United States Patent
Gérard et al.

(10) Patent No.: US 10,081,640 B2
(45) Date of Patent: Sep. 25, 2018

(54) METHODS OF PREPARING CYTOTOXIC BENZODIAZEPINE DERIVATIVES

(71) Applicant: ImmunoGen, Inc., Waltham, MA (US)

(72) Inventors: Baudouin Gérard, Belmont, MA (US); Manami Shizuka, Belmont, MA (US); Michael Louis Miller, Framingham, MA (US); Richard A. Silva, Needham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/216,548

(22) Filed: Jul. 21, 2016

(65) Prior Publication Data

US 2017/0051011 A1    Feb. 23, 2017

Related U.S. Application Data

(60) Provisional application No. 62/327,973, filed on Apr. 26, 2016, provisional application No. 62/195,023, filed on Jul. 21, 2015.

(51) Int. Cl.

| | |
|---|---|
| *C07K 17/00* | (2006.01) |
| *A61K 38/06* | (2006.01) |
| *C07K 5/00* | (2006.01) |
| *C07K 7/00* | (2006.01) |
| *C07K 16/00* | (2006.01) |
| *C07D 519/00* | (2006.01) |
| *C07D 487/04* | (2006.01) |
| *C07K 5/083* | (2006.01) |

(52) U.S. Cl.
CPC ......... *C07D 519/00* (2013.01); *C07D 487/04* (2013.01); *C07K 5/0804* (2013.01)

(58) Field of Classification Search
CPC ........... A61K 38/00; C07K 7/00; C07K 16/18
See application file for complete search history.

(56) References Cited

U.S. PATENT DOCUMENTS 8,889,669 B2 * 11/2014 Li .................. C07D 487/04
                                                    514/219
9,353,127 B2    5/2016 Fishkin et al.
2016/0106863 A1 4/2016 Chari et al.

FOREIGN PATENT DOCUMENTS

| EP | 2 511 260 A1 | 10/2012 |
|---|---|---|
| WO | 2010/091150 A1 | 8/2010 |
| WO | 2011/064141 A1 | 6/2011 |
| WO | 2012/128868 A1 | 9/2012 |
| WO | 2015/051045 A2 | 4/2015 |
| WO | 2016/036794 A1 | 3/2016 |
| WO | 2016/036801 A1 | 3/2016 |

OTHER PUBLICATIONS

Philou, Sciencemadness Discussion Board—Reaction of esters with hydrazine, Oct. 4, 2003, available online at: https://sciencemadness.org/talk/viewthread.php?tid=161, accessed on Oct. 22, 2017.*
Behrens et al.; "Synthesis of Achiral Linker Reagents for Direct Labelling of Oligonucleotides on Solid Supports"; Nucleosides & Nucleotides; 18(2):291-305 (Feb. 1, 1999).
Ueno et al.; "Synthesis and Properties of Nucleic Acid Analogues Consisting of a Benzene-Phosphate Backbone"; The Journal of Organic Chemistry, American Chemical Society; 70(20):7925-7935 (Jan. 1, 2005).

* cited by examiner

*Primary Examiner* — Hasan Syed Ahmed
*Assistant Examiner* — Kaipeen E Yang
(74) *Attorney, Agent, or Firm* — McCarter & English, LLP; Steven G. Davis; Xin Zhang

(57) ABSTRACT

The invention relates to novel methods for preparing indolinobenzodiazepine dimer compounds and their synthetic precursors.

18 Claims, 13 Drawing Sheets

METHODS OF PREPARING CYTOTOXIC BENZODIAZEPINE DERIVATIVES

REFERENCE TO RELATED APPLICATIONS

This application claims the benefit of the filing date, under 35 U.S.C. § 119(e), of U.S. Provisional Application No. 62/327,973, filed on Apr. 26, 2016, and U.S. Provisional Application No. 62/195,023, filed on Jul. 21, 2015. The entire contents of each of the above-referenced applications are incorporated herein by reference.

FIELD OF THE INVENTION

The present invention relates to novel methods for preparing cytotoxic indolinobenzodiazepine derivatives.

BACKGROUND OF THE INVENTION

It has been shown that cell-binding agent conjugates of indolinobenzodiazepine dimers that have one imine functionality and one amine functionality display a much higher therapeutic index (ratio of maximum tolerated dose to minimum effective dose) in vivo compared to previously disclosed benzodiazepine derivatives having two imine functionalities. See, for example, WO 2012/128868. The previously disclosed method for making the indolinobenzodiazepine dimers with one imine functionality and one amine functionality involves partial reduction of indolinobenzodiazepine dimers having two imine functionalities. The partial reduction step generally leads to the formation of fully reduced by-product and unreacted starting material, which requires cumbersome purification step and results in low yield.

Thus, there exists a need for improved methods for preparing the indolinobenzodiazepine dimers that are more efficient and suitable for large scale manufacturing process.

SUMMARY OF THE INVENTION

The present invention provides various methods for preparing indolinobenzodiazepine dimer compounds and their synthetic precursors. Compared to the previously disclosed method, the methods of the present invention can produce the desired dimer compounds with higher yield without the need of cumbersome purification steps. These methods are more suitable for large scale manufacturing process.

In a first embodiment, the present invention provides a method of preparing a compound of formula (2d),

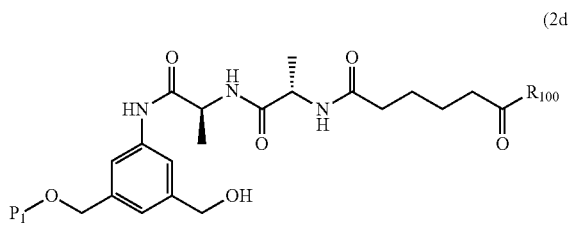

(2d)

or a salt thereof, said method comprising introducing an alcohol protecting group onto one of the primary alcohols of a compound of formula (1d) by reacting the compound of formula (1d) with an alcohol protecting reagent, (1d)

wherein $P_1$ is the alcohol protecting group; and $R_{100}$ is $(C_1-C_3)$alkoxy.

In a second embodiment, the present invention provides a method of preparing a compound of formula (3d), (3d)

or a salt thereof, said method comprising reacting a halogenating reagent, a sulfonating reagent or an esterification reagent with a compound of formula (2d), (2d)

wherein $P_1$ is an alcohol protecting group; $X_1$ is a leaving group selected from the group consisting of: —Br, —I, —Cl, a sulfonate ester, and an activated ester (preferably, $X_1$ is —Br, —I, or a sulfonate ester); and $R_{100}$ is $(C_1-C_3)$alkoxy.

In a third embodiment, the present invention provides a method of preparing a compound of formula (4d), (4d)

or a salt thereof, said method comprising reacting a compound of formula (3d)

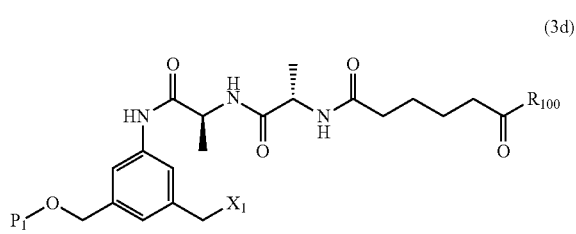

with a monomer compound of the formula (a₁),

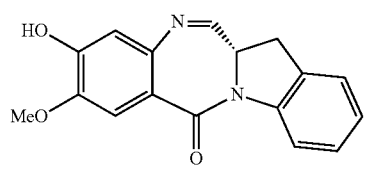

wherein $P_1$ is an alcohol protecting group; $X_1$ is a leaving group selected from the group consisting of: —Br, —I, —Cl, a sulfonate ester, and an activated ester (preferably, $X_1$ is —Br, —I, or a sulfonate ester); and $R_{100}$ is $(C_1-C_3)$alkoxy.

In a fourth embodiment, the present invention provides a method of preparing a compound of formula (5d),

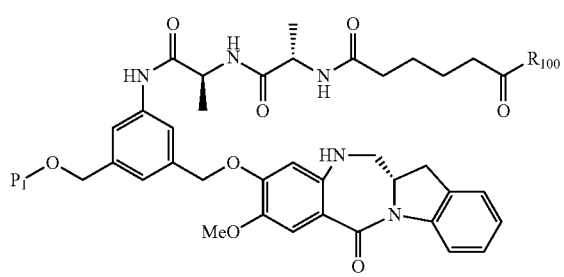

or a salt thereof, said method comprising reacting a compound of formula (4d),

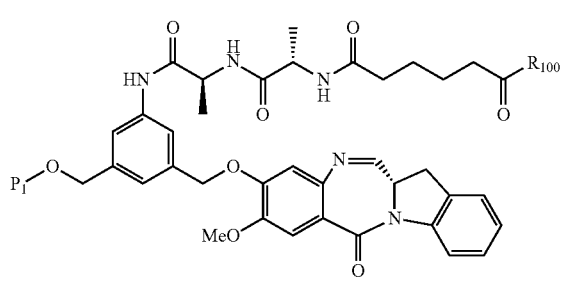

with an imine reducing agent, wherein $P_1$ is an alcohol protecting group; and $R_{100}$ is $(C_1-C_3)$alkoxy.

In a fifth embodiment, the present invention provides method of preparing a compound of formula (6d),

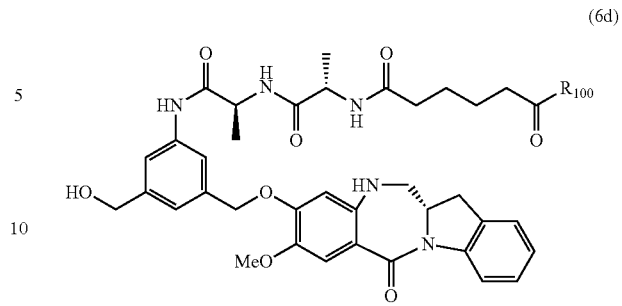

or a salt thereof, said method comprising reacting a compound of formula (5d),

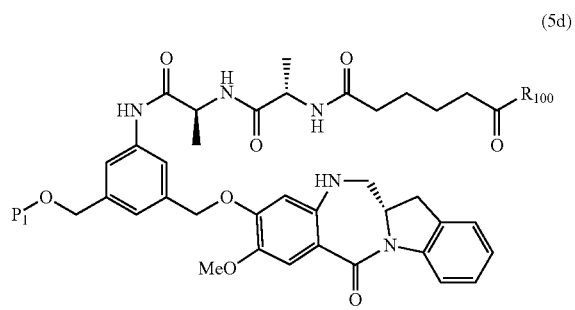

with an alcohol deprotecting reagent, wherein $P_1$ is an alcohol protecting group; and $R_{100}$ is $(C_1-C_3)$alkoxy.

In a sixth embodiment, the present invention provides a method of preparing a compound of formula (7d),

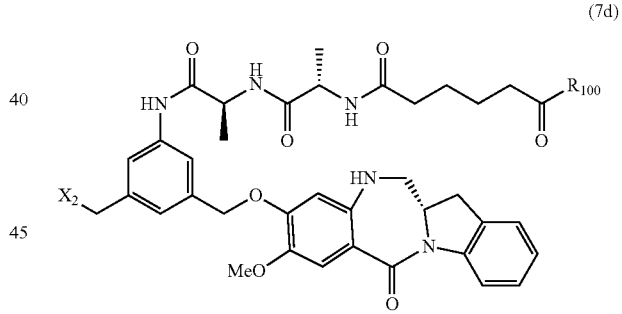

or a salt thereof, said method comprising reacting a halogenating reagent, a sulfonating reagent or an esterification reagent with the primary alcohol compound of formula (6d),

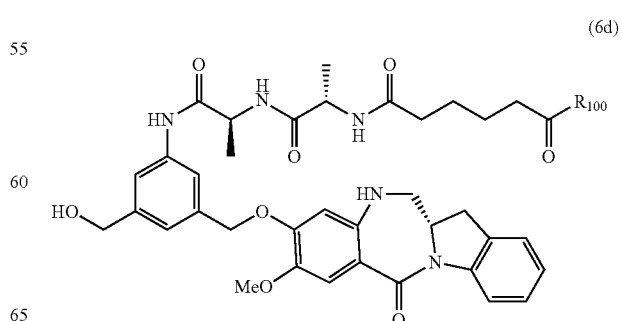

wherein X₂ is a leaving group selected from the group consisting of: —Br, —I, —Cl, a sulfonate ester, and an activated ester (preferably, X₂ is —Br, —I, or a sulfonate ester); and $R_{100}$ is $(C_1-C_3)$alkoxy.

In a seventh embodiment, the present invention provides a method of preparing a compound of formula (7d")

or a pharmaceutically acceptable salt thereof, said method comprising reacting a compound of formula (7d)

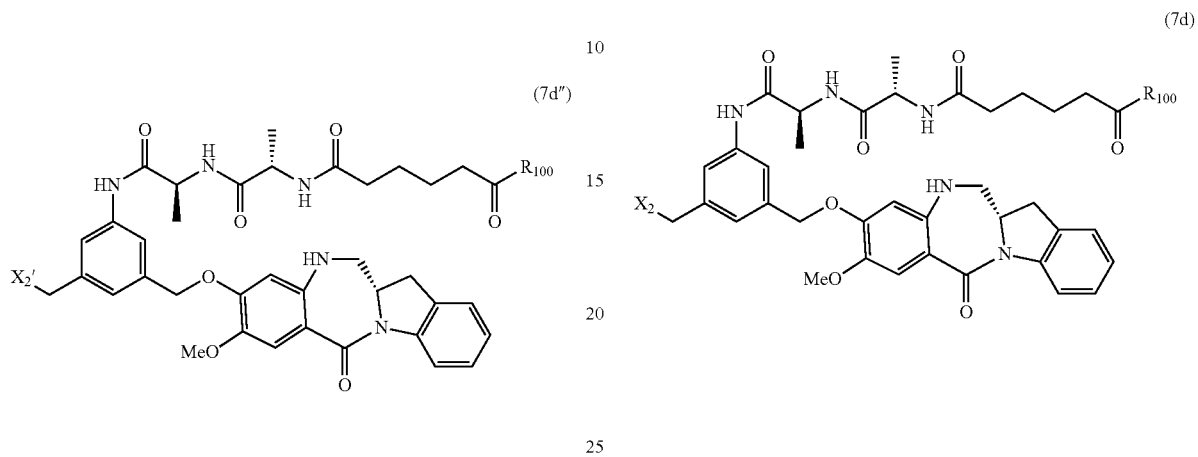

or a salt thereof, said method comprising reacting a compound of formula (5d")

with a monomer compound of the formula (a₁),

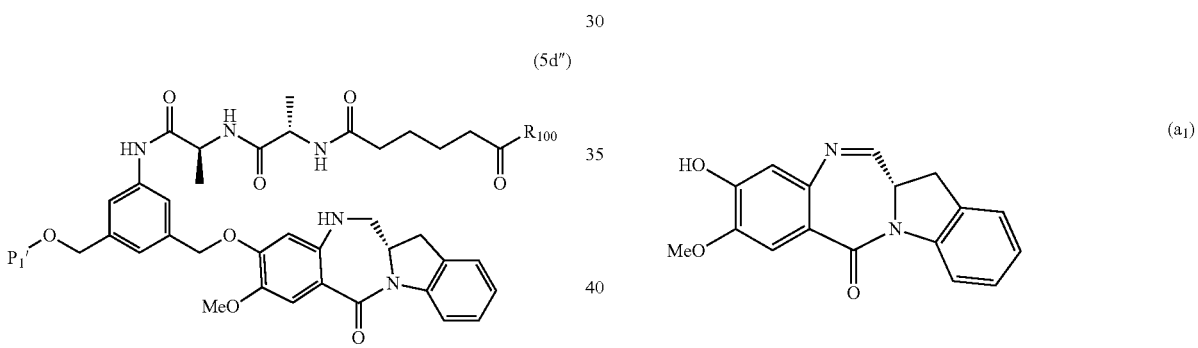

with an alcohol deprotecting reagent and a halogenating reagent, wherein $P_1'$ is an acid labile alcohol protecting group; $X_2'$ is —Br or —I; and $R_{100}$ is $(C_1-C_3)$alkoxy.

In a eighth embodiment, the present invention provides a method of preparing a compound of formula (Id'), wherein $R_{100}$ is $(C_1-C_3)$alkoxy; and, X₂ is a leaving group selected from the group consisting of: —Br, —I, —Cl, a sulfonate ester, and an activated ester (preferably, X₂ is —Br, —I, or a sulfonate ester).

In a ninth embodiment, the present invention provides a method of forming a compound of formula (Id'),

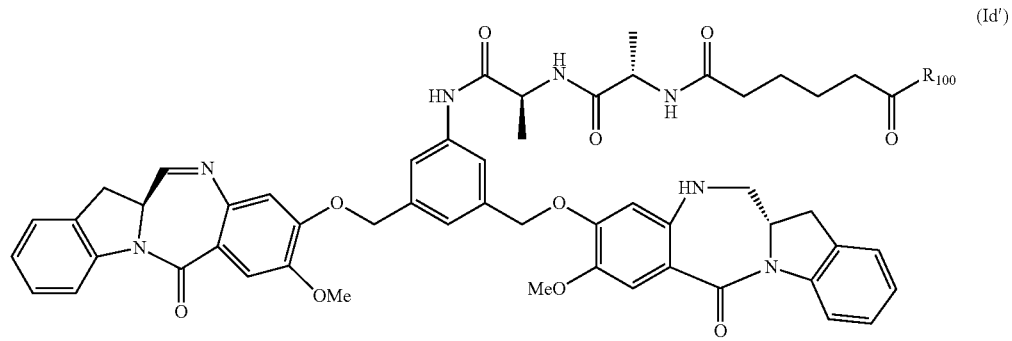

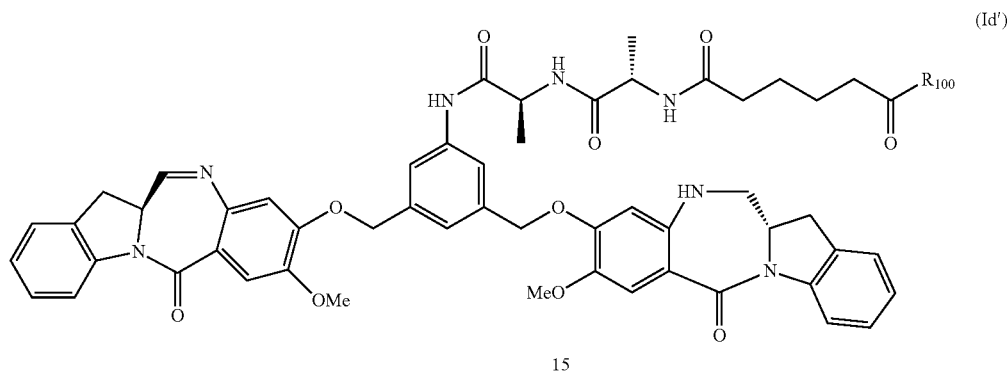

or a pharmaceutically acceptable salt thereof, said method comprising the steps of:

(1) introducing an alcohol protecting group onto one of the primary alcohols of a compound of formula (1d),

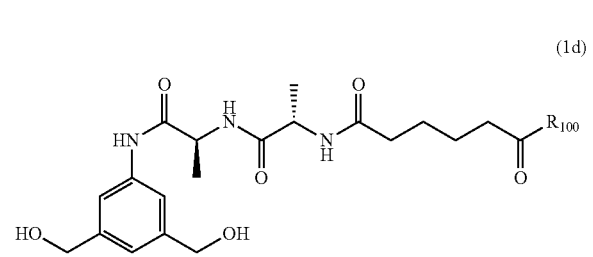

to form a compound of formula (2d),

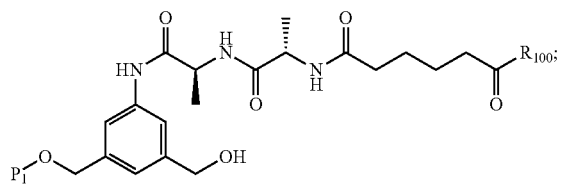

(2) reacting the compound of formula (2d) with a halogenating reagent, a sulfonating reagent or an esterification reagent to form a compound of formula (3d),

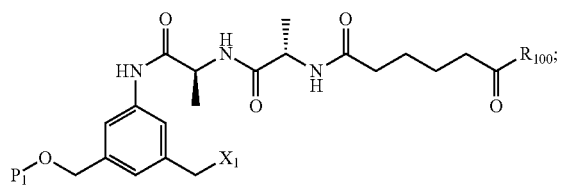

(3) reacting the compound of formula (3d) with a monomer compound of the formula ($a_1$),

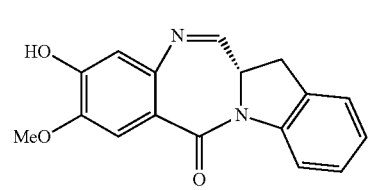

to form a compound of formula (4d),

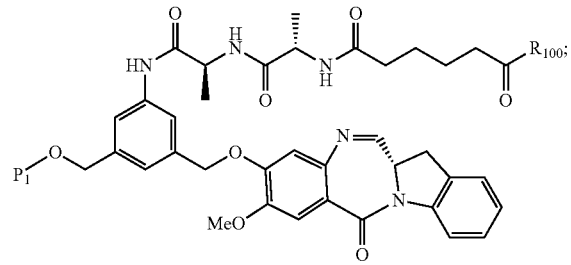

(4) reacting the compound of formula (4d) with an imine reducing agent to form a compound of formula (5d),

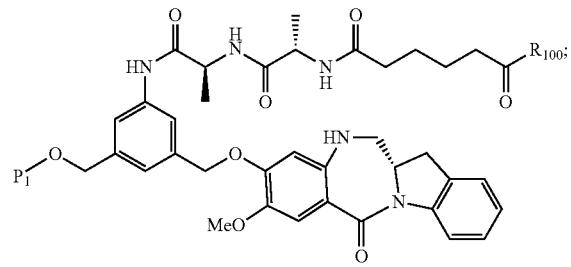

(5) reacting the compound of formula (5d) with an alcohol deprotecting reagent to form a compound of formula (6d),

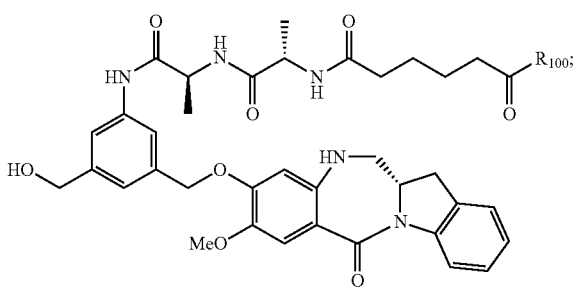

(6) reacting the compound of formula (6d) with a second halogenating reagent, a second sulfonating reagent, or a second esterification reagent to form a compound of formula (7d),

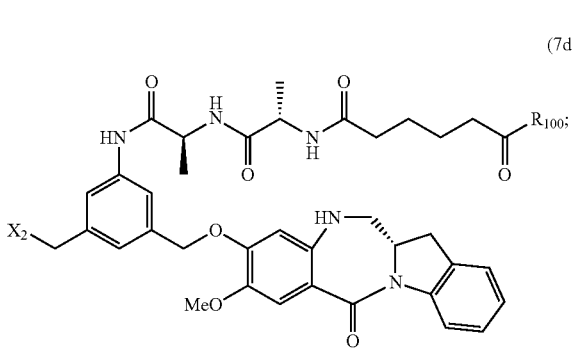

(7d)

and (7) reacting the compound of formula (7d) with a monomer compound of the formula (a₁),

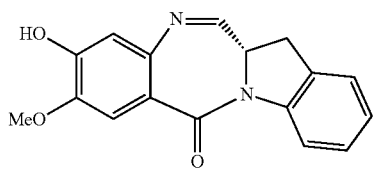

(a₁)

to form the compound of formula (Id'); wherein $P_1$ is an alcohol protecting group; $X_1$ and $X_2$ are each independently a leaving group selected from the group consisting of: —Br, —I, —Cl, a sulfonate ester, and an activated ester (preferably, $X_1$ and $X_2$ are each independently —Br, —I, or a sulfonate ester); and $R_{100}$ is $(C_1-C_3)$alkoxy.

In a tenth embodiment, the present invention provides a method of preparing a compound of formula (Id'), or a pharmaceutically acceptable salt thereof, said method comprising the steps of:

(1) introducing an alcohol protecting group onto one of the primary alcohols of a compound of formula (1d),

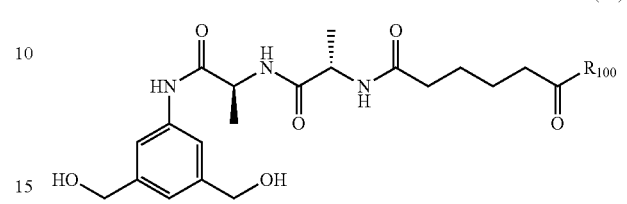

(1d)

to form a compound of formula (2d"),

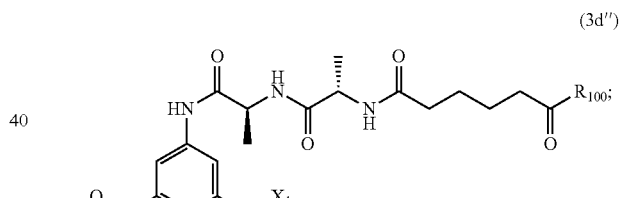

(2d")

(2) reacting the compound of formula (2d") with a halogenating reagent, a sulfonating reagent or an esterification reagent to form a compound of formula (3d"), (3d")

(3) reacting the compound of formula (3d") with a monomer compound of the formula (a₁),

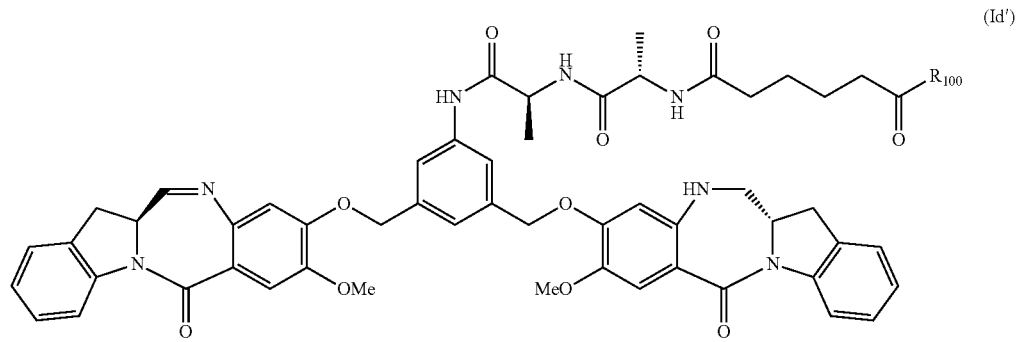

(Id')

(a₁)

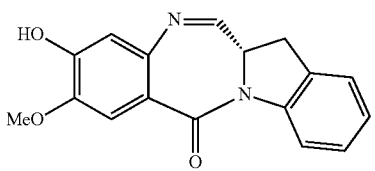

to form a compound of formula (4d''), (4d'')

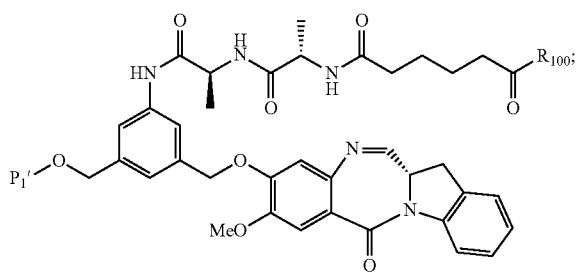

(4) reacting the compound of formula (4d'') with an imine reducing agent to form a compound of formula (5d''), (5d'')

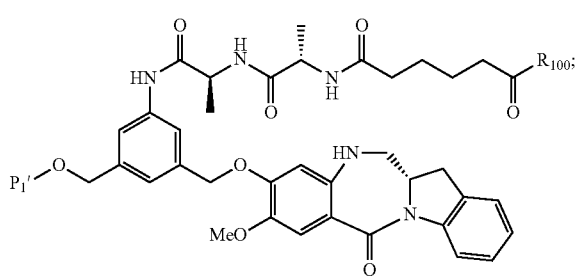

(5) reacting the compound of formula (5d'') with an alcohol deprotecting reagent and a halogenating reagent to form a compound of formula (7d''), (7d'')

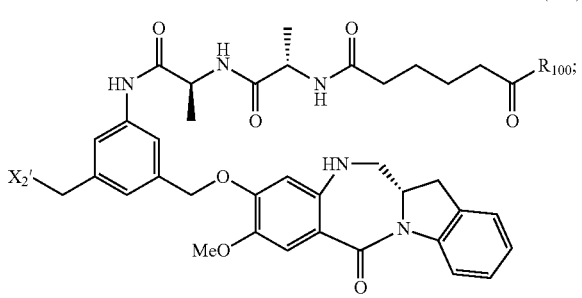

(6) reacting a compound of formula (7d'') with a monomer compound of the formula (a₁), (a₁)

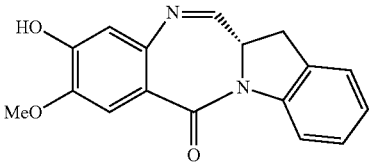

to form the compound of formula (Id'), wherein $X_2'$ is —Br or —I; and the remaining variables are as described above in the ninth embodiment.

In a eleventh embodiment, the present invention provides a method of preparing a compound of formula (9d), (9d)

or a salt thereof, said method comprising reacting a compound of formula (4d), (4d)

with an alcohol deprotecting reagent, wherein $P_1$ is an alcohol protecting group; and $R_{100}$ is $(C_1\text{-}C_3)$alkoxy.

In a twelfth embodiment, the present invention provides a method of preparing a compound of formula (10d),

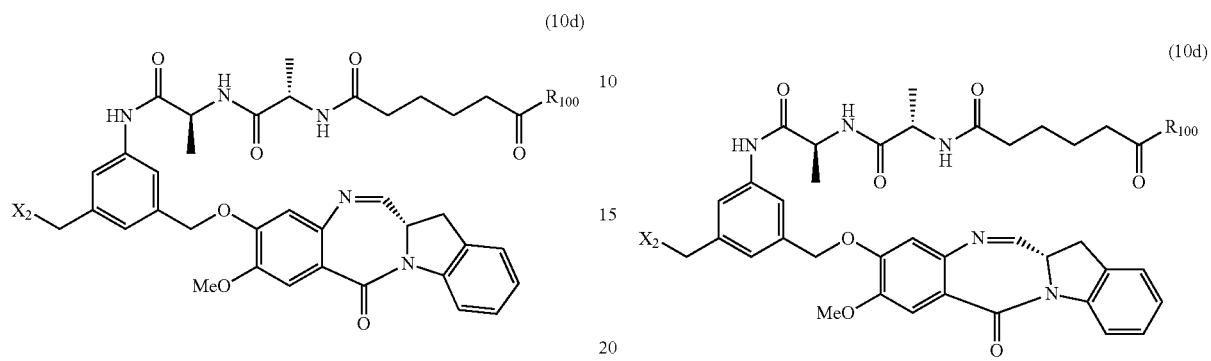

(10d)

or a salt thereof, said method comprising reacting the compound of formula (9d) with a halogenating reagent, a sulfonating reagent or an esterification reagent, (9d)

wherein $X_2$ is —Br, —I, —Cl, a sulfonate ester, and an activated ester (preferably, $X_2$ is —Br, —I, or a sulfonate ester); and $R_{100}$ is $(C_1-C_3)$alkoxy.

In a thirteenth embodiment, the present invention provides a method of preparing a compound of formula (18d), or a salt thereof, said method comprising reacting a compound of formula (10d)

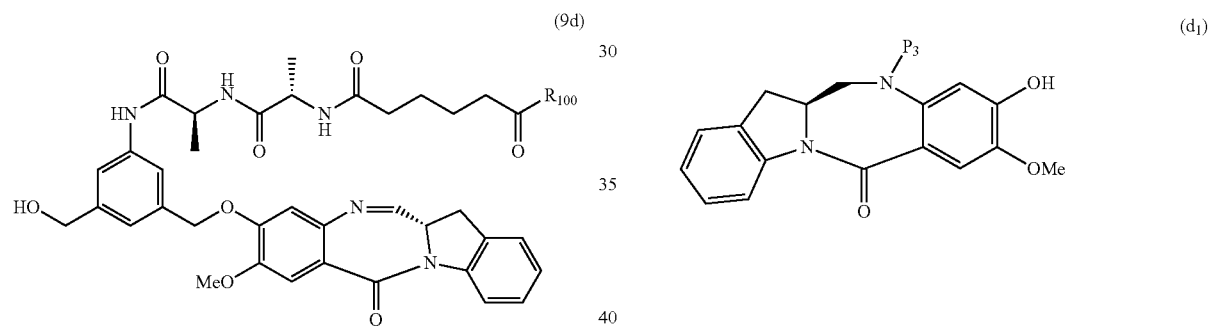

(10d)

with a monomer compound of the formula $(d_1)$, $(d_1)$ wherein $X_2$ is a leaving group selected from the group consisting of: —Br, —I, —Cl, a sulfonate ester, and an activated ester (preferably, $X_2$ is —Br, —I, or a sulfonate ester); $P_3$ is H or $P_2$; $P_2$ is an amine protecting group; and $R_{100}$ is $(C_1-C_3)$alkoxy.

In a fourteenth embodiment, the present invention provides a method of preparing a compound of formula (Id'),

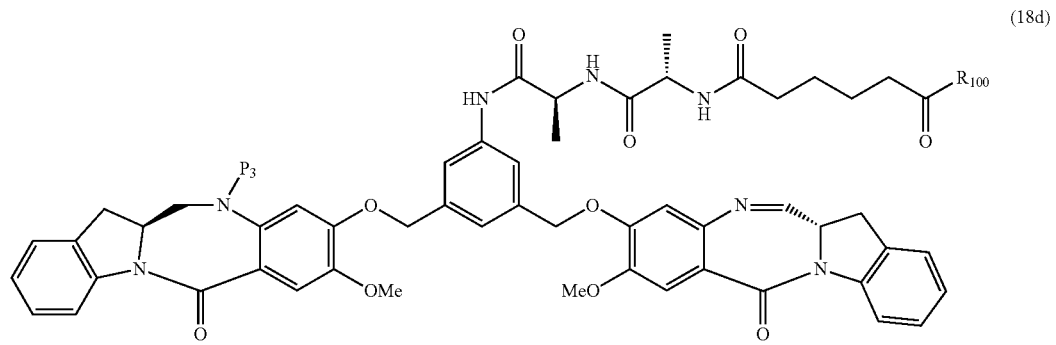

(18d)

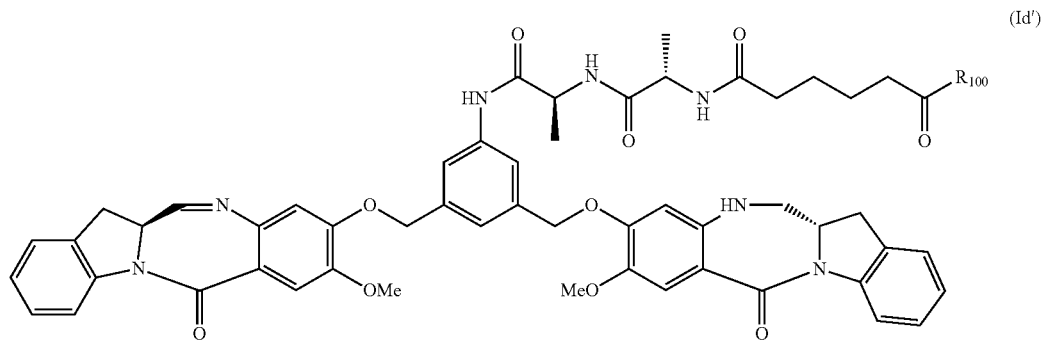

(Id')

or a pharmaceutically acceptable salt thereof, said method comprising reacting a compound of formula (11d),

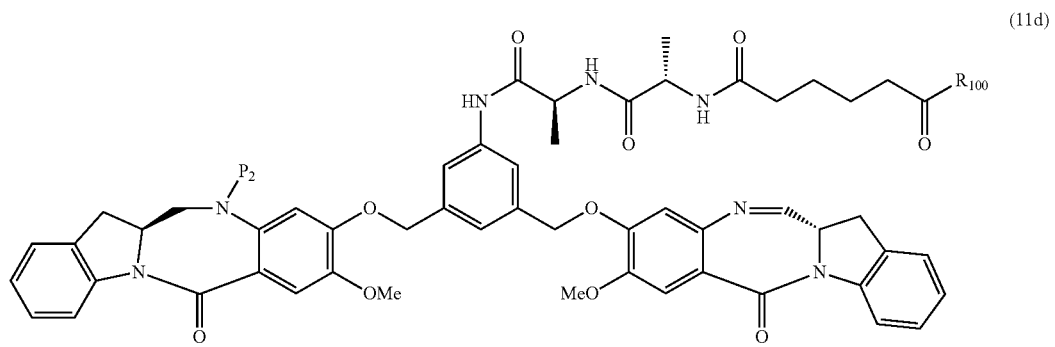

(11d)

with an amine deprotecting reagent, wherein $P_2$ is an amine protecting group; and $R_{100}$ is $(C_1-C_3)$alkoxy.

In a fifteenth embodiment, the present invention provides a method of preparing a compound of formula (Id'),

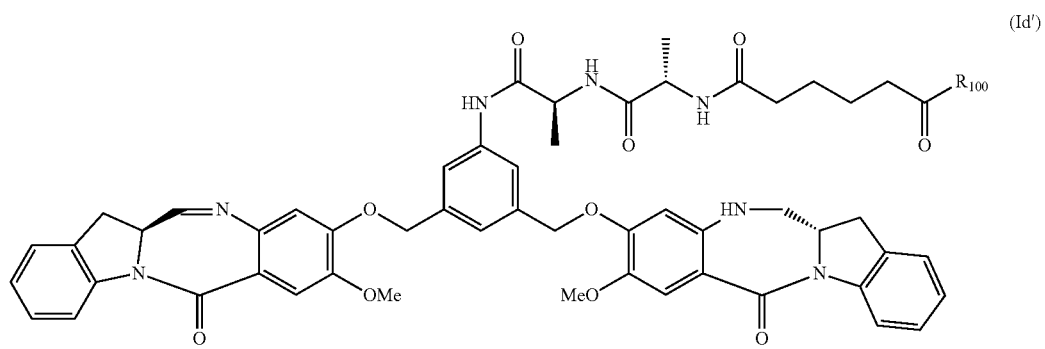

(Id')

or a pharmaceutically acceptable salt thereof, said method comprising the steps of:

(1) introducing an alcohol protecting group onto one of the primary alcohols of the compound of formula (1d), (1d)

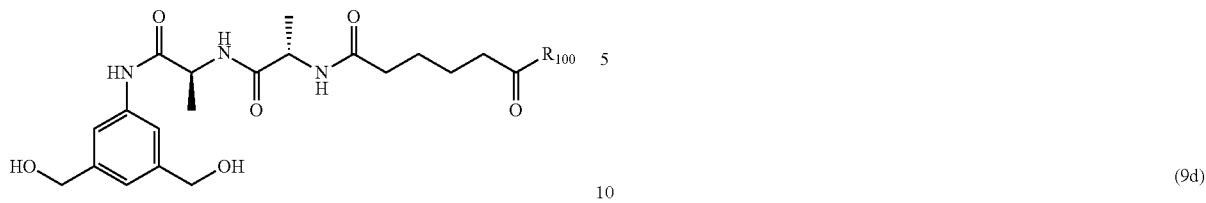

to form a compound of formula (2d), (2d)

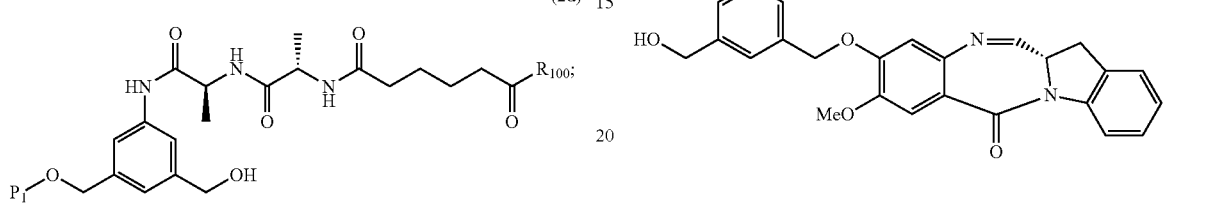

(2) reacting the compound of formula (2d) with a halogenating reagent, a sulfonating reagent or an esterification reagent to form a compound of formula (3d), (3d)

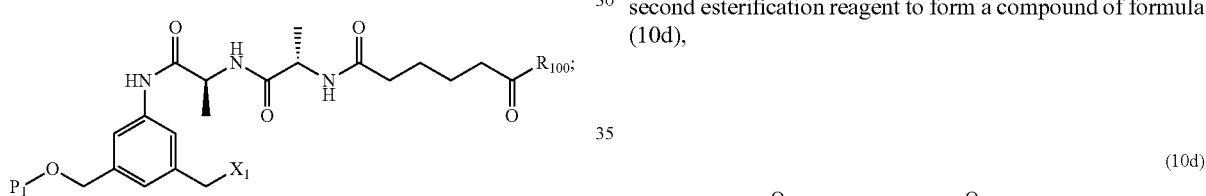

(3) reacting the compound of formula (3d) with a monomer compound of the formula ($a_1$), (a₁)

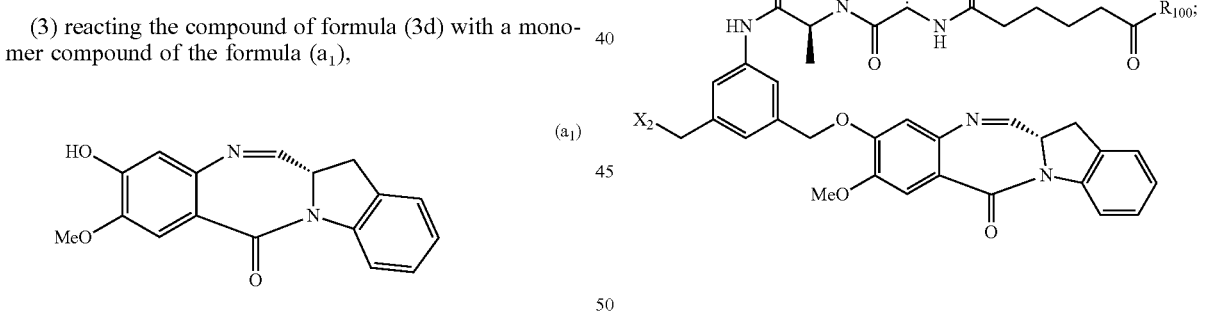

to form a compound of formula (4d), (4d)

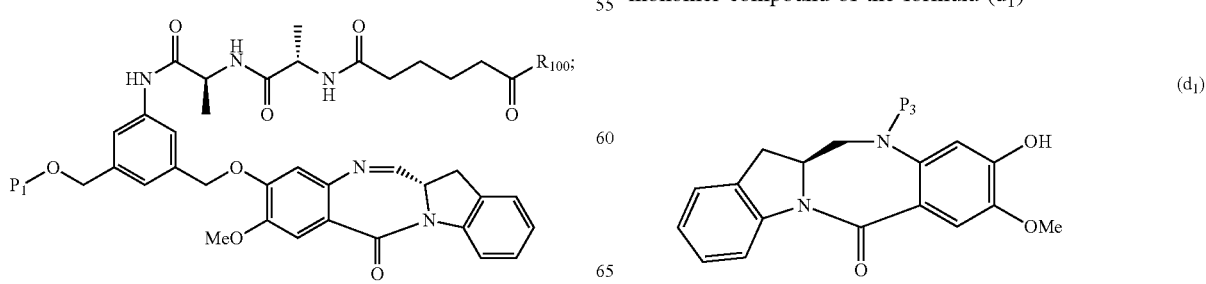

(4) reacting the compound of formula (4d) with an alcohol deprotecting reagent to form a compound of formula (9d), (9d)

(5) reacting the compound of formula (9d) with a second halogenating reagent, a second sulfonating reagent or a second esterification reagent to form a compound of formula (10d), (10d)

(6) reacting the compound of formula (10d) with a monomer compound of the formula ($d_1$)

(d₁)

to form a compound of formula (18d),

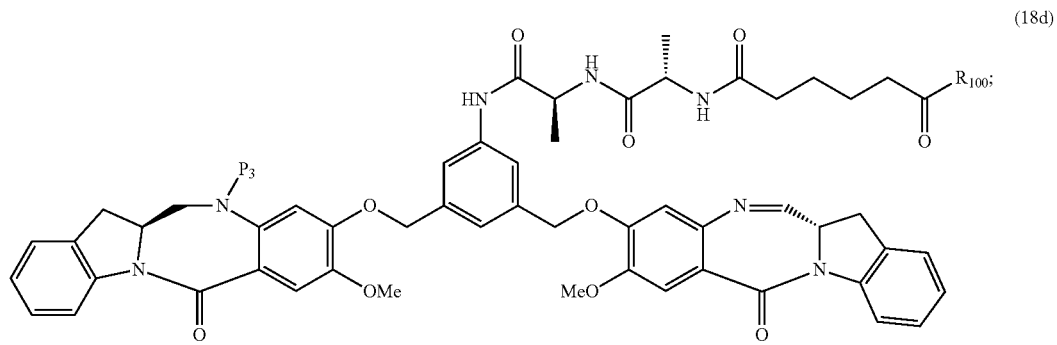

and (7) when $P_3$ is an amine protecting group, reacting the compound of formula (18d) to an amine deprotecting reagent to form the compound of formula (Id'), wherein $P_1$ is an alcohol protecting group; $X_1$ and $X_2$ are each independently a leaving group selected from the group consisting of: —Br, —I, —Cl, a sulfonate ester, and an activated ester (preferably, $X_1$ is —Br, —I, or a sulfonate ester); $P_3$ is H or an amine protecting group; and $R_{100}$ is $(C_1-C_3)$alkoxy.

In a sixteenth embodiment, the present invention provides a method of preparing a compound of formula (12d),

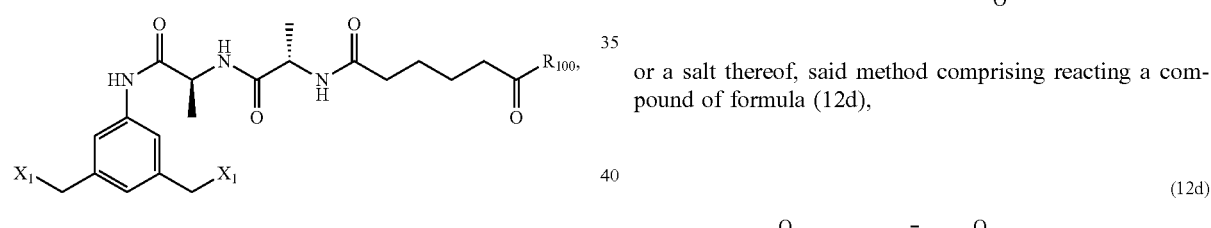

or a salt thereof, said method comprising reacting a compound of formula (1d),

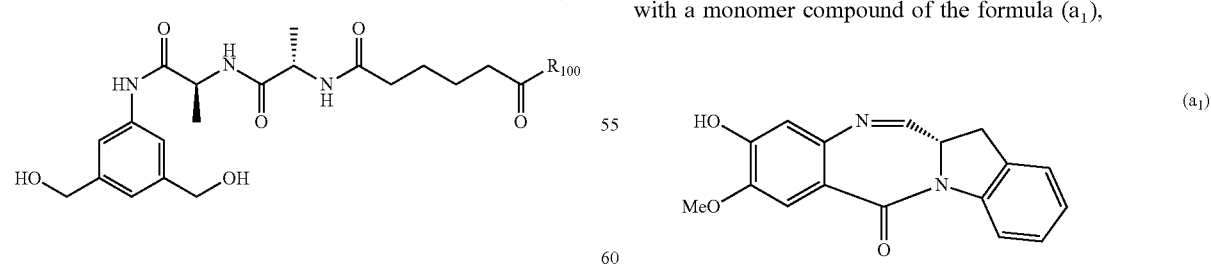

with a halogenating reagent, a sulfonating reagent or an esterification reagent, wherein $X_1$ is —Br, —I, a sulfonate ester or an activated ester (preferably, $X_1$ is —Br, —I, or a sulfonate ester); and $R_{100}$ is $(C_1-C_3)$alkoxy.

In a seventeenth embodiment, the present invention provides a method of preparing a compound of formula (10d'),

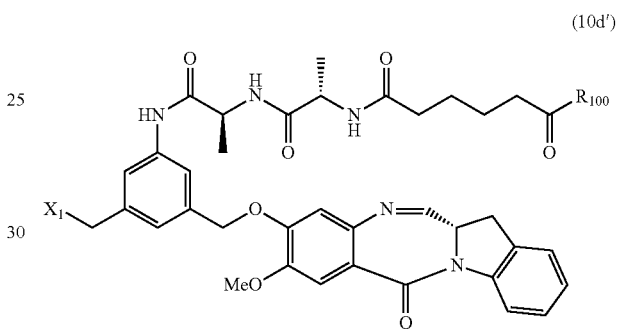

or a salt thereof, said method comprising reacting a compound of formula (12d),

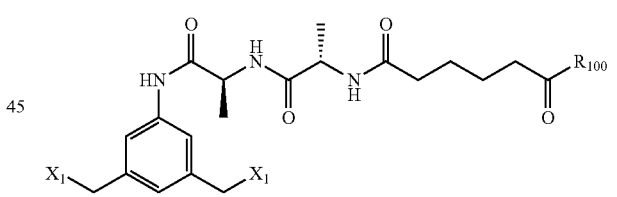

with a monomer compound of the formula ($a_1$),

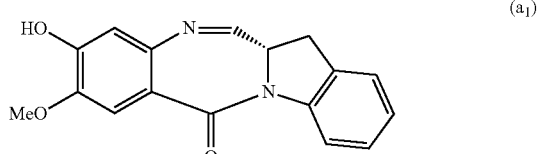

wherein $X_1$ is —Br, —I, —Cl, a sulfonate ester, and an activated ester (preferably, $X_1$ is —Br, —I, or a sulfonate ester); and $R_{100}$ is $(C_1-C_3)$alkoxy.

In a eighteenth embodiment, the present invention provides a method of preparing a compound of formula (7d'), (7d')

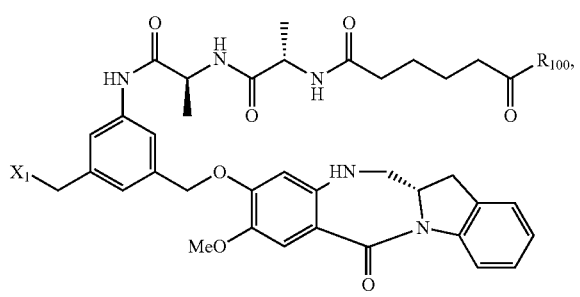

or a salt thereof, said method comprising reacting a compound of formula (10d'),

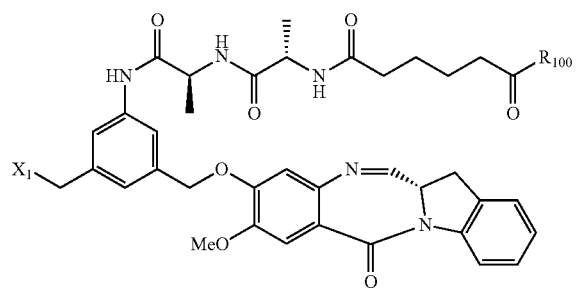

(10d')

or a salt thereof, with an imine reducing agent, wherein $X_1$ is —Br, —I, —Cl, a sulfonate ester, and an activated ester (preferably, $X_1$ is —Br, —I, or a sulfonate ester); and $R_{100}$ is $(C_1\text{-}C_3)$alkoxy.

In a nineteenth embodiment, the present invention provides a method of preparing a compound of formula (Id'), or a pharmaceutically acceptable salt thereof, said method comprising the steps of:

(1) reacting a compound of formula (1d) with a halogenating reagent, a sulfonating reagent or an esterification reagent, (1d)

[structure of compound 1d]

to form a compound of formula (12d), (12d)

[structure of compound 12d]

(2) reacting the compound of formula (12d) with a monomer compound of the formula ($a_1$),

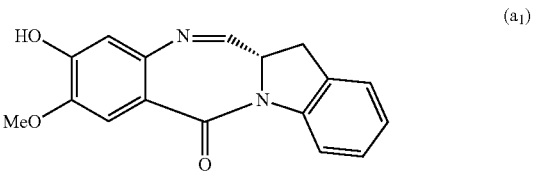 [SMILES: COc1cc2c(cc1O)N=C[C@@H]1Cc3ccccc3N1C2=O]

(Id')

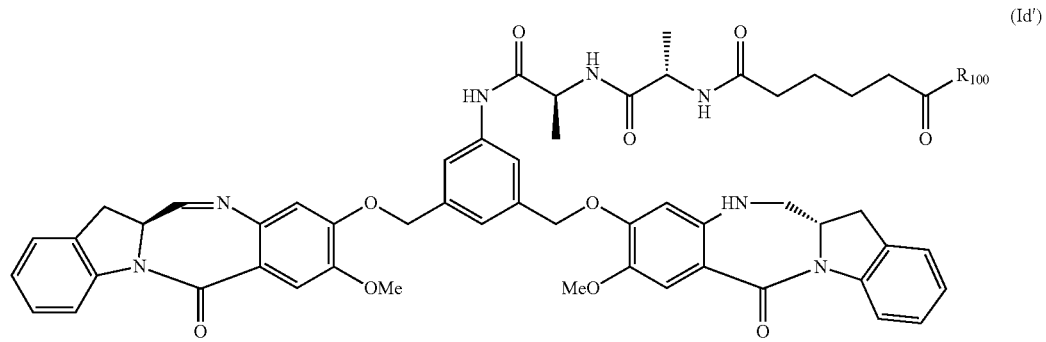

to form a compound of a formula (10d'), (10d')

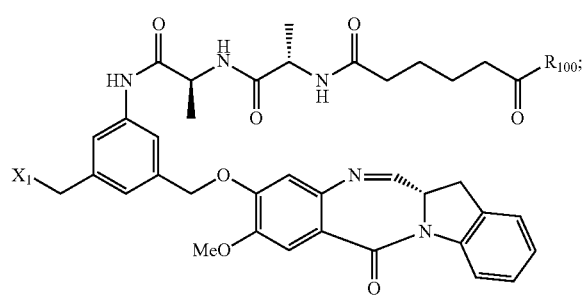

(3) reacting the compound of formula (10d') with a monomer compound of the formula ($d_1$), ($d_1$)

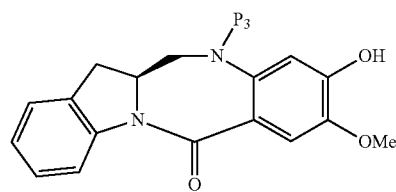

to form a compound of formula (18d), (18d)

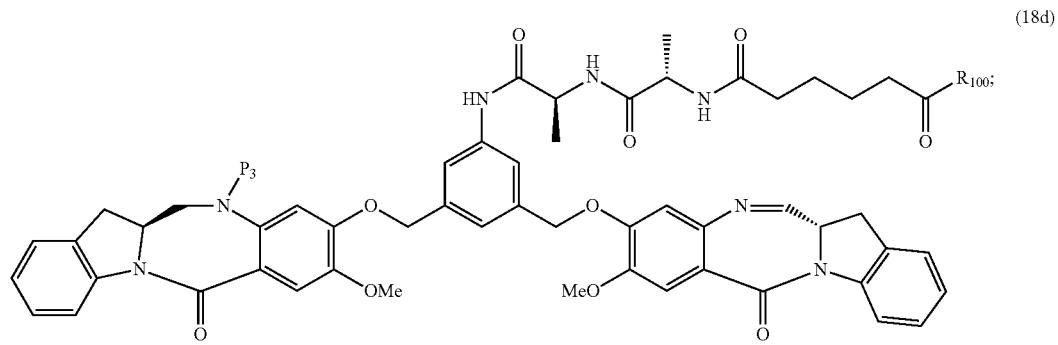

and (4) when $P_3$ is an amine protecting group, reacting the compound of formula (18d) with an amine deprotecting reagent to form the compound of formula (Id'), wherein $X_1$ is —Br, —I, —Cl, a sulfonate ester, and an activated ester (preferably, $X_1$ is —Br, —I, or a sulfonate ester); $P_3$ is H or an amine protecting group; and $R_{100}$ is ($C_1$-$C_3$)alkoxy.

In a twentieth embodiment, the present invention provides a method of preparing a compound of formula (Id'), or a pharmaceutically acceptable salt thereof, said method comprising the steps of:

(1) reacting a halogenating reagent, a sulfonating reagent or an esterification reagent with a compound of formula (1d), (1d)

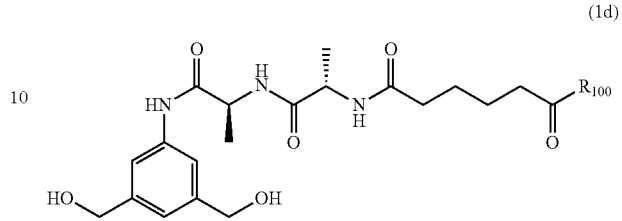

to form a compound of formula (12d), (12d)

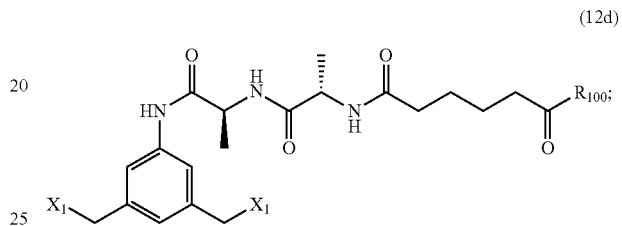

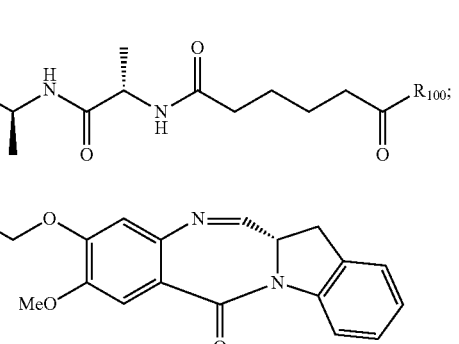

(Id')

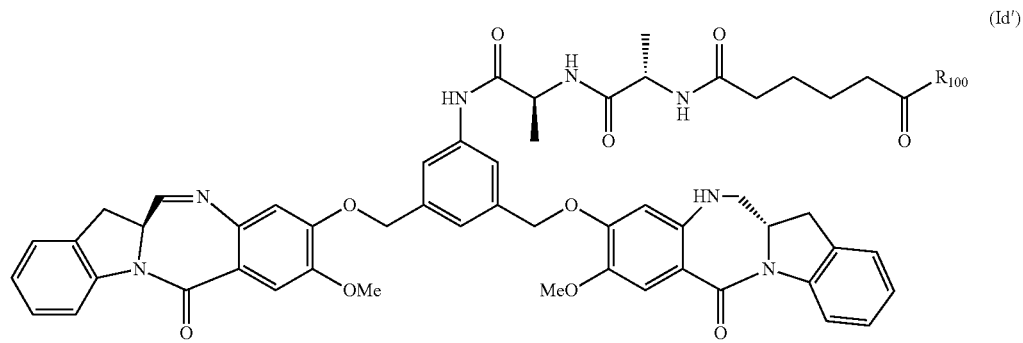

(2) reacting the compound of formula (12d) with a monomer compound of the formula (a₁),

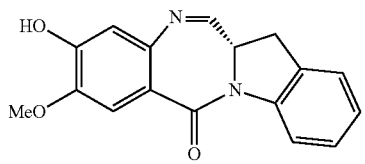
(a₁)

to form a compound of a formula (10d'),

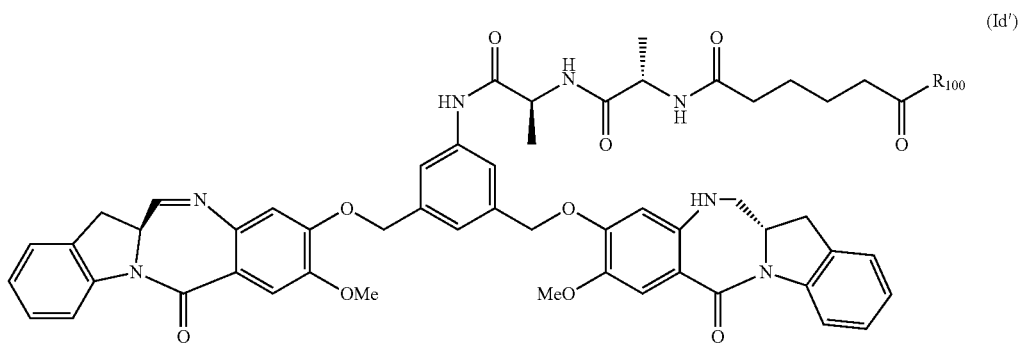
(10d')

(3) reacting the compound (10d') with an imine reducing reagent to form a compound (7d'),

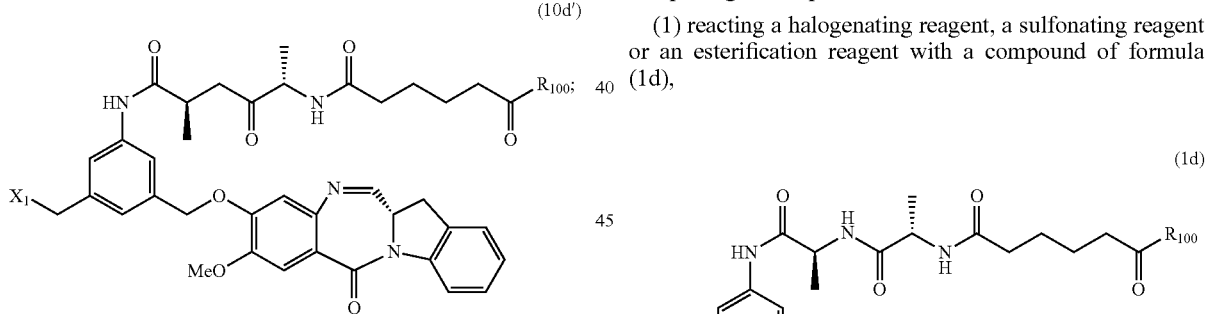
(7d')

(4) reacting the compound of formula (7d') with a monomer compound of the formula (a₁),

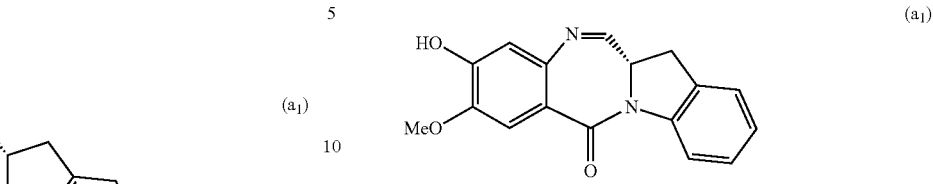
(a₁)

to form a compound of formula (Id'), or a pharmaceutically acceptable salt thereof, wherein $X_1$ is —Br, —I, —Cl, a sulfonate ester, or an activated ester (preferably, $X_1$ is —Br, —I, or a sulfonate ester); and $R_{100}$ is $(C_1$-$C_3)$alkoxy.

In a twenty-first embodiment, the present invention provides a method of preparing a compound of formula (Id'),

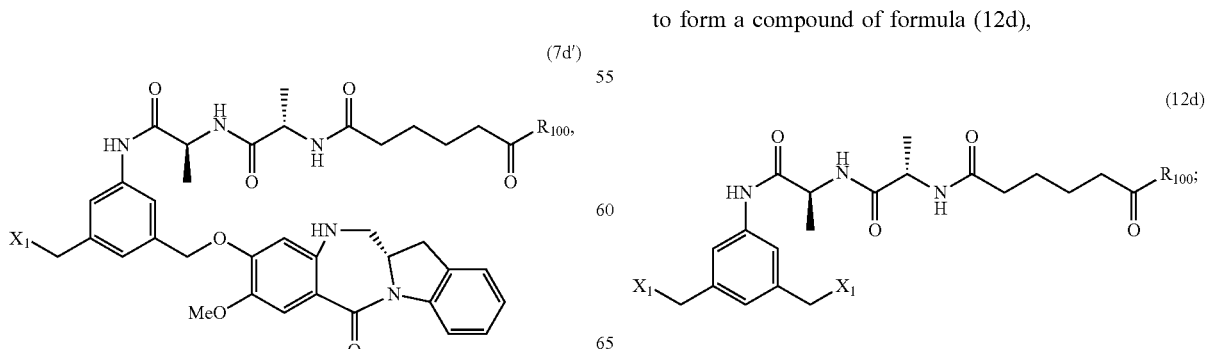
(Id')

or a pharmaceutically acceptable salt thereof, said method comprising the steps of:

(1) reacting a halogenating reagent, a sulfonating reagent or an esterification reagent with a compound of formula (1d),

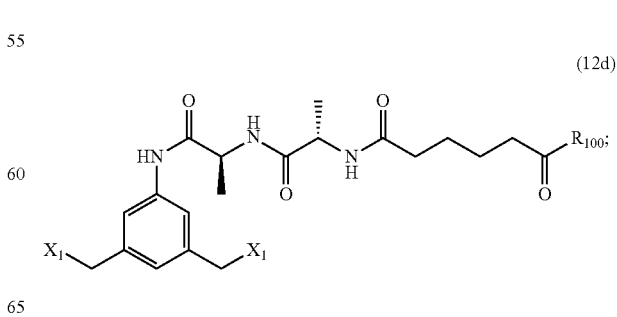
(1d)

to form a compound of formula (12d), (12d)

(2) reacting the compound of formula (12d) with a monomer compound of the formula (d₁),

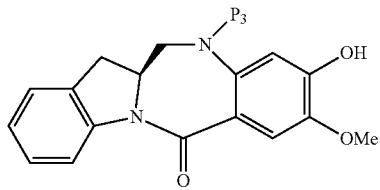

to form a compound of a formula (7d1'),

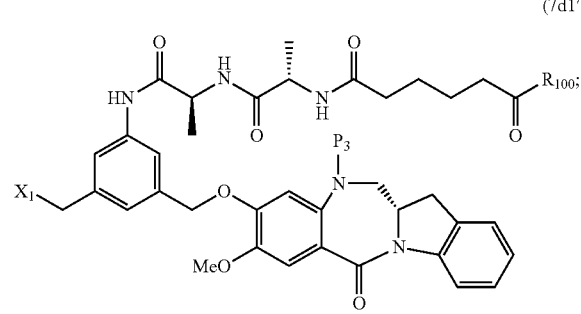

(3) reacting the compound of formula (7d1') with a monomer compound of the formula ($a_1$),

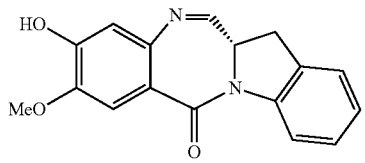

to form a compound of formula (18d),

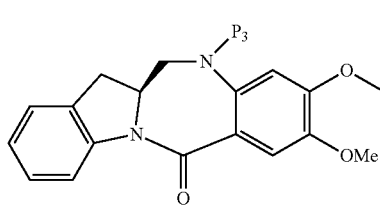

and
(4) when $P_3$ is an amine protecting group, reacting the compound of formula (18d) with an amine deprotecting reagent to form the compound of formula (Id'); wherein $X_1$ is —Br, —I, —Cl, a sulfonate ester, or an activated ester (preferably, $X_1$ is —Br, —I, or a sulfonate ester); $P_3$ is H or an amine protecting group; and $R_{100}$ is ($C_1$-$C_3$)alkoxy.

In a twenty-second embodiment, the present invention provides a method of preparing a compound of formula (13d),

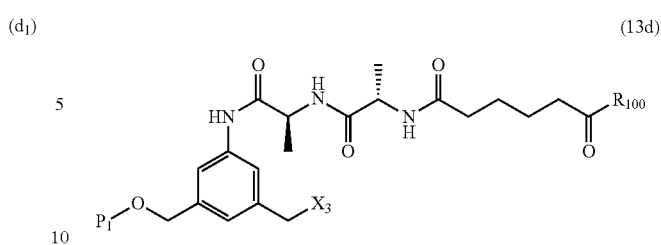

or a salt thereof, said method comprising reacting a chlorinating reagent with a compound of formula (2d),

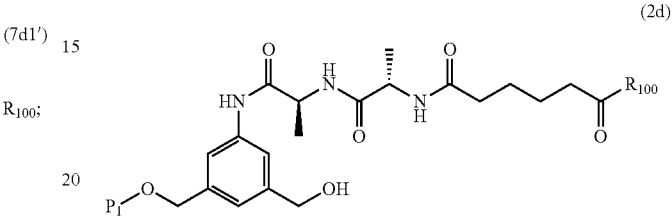

wherein $P_1$ is an alcohol protecting group; $X_3$ is —Cl; and $R_{100}$ is ($C_1$-$C_3$)alkoxy.

In a twenty-third embodiment, the present invention provides a method of preparing a compound of formula (14d),

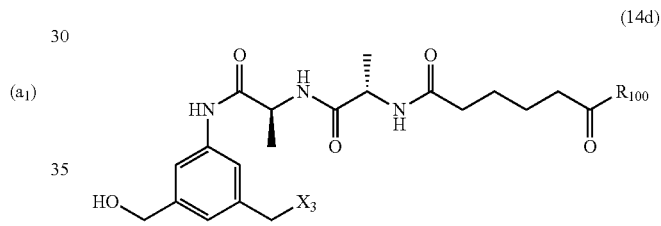

or a salt thereof, said method comprising reacting a compound of formula (13d)

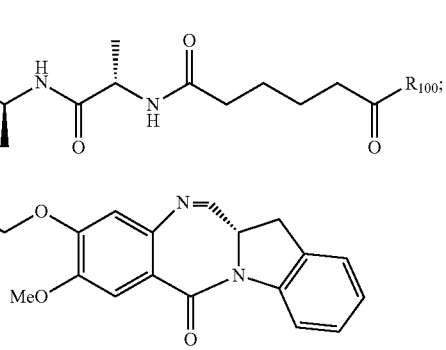

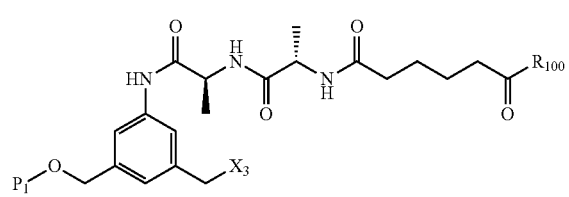

with an alcohol deprotecting reagent, wherein $P_1$ is an alcohol protecting group; $X_3$ is —Cl; and $R_{100}$ is $(C_1$-$C_3)$ alkoxy.

In a twenty-fourth embodiment, the present invention provides a method of preparing a compound of formula (15d):

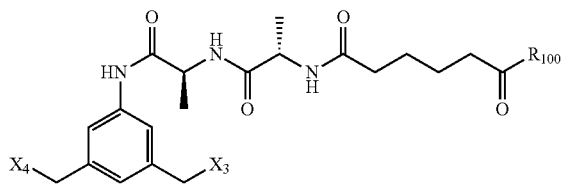

or a salt thereof, said method comprising reacting a sulfonating reagent or an esterification reagent with a compound of formula (14d),

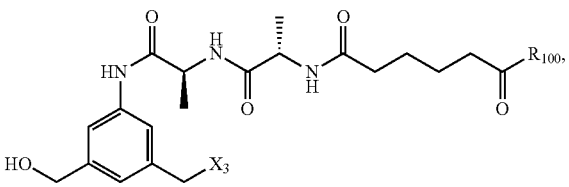

wherein $X_3$ is —Cl; $X_4$ is a sulfonate ester or an activated ester (preferably, $X_4$ is a sulfonate ester); and $R_{100}$ is $(C_1$-$C_3)$alkoxy.

In a twenty-fifth embodiment, the present invention provides a method of preparing a compound of formula (20d):

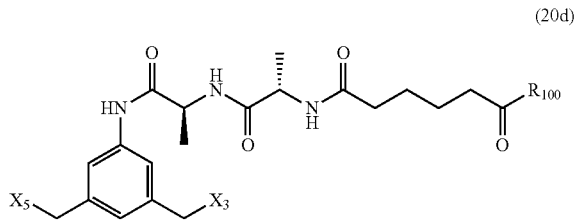

or a salt thereof, said method comprising reacting a brominating or iodinating reagent with a compound of formula (14d),

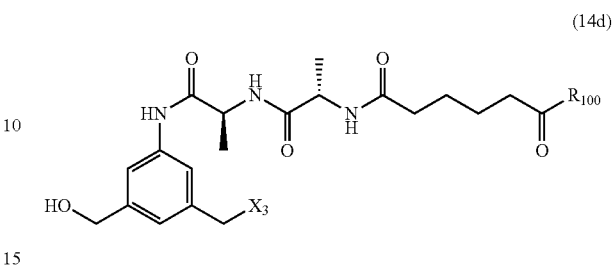

wherein $X_3$ is —Cl; $X_5$ is —Br or —I; and $R_{100}$ is $(C_1$-$C_3)$ alkoxy.

In a twenty-sixth embodiment, the present invention provides a method of preparing a compound of formula (16d):

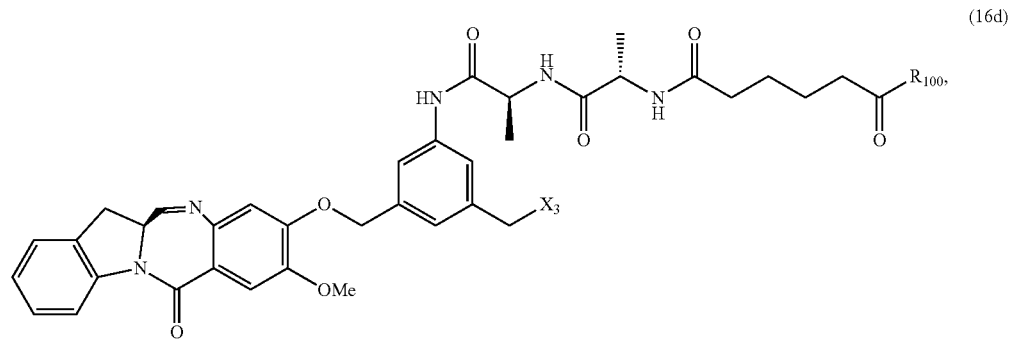

or a salt thereof, said method comprising reacting a compound of formula (15d)

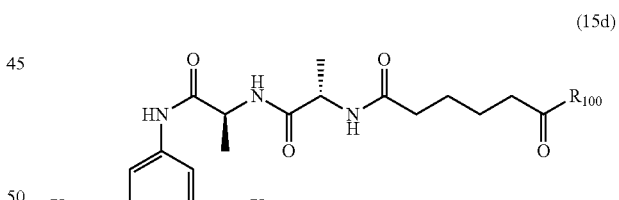

with a monomer compound of formula $(a_1)$,

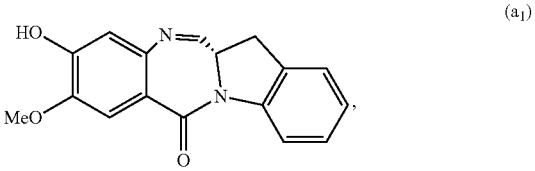

wherein $X_3$ is —Cl; $X_4$ is a sulfonate ester or an activated ester (preferably, $X_4$ is a sulfonate ester); and $R_{100}$ is $(C_1$-$C_3)$alkoxy.

In a twenty-seventh embodiment, the present invention provides a method of preparing a compound of formula (16d),

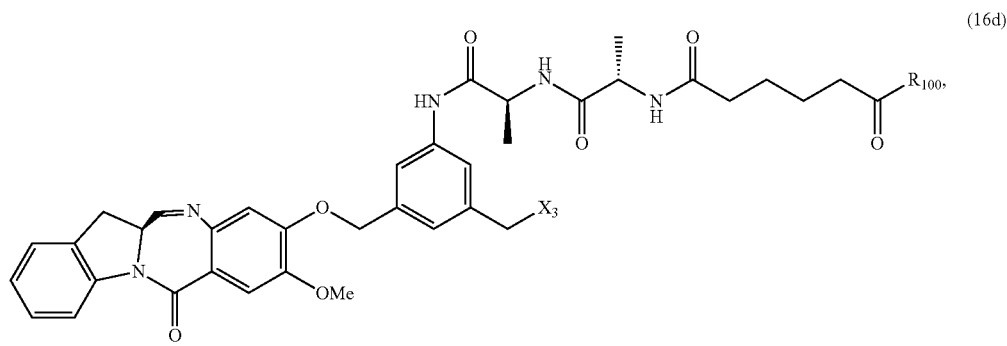

or a salt thereof, said method comprising reacting a compound of formula (20d)

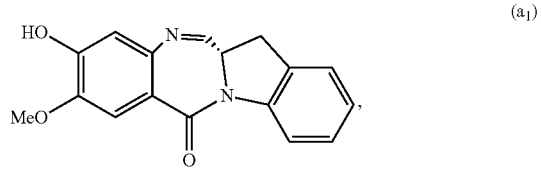 [SMILES: COc1cc2c(cc1O)N=C[C@@H]1Cc3ccccc3N1C2=O]

with a monomer compound of formula (a₁), wherein $X_3$ is —Cl; $X_5$ is —Br or —I; and $R_{100}$ is $(C_1$-$C_3)$ alkoxy.

In a twenty-eighth embodiment, the present invention provides a method of preparing a compound of formula (16d), or a salt thereof, said method comprising reacting a compound of formula (14d)

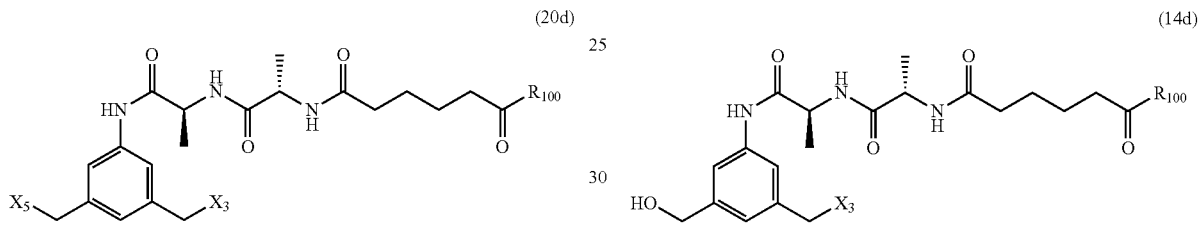

with a monomer compound of formula (a₁), wherein $X_3$ is —Cl; and $R_{100}$ is $(C_1$-$C_3)$alkoxy.

In a twenty-ninth embodiment, the present invention provides a method of preparing a compound of formula (18d):

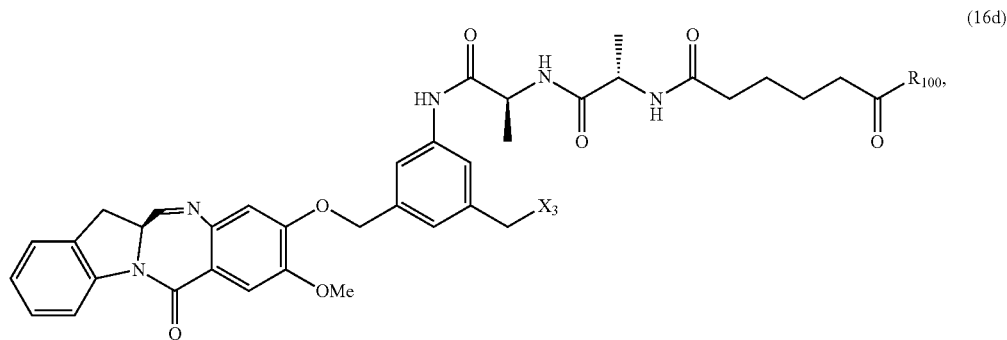

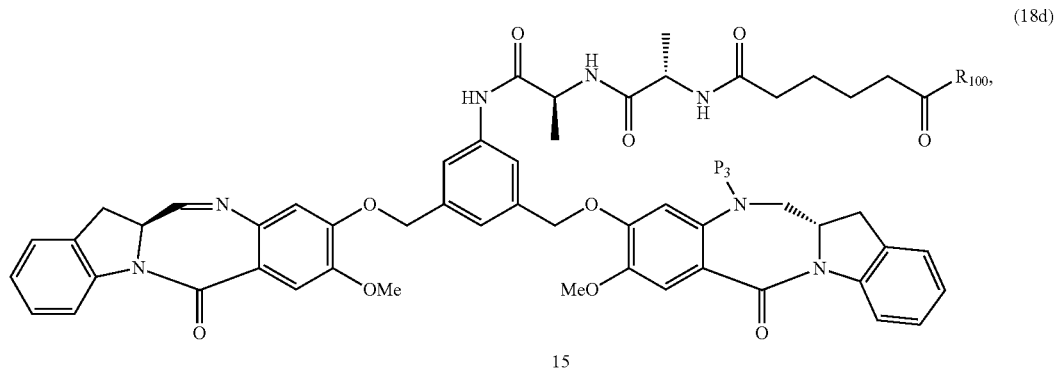

(18d)

a pharmaceutically acceptable salt thereof, said method comprising reacting a compound of formula of (16d):

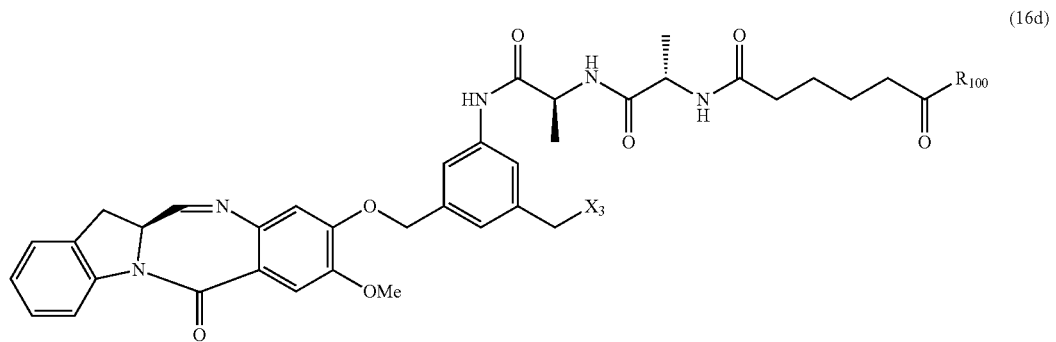

(16d)

with a reduced monomer of formula (d₁):

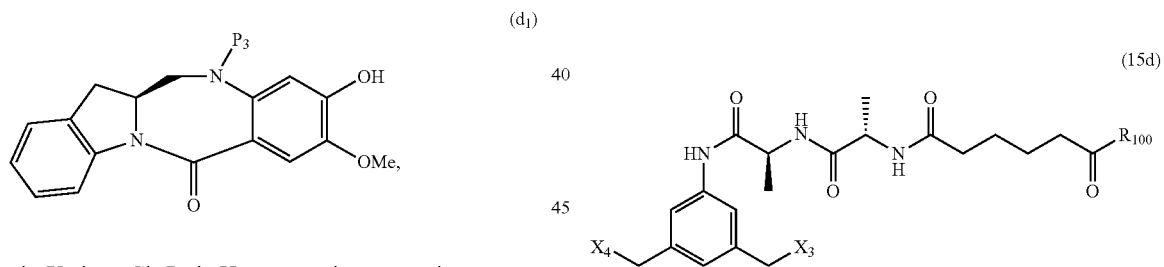

(d₁)

wherein $X_3$ is —Cl; $P_3$ is H or an amine protecting group; and $R_{100}$ is $(C_1-C_3)$alkoxy.

In a thirtieth embodiment, the present invention provides a method for preparing a compound of formula (17d):

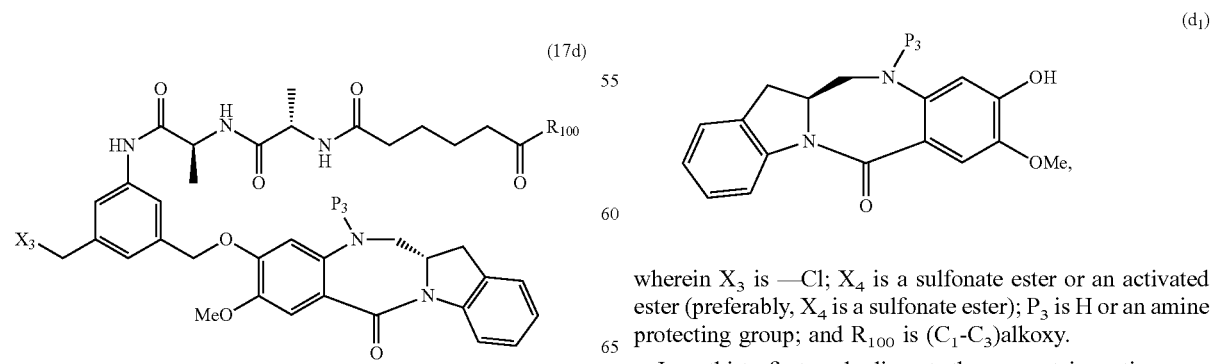

(17d)

or a salt thereof, said method comprising reacting a compound of formula (15d)

(15d)

with a monomer compound of formula (d₁), (d₁)

wherein $X_3$ is —Cl; $X_4$ is a sulfonate ester or an activated ester (preferably, $X_4$ is a sulfonate ester); $P_3$ is H or an amine protecting group; and $R_{100}$ is $(C_1-C_3)$alkoxy.

In a thirty-first embodiment, the present invention provides a method of preparing a compound of formula (17d),

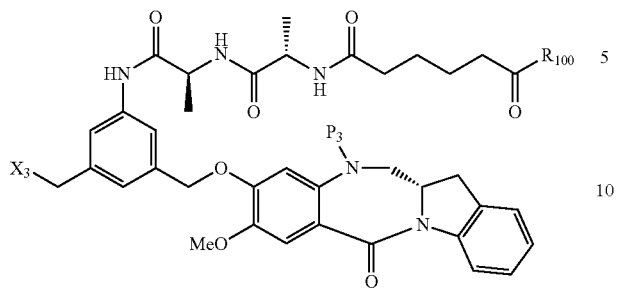

(17d)

or a salt thereof, said method comprising reacting a compound of formula (14d)

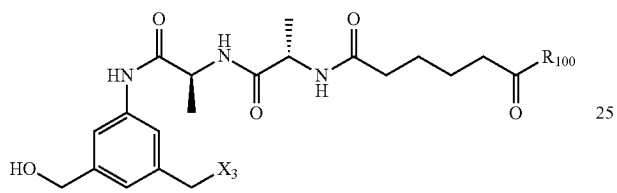

(14d)

with a monomer compound of formula (d₁),

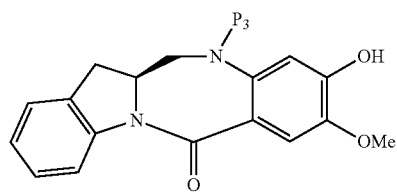

(d₁)

wherein $X_3$ is —Cl; $P_3$ is H or an amine protecting group; and $R_{100}$ is $(C_1$-$C_3)$alkoxy.

In a thirty-second embodiment, the present invention provides a method of preparing a compound of formula (17d):

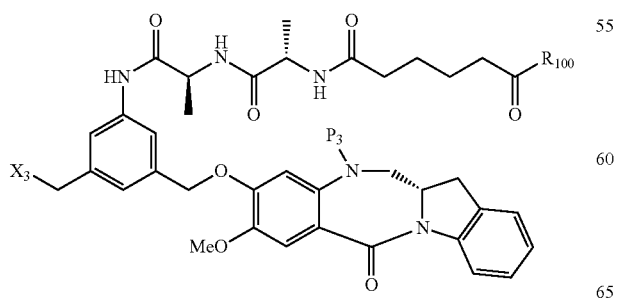

(17d)

or a salt thereof, said method comprising reacting a compound of formula (20d)

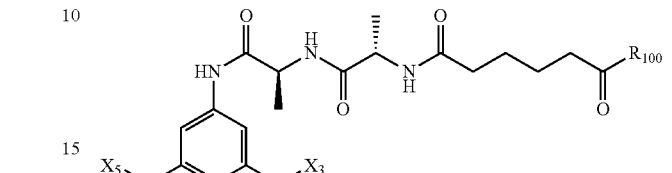

(20d)

with a monomer compound of formula (d₁),

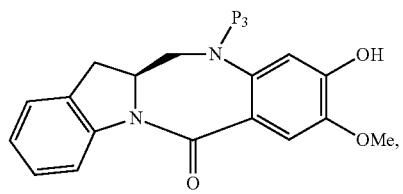

(d₁)

wherein $X_3$ is —Cl; $X_5$ is —Br or —I; $P_3$ is H or an amine protecting group; and $R_{100}$ is $(C_1$-$C_3)$alkoxy.

In a thirty-third embodiment, the present invention provides a method of preparing a compound of formula (17d'):

(17d')

or a salt thereof, said method comprising reacting a compound of formula (16d)

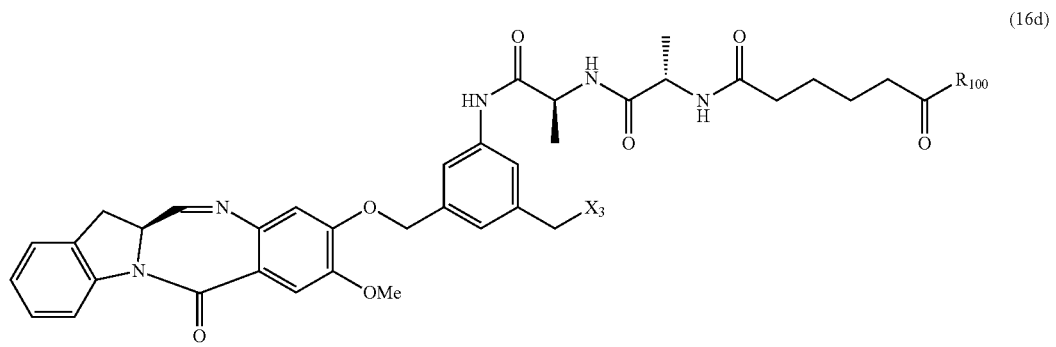

(16d)

with an imine reducing agent, wherein $X_3$ is —Cl; and $R_{100}$ is $(C_1\text{-}C_3)$alkoxy.

In a thirty-fourth embodiment, the present invention provides a method of preparing a compound of formula (18d),

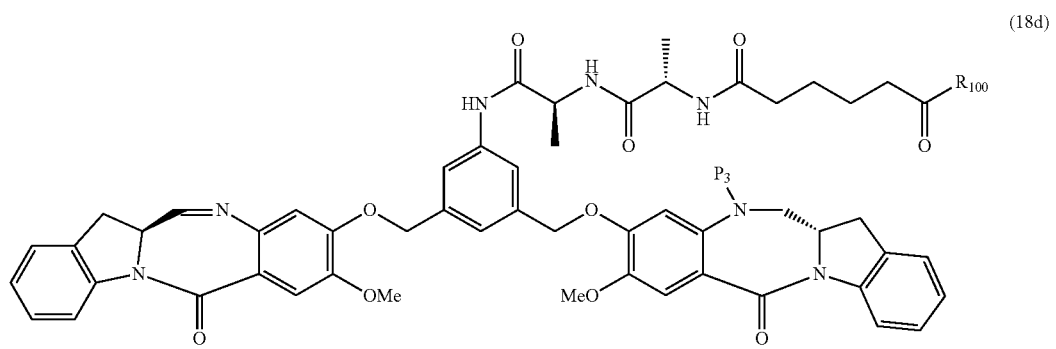

(18d)

or a pharmaceutically acceptable salt thereof, said method comprising reacting a compound of formula of (17d):

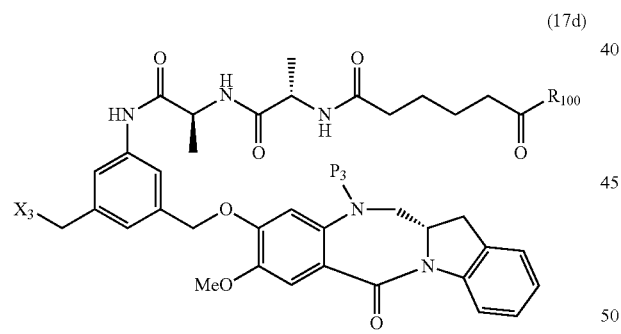

(17d)

with a monomer of formula $(a_1)$:

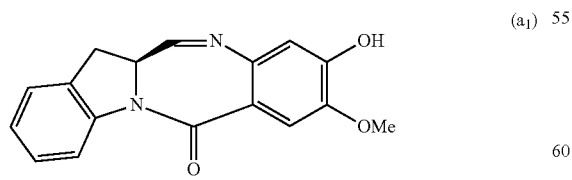

$(a_1)$ wherein $X_3$ is —Cl; $P_3$ is H or an amine protecting group; and $R_{100}$ is $(C_1\text{-}C_3)$alkoxy.

In a thirty-fifth embodiment, the present invention provides a method of preparing a compound of formula (18d),

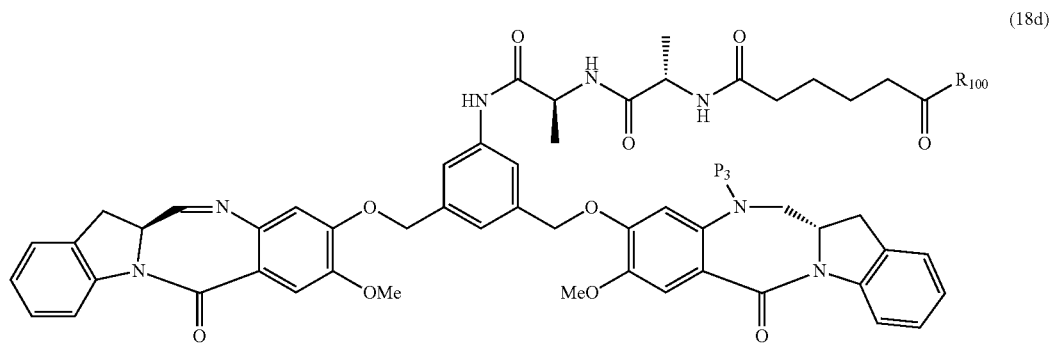

or a pharmaceutically acceptable salt thereof, said method comprising the steps of:

(1) reacting a sulfonating reagent or an esterification reagent with the compound of formula (14d):

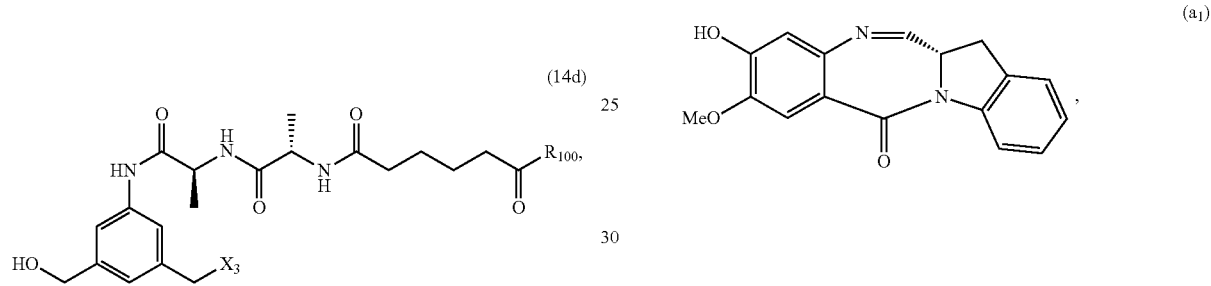

or a salt thereof, to form a compound of formula (15d):

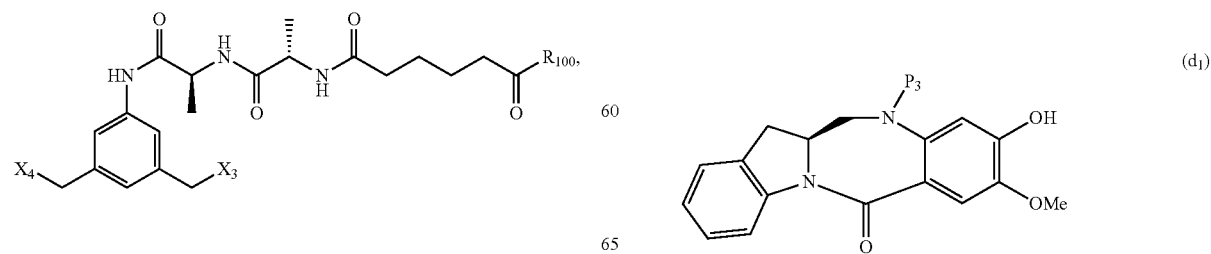

or a salt thereof;

(2) reacting the compound of formula (15a) with a monomer compound of formula (a₁),

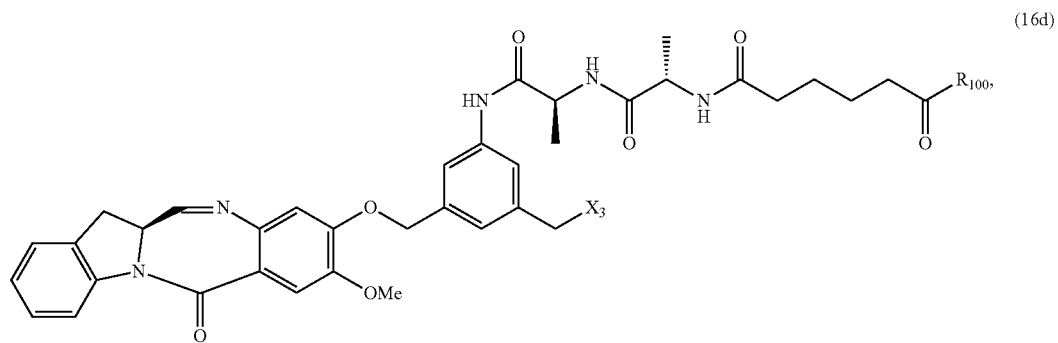

to form a compound of formula (16d):

or a salt thereof; and (3) reacting the compound of formula of (16d) with a reduced monomer of formula (d₁):

to form a compound of formula (18d), or a pharmaceutically acceptable salt thereof, wherein $X_3$ is —Cl; $X_4$ is a sulfonate ester or an activated ester (preferably, a sulfonate ester); $P_1$ is an alcohol protecting group; $P_3$ is H or an amine protecting group; and $R_{100}$ is $(C_1-C_3)$alkoxy.

In a thirty-sixth embodiment, the present invention provides a method of preparing a compound of formula (18d),

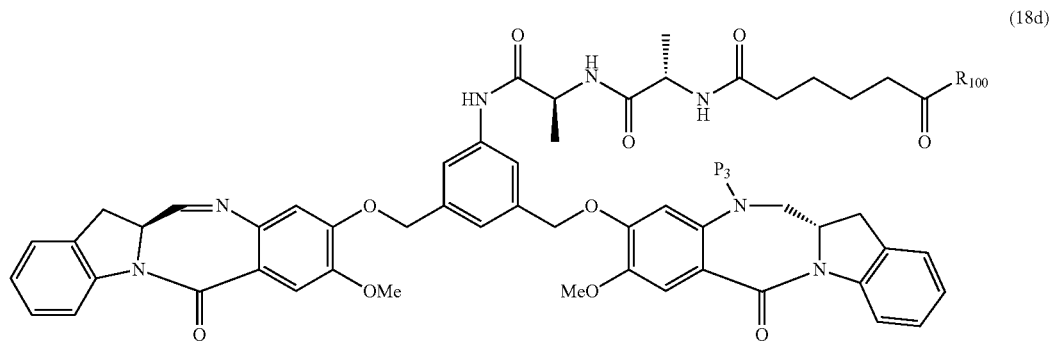
(18d)

or a pharmaceutically acceptable salt thereof, said method comprising the steps of:

(1) reacting the compound of formula (14d):

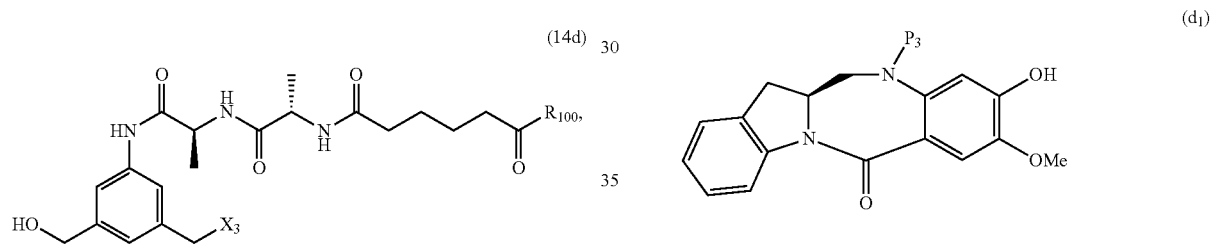
(14d)

or a salt thereof, with a monomer compound of formula $(a_1)$,

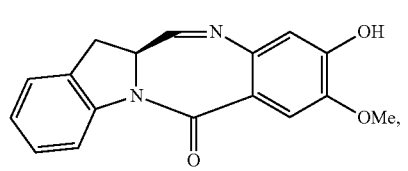
$(a_1)$ to form a compound of formula (16d):

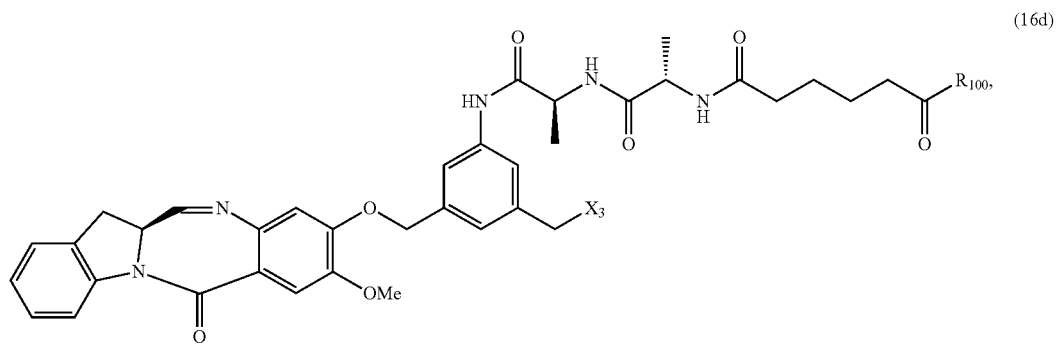
(16d)

or a salt thereof; and (2) reacting the compound of formula of (16d) with a reduced monomer of formula $(d_1)$:

$(d_1)$ to form a compound of formula (18d), or a pharmaceutically acceptable salt thereof, wherein $X_3$ is —Cl; $P_1$ is an alcohol protecting group; $P_3$ is H or an amine protecting group; and $R_{100}$ is $(C_1-C_3)$alkoxy.

In a thirty-seventh embodiment, the present invention provides a method of preparing a compound of formula (18d),

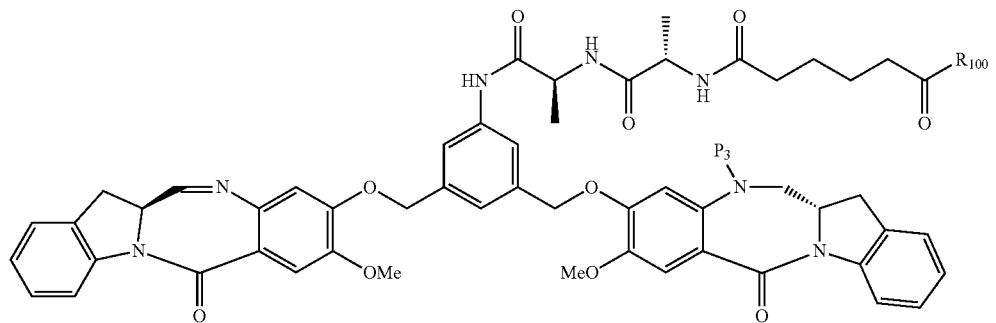
(18d)

or a pharmaceutically acceptable salt thereof, said method comprising the steps of:

(1) reacting a halogenating reagent with the compound of formula (14d):

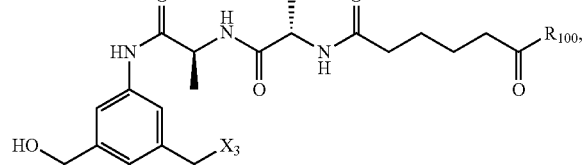
(14d)

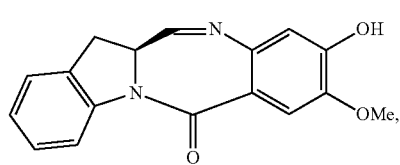
(a₁)

to form a compound of formula (16d):

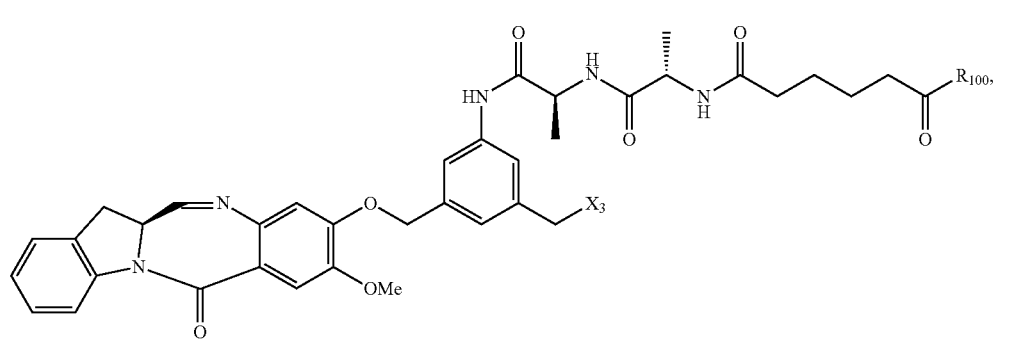
(16d)

or a salt thereof, to form a compound of formula (20d):

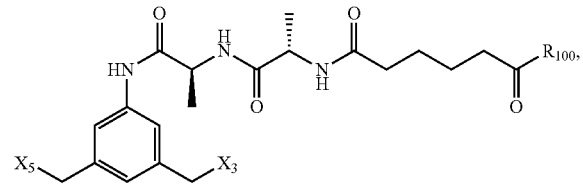
(20d)

or a salt thereof;

(2) reacting a compound of formula (20d) or a salt thereof with a monomer compound of formula (a₁), or a salt thereof; and (3) reacting the compound of formula of (16d) with a reduced monomer of formula (d₁):

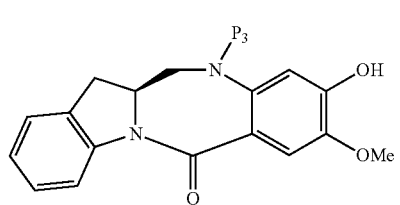
(d₁)

to form a compound of formula (18d), or a pharmaceutically acceptable salt thereof, wherein $X_3$ is —Cl; $X_5$ is —Br or —I; $P_3$ is H or an amine protecting group; and $R_{100}$ is ($C_1$-$C_3$)alkoxy.

In a thirty-eighth embodiment, the present invention provides a method of preparing a compound of formula (18d),

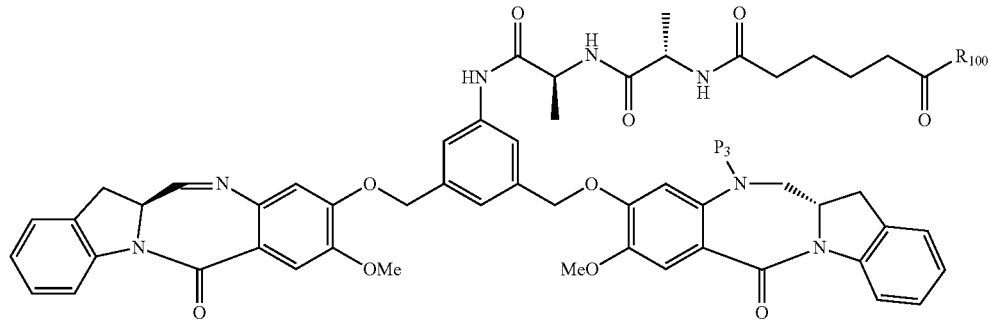

(18d)

or a pharmaceutically acceptable salt thereof, said method comprising the steps of:

(1) reacting a sulfonating reagent or an esterification reagent with the compound of formula (14d):

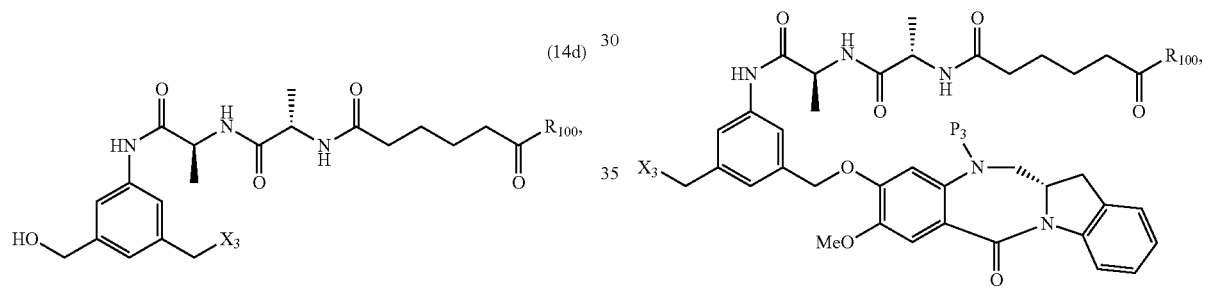

(14d)

or a salt thereof, to form a compound of formula (15d):

(15d)

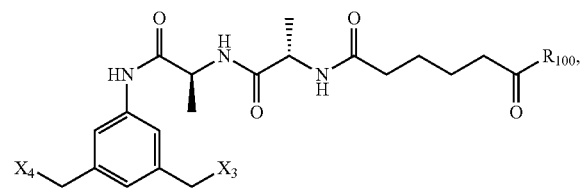

or a salt thereof;

(2) reacting the compound of formula (15d) with a reduced monomer compound of formula ($d_1$), ($d_1$)

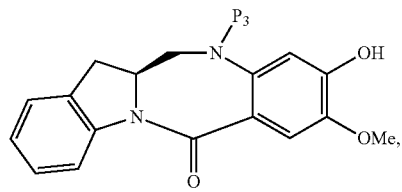

to form a compound of formula (17d):

(17d)

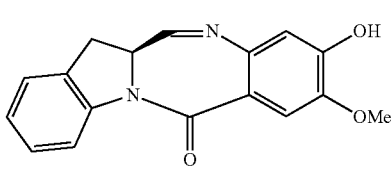

or a salt thereof; and (3) reacting the compound of formula of (17d) with a monomer of formula ($a_1$):

($a_1$)

to form a compound of formula (18d), or a pharmaceutically acceptable salt thereof, wherein $X_3$ is —Cl; $X_4$ is a sulfonate ester or an activated ester (preferably, a sulfonate ester); $P_1$ is an alcohol protecting group; $P_3$ is H or an amine protecting group; and $R_{100}$ is ($C_1$-$C_3$)alkoxy.

In a thirty-ninth embodiment, the present invention provides method of preparing a compound of formula (18d),

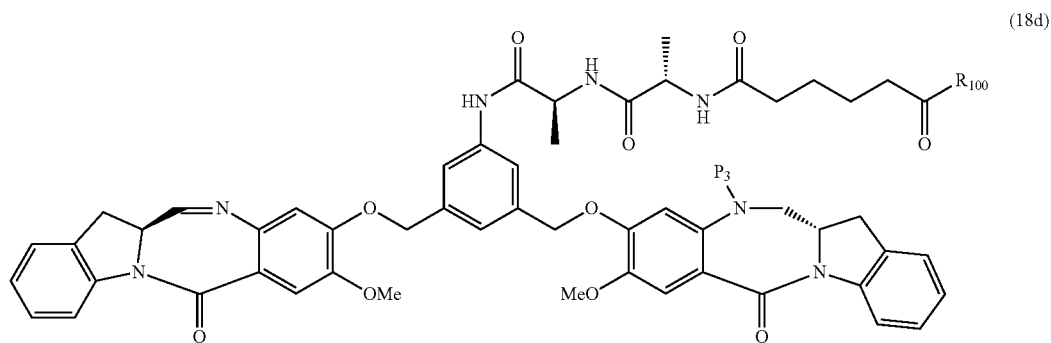

or a pharmaceutically acceptable salt thereof, said method comprising the steps of:

(1) reacting the compound of formula (14d):

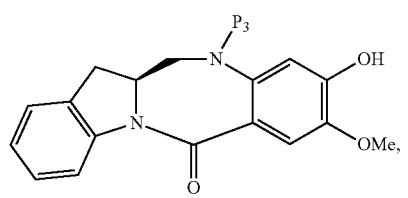

or a salt thereof, with a reduced monomer compound of formula ($d_1$),

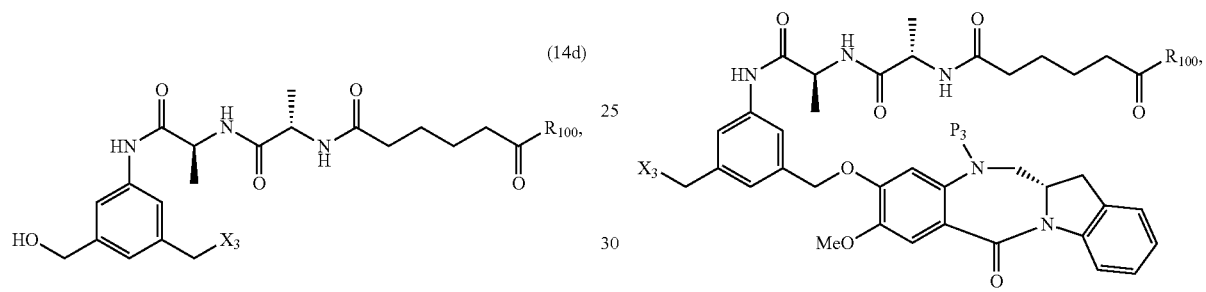

to form a compound of formula (17d):

or a salt thereof; and (2) reacting the compound of formula of (17d) with a monomer of formula ($a_1$):

to form a compound of formula (18d), or a pharmaceutically acceptable salt thereof, wherein $X_3$ is —Cl; $P_1$ is an alcohol protecting group; $P_3$ is H or an amine protecting group; and $R_{100}$ is ($C_1$-$C_3$)alkoxy.

In a fortieth embodiment, the present invention provides a method of preparing a compound of formula (18d),

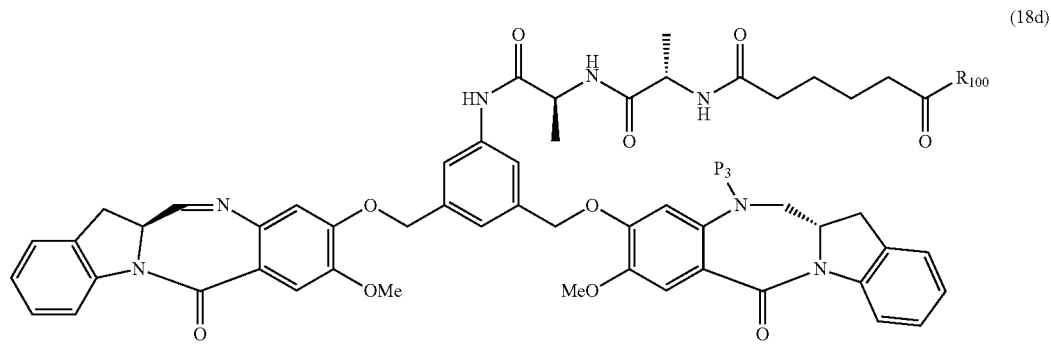

or a pharmaceutically acceptable salt thereof, said method comprising the steps of:

(1) reacting a brominating or iodinating reagent with the compound of formula (14d):

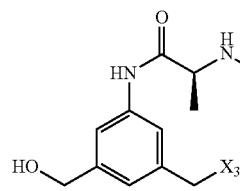
(14d)

or a salt thereof, to form a compound of formula (20d):

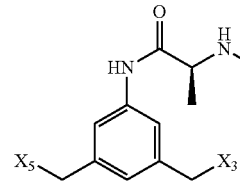
(20d)

or a salt thereof;

(2) reacting the compound of formula (20d) with a reduced monomer compound of formula (d₁),

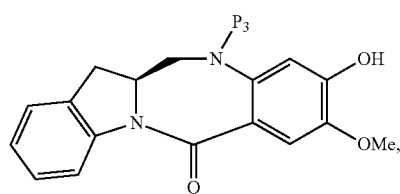
(d₁)

to form a compound of formula (17d):

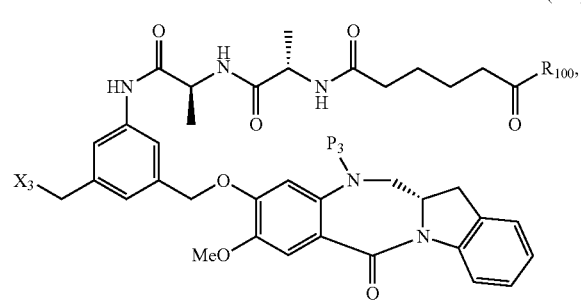
(17d)

or a salt thereof; and (3) reacting the compound of formula of (17d) with a monomer of formula (a₁):

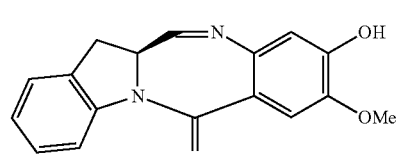
(a₁)

to form a compound of formula (18d), or a pharmaceutically acceptable salt thereof, wherein $X_3$ is —Cl; $X_5$ is —Br or —I; $P_1$ is an alcohol protecting group; $P_3$ is H or an amine protecting group; and $R_{100}$ is $(C_1$-$C_3)$alkoxy.

In a forty-first embodiment, the present invention provides a method of preparing a compound of formula (Id'),

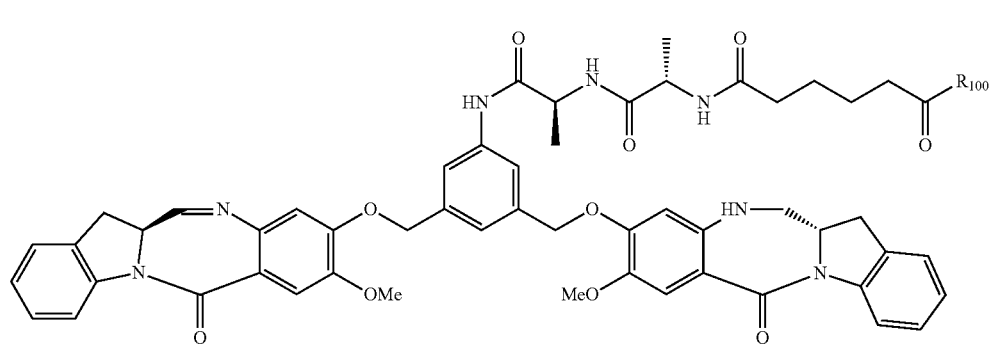
(Id')

or a pharmaceutically acceptable salt thereof, said method comprising the steps of:

(1) reacting a sulfonating reagent or an esterification reagent with the compound of formula (14d):

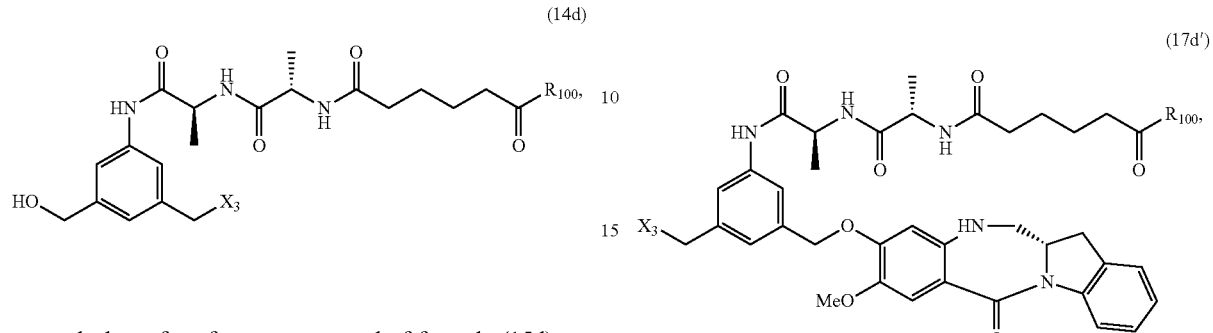

or a salt thereof, to form a compound of formula (15d):

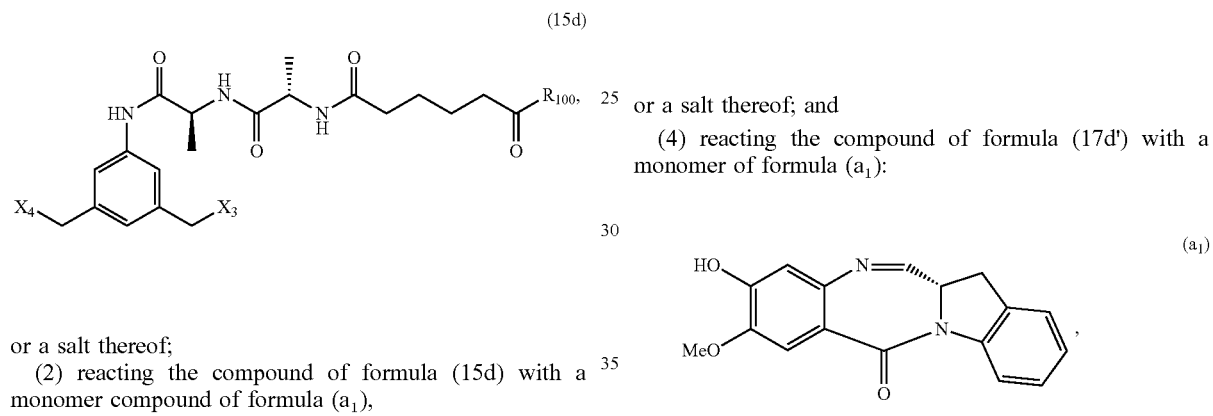

or a salt thereof;

(2) reacting the compound of formula (15d) with a monomer compound of formula ($a_1$),

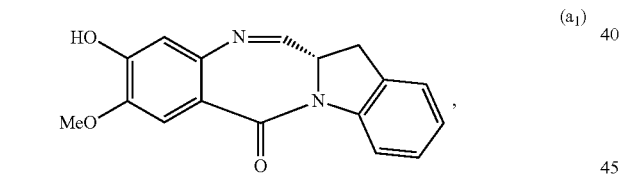

to form a compound of formula (16d):

(3) reacting the compound of formula (16d) with an imine reducing agent to form a compound of formula (17d'):

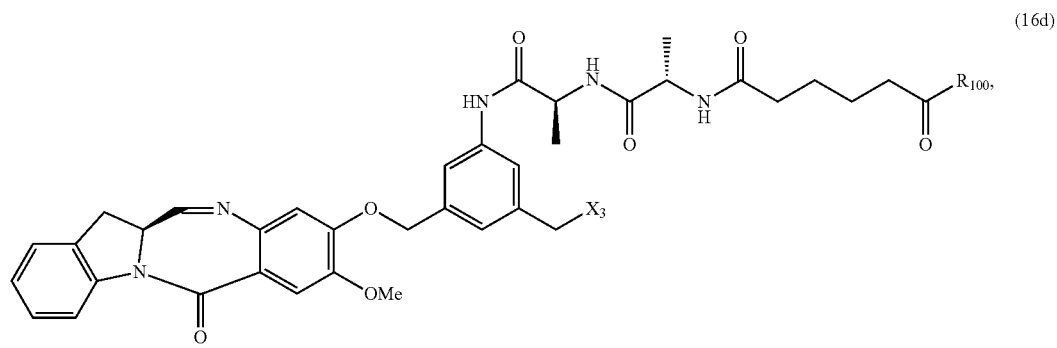

or a salt thereof; and (4) reacting the compound of formula (17d') with a monomer of formula ($a_1$):

to form the compound of formula (Id'); wherein $X_3$ is —Cl; $X_4$ is a sulfonate ester or an activated ester (preferably, a sulfonate ester); $P_1$ is an alcohol protecting group; $P_2$ is an amine protecting group; and $R_{100}$ is ($C_1$-$C_3$)alkoxy.

In a forty-second embodiment, the present invention provides a method of preparing a compound of formula (Id'), or a salt thereof;

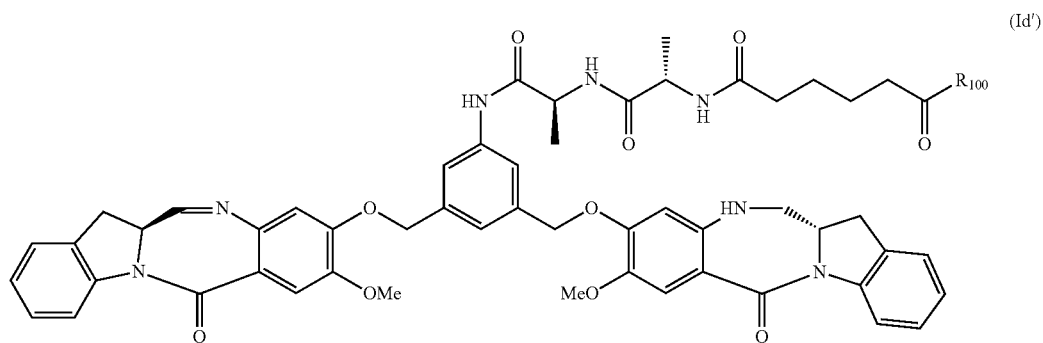

(Id')

or a pharmaceutically acceptable salt thereof, said method comprising the steps of:
(1) reacting the compound of formula (14d):

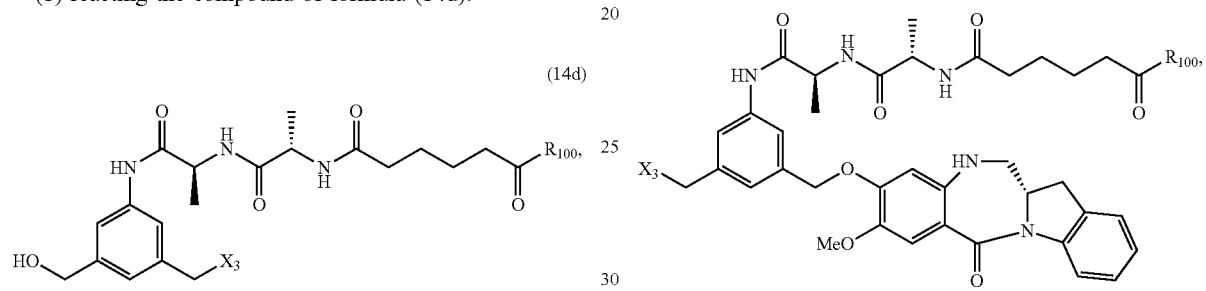

(14d)

or a salt thereof, with a monomer compound of formula (a₁), (a₁)

to form a compound of formula (16d):

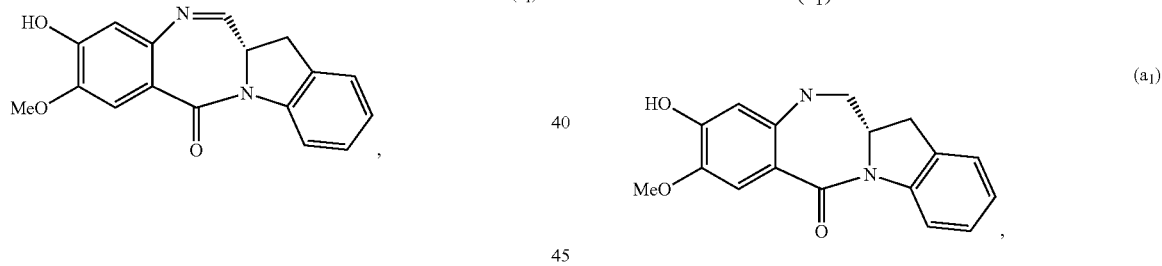

(16d)

or a salt thereof;
(2) reacting the compound of formula (16d) with an imine reducing agent to form a compound of formula (17d'):

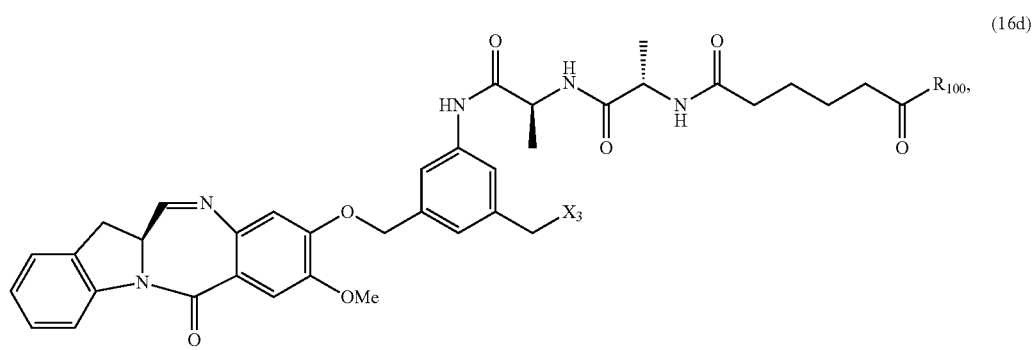

(17d')

or a salt thereof; and
(3) reacting the compound of formula (17d') with a monomer of formula (a₁):

(a₁)

to form the compound of formula (Id'); wherein $X_3$ is —Cl; $P_1$ is an alcohol protecting group; and $R_{100}$ is $(C_1\text{-}C_3)$alkoxy.

In a forty-third embodiment, the present invention provides a method of preparing a compound of formula (Id'),

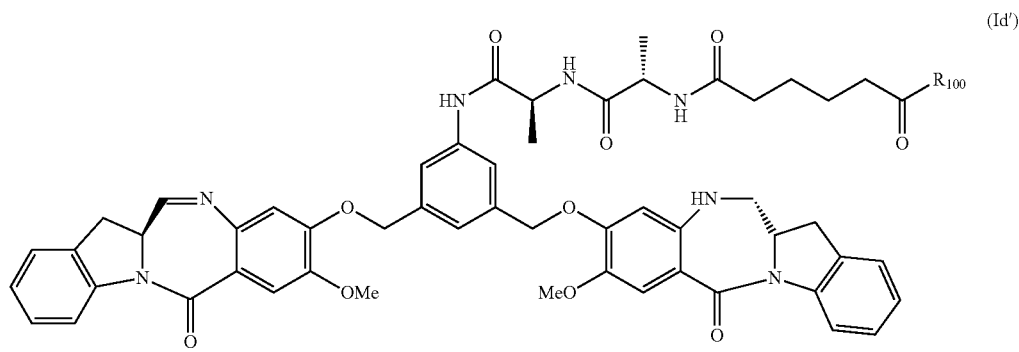
or a pharmaceutically acceptable salt thereof, said method comprising the steps of:
(1) reacting a brominating or iodinating reagent with the compound of formula (14d):
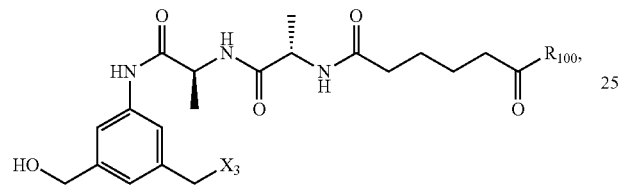
or a salt thereof, to form a compound of formula (20d):
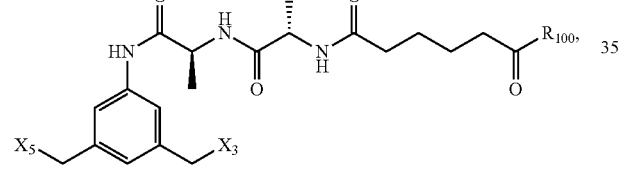
or a salt thereof;
(2) reacting a compound of formula (20d) or a salt thereof with a monomer compound of formula ($a_1$),
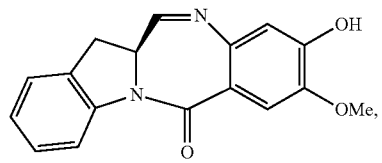
to form a compound of formula (16d):
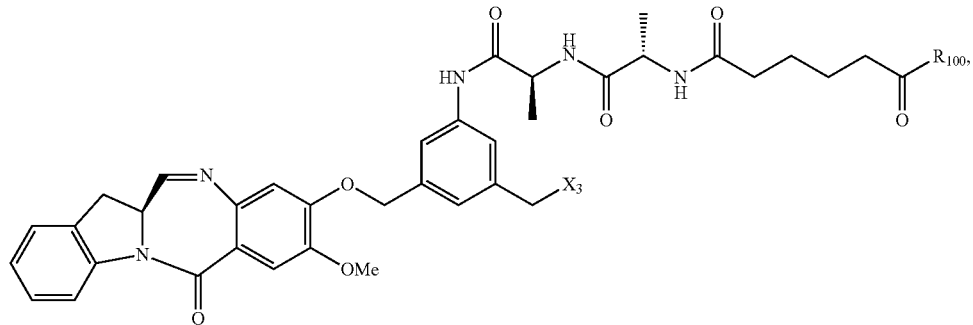

(3) reacting the compound of formula (16d) with an imine reducing agent to form a compound of formula (17d'):

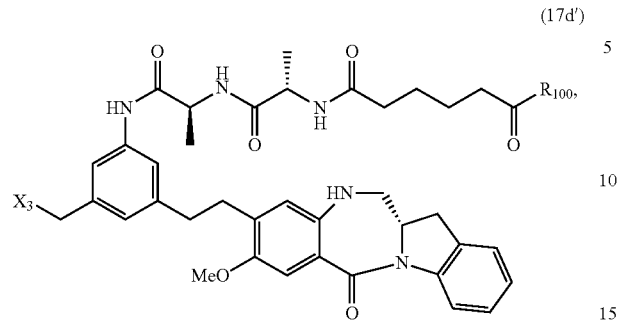
(17d')

or a salt thereof; and (4) reacting the compound of formula (17d') with a monomer of formula (a₁):

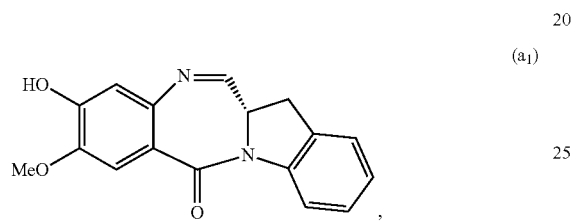
(a₁)

to form the compound of formula (Id'); wherein $X_3$ is —Cl; $P_1$ is an alcohol protecting group; and $R_{100}$ is $(C_1-C_3)$alkoxy.

In a forty-fourth embodiment, the present invention provides a method of

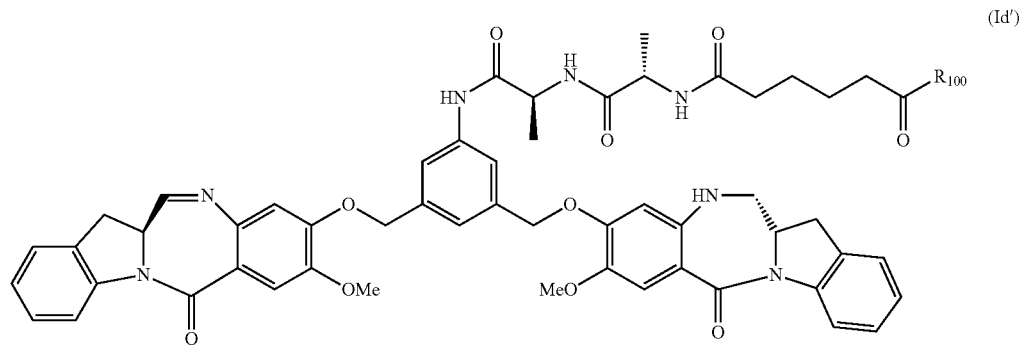
(Id')

or a pharmaceutically acceptable salt thereof, said method comprising the steps of:

(1) reacting a compound of formula (IA):

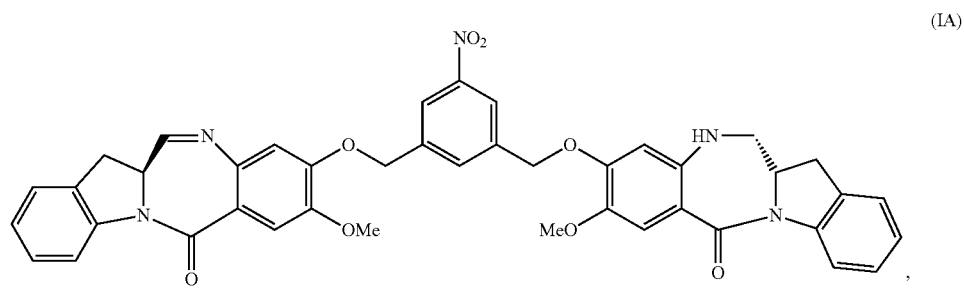
(IA)

with a reducing agent to form a compound of formula (IB):

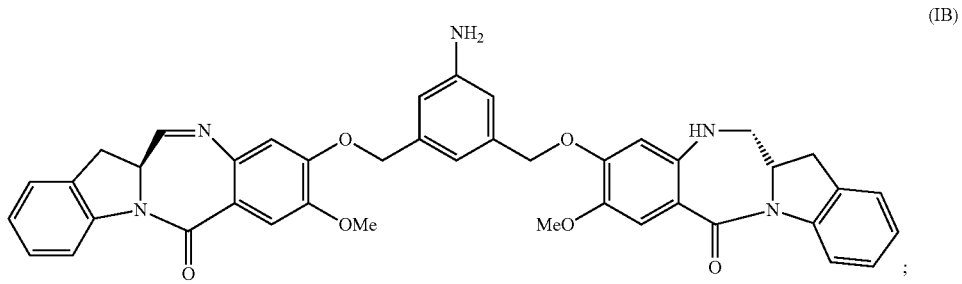

(IB)

and (2) reacting the compound of formula (IB) with a compound of formula (L1):

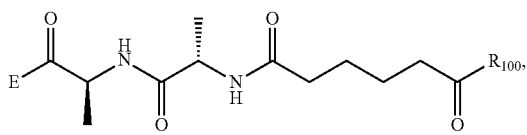

to form the compound of formula (Id), wherein E is —OH, halide or —C(=O)E is an activated ester; and $R_{100}$ is $(C_1-C_3)$alkoxy.

Also included in the present invention are compounds described in the methods of the present invention.

DETAILED DESCRIPTION OF THE INVENTION

Figure 1:
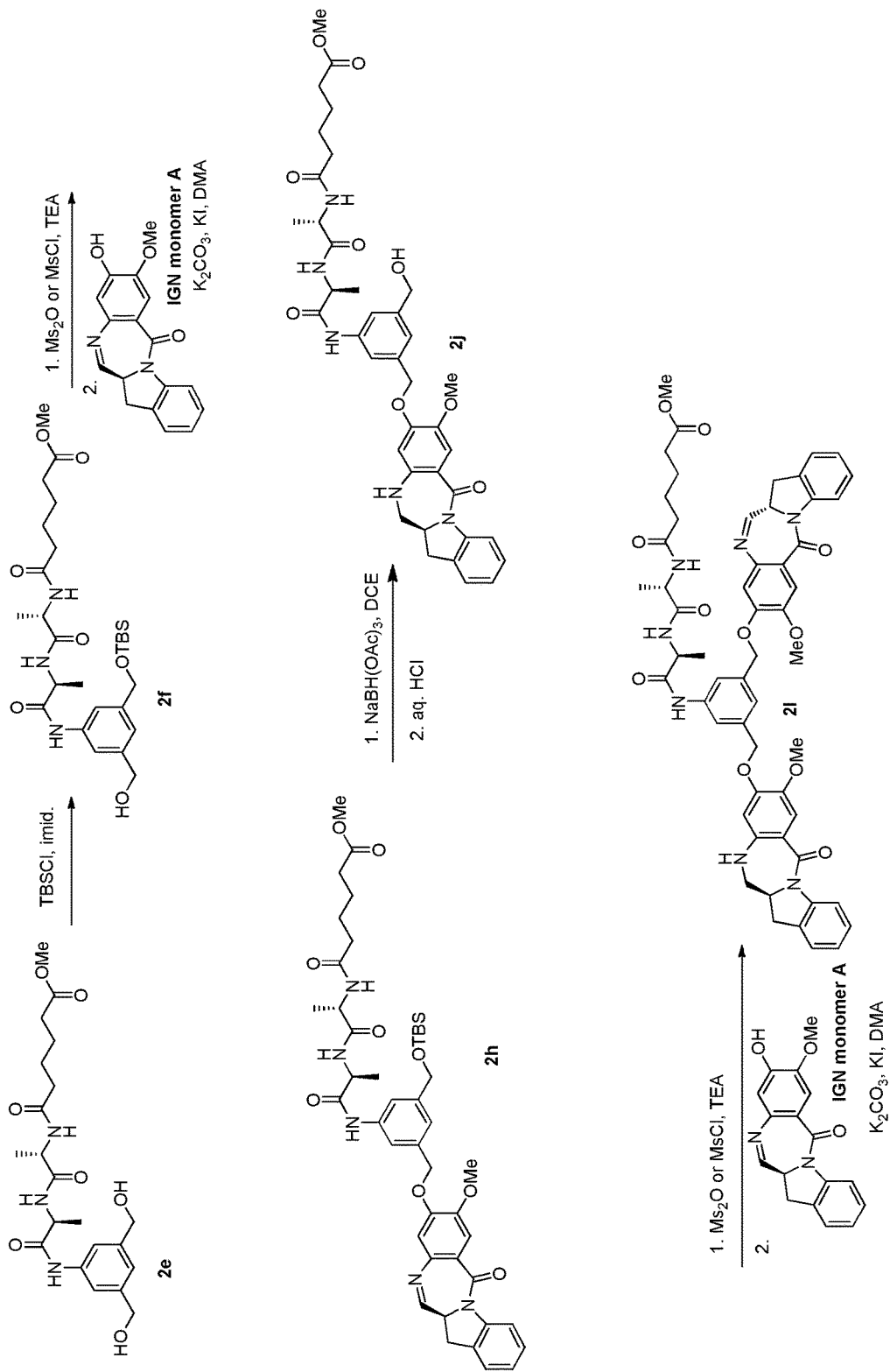
FIGS. 1-13 show exemplary schemes for the methods of the present invention.
Figure 2:
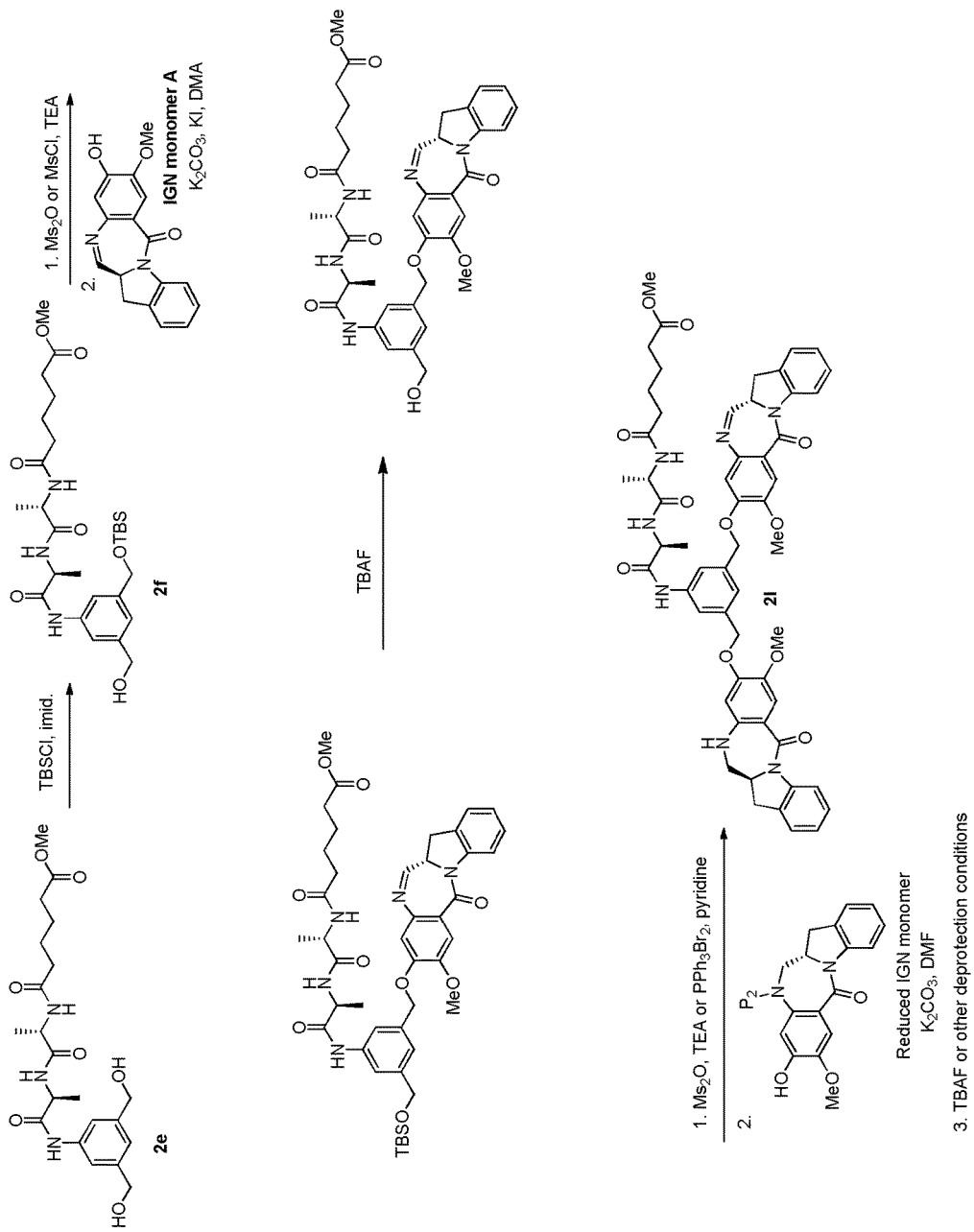
Figure 3:
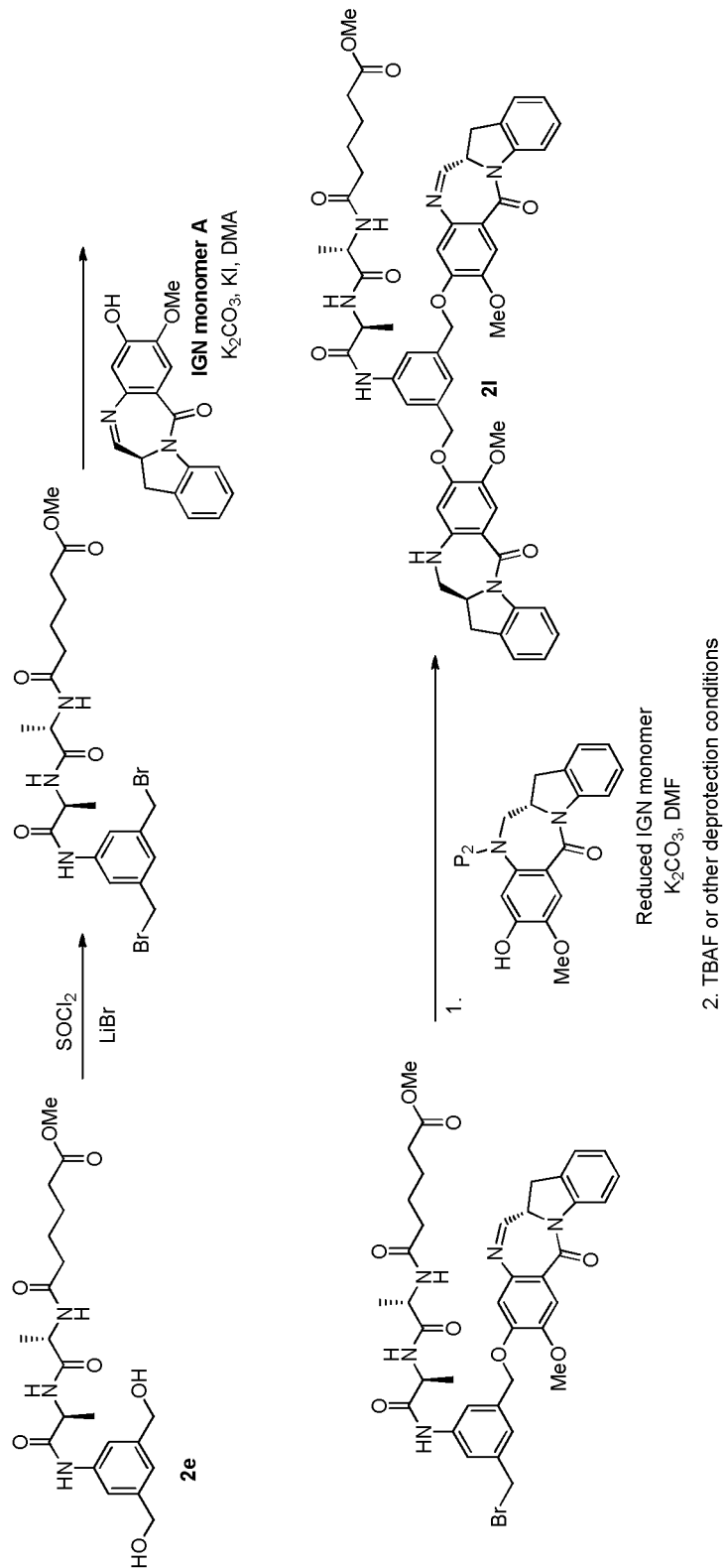
Figure 4:
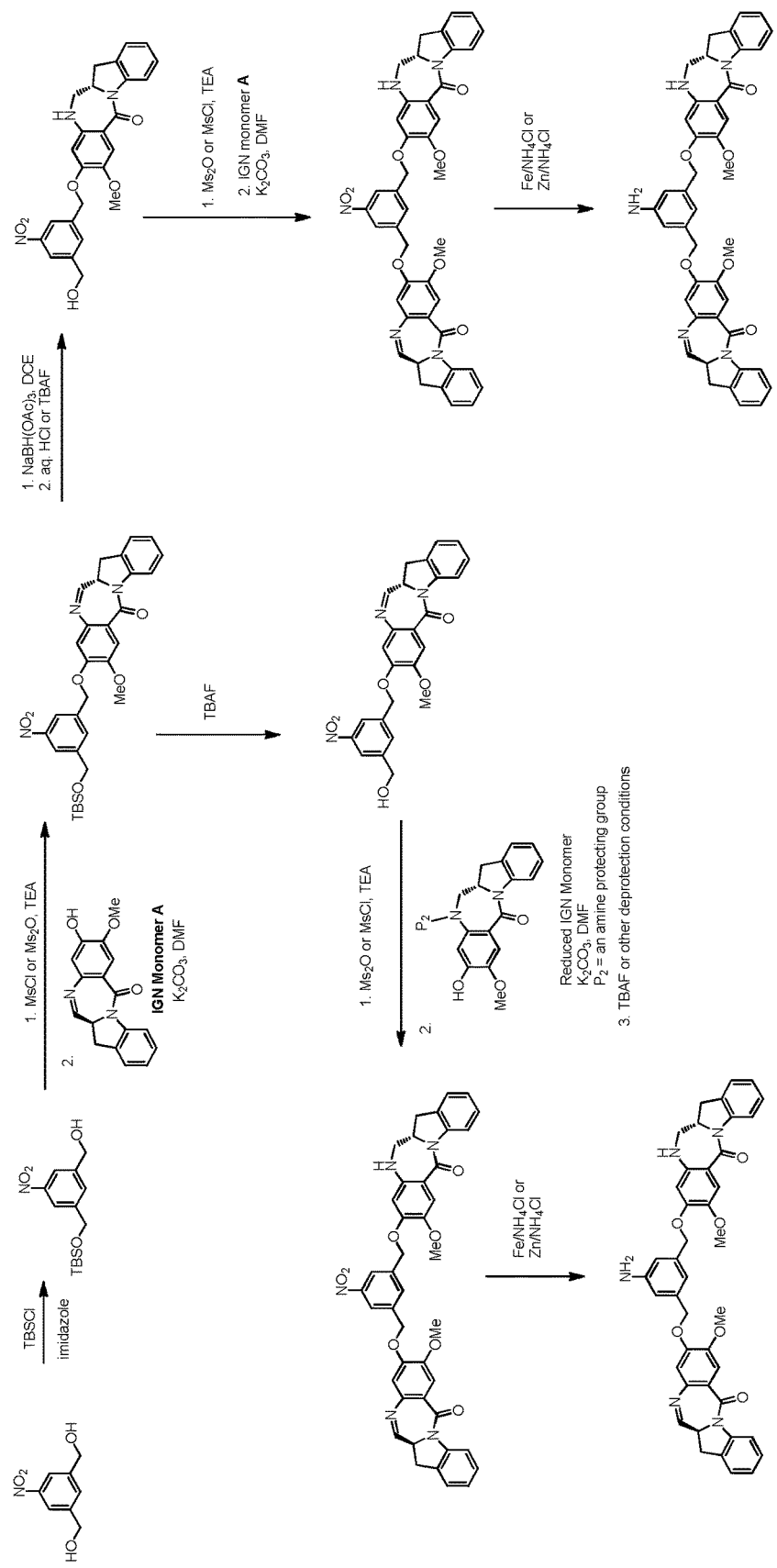
Figure 5:
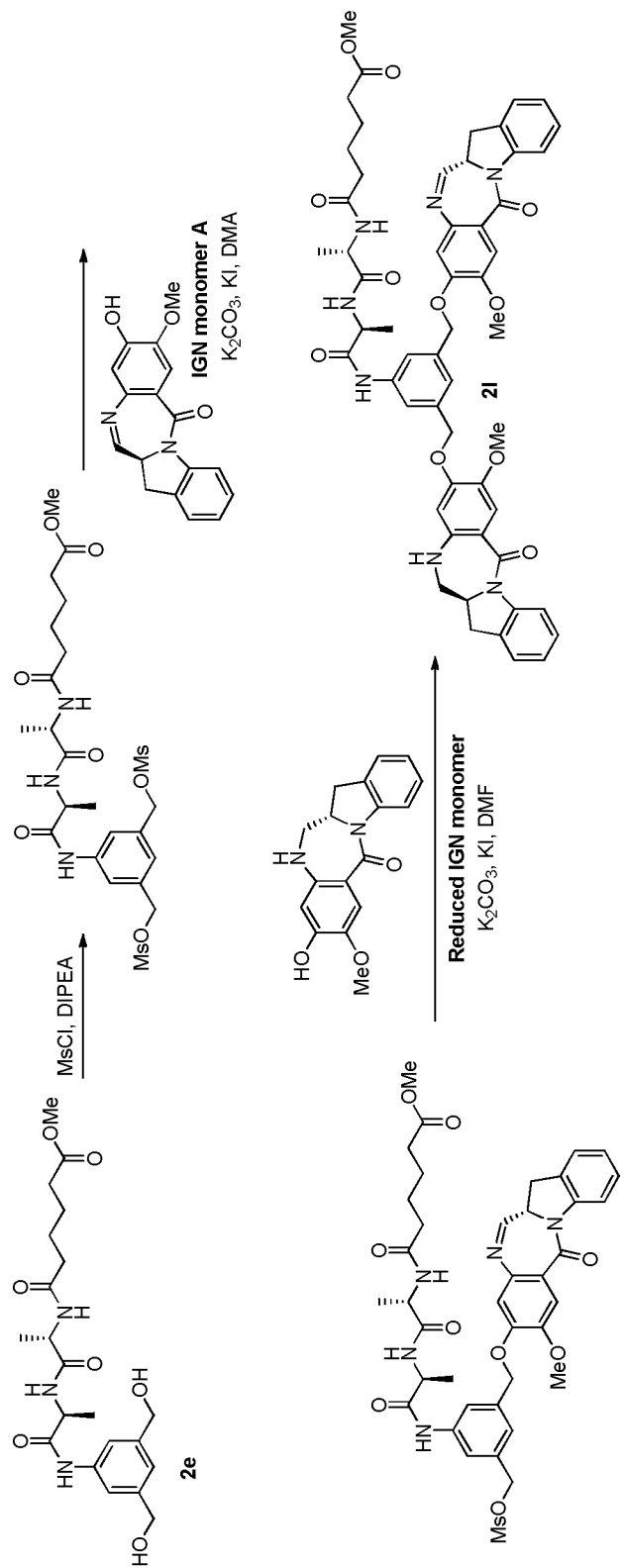
Figure 6:
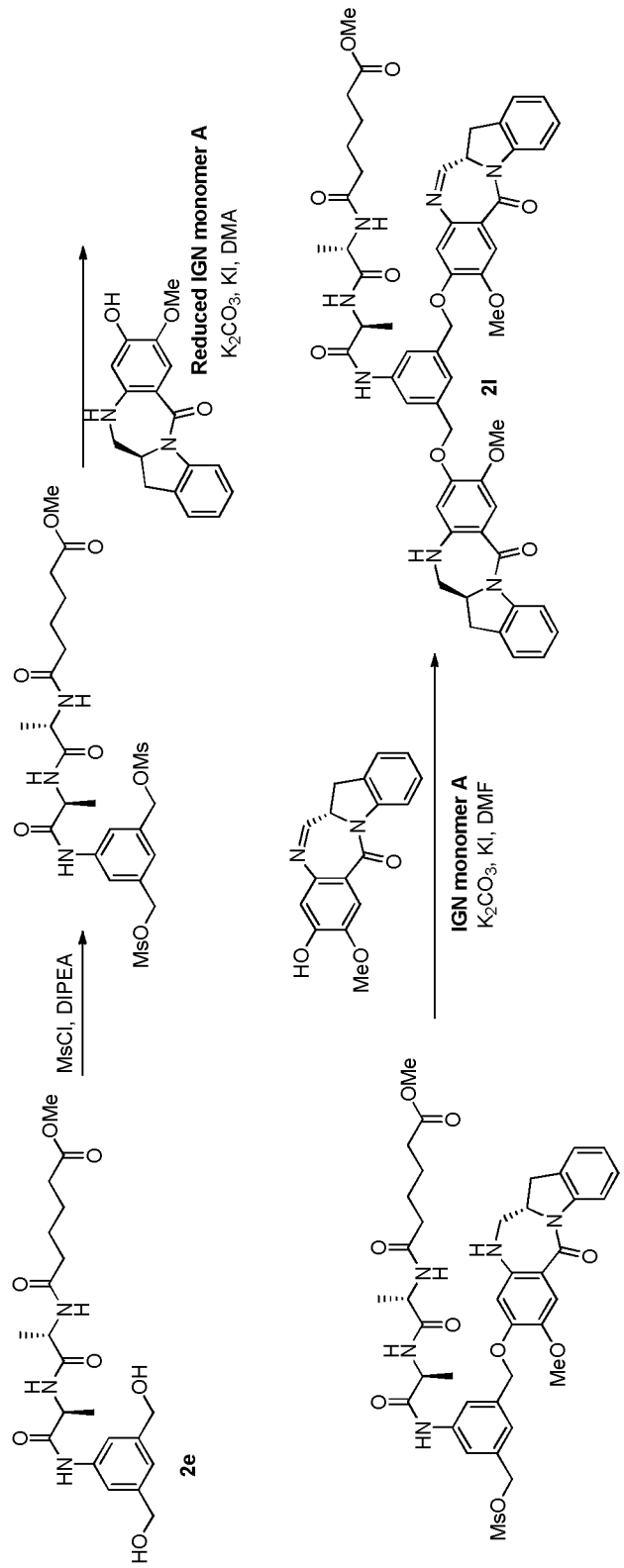
Figure 7:
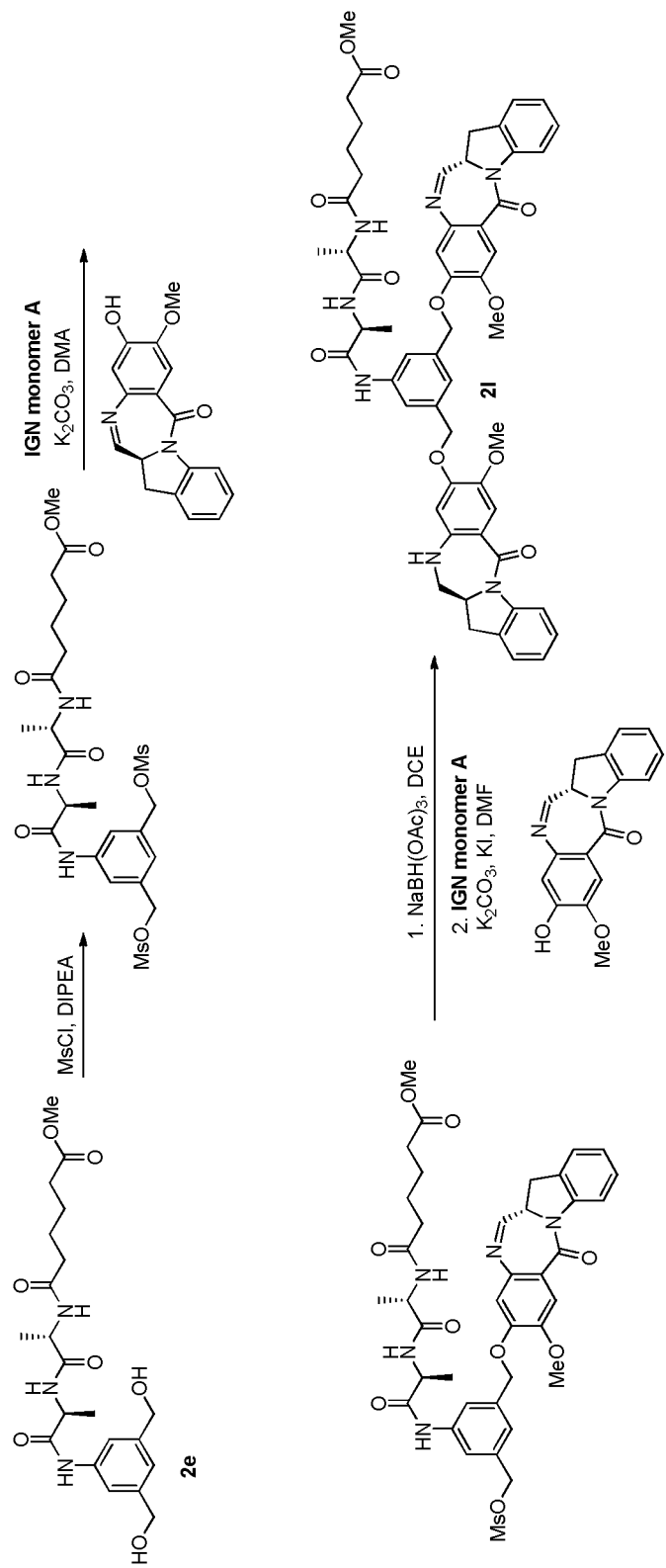
Figure 8:
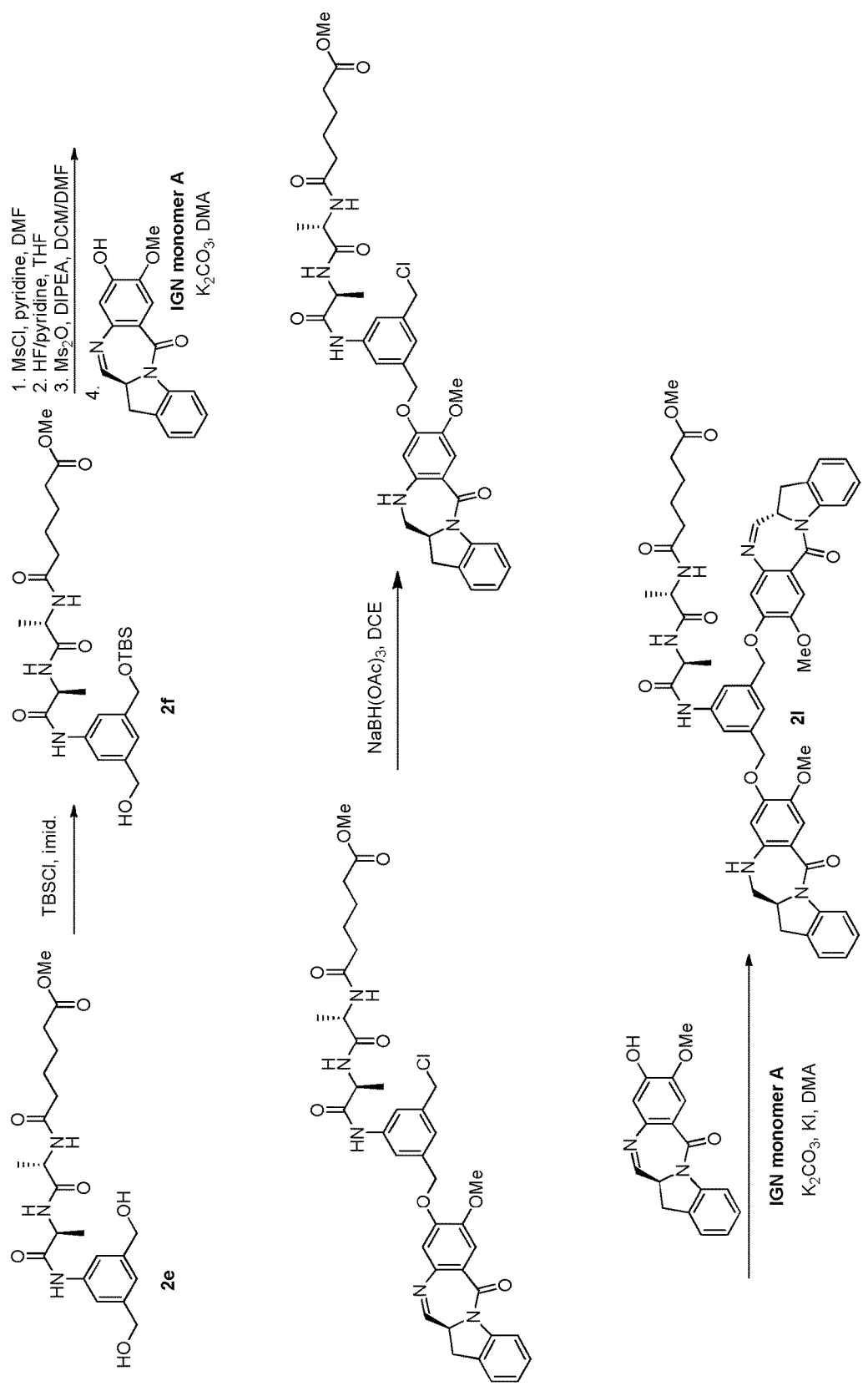
Figure 9:
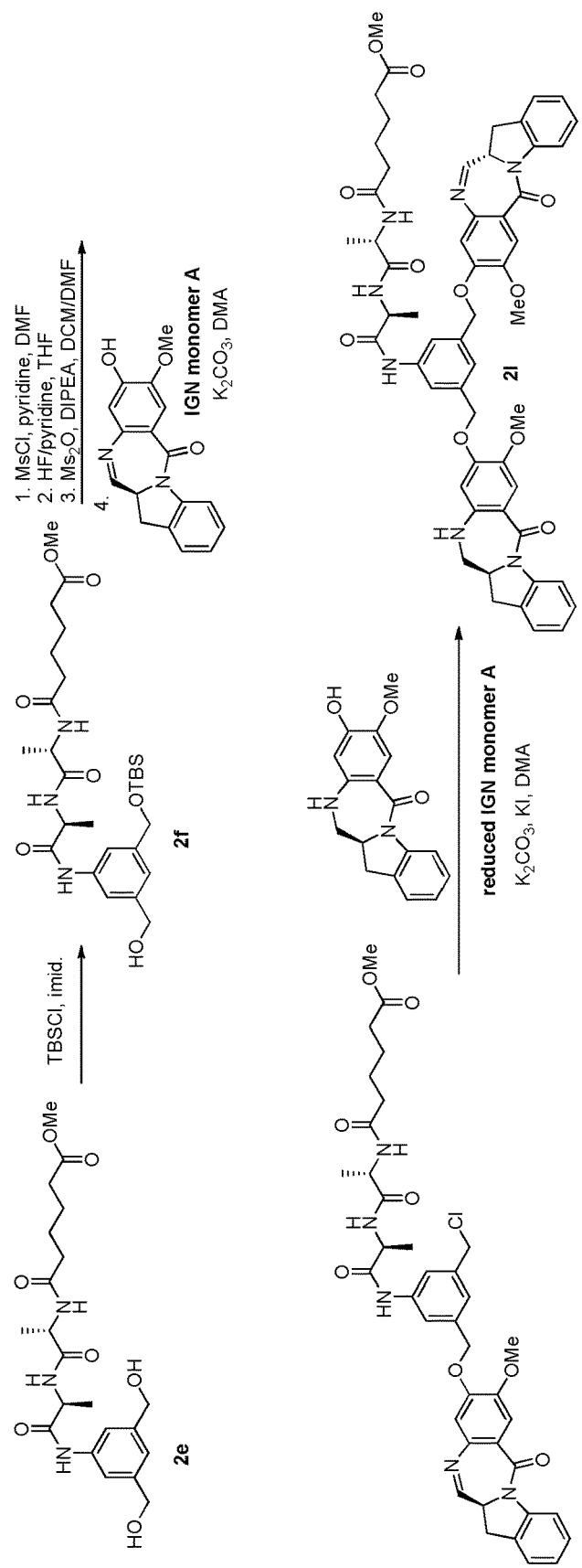
Figure 10:
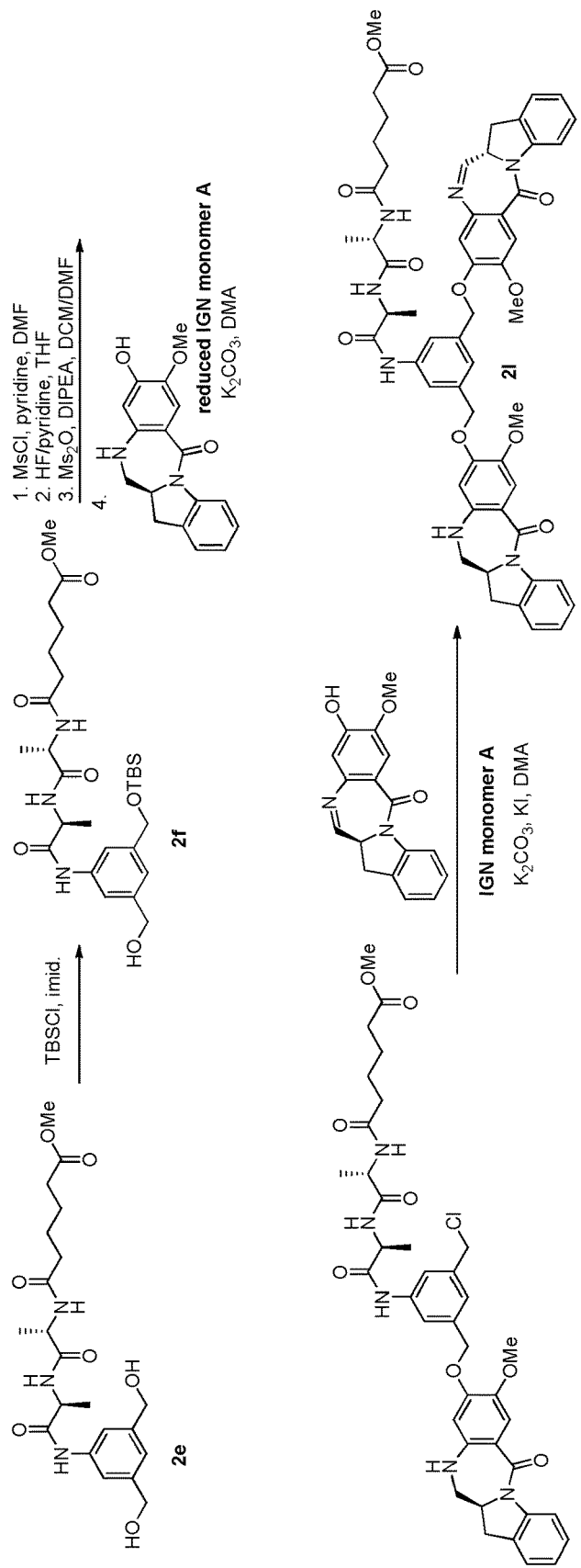
Figure 11:
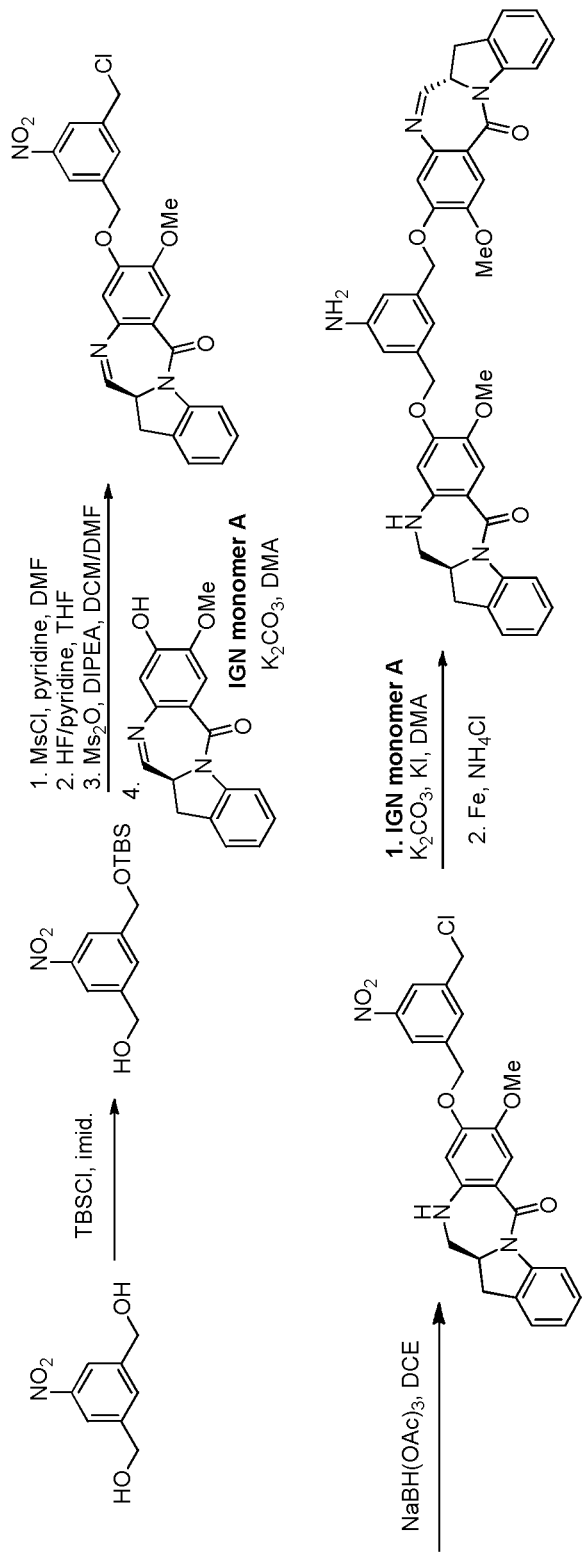
Figure 12:
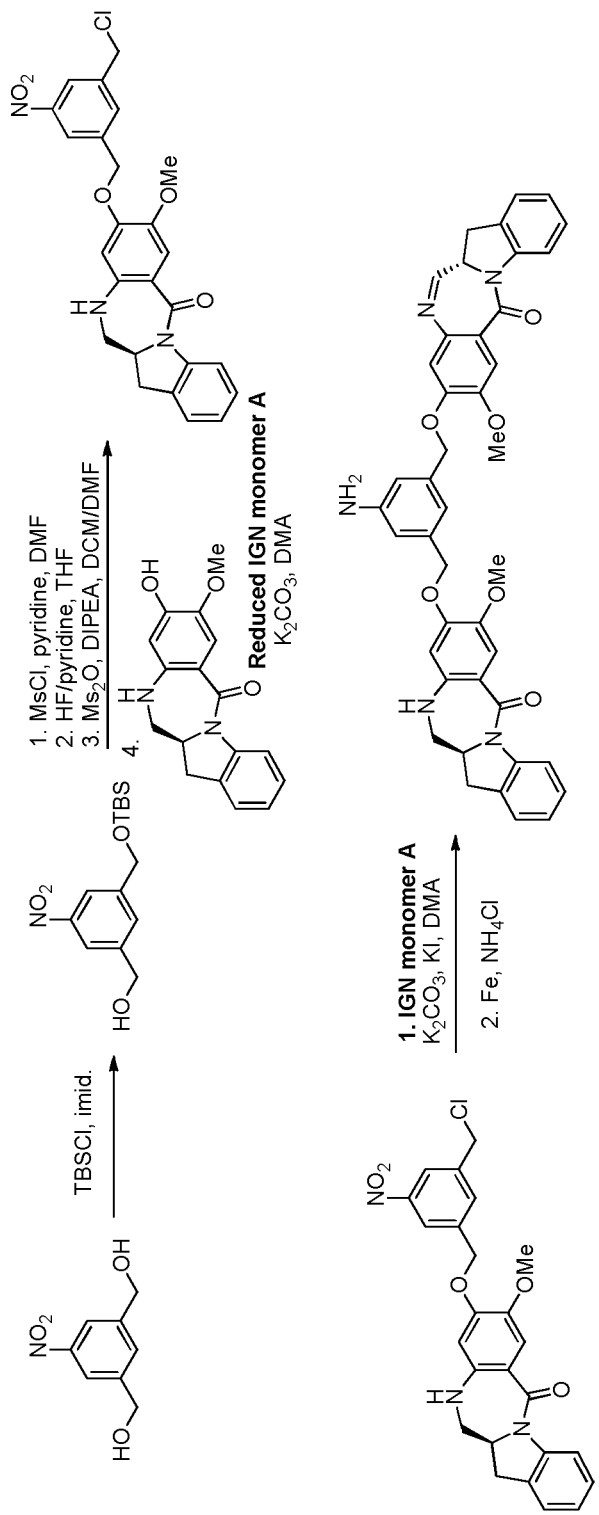
Figure 13:
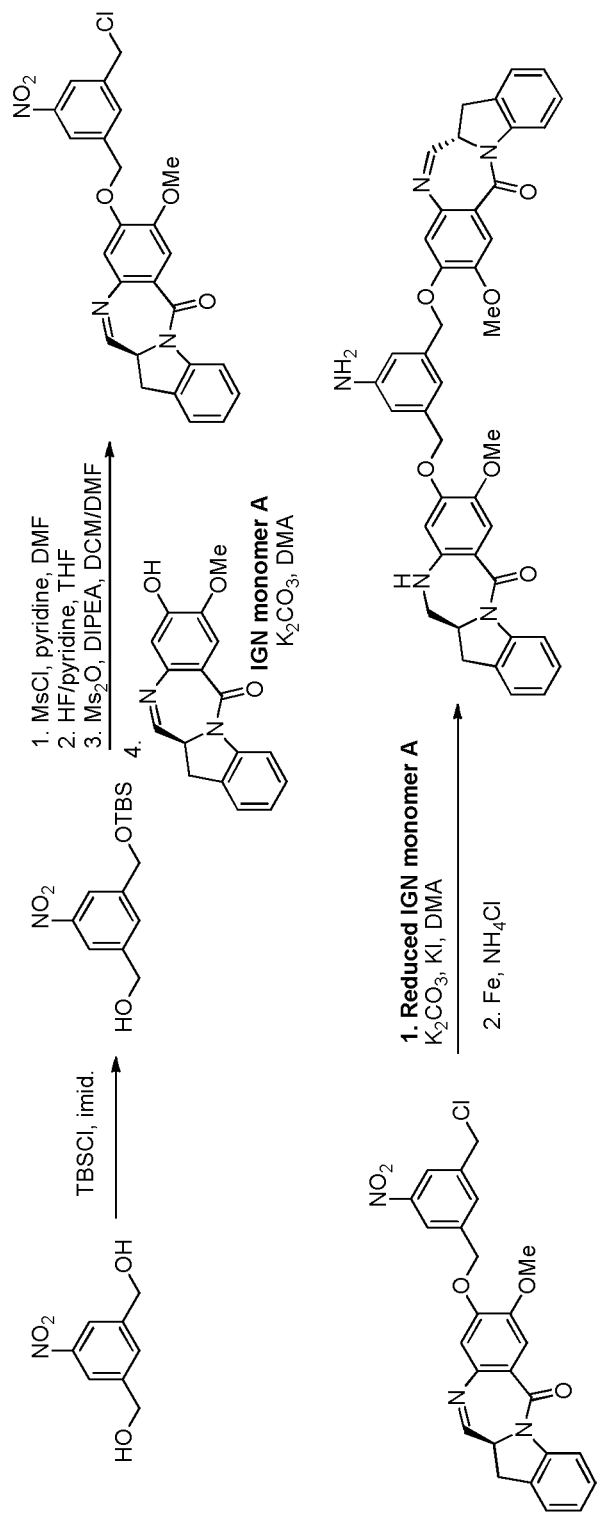

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

DEFINITIONS

"Alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The term "halo" or "halogen" refers to F, Cl, Br or I. In one embodiment, the halogen is Br or I.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "precursor" of a given group refers to any group which may lead to that group by any deprotection, a chemical modification, or a coupling reaction.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "imine reducing reagent" refers to a reagent that is capable of reducing an imine functional group to an amine functional group. In certain embodiments, the imine reducing reagent is a hydride reducing reagent. Examples of such imine reducing reagents include, but are not limited to, borohydrides (e.g., sodium borohydride, sodium triacetoxy borohydride, sodium cyanoborohydride, lithium borohydride (LiBH$_4$), potassium borohydride (KBH$_4$)), hydrogen gas, and lithium aluminum hydride, ammonium formate, borane, 9-borabicyclo[3.3.1]nonane (9-BBN), diisobutylaluminium hydride (DIBAL), and sodium bis(2-methoxyethoxy)aluminumhydride (Red-Al). In certain embodiments, the imine reducing reagent is sodium triacetoxy borohydride.

The term "protecting group" or "protecting moiety" refers to a substituent that is commonly employed to block or protect a particular functionality while reacting other functional groups on the compound, a derivative thereof, or a conjugate thereof. For example, an "amine protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc), 2-trimethylsilylethyl, (2-phenyl-2-trimethylsilyeethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2, 2,2,2-trichloroethoxycarbonyl. For a general description of protecting groups and their use, see P. G. M. Wuts & T. W. Greene, Protective Groups in Organic Synthesis, John Wiley & Sons, New York, 2007.

An "alcohol protecting group" or an "alcohol-protecting moiety" is a substituent attached to an alcohol group that blocks or protects the alcohol functionality in the compound. Such groups are well known in the art (see for example, P. Wuts and T. Greene, 2007, Protective Groups in Organic Synthesis, Chapter 2, J. Wiley & Sons, NJ). Suitable alcohol protecting group include, but are not limited to, pivaloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris(4-tert-butylphenyl)methyl and various silyl protecting groups (for example, dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl). In certain embodiments, the alcohol protecting group is sterically hindered. In certain embodiments, the alcohol protecting group is preferably methoxymethyl, tetrahydropyranyl, 2-methoxyethoxymethyl, p-methoxybenzyl, benzyloxymethyl, or 2,2,2-trichloroethoxycarbonyl. More preferably, the alcohol protecting group is 2,2,2-trichloroethoxycarbonyl. In certain embodiments, the alcohol protecting group is a silyl protecting group, preferably, triethylsilyl, triisopropylsilyl, or tert-butyldimethylsilyl. More preferably, the alcohol protecting group is tert-butyldimethylsilyl.

An "alcohol protecting reagent" as used herein refers to a reagent that introduces an alcohol protecting group onto an alcohol group.

An "acid labile alcohol protecting group" is an alcohol protecting group that is not stable under acidic condition and releases the alcohol protecting group to form free alcohol. Examples of an acid labile alcohol protecting group include, but are not limited to, acetate, allyl, methoxymethyl, tetrahydrofuranyl, tetrahydropyranyl, 5-dibenzosuberyl, 1-ethoxyethyl, 1-methyl-1methoxylethyl, 2-(phenylselenyl) ethyl, trityl/triphenylmethyl, tris(4-tert-butylphenyl)methyl, and various silyl protecting group (for example, dimethylisopropylsilyl, diethylisopropylsilyl, dimethylhexylsilyl, trimethylsilyl, triethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl). In certain embodiments, the alcohol protecting group is a silyl protecting group, preferably, triethylsilyl, triisopropylsilyl, or tert-butyldimethylsilyl. More preferably, the alcohol protecting group is tert-butyldimethylsilyl.

As used herein, the term "alcohol deprotecting reagent" refers to a reagent that is capable of cleaving an alcohol protecting group to form free alcohol. Such reagents are well known in the art (see for example P. Wuts and T. Greene, 2007, Protective Groups in Organic Synthesis, Chapter 2, J. Wiley & Sons, NJ). Examples of such alcohol deprotecting reagents include, but are not limited to, tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, periodic acid. In certain embodiments, the alcohol deprotecting reagent is hydrochloric acid or tetra-n-butylammonium fluoride (TBAF). In certain embodiments, the alcohol deprotecting agent is hydrogen fluoride-pyridine (HF-pyridine).

As used herein, "amine deprotecting group" refers a reagent that is capable of cleaving an amine protecting group to form free amine Such reagents are well known in the art (see for example P. Wuts and T. Greene, 2007, Protective Groups in Organic Synthesis, Chapter 7, J. Wiley & Sons, NJ). Examples of such amine deprotecting reagents include, but are not limited to, tetra-n-butylammonium fluoride, acetic acid, hydrogen fluoride pyridine, cesium fluoride, piperidine, morpholine, or trifluoroacetic acid.

As used herein, "alcohol activating agent" refers a reagent that increases the reactivity of a hydroxyl group thereby making the hydroxyl group a better leaving group. Examples of such alcohol activating agents include p-toluenesulfonyl chloride, thionyl chloride, triflic anhydride, mesyl chloride, mesyl anhydride, triphenylphosphine, acyl chloride, 4-dimethylaminopyridine, and others. In certain embodiments, the alcohol activating agent is thionyl chloride. In certain embodiment, the alcohol activating agent is triphenylphosphine.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The term "leaving group" refers to a group of charged or uncharged moiety that departs during a nucleophilic substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

As used herein, the term "halogenating reagent" refers to a reagent that converts an alcohol group to a halide group. A "brominating reagent" is a reagent that converts an alcohol group to a bromide group. A "iodinating reagent" is a reagent that converts an alcohol group to a iodide group. A "chlorinating reagent" is a reagent that converts an alcohol group to a chloride group. Exemplary brominating reagents include, but are not limited to, bromine, hydrobromic acid, carbon tetrabromide, phosphorus tribromide, and potassium bromide. Exemplary iodinating reagent include, but are not limited to, hydroiodic acid, iodine, carbon tetraiodide, phosphorus triiodide, sodium iodide, or potassium iodide. Exemplary chlorinating reagent include, but are not limited to, carbon tetrachloride, methanesulfonyl chloride, sulfuryl chloride, thionyl chloride, cyanuric chloride, N-chlorosuccinimide, phosphorus(V) oxychloride, phosphorus pentachloride, and phosphorus trichloride. In a specific embodiment, the chlorinating reagent is methanesulfonyl chloride.

As used herein, a "sulfonating reagent" refers to a reagent that converts an alcohol group to a sulfonate ester group. Preferably, the sulfonating reagent is a sulfonic anhydride, such as methanesulfonic anhydride, or a sulfonic chloride, such as methanesulfonyl chloride (MsCl).

As used herein, an "activated ester" refers to an ester group that is readily displaced by a hydroxyl or an amine group. Exemplary activated esters include, but are not limited to nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, pentafluorophenyl ester, nitropyridyl (e.g., 4-nitropyridyl) ester, trifluoroacetate, and acetate.

As used herein, an "esterification reagent" refers to a reagent that converts an alcohol group to an ester group.

Exemplary esterification reagent include, but are not limited to, nitrobenzoid acid (e.g., 2 or 4-nitrobenzoic acid), dinitrobenzoid acid (e.g., 2,4-dinitrobenzoic acid), sulfo-tetraflurobenzoid acid (e.g., 4-sulfo-2,3,5,6-tetrafluorobenzoic acid), pentafluorobenzoic acid, nitropyridine carboxylic acid (e.g., 4-nitro-2-pyridine carboxylic acid, trifluoroacetic acid, and acetic acid, or acyl chloride, acid anhydride or other activated carboxylic acid derivatives thereof.

Methods of the Present Invention

The present invention provides novel methods for preparing indolinobenzodiazepine dimer compounds that have one imine functionality and one amine functionality. As compared to the methods known in the art, the present methods can produce the desired dimer compounds with higher yield and without the use of HPLC purification.

In a first embodiment, the present invention provides a method of preparing a compound of formula (2d),

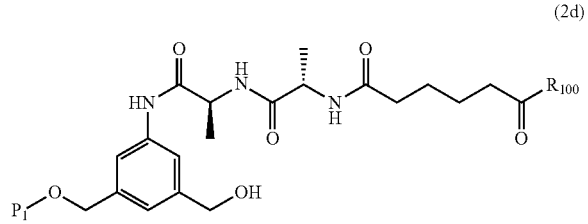

(2d)

or a salt thereof, said method comprising introducing an alcohol protecting group onto one of the primary alcohols of a compound of formula (1d) by reacting the compound of formula (1d) with an alcohol protecting reagent,

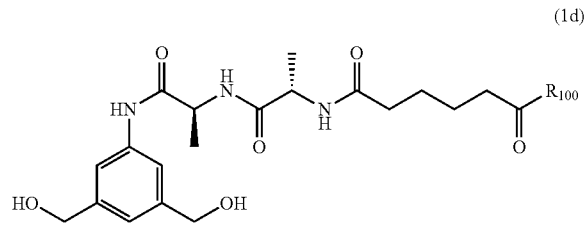

(1d)

wherein $P_1$ is the alcohol protecting group; and $R_{100}$ is ($C_1$-$C_3$)alkoxy.

Also provided in the first embodiment is a method of preparing a compound of formula (2A),

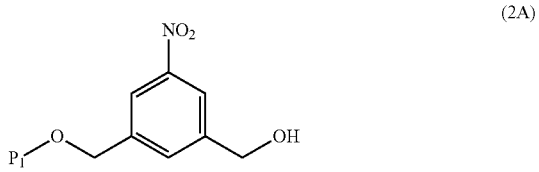

(2A)

or a salt thereof, comprising introducing an alcohol protecting group onto one of the primary alcohols of a compound of formula (1A) by reacting the compound of formula (1A) with an alcohol protecting reagent,

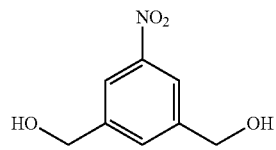

(1A)

wherein $P_1$ is the alcohol protecting group.

In a specific embodiment, for methods of preparing compound of formula (2d) or (2A) described above the alcohol protecting group is sterically hindered.

In another specific embodiment, the alcohol protecting group is pivaloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris (4-tert-butylphenyl)methyl. Preferably, the alcohol protecting group is methoxymethyl, tetrahydropyranyl, 2-methoxyethoxymethyl, p-methoxybenzyl, benzyloxymethyl, or 2,2, 2-trichloroethoxycarbonyl. Even more preferably, the alcohol protecting group is 2,2,2-trichloroethoxycarbonyl.

In another specific embodiment, the alcohol protecting group is a silyl protecting group. For example, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

The silyl protecting group can be introduced by reacting the compound of formula (1d) or (1A) with $R^3$—Cl, $R^3$—Br, $R^3$—I or $R^3$—$OSO_2CF_3$ (collectively the alcohol protecting reagent) in the presence of a base, wherein $R^3$ is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl or [2-(trimethylsilyl)ethoxy]methyl. In certain embodiments, the molar ratio of the alcohol protecting reagent to the compound of formula (1d) or (1A) is between 0.8-1.2, between 1 to 5, between 1 to 2, between 1 to 1.5, between 1 to 1.4, between 1 to 1.3, between 1 to 1.2, or between 1 to 1.1. In certain embodiment, less than 2 molar equivalents of the alcohol protecting reagent is used relative to the compound of formula (1d) or (1A). Preferably, 1.5, 1.4, 1.3, 1.2, 1.1 or 1.0 molar equivalent of the alcohol protecting reagent relative to the compound of formula (1d) or (1A) is used. In one embodiment, the base can be a non-nucleophilic base. Examples of non-nucleophilic base include, but are not limited to, imidazole, triethylamine, diisopropylethylamine, pyridine, 2,6-lutidine, 1,8-diazabicycloundec-7-ene, or tetramethylpiperidine. Preferably, the non-nucleophilic base is imidazole. Molar excess amount of the base can be used. In certain embodiments, more than 2 molar equivalents of the base (e.g., non-nucleophilic base) are used relative to the compound of formula (1d) or (1A).

In another embodiment, the reaction between the compound of formula (1d) or (1A) and $R^3$—Cl, $R^3$—Br, $R^3$—I or $R^3$—$OSO_2CF_3$ is carried out in the presence of a catalyst that facilitates the introduction of the silyl protecting group. Any suitable catalysts known in the art (see, for example, P.

Wuts and T. Greene, 2007, Protective Groups in Organic Synthesis, Chapter 2, J. Wiley & Sons, NJ) can be used in the reaction. Exemplary catalysts include, but are not limited to, 4-dimethylaminopyridine (DMAP), 1,1,3,3-tetramethylguanidine and 1,8-diazabicyclo[5.4.0]undec-7-ene (DBU).

Any suitable organic solvents can be used for the methods of the first embodiment. Exemplary solvents include, but are not limited to, DMF, $CH_2Cl_2$, dichloroethane, THF, dimethylacetamide, etc. In certain embodiments, DMF is used as the solvent.

In another specific embodiment, the method of preparing the compound of formula (2d) or (2A) comprising reacting the compound of (1d) or (1A) with TBSCl in the presence of a non-nucleophilic base. In one embodiment, the base is imidazole or DIPEA. In a specific embodiment, the base is imidazole. In another specific embodiment, the base is DIPEA.

In a second embodiment, the present invention provides a method of preparing a compound of formula (3d),

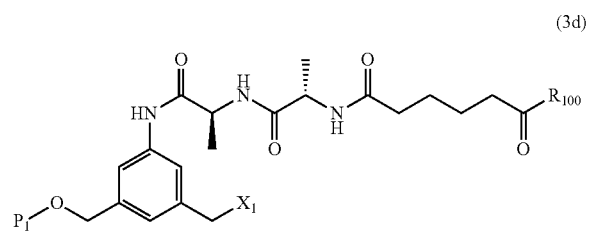

(3d)

or a salt thereof, said method comprising reacting a halogenating reagent, a sulfonating reagent or an esterification reagent with a compound of formula (2d),

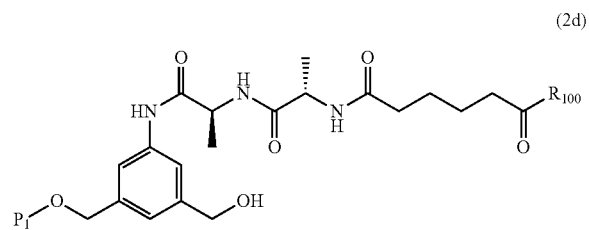

(2d)

wherein $P_1$ is an alcohol protecting group; $X_1$ is a leaving group selected from the group consisting of: —Br, —I, —Cl, a sulfonate ester, and an activated ester; and $R_{100}$ is ($C_1$-$C_3$) alkoxy.

Also provided in the second embodiment is a method of preparing a compound of formula (3A),

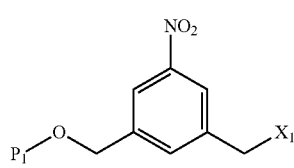

(3A)

or a salt thereof, comprising reacting the compound of formula (2A) with a halogenating reagent, a sulfonating reagent or an esterification reagent,

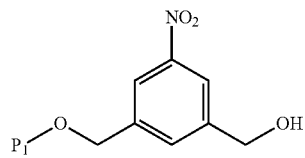

(2A)

wherein $P_1$ and $R_{100}$ are as defined in the first embodiment, and $X_1$ is a leaving group selected from the group consisting of: —Br, —I, —Cl a sulfonate ester, and an activated ester.

In a specific embodiment, for methods of preparing compound of formula (3d) or (3A) described above, $X_1$ is —Br, —I or a sulfonate ester.

In a specific embodiment, for methods of making compound of formula (3d) or (3A) described above, $X_1$ is mesylate, tosylate, brosylate, or triflate. Preferably, $X_1$ is mesylate.

In another specific embodiment, the method of the second embodiment comprises reacting the compound of formula (2d) or (2A) with a halogenating reagent. Exemplary halogenating reagents include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In yet another specific embodiment, the method of the second embodiment comprises reacting the compound of formula (2d) or (2A) with a sulfonating reagent. Preferably, the sulfonating reagent is a sulfonic anhydride, such as methanesulfonic anhydride, or a sulfonic chloride, such as methanesulfonyl chloride (MsCl).

In certain embodiment, the reaction between the compound of formula (2d) or (2A) and the sulfonating reagent can be carried out in the presence of a base. In one embodiment, the base is a non-nucleophilic base. Exemplary non-nucleophilic bases include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine.

Any suitable organic solvents can be used in the method of the second embodiment. In one embodiment, the solvent is dichloromethane.

In a third embodiment, the present invention provides a method of preparing a compound of formula (4d),

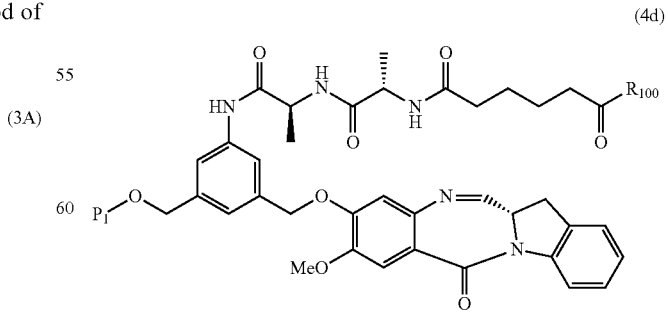

(4d)

or a salt thereof, said method comprising reacting a compound of formula (3d)

(3d)

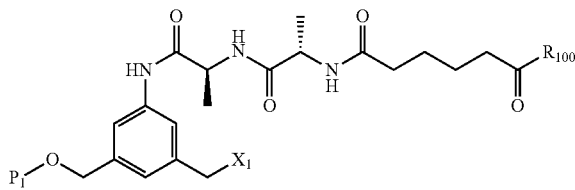

with a monomer compound of the formula (a₁), (a1)

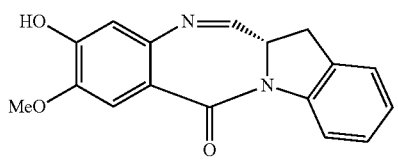

wherein $P_1$ is an alcohol protecting group; $X_1$ is a leaving group selected from the group consisting of: —Br, —I, —Cl, a sulfonate ester and an activated ester; and $R_{100}$ is $(C_1$-$C_3)$ alkoxy.

Also provided in the third embodiment is a method of preparing a compound of formula (4A), (4A)

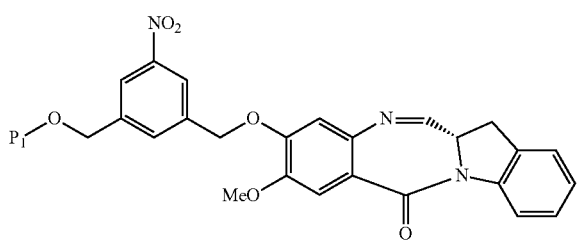

or a salt thereof, said method comprising reacting a compound of formula (3A)

(3A)

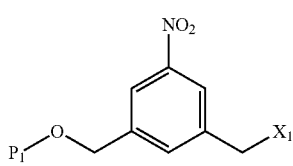

with a monomer compound of the formula (a₁), (a₁)

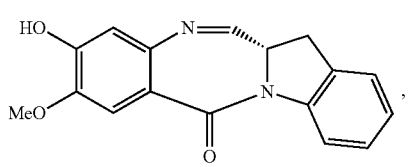

wherein $P_1$ is an alcohol protecting group; and $X_1$ is a leaving group selected from the group consisting of: —Br, —I, —Cl, a sulfonate ester and an activated ester.

In a specific embodiment, for methods of the third embodiment, $X_1$ is —Br, —I, or a sulfonate ester.

In a specific embodiment, for method of preparing compound of formula (4d) or (4A), the compound of formula (3d) or (3A) is reacted with the monomer compound of formula (a₁) in the presence of a base. Any suitable base can used. Exemplary bases include, but are not limited to, sodium carbonate, potassium carbonate, cesium carbonate, sodium hydride, or potassium hydride. In one embodiment, the base is potassium carbonate.

Any suitable solvents can be use in the method of third embodiment. In one embodiment, the solvent is dimethylacetamide (DMA).

In a specific embodiment, the method of preparing compound of formula (4d) or (4A) described above comprises reacting the compound of formula (3d) or (3A) with the monomer compound (a₁) in the presence of potassium carbonate in DMA. In one embodiment, the reaction is carried out in the presence of potassium iodide.

In a fourth embodiment, the present invention provides a method of preparing a compound of formula (5d), (5d)

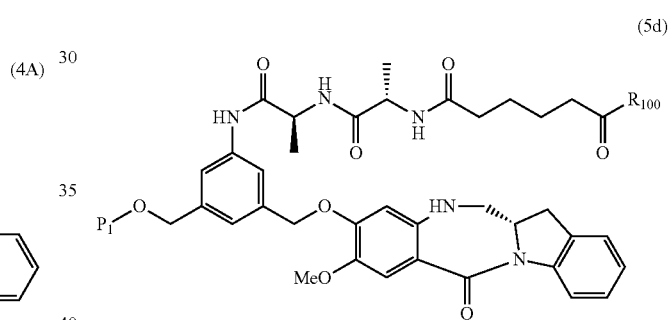

or a salt thereof, said method comprising reacting a compound of formula (4d), (4d)

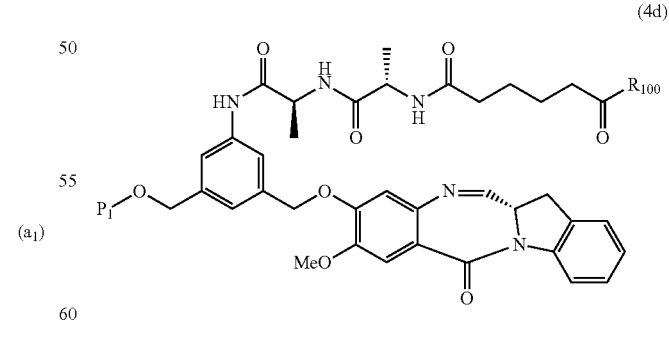

with an imine reducing agent, wherein $P_1$ is an alcohol protecting group; and $R_{100}$ is $(C_1$-$C_3)$alkoxy.

Also provided in the fourth embodiment is a method of preparing a compound of formula (5A),

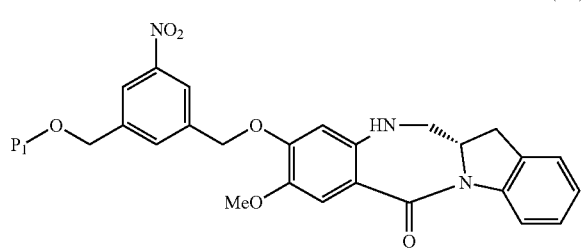

(5A)

or a salt thereof, said method comprising reacting a compound of formula (4A),

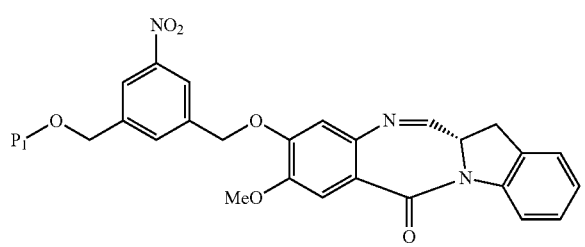

(4A)

with an imine reducing agent, wherein the variables are as described above in the third embodiment.

In a specific embodiment, for methods of preparing compound of formula (5d) or (5A) described above, the imine reducing reagent is a hydride reducing reagent.

In another specific embodiment, the imine reducing reagent is sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH$_4$), potassium borohydride (KBH$_4$), or sodium bis(2-methoxyethoxy)aluminumhydride (Red-Al). Preferably, the imine reducing reagent is sodium triacetoxy borohydride (NaBH(OAc)$_3$).

Any suitable solvents can be use in the method of fourth embodiment. In one embodiment, the solvent is dichloroethane.

In a fifth embodiment, the present invention provides a method of preparing a compound of formula (6d),

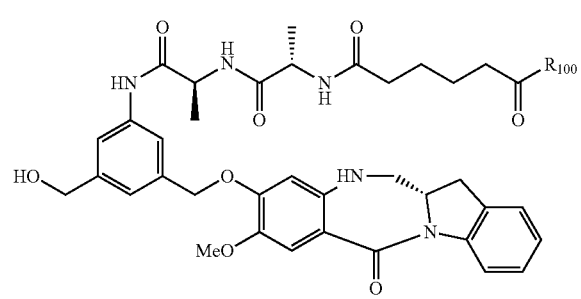

(6d)

or a salt thereof, said method comprising reacting a compound of formula (5d),

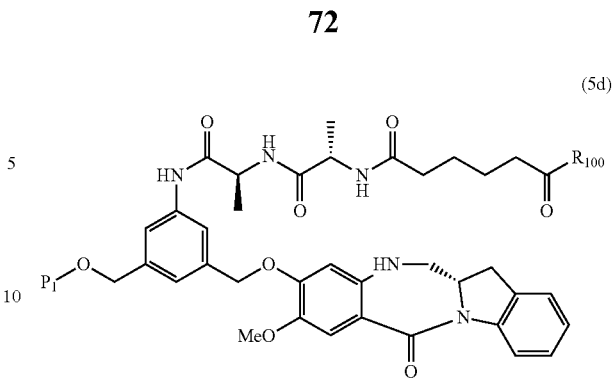

(5d)

with an alcohol deprotecting reagent, wherein P$_1$ is an alcohol protecting group; and R$_{100}$ is (C$_1$-C$_3$)alkoxy.

Also provided in the fifth embodiment is a method of preparing a compound of formula (6A),

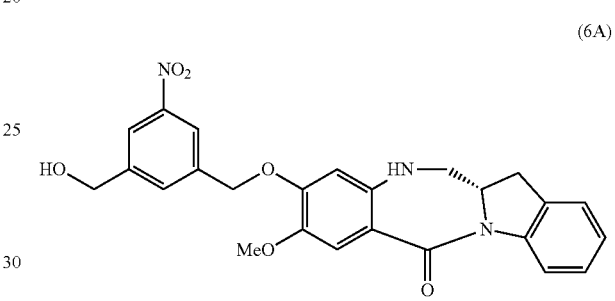

(6A)

or a salt thereof, said method comprising reacting a compound of formula (5A),

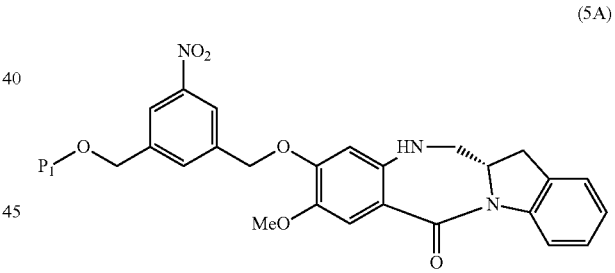

(5A)

with an alcohol deprotecting reagent, wherein the variables are as described above in the fourth embodiment In a specific embodiment, for methods of preparing a compound of formula (6d) or (6A) described above, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, or periodic acid. Preferably, the alcohol deprotecting reagent is hydrochloric acid or tetra-n-butylammonium fluoride. In a more specific embodiment, the alcohol deprotecting reagent is aqueous hydrochloric acid.

Any suitable solvents can be used in the deprotection reaction described above. In one embodiment, the solvent is THF.

In a sixth embodiment, the present invention provides a method of preparing a compound of formula (7d),

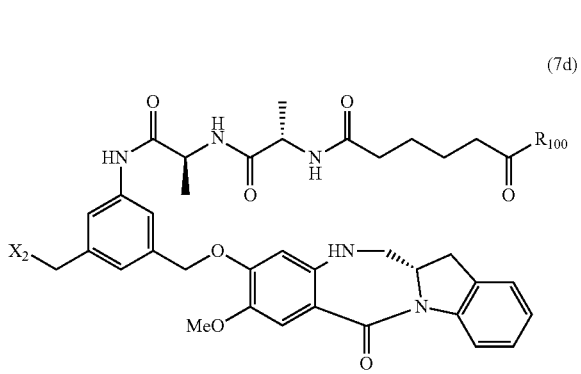
(7d)

or a salt thereof, said method comprising reacting a halogenating reagent, a sulfonating reagent or an esterification reagent with the primary alcohol compound of formula (6d),

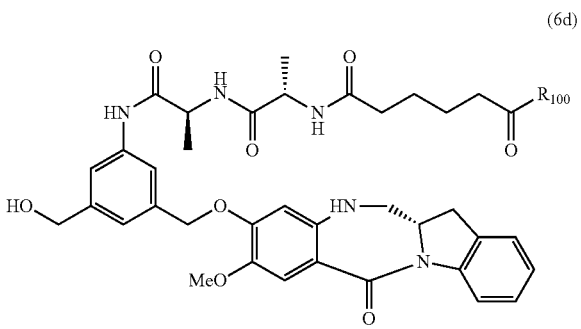
(6d)

wherein $X_2$ is a leaving group selected from the group consisting of: —Br, —I, —Cl, a sulfonate ester and an activated ester; and $R_{100}$ is $(C_1-C_3)$alkoxy.

Also provided in the sixth embodiment is a method of preparing a compound of formula (7A),

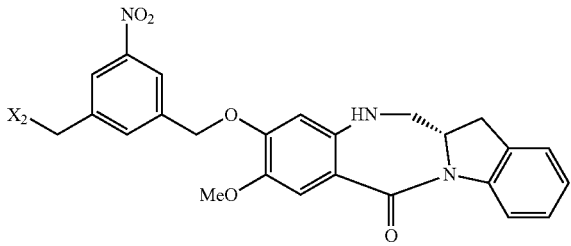
(7A)

or a salt thereof, said method comprising reacting a halogenating reagent, a sulfonating reagent or an esterification reagent with the primary alcohol compound of formula (6A),

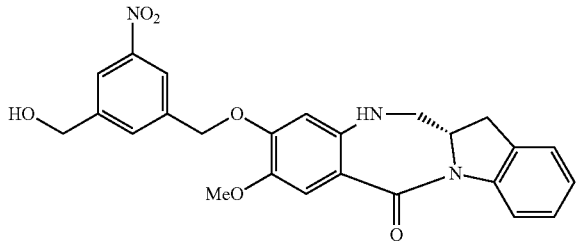
(6A)

wherein $X_2$ is —Br, —I, —Cl, a sulfonate ester or an activated ester; and the remaining variables are as described above in the fifth embodiment.

In a specific embodiment, for methods of preparing a compound of formula (7d) or (7A), $X_2$ is —Br, —I or a sulfonate ester.

In a specific embodiment, for methods of preparing a compound of formula (7d) or (7A), $X_2$ is mesylate, tosylate, brosylate, or triflate. Preferably, $X_2$ is mesylate.

In another specific embodiment, the method of the sixth embodiment comprises reacting the compound of formula (6d) or (6A) with a halogenating reagent. Exemplary halogenating reagent include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In yet another specific embodiment, the method of the sixth embodiment comprises reacting the compound of formula (6d) or (6A) with a sulfonating reagent. Preferably, the sulfonating reagent is a sulfonic anhydride, such as methanesulfonic anhydride, or a sulfonic chloride, such as methanesulfonyl chloride (MsCl).

In one embodiment, the reaction between the compound of formula (6d) or (6A) and the sulfonating reagent is carried out in the presence of a base. Preferably, the base is a non-nucleophilic base. Exemplary non-nucleophilic base include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine.

Any suitable solvents can be used in the reactions described in the sixth embodiment above. In one embodiment, the solvent is dichloromethane. In another embodiment, the solvent is DMF. In yet another embodiment, the solvent is a mixture of dichloromethane and DMF.

In a seventh embodiment, the present invention provides a method of preparing a compound of formula (7d")

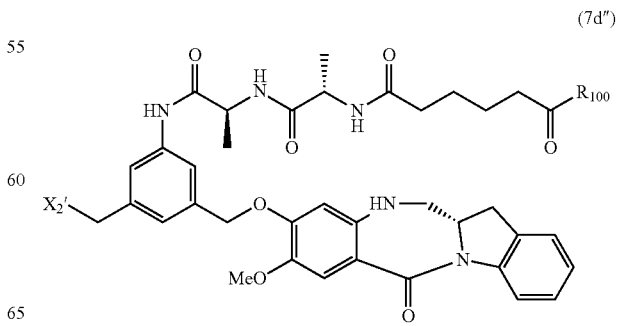
(7d")

or a salt thereof, said method comprising reacting a compound of formula (5d″)

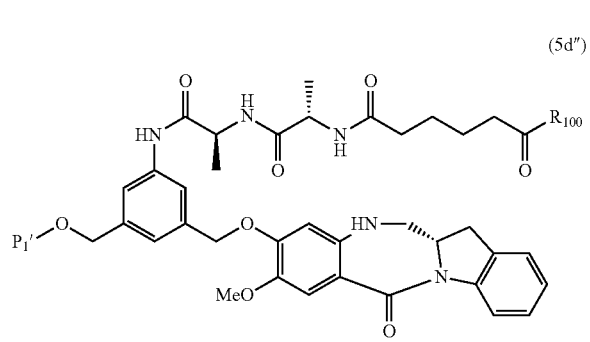
(5d″)

with an alcohol deprotecting reagent and a halogenating reagent, wherein $P_1'$ is an acid labile alcohol protecting group; $X_2'$ is —Br or —I; and $R_{100}$ is $(C_1-C_3)$alkoxy.

Also provided in the seventh embodiment is a method of preparing a compound of formula (7A″):

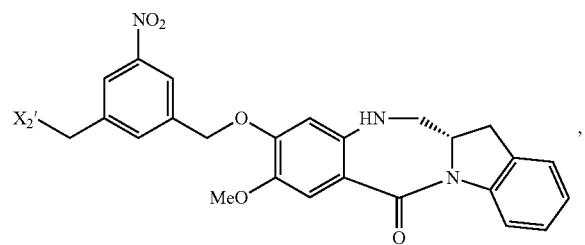
(7A″)

or a salt thereof, said method comprising reacting a compound of formula (5A″)

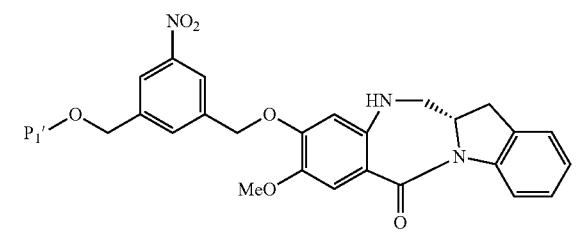
(5A″)

with an alcohol deprotecting reagent and a halogenating reagent, wherein $P_1'$ is an acid labile alcohol protecting group; $X_2'$ is —Br or —I; and the remaining variables are as described above in the sixth embodiment.

The method of the seventh embodiment combines the alcohol deprotection step described in the fifth embodiment and the halogenation reaction of the resulting alcohol described in the sixth embodiment into one step.

In a specific embodiment, for the method of the seventh embodiment, the compound of formula (7d″) is represented by the following formula:

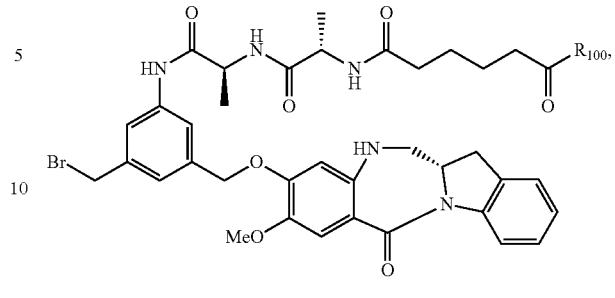
(7d‴)

and the method comprising reacting the compound of formula (5d″) with an alcohol deprotecting reagent and a bromination reagent.

In another specific embodiment, for the method of the seventh embodiment, the compound of formula (7A‴) is represented by the following formula:

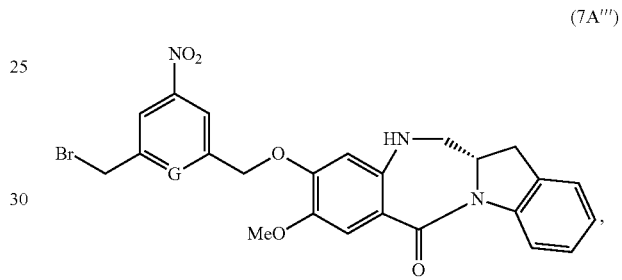
(7A‴)

and the method comprising reacting the compound of formula (5A″),

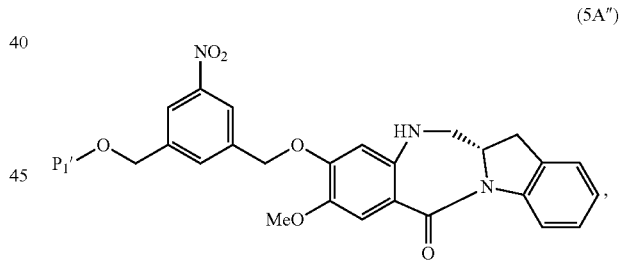
(5A″)

with an alcohol deprotecting reagent and a bromination reagent.

In one embodiment, for the methods described in the seventh embodiment, the acid labile alcohol protecting group is acetate, allyl, methoxymethyl, tetrahydrofuranyl, tetrahydropyranyl, 5-dibenzosuberyl, 1-ethoxyethyl, 1-methyl-1methoxylethyl, 2-(phenylselenyl)ethyl, trityl/triphenylmethyl, or tris(4-tert-butylphenyl)methyl.

In another embodiment, the acid labile alcohol protecting group is a silyl protecting group. Exemplary silyl protecting groups include, but are not limited to, dimethylisopropylsilyl, diethylisopropylsilyl, dimethylhexylsilyl, trimethylsilyl, triethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl(TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

In one embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, pyridinium p-toluensulfonate, formic acid, periodic acid, trifluoroacetic acid, or .p-toluenesulfonic acid (p-TsOH). Preferably, the alcohol deprotecting reagent is acetic acid.

In yet another embodiment, the bromination reagent is HBr.

In one specific embodiment, the methods of the seventh embodiment comprises reacting the compound of formula (5d″) with a mixture of acetic acid and HBr to give the compound of formula (7d′″).

In another specific embodiment, the methods of the seventh embodiment comprises reacting the compound of formula (5A″) with a mixture of acetic acid and HBr to give the compound of formula (7A′″)

In a eighth embodiment, the present invention provides a method of preparing a compound of formula (Id′),

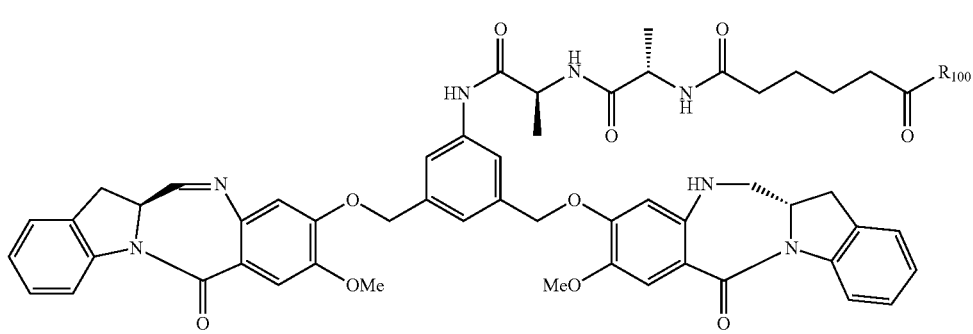

(Id′)

or a pharmaceutically acceptable salt thereof, said method comprising reacting a compound of formula (7d)

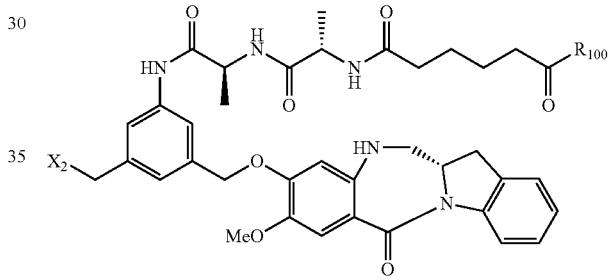

(7d)

with a monomer compound of the formula ($a_1$),

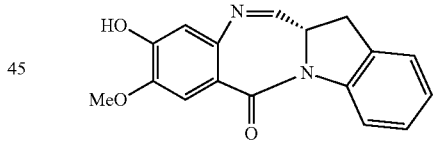

($a_1$)

wherein $R_{100}$ is ($C_1$-$C_3$)alkoxy; and, $X_2$ is a leaving group selected from the group consisting of: —Br, —I, —Cl, a sulfonate ester, and an activated ester.

Also provided in the eighth embodiment is a method of preparing a compound of formula (IA),

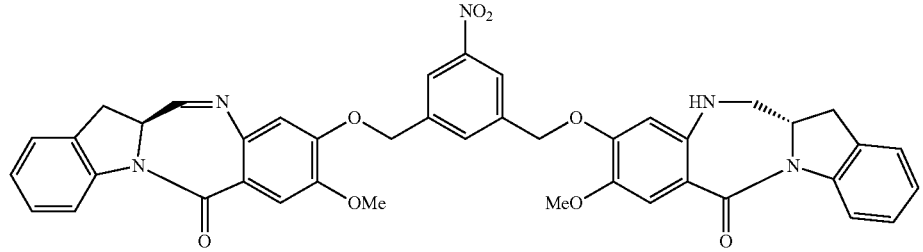

(IA)

or a pharmaceutically acceptable salt thereof, said method comprising reacting a compound of formula (7A)

(7A)

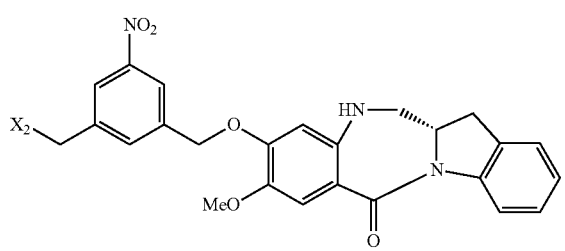

with a monomer compound of the formula (a₁), (a₁)

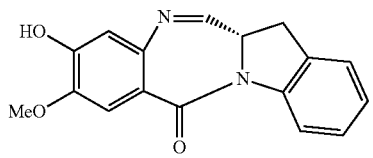

wherein $R_{100}$ is $(C_1$-$C_3)$alkoxy; and, $X_2$ is a leaving group selected from the group consisting of: —Br, —I, —Cl, a sulfonate ester, and an activated ester.

In one embodiment, for methods of the eighth embodiment, $X_2$ is —Br, —I or a sulfonate ester.

In one embodiment, for methods of the eighth embodiment, the compound of formula (7d) or (7A) is reacted with the monomer compound of formula (a₁) in the presence of a base. Examples of the base include, but are not limited to, sodium carbonate, potassium carbonate, cesium carbonate, sodium hydride, or potassium hydride. In one embodiment, the base is potassium carbonate.

Any suitable solvents can be used in the methods of eighth embodiment described above. In one embodiment, the solvent is DMF. In another embodiment, the solvent is DMA.

In a ninth embodiment, the present invention provides a method of preparing a compound of formula (Id'), or a pharmaceutically acceptable salt thereof, said method comprising the steps of:

(1) introducing an alcohol protecting group onto one of the primary alcohols of a compound of formula (1d), (1d)

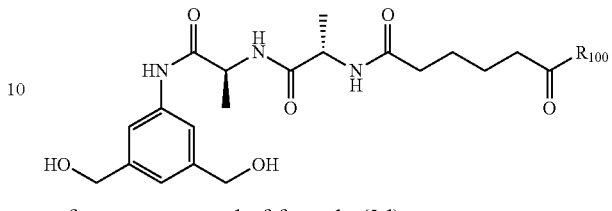

to form a compound of formula (2d), (2d)

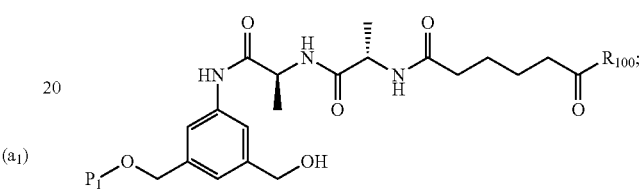

(2) reacting the compound of formula (2d) with a halogenating reagent, a sulfonating reagent or an esterification reagent to form a compound of formula (3d), (3d)

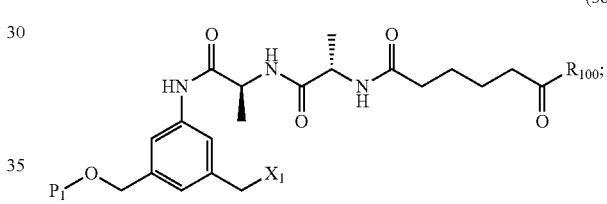

(3) reacting the compound of formula (3d) with a monomer compound of the formula (a₁), (a₁)

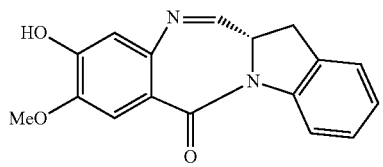

(Id')

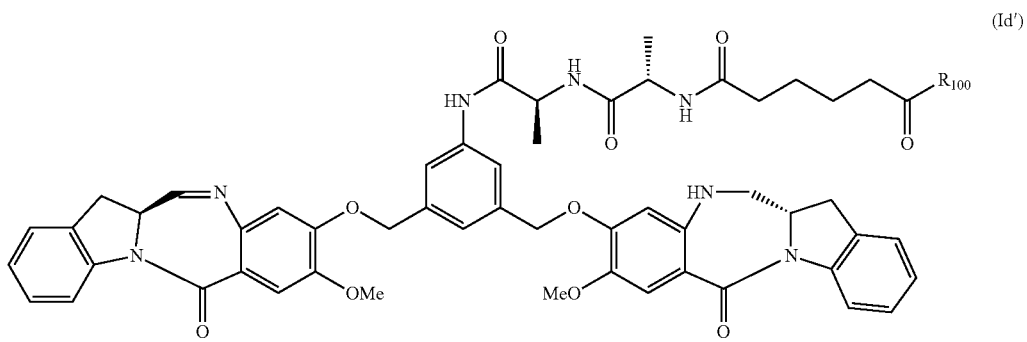

to form a compound of formula (4d), (4d)

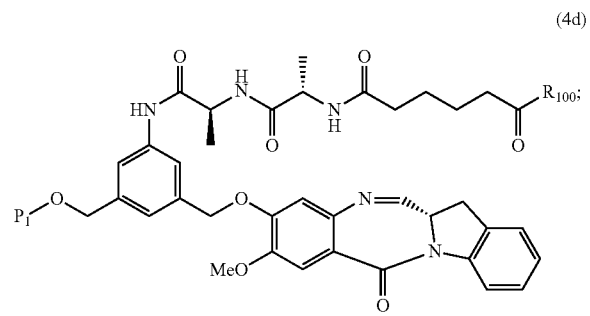

(4) reacting the compound of formula (4d) with an imine reducing agent to form a compound of formula (5d), (5d)

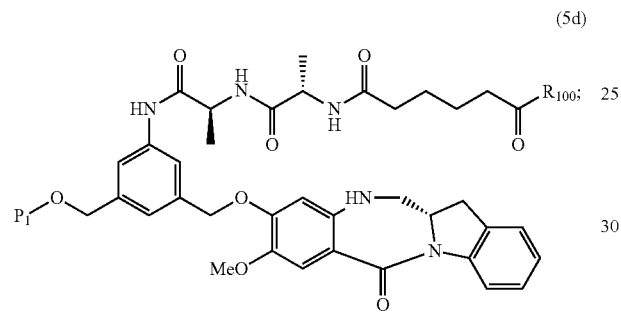

(5) reacting the compound of formula (5d) with an alcohol deprotecting reagent to form a compound of formula (6d), (6d)

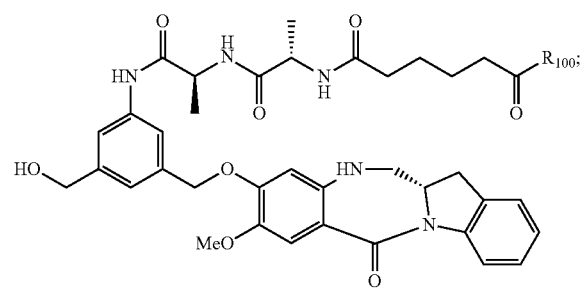

(6) reacting a second halogenating reagent, a second sulfonating reagent or a second esterification reagent with the compound of formula (6d) to form a compound of formula (7d), (7d)

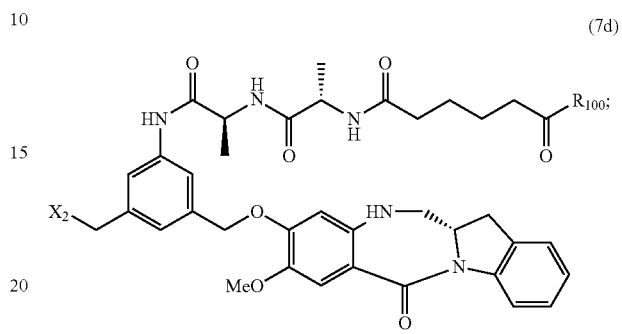

and (7) reacting the compound of formula (7d) with a monomer compound of the formula ($a_1$), ($a_1$)

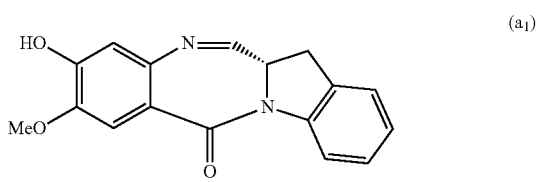 [SMILES: COc1cc2c(cc1O)N=C[C@@H]1Cc3ccccc3N1C2=O]

to form the compound of formula (Id'), wherein $P_1$ is an alcohol protecting group; $X_1$ and $X_2$ are each independently a leaving group selected from the group consisting of: —Br, —I, —Cl, a sulfonate ester and an activated ester; and $R_{100}$ is ($C_1$-$C_3$)alkoxy.

Also provided in the ninth embodiment is a method of preparing a compound of formula (IA):

(IA)

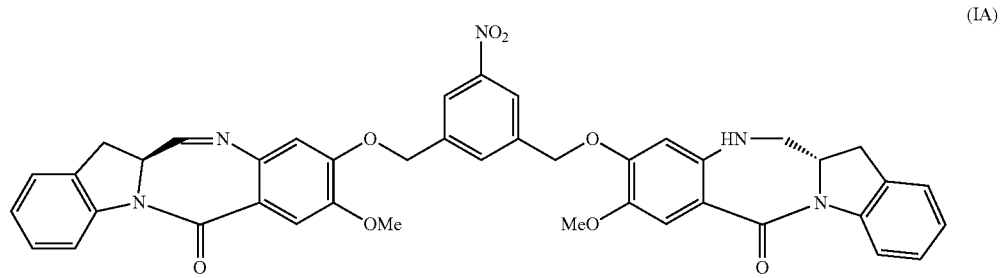 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

or a pharmaceutically acceptable salt thereof, said method comprising the steps of:

(1) introducing an alcohol protecting group onto one of the primary alcohols of a compound of formula (1A),

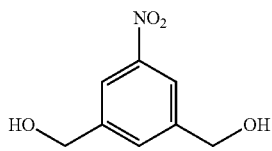
(1A)

to form a compound of formula (2A),

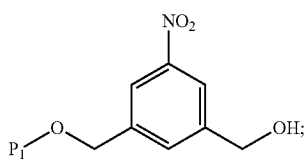
(2A)

(2) reacting the compound of formula (2A) with a halogenating reagent, a sulfonating reagent or an esterification reagent to form a compound of formula (3A),

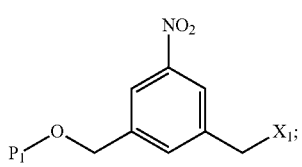
(3A)

(3) reacting the compound of formula (3A) with a monomer compound of the formula ($a_1$),

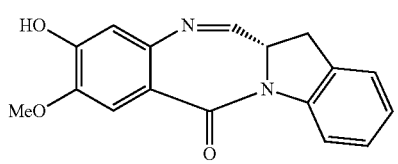
($a_1$)

to form a compound of formula (4A),

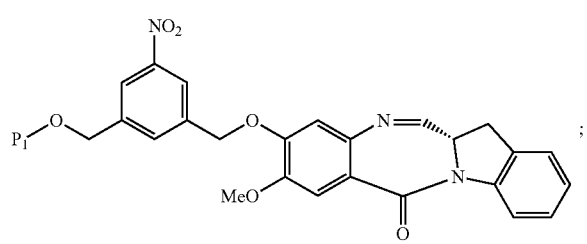
(4A)

(4) reacting the compound of formula (4A) with an imine reducing agent to form a compound of formula (5A),

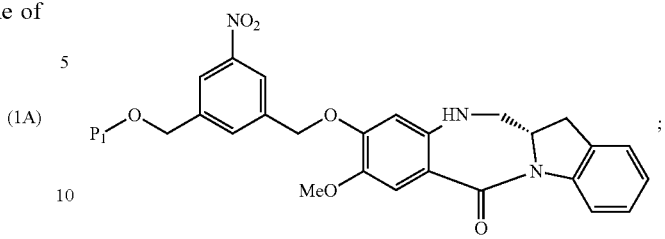
(5A)

(5) reacting the compound of formula (5A) with an alcohol deprotecting reagent to form a compound of formula (6A),

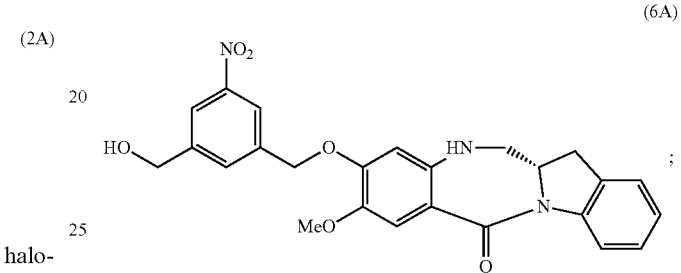
(6A)

(6) reacting a second halogenating reagent, a second sulfonating reagent or an esterification reagent with the compound of formula (6A) to form a compound of formula (7A),

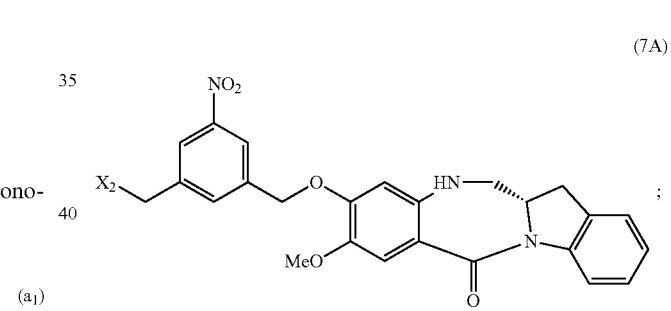
(7A)

and (7) reacting the compound of formula (7A) with a monomer compound of the formula ($a_1$),

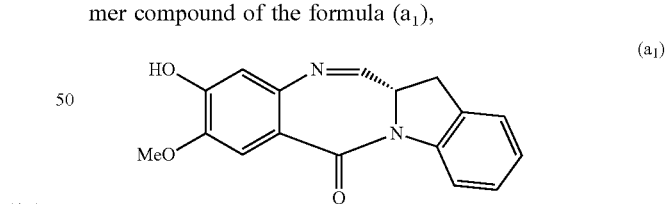
($a_1$)

to form the compound of formula (IA), wherein $P_1$ is an alcohol protecting group; and $X_1$ and $X_2$ are each independently a leaving group selected from the group consisting of: —Br, —I, —Cl, a sulfonate ester and an activated ester.

In one embodiment, for methods of the ninth embodiment, $X_1$ and $X_2$ are each independently —Br, —Cl or a sulfonate ester.

The reaction conditions and reagents for each step in the method of the ninth embodiment are as described in the first, second, third, fourth, fifth, sixth and/or eighth embodiment or any specific embodiments described therein.

In a tenth embodiment, the present invention provides a method of preparing a compound of formula (Id'),

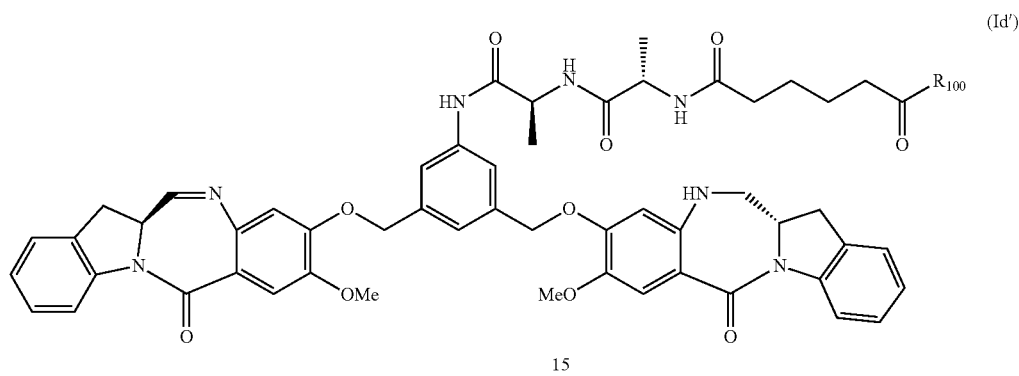

or a pharmaceutically acceptable salt thereof, said method comprising the steps of:

(1) introducing an alcohol protecting group onto one of the primary alcohols of a compound of formula (1d),

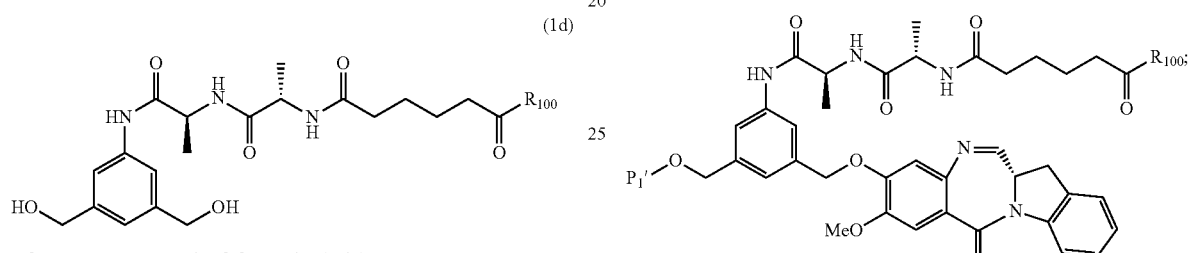

to form a compound of formula (2d″),

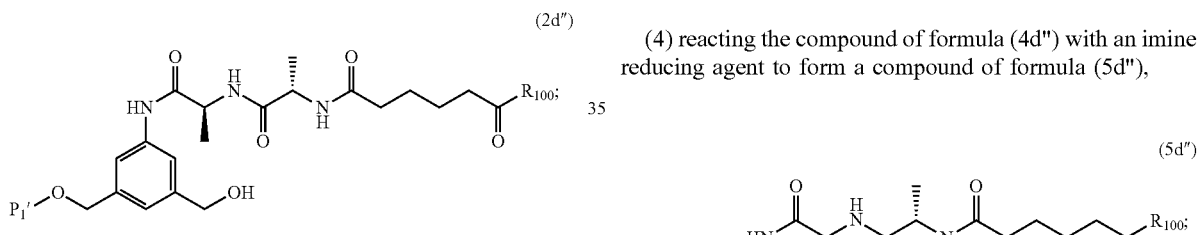

(2) reacting the compound of formula (2d″) with a halogenating reagent, a sulfonating reagent or an esterification reagent to form a compound of formula (3d″),

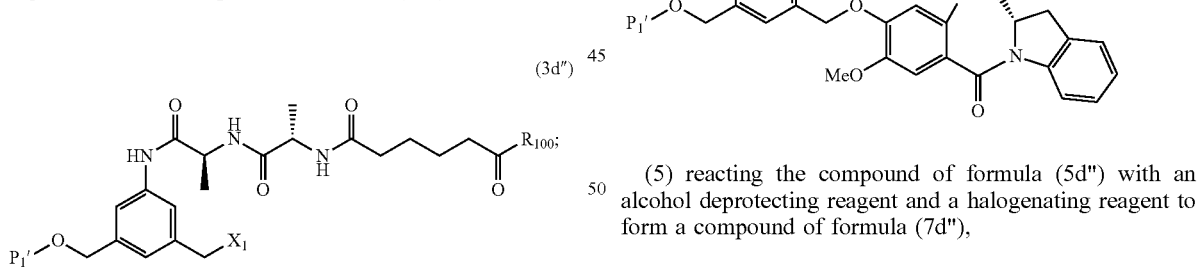

(3) reacting the compound of formula (3d″) with a monomer compound of the formula ($a_1$),

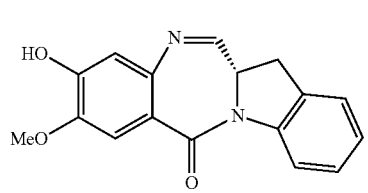

to form a compound of formula (4d″),

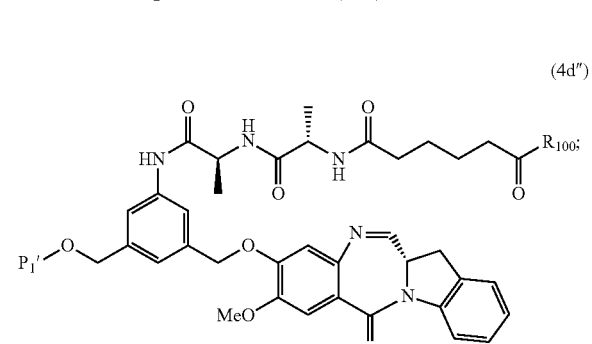

(4) reacting the compound of formula (4d″) with an imine reducing agent to form a compound of formula (5d″),

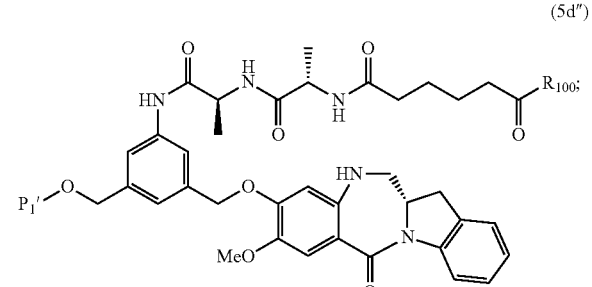

(5) reacting the compound of formula (5d″) with an alcohol deprotecting reagent and a halogenating reagent to form a compound of formula (7d″),

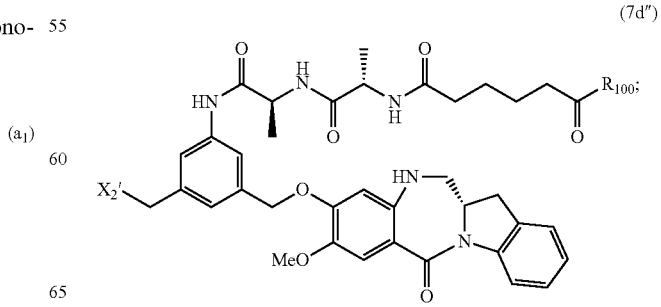

(6) reacting a compound of formula (7d″) with a monomer compound of the formula (a₁),

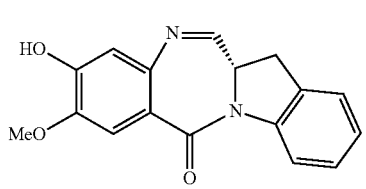

(a₁)

to form the compound of formula (Id′), wherein X₂′ is —Br or —I; and the remaining variables are as described above in the ninth embodiment.

Also provided in the tenth embodiment is a method of preparing a compound of formula (IA):

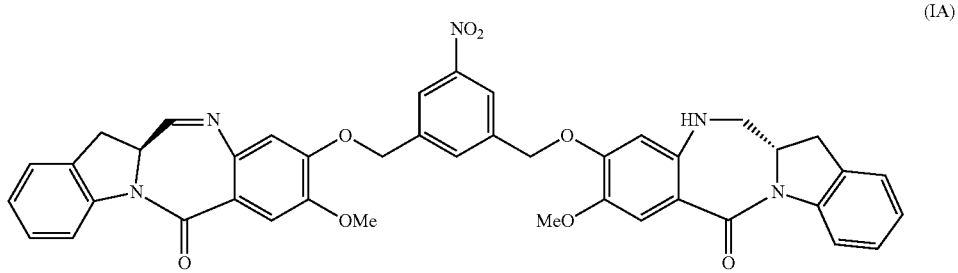 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

(IA)

or a pharmaceutically acceptable salt thereof, said method comprising the steps of:

(1) introducing an alcohol protecting group onto one of the primary alcohols of a compound of formula (1A),

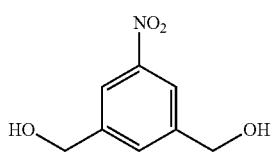

(1A)

to form a compound of formula (2A″),

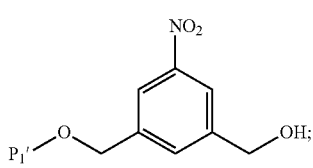

(2A″)

(2) reacting the compound of formula (2A″) with a halogenating reagent, a sulfonating reagent or an esterification reagent to form a compound of formula (3A″),

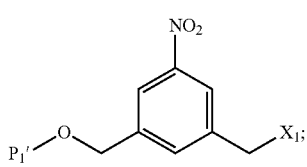

(3A″)

(3) reacting the compound of formula (3A″) with a monomer compound of the formula (a₁),

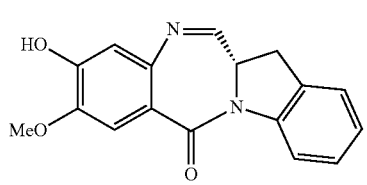

(a₁)

to form a compound of formula (4A″),

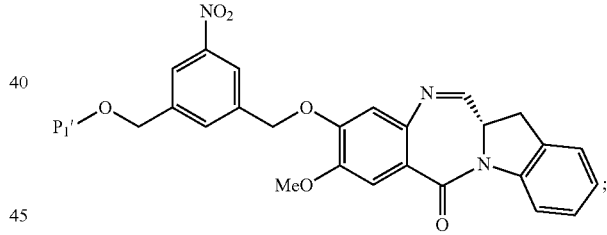

(4A″)

(4) reacting the compound of formula (4A″) with an imine reducing agent to form a compound of formula (5A″),

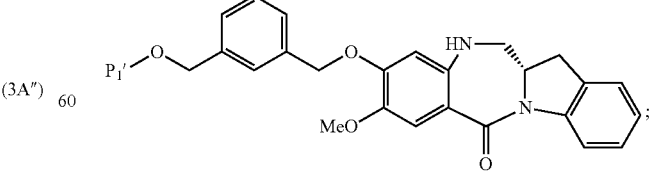

(5A″)

(5) reacting the compound of formula (5A″) with an alcohol deprotecting reagent and a halogenating reagent to form a compound of formula (7A″), (7A″)

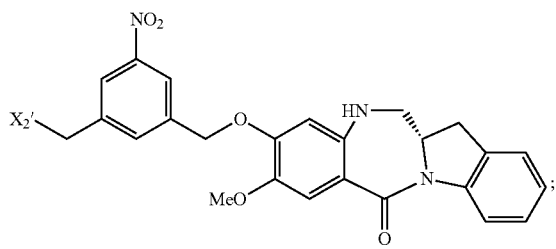

(6) reacting a compound of formula (7A″) with a monomer compound of the formula (a₁), (a₁)

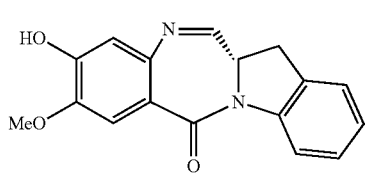

to form the compound of formula (IA), wherein $X_2'$ is —Br or —I; and the remaining variables are as described above in the ninth embodiment.

The conditions and reagents for the methods of tenth embodiment are as described above in the first, second, third, fourth, seventh and/or eighth embodiment(s) and any specific embodiments described therein.

In a eleventh embodiment, the present invention provides a method of preparing a compound of formula (9d), (9d)

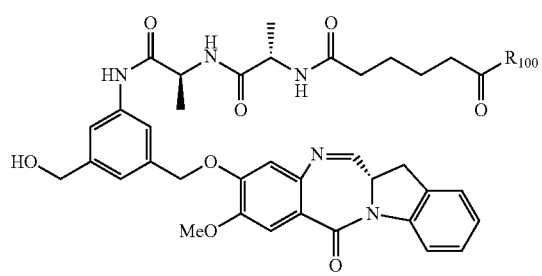

or a salt thereof, said method comprising reacting a compound of formula (4d), (4d)

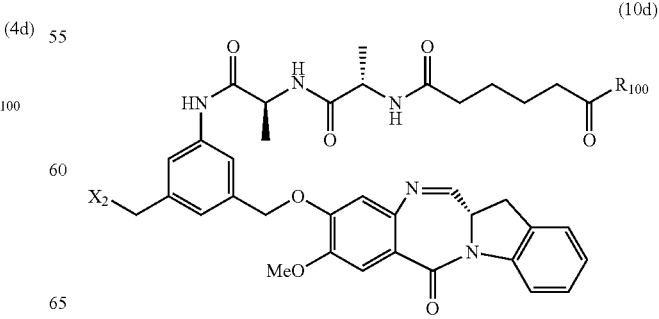

with an alcohol deprotecting reagent, wherein $P_1$ is an alcohol protecting group; and $R_{100}$ is $(C_1-C_3)$alkoxy.

Also provided in the eleventh embodiment is a method of preparing a compound of (9A):

(9A)

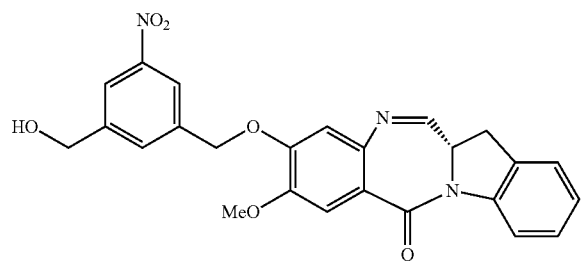

or a salt thereof, said method comprising reacting a compound of formula (4A), (4A)

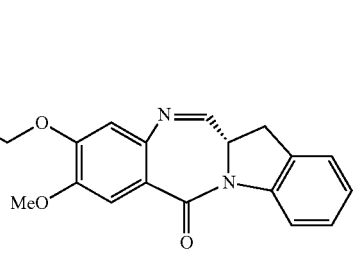

with an alcohol deprotecting reagent, wherein $P_1$ is an alcohol protecting group.

In a specific embodiment, for the methods of the eleventh embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, pyridinium p-toluensulfonate, formic acid, periodic acid, trifluoroacetic acid, or p-toluenesulfonic acid (p-TsOH). More specifically, the alcohol deprotecting reagent is hydrochloric acid or tetra-n-butylammonium fluoride.

In a twelfth embodiment, the present invention provides a method of preparing a compound of formula (10d), (10d)

or a salt thereof, said method comprising reacting the compound of formula (9d) with a halogenating reagent, a sulfonating reagent or an esterification reagent,

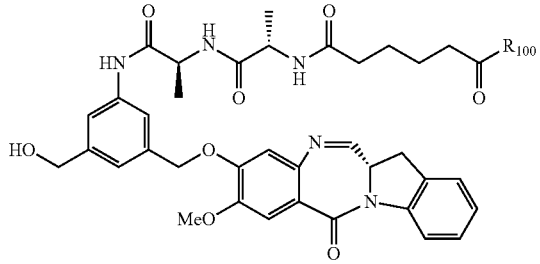

(9d)

wherein $X_2$ is —Br, —I, —Cl, a sulfonate ester or an activated ester; and $R_{100}$ is $(C_1$-$C_3)$alkoxy.

Also provided in the twelfth embodiment is a method of preparing a compound of formula (10A):

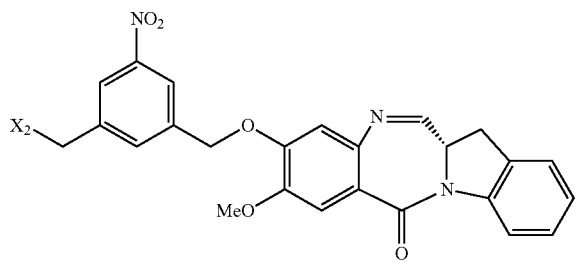

(10A)

or a salt thereof, said method comprising reacting the compound of formula (9A) with a halogenating reagent, a sulfonating reagent or an esterification reagent,

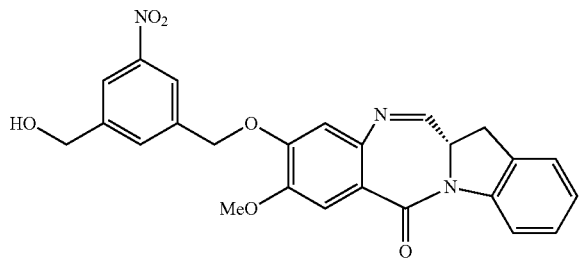

(9A)

wherein $X_2$ is —Br, —I, —Cl, a sulfonate ester or an activated ester.

In a specific embodiment, for the methods of the twelfth embodiment, $X_2$ is —Br, —I or a sulfonate ester.

In a specific embodiment, for the methods of the twelfth embodiment, $X_2$ is mesylate, tosylate, brosylate, or triflate. Preferably, $X_2$ is mesylate.

In another specific embodiment, the method described in the twelfth embodiment comprises reacting the compound of formula (9d) or (9A) with a halogenating reagent. Exemplary halogenating reagent include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In yet another specific embodiment, the method of the twelfth embodiment comprises reacting the compound of formula (9d) or (9A) with a sulfonating reagent. Preferably, the sulfonating reagent is a sulfonic anhydride, such as methanesulfonic anhydride, or a sulfonic chloride, such as methanesulfonyl chloride (MsCl).

In one embodiment, the reaction between the compound of formula (9d) or (9A) and the sulfonating reagent is carried out in the presence of a base. Preferably, the base is a non-nucleophilic base. Exemplary non-nucleophilic base include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine.

In a thirteenth embodiment, the present invention provides a method of preparing a compound of formula (18d),

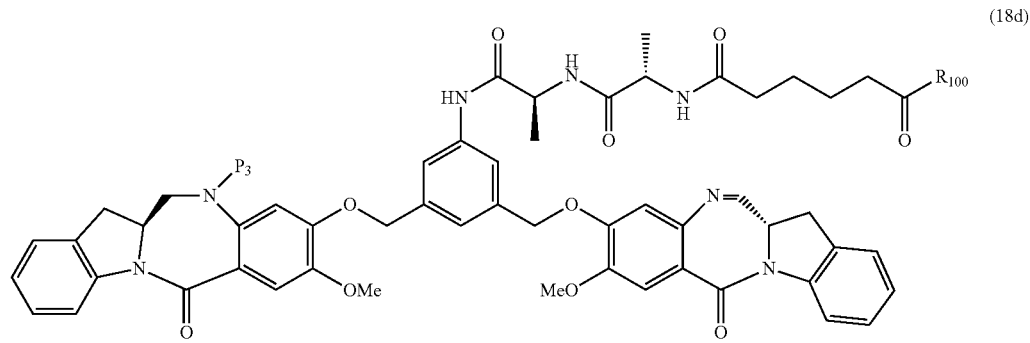

(18d)

or a salt thereof, said method comprising reacting a compound of formula (10d)

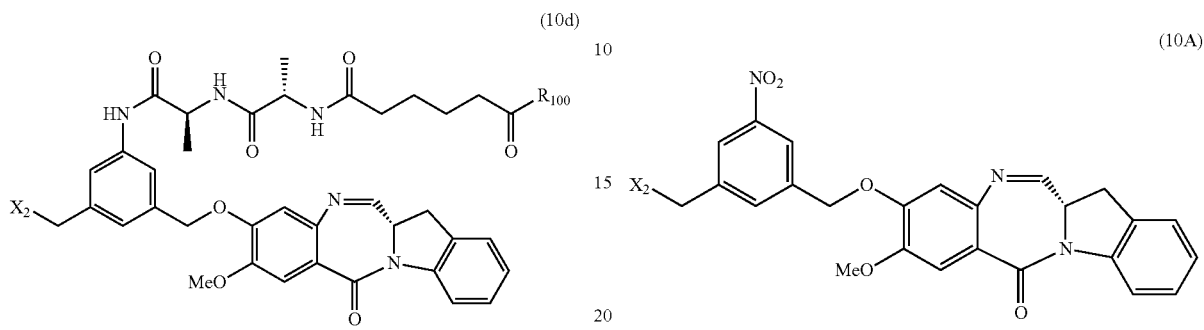

(10d)

with a monomer compound of the formula (d₁), (c₁)

wherein $X_2$ is a leaving group selected from the group consisting of: —Br, —I, —Cl, a sulfonate ester and an activated ester; $P_3$ is H or $P_2$; $P_2$ is an amine protecting group; and $R_{100}$ is ($C_1$-$C_3$)alkoxy. In one embodiment, $X_2$ is —Br, —I, or a sulfonate ester.

Also provided in the thirteenth embodiment is a method of preparing a compound of formula (18A):

or a salt thereof, said method comprising reacting a compound of formula (10A)

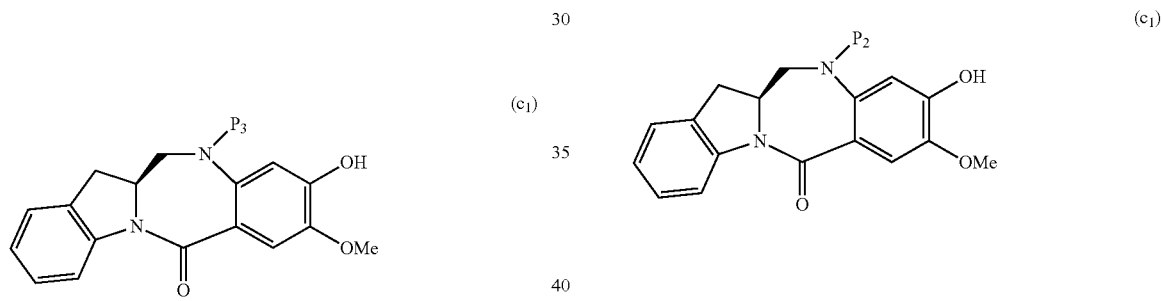

(10A)

with a monomer compound of the formula (d₁), (c₁)

herein $X_2$ is a leaving group selected from the group consisting of: —Br, —I, —Cl, a sulfonate ester or an activated ester; and $P_3$ is H or $P_2$; and $P_2$ is an amine protecting group. In one embodiment, $X_2$ is —Br, —I, or a sulfonate ester.

In a specific embodiment, for methods of the thirteenth embodiment, $P_3$ is H and the compound of (10d) or (10A) is reacted with the monomer compound of (d₁) to form a compound of (Id') or (IA), respectively:

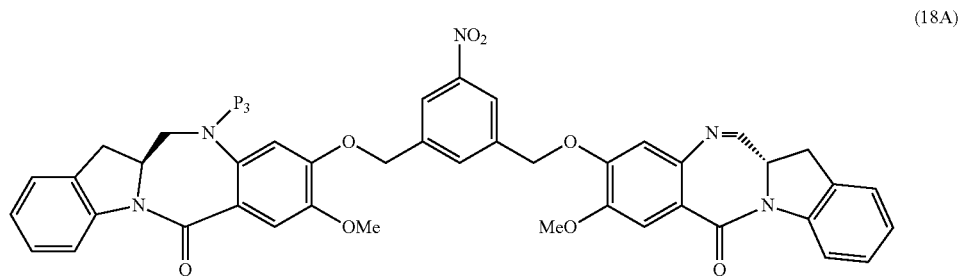

(18A)

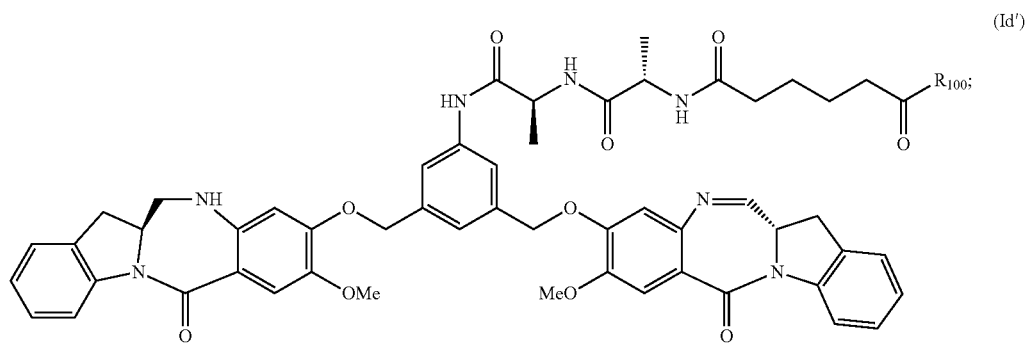
(Id′)
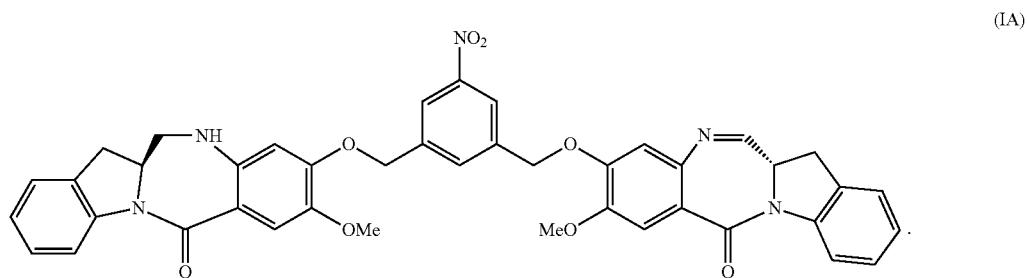
(IA)
In another specific embodiment, $P_3$ is an amine protecting group represented by $P_2$; the monomer compound is represented by formula $(c_1)$:
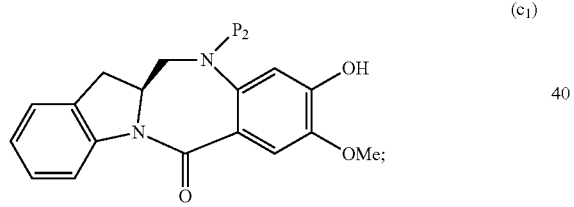
(c₁)
and the compound of formula (18d) or (18A) is represented by formula (11d) or (11A), respectively,
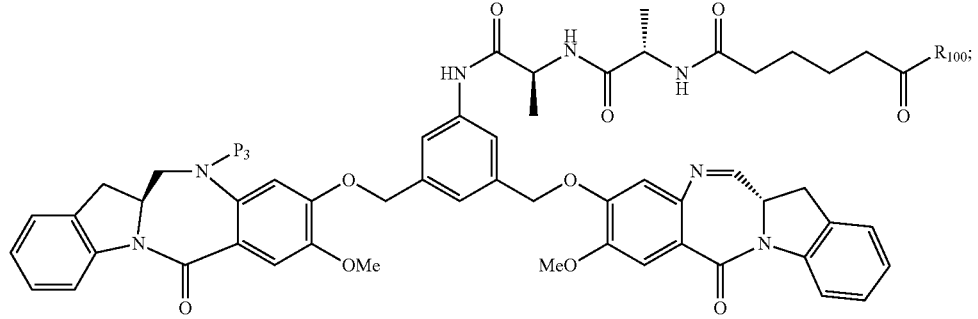
(11d)

(11A)

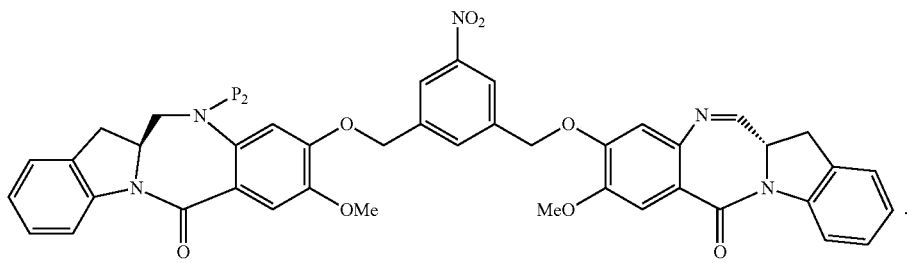

Any suitable amine protecting group can be used in the methods of the thirteenth embodiment described above. In one embodiment, the amine protecting group is 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2, 2,2-trichloroethoxycarbonyl.

In a specific embodiment, the compound of formula (10d) or (10A) is reacted with the monomer compound of formula ($d_1$) or ($c_1$) in the presence of a base. Examples of the base include, but are not limited to sodium carbonate, potassium carbonate, cesium carbonate, sodium hydride, or potassium hydride.

Any suitable solvents can be used in the reaction described above. In one embodiment, the solvent is DMF.

In a fourteenth embodiment, the present invention provides a method of preparing a compound of formula (Id'), (1d')

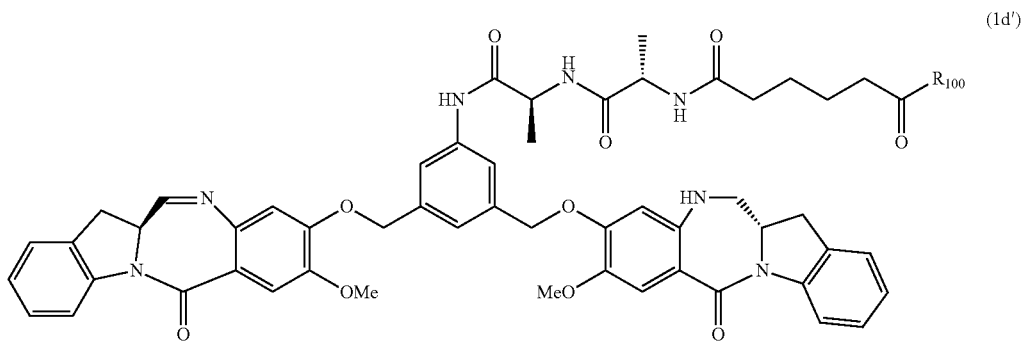

or a pharmaceutically acceptable salt thereof, said method comprising reacting a compound of formula (11d), (11d)

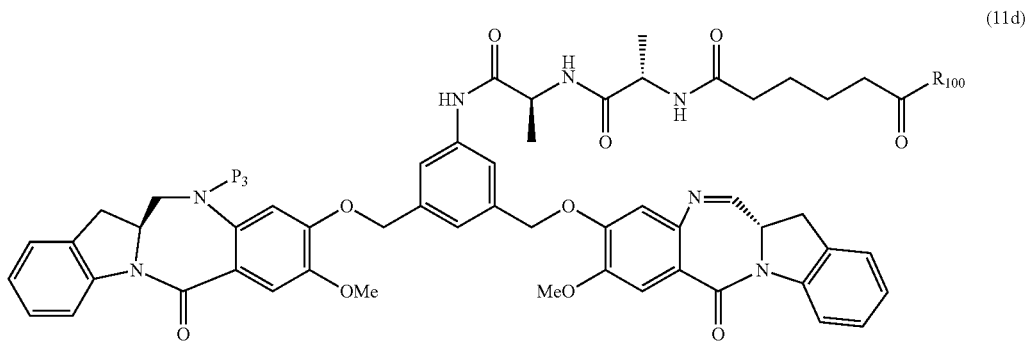

with an amine deprotecting reagent, wherein $P_2$ is an amine protecting group; and $R_{100}$ is $(C_1-C_3)$alkoxy.

Also provided in the fourteenth embodiment is a method of preparing a compound of formula (IA):

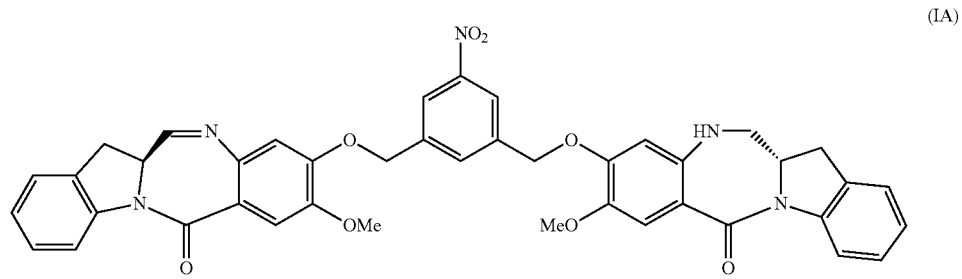 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

(IA)

or a pharmaceutically acceptable salt thereof, said method comprising reacting a compound of formula (11d),

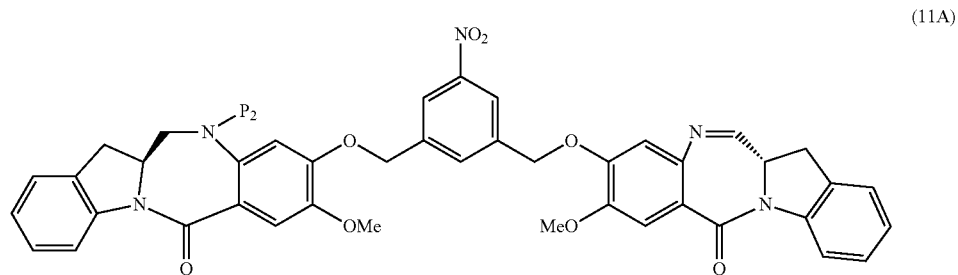

(11A)

with an amine deprotecting reagent, wherein $P_2$ is an amine protecting group.

Any suitable amine deprotecting reagent can be used in the method described above. In one embodiment, the amine deprotecting reagent is tetra-n-butylammonium fluoride, acetic acid, hydrogen fluoride pyridine, cesium fluoride, piperidine, morpholine, or trifluroacetic acid.

In a fifteenth embodiment, the present invention provides a method of preparing a compound of formula (Id'),

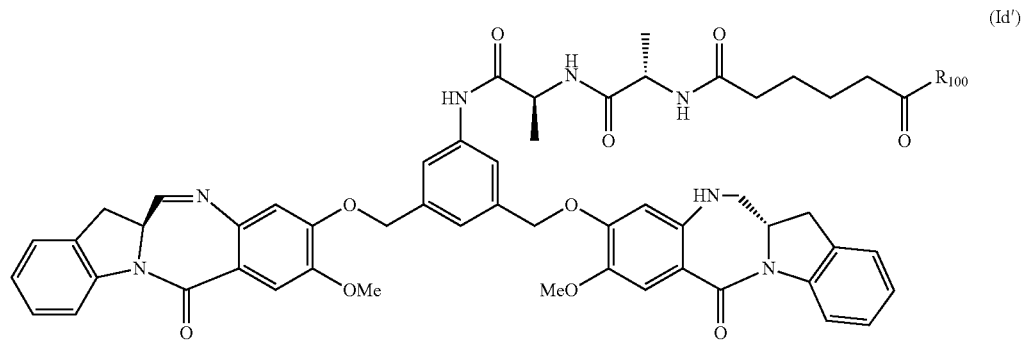

(Id')

or a pharmaceutically acceptable salt thereof, said method comprising the steps of:

(1) introducing an alcohol protecting group onto one of the primary alcohols of the compound of formula (1d), (1d)

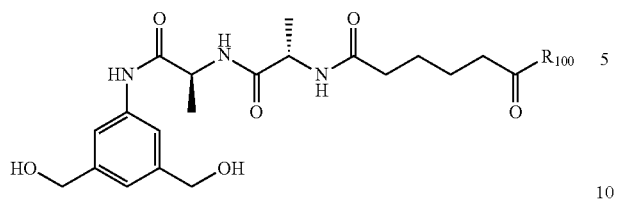

to form a compound of formula (2d), (2d)

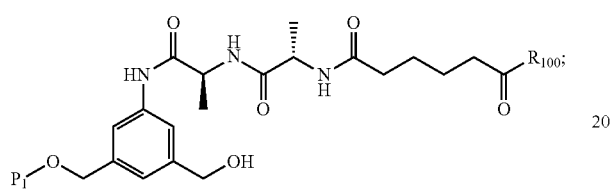

(2) reacting the compound of formula (2d) with a halogenating reagent, a sulfonating reagent or an esterification reagent to form a compound of formula (3d), (3d)

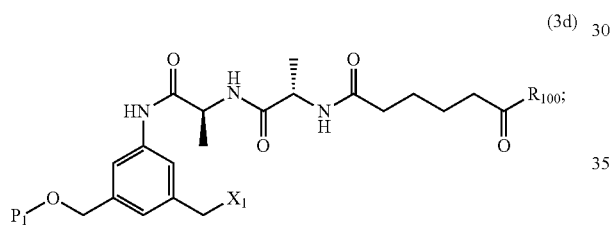

(3) reacting the compound of formula (3d) with a monomer compound of the formula (a₁), (a₁)

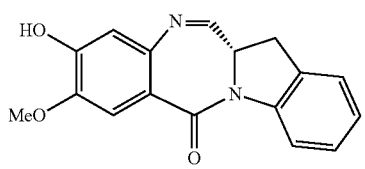

to form a compound of formula (4d), (4d)

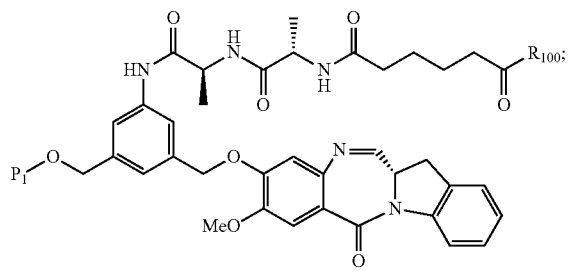

(4) reacting the compound of formula (4d) with an alcohol deprotecting reagent to form a compound of formula (9d), (9d)

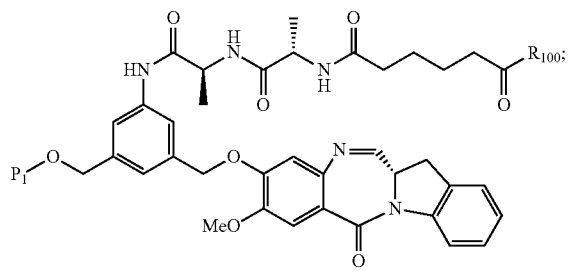

(5) reacting the compound of formula (9d) with a second halogenating reagent, a second sulfonating reagent or a second esterification reagent to form a compound of formula (10d), (10d)

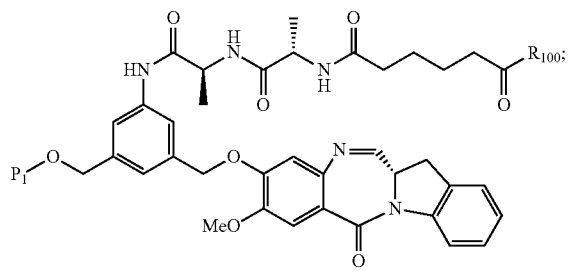

(6) reacting the compound of formula (10d) with a monomer compound of the formula (d₁)

(d₁)

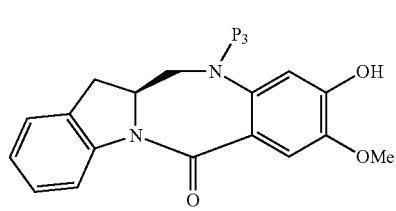

to form a compound of formula (18d),

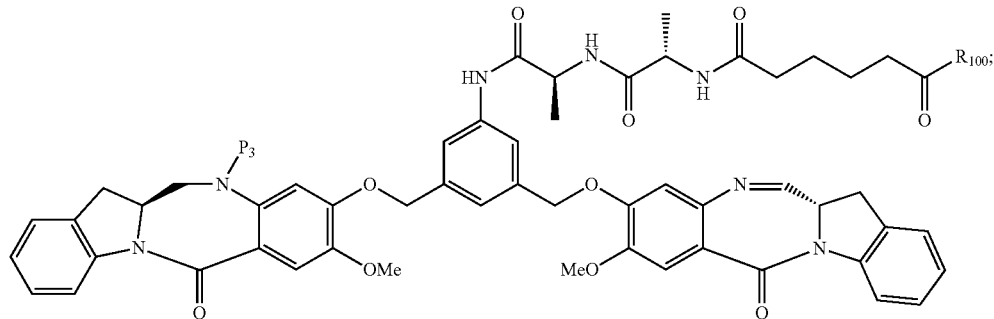

and (7) when $P_3$ is an amine protecting group, reacting the compound of formula (18d) to an amine deprotecting reagent to form the compound of formula (Id'), wherein $P_1$ is an alcohol protecting group; $X_1$ and $X_2$ are each independently a leaving group selected from the group consisting of: —Br, —I, —Cl, a sulfonate ester and an activated ester; $P_3$ is H or an amine protecting group; and $R_{100}$ is $(C_1$-$C_3)$ alkoxy.

Also included in the fifteenth embodiment is a method of preparing a compound of formula (IA):

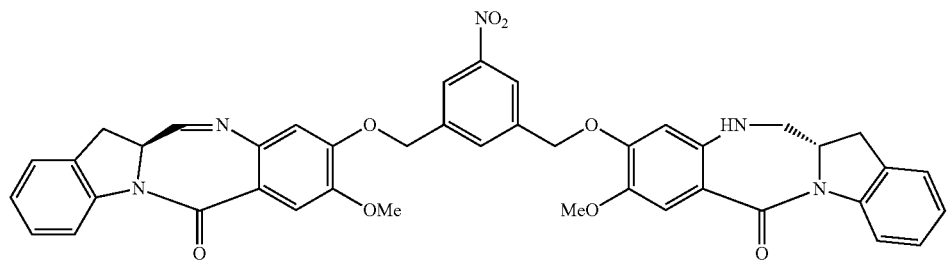

or a pharmaceutically acceptable salt thereof, said method comprising the steps of:

(1) introducing an alcohol protecting group onto one of the primary alcohols of the compound of formula (1A),

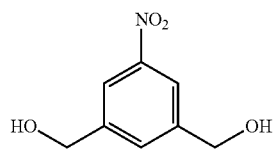

to form a compound of formula (2A),

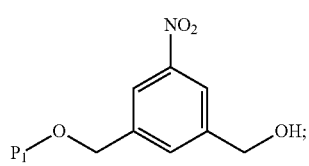

(2) reacting the compound of formula (2A) with a halogenating reagent, a sulfonating reagent or an esterification reagent to form a compound of formula (3A),

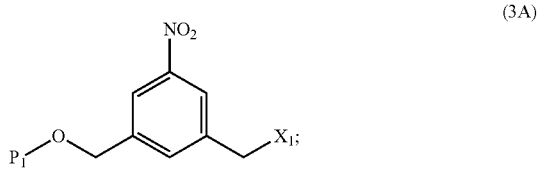

(3) reacting the compound of formula (3A) with a monomer compound of the formula ($a_1$),

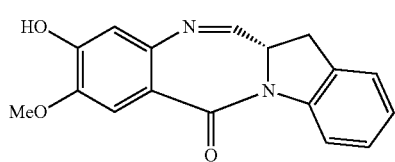

to form a compound of formula (4A),

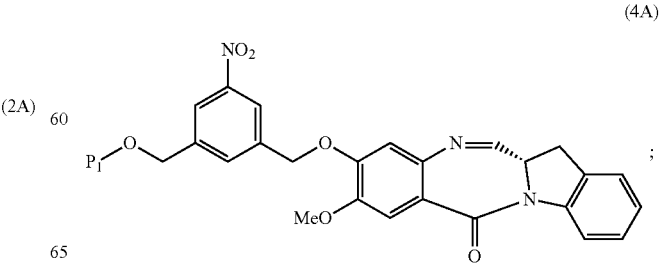

(4) reacting the compound of formula (4A) with an alcohol deprotecting reagent to form a compound of formula (9A).

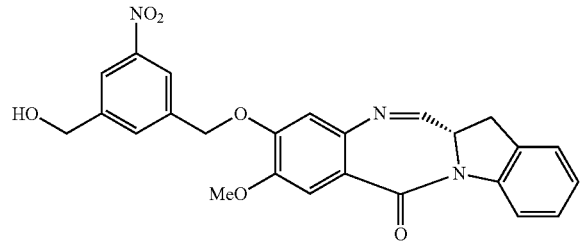
(9A)

(5) reacting the compound of formula (9A) with a second halogenating reagent, a second sulfonating reagent or a second esterification reagent to form a compound of formula (10A),

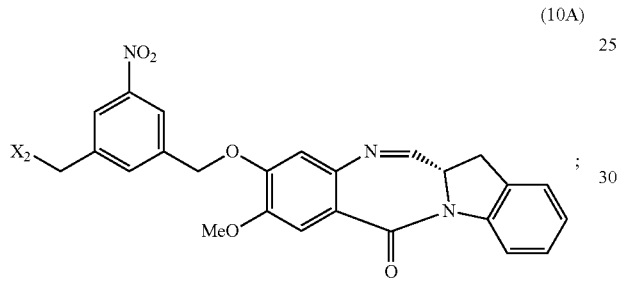
(10A)

(6) reacting the compound of formula (10A) with a monomer compound of the formula ($d_1$)

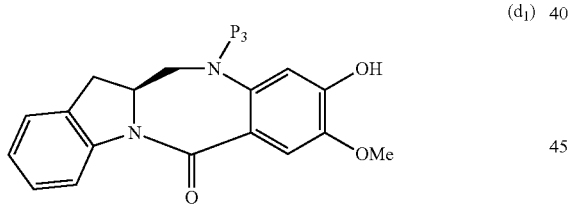
($d_1$)

to form a compound of formula (18A), and (7) reacting the compound of formula (18A) to an amine deprotecting reagent to form the compound of formula (IA), wherein $P_1$ is an alcohol protecting group; $X_1$ and $X_2$ are each independently a leaving group selected from the group consisting of: —Br, —I, —Cl, a sulfonate ester and an activated ester; and $P_3$ is H or an amine protecting group.

In a specific embodiment, for methods of the fifteenth embodiment, $X_1$ and $X_2$ are each independently —Br, —I or a sulfonate ester.

In a specific embodiment, for methods of the fifteenth embodiment, $P_3$ is H and the compound of (10d) or (10A) is reacted with the monomer compound of ($d_1$) to form a compound of (Id') or (IA), respectively.

In another specific embodiment, for methods of the fifteenth embodiment, $P_3$ is $P_2$; the monomer compound is represented by formula ($c_1$):

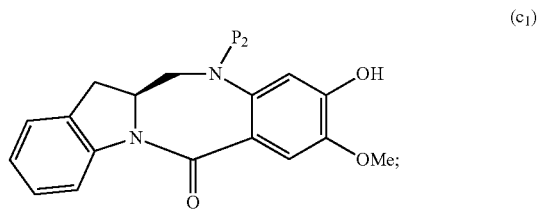
($c_1$)

and the compound of formula (18d) or (18A) is represented by formula (11d) or (11A), respectively:

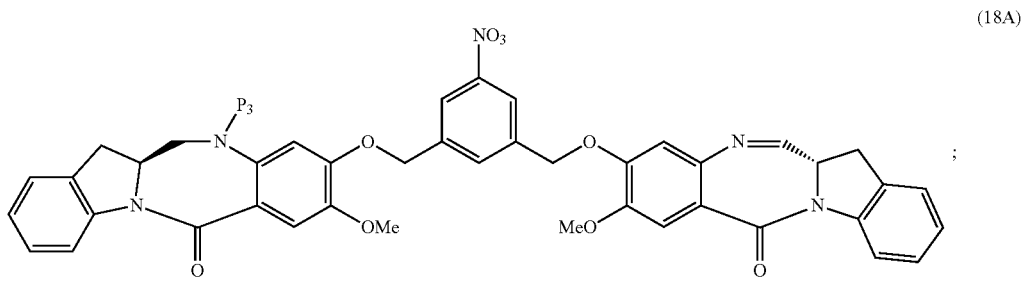
(18A)

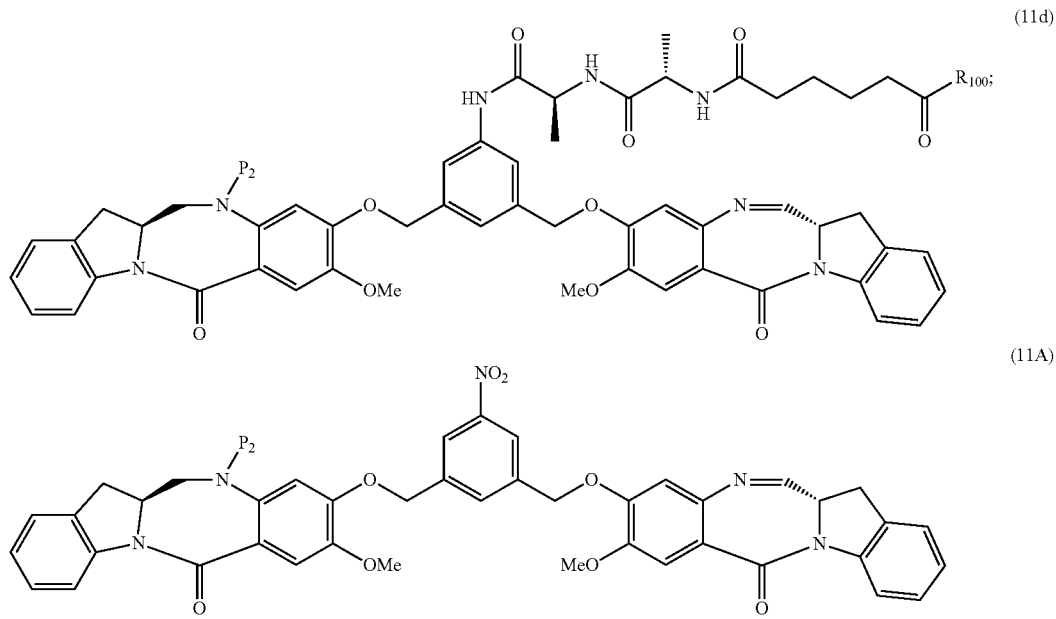

wherein P₂ is an amine protecting group.

The conditions and reagents for the methods of the fifteenth embodiment are as described above in the first, second, third, eleventh, twelfth, thirteenth, and/or fourteenth, embodiment(s) and any specific embodiments described therein.

In a sixteenth embodiment, the present invention provides a method of preparing a compound of formula (12d),

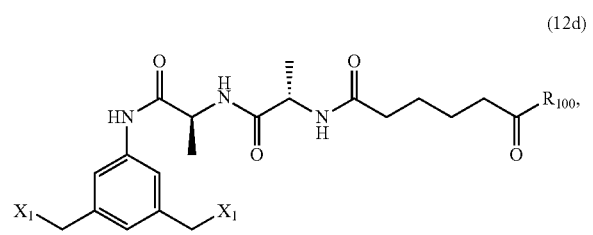

or a salt thereof, said method comprising reacting a compound of formula (1d),

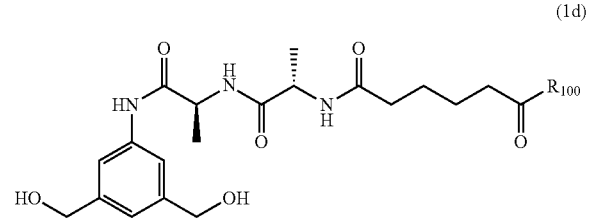

with a halogenating reagent or a sulfonating reagent, wherein $X_1$ is —Br, —I, —Cl, a sulfonate ester or an activated ester; and $R_{100}$ is $(C_1$-$C_3)$alkoxy.

Also provided in the sixteenth embodiment is a method of preparing a compound of formula (12A):

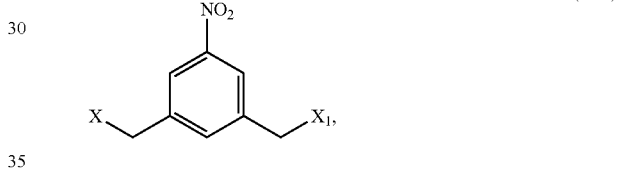

or a salt thereof, said method comprising reacting a compound of formula (1A),

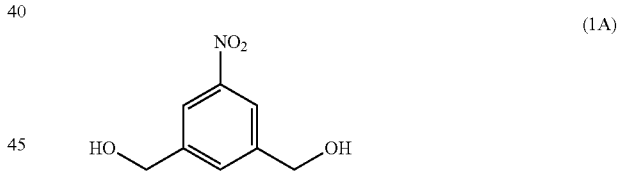

with a halogenating reagent or a sulfonating reagent, wherein $X_1$ is —Br, —I, —Cl, a sulfonate ester or an activated ester.

In a specific embodiment, for the methods of the sixteenth embodiment, $X_1$ is —Br, —I, or a sulfonate ester. In another specific embodiment, $X_1$ is —Br or —I. In yet another specific embodiment, $X_1$ is a sulfonate ester, preferably mesylate. In another specific embodiment, $X_1$ is —Cl.

In another specific embodiment, the halogenating reagent reacts with the primary alcohols of the compound of formula (1d) or (1A) in the presence of an alcohol activating agent. In one embodiment, the alcohol activating agent is thionyl chloride. In another specific embodiment, halogenating reagent is lithium bromide, sodium bromide, potassium bromide, potassium iodide, or sodium iodide. In another specific embodiment, the halogenating reagent is carbon tetrachloride/triphenylphosphine, methanesulfonyl (mesyl) chloride/lithium chloride, or methanesulfonyl (mesyl) chloride/pyridine.

In yet another specific embodiment, the methods of the sixteenth embodiment comprise reacting the compound of formula (1d) or (1A) with LiBr in the presence of thionyl chloride.

Any suitable solvents can be used in the methods of the sixteenth embodiment described above. Exemplary solvents include, but are not limited to, DMF, CH$_2$Cl$_2$, THF, dichloroethane, etc.

In a seventeenth embodiment, the present invention provides a method of preparing a compound of formula (10d'),

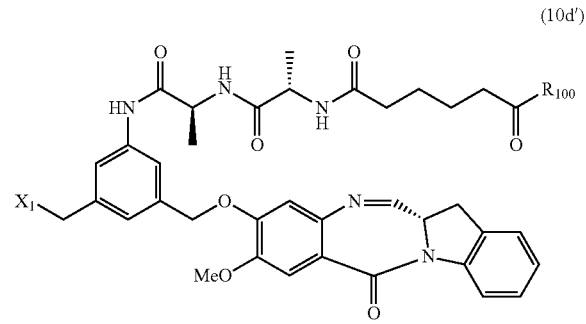

(10d')

or a salt thereof, said method comprising reacting a compound of formula (12d),

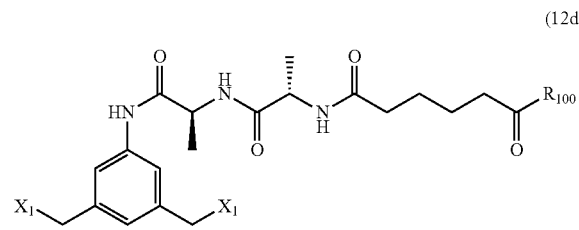

(12d)

with a monomer compound of the formula (a$_1$),

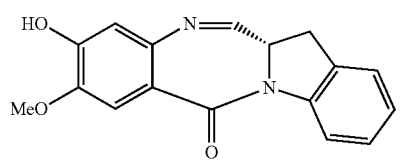

(a$_1$)

wherein X$_1$ is —Br, —I, —Cl, a sulfonate ester or an activated ester; and R$_{100}$ is (C$_1$-C$_3$)alkoxy.

Also provided in the seventeenth embodiment is a method of preparing a compound of formula (10A')

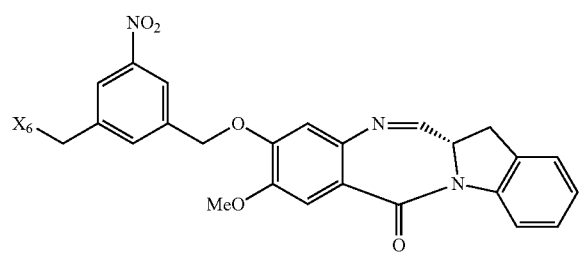

(10A')

or a salt thereof, said method comprising reacting a compound of formula (12A),

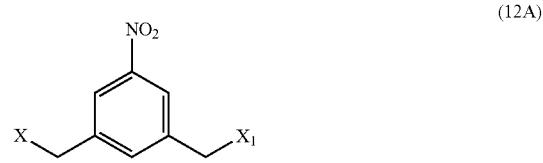

(12A)

with a monomer compound of the formula (a$_1$),

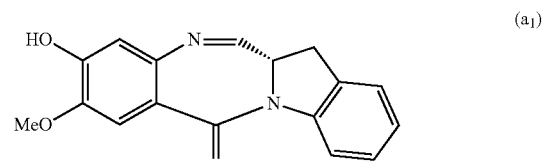

(a$_1$)

wherein X$_1$ is —Br, —I, —Cl, a sulfonate ester or an activated ester.

Also provided in the seventeenth embodiment is a method of preparing a compound of formula (7d1'),

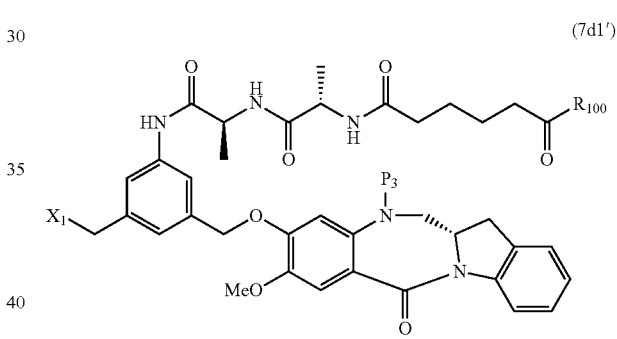

(7d1')

or a salt thereof, said method comprising reacting a compound of formula (12d) with a monomer compound of formula (d$_1$), wherein X$_1$ is —Br, —I, —Cl, a sulfonate ester or an activated ester; P$_3$ is H or an amine protecting group; and R$_{100}$ is a (C$_1$-C$_3$)alkoxy.

Also provided in the seventeenth embodiment is a method of preparing a compound of formula (7A1'),

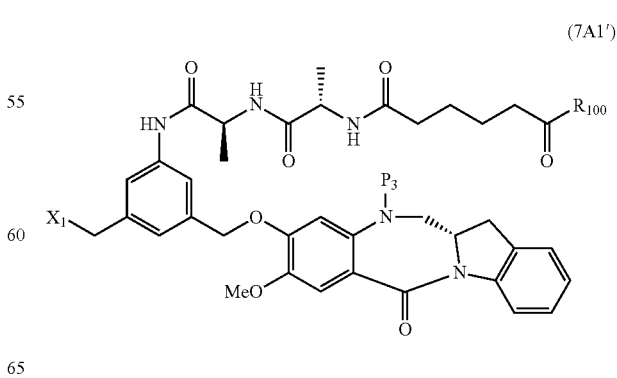

(7A1')

or a salt thereof, said method comprising reacting a compound of formula (12A) with a monomer compound of formula (d₁), wherein X₁ is —Br, —I, —Cl, a sulfonate ester or an activated ester; and P₃ is H or an amine protecting group.

In a specific embodiment, for formula (7d1') or (7A1'), P₃ is H. In another specific embodiment, P₃ is an amine protecting group as described herein.

In a specific embodiment, for methods of the seventeenth embodiment, X₁ is —Br, —I, or a sulfonate ester. In another specific embodiment, X₁ is a sulfonate ester. In a more specific embodiment, X₁ is mesylate.

In a specific embodiment, the compound of formula (12d) or (12A) is reacted with the monomer compound of formula (a₁) in the presence of a base. Examples of suitable base include, but are not limited to, sodium carbonate, potassium carbonate, cesium carbonate, sodium hydride, or potassium hydride. In one embodiment, the base is potassium carbonate.

In another specific embodiment, the compound of formula (12d) or (12A) is reacted with the monomer compound of formula (d₁) in the presence of a base. Examples of suitable base include, but are not limited to, sodium carbonate, potassium carbonate, cesium carbonate, sodium hydride, or potassium hydride. In one embodiment, the base is potassium carbonate.

For the methods of the seventeenth embodiment, any suitable solvents can be used. In one embodiment, the solvent is DMF.

In another specific embodiment, excess molar equivalent of the compound of formula (12d) or (12A) relative to the monomer compound of formula (a₁) or (d₁) is used in the reaction.

In a eighteenth embodiment, the present invention provides a method of preparing a compound of formula (7d'),

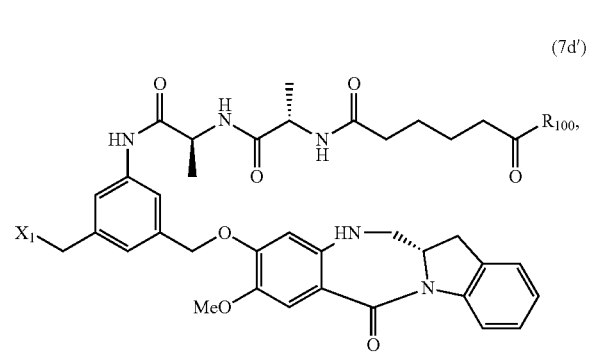

(7d')

or a salt thereof, said method comprising reacting a compound of formula (10d'),

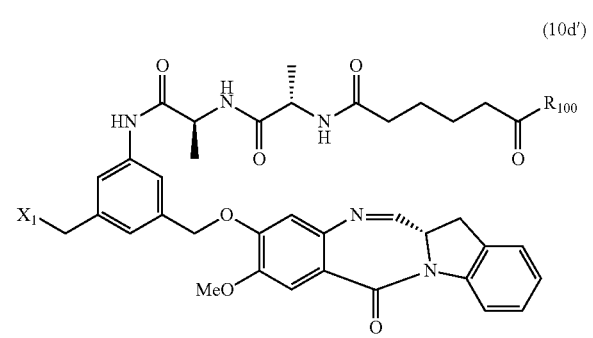

(10d')

or a salt thereof, with an imine reducing agent, wherein X₁ is —Br, —I, —Cl, a sulfonate ester or an activated ester; and R₁₀₀ is (C₁-C₃)alkoxy.

Also provided in the eighteenth embodiment is a method of preparing a compound of formula (7A'),

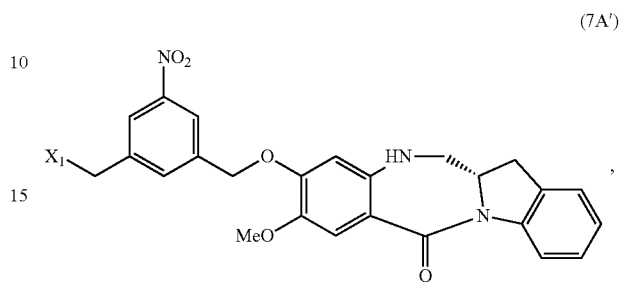

(7A')

or a salt thereof, said method comprising reacting a compound of formula (10A'),

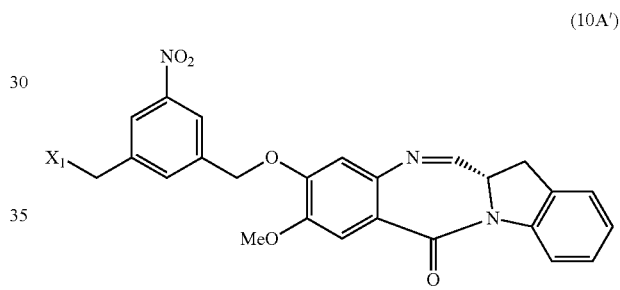

(10A')

or a salt thereof, with an imine reducing agent, wherein X₁ is —Br, —I, —Cl, a sulfonate ester or an activated ester.

In a specific embodiment, for methods of the eighteenth embodiment, X₁ is —Br, —I, or a sulfonate ester. In another specific embodiment, X₁ is a sulfonate ester. Preferably, X₁ is mesylate.

In another specific embodiment, for methods of the eighteenth embodiment, the imine reducing reagent is a hydride reducing reagent. In a more specific embodiment, the imine reducing reagent is sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH₄), potassium borohydride (KBH₄), or sodium bis(2-methoxyethoxy)aluminumhydride (Red-Al). Even more specifically, the imine reducing reagent is sodium triacetoxy borohydride (NaBH(OAc)3).

Any suitable solvents can be used in the methods of the eighteenth embodiment. In one embodiment, the solvent is dichloroethane.

In a nineteenth embodiment, the present invention provides a method of preparing a compound of formula (Id'),

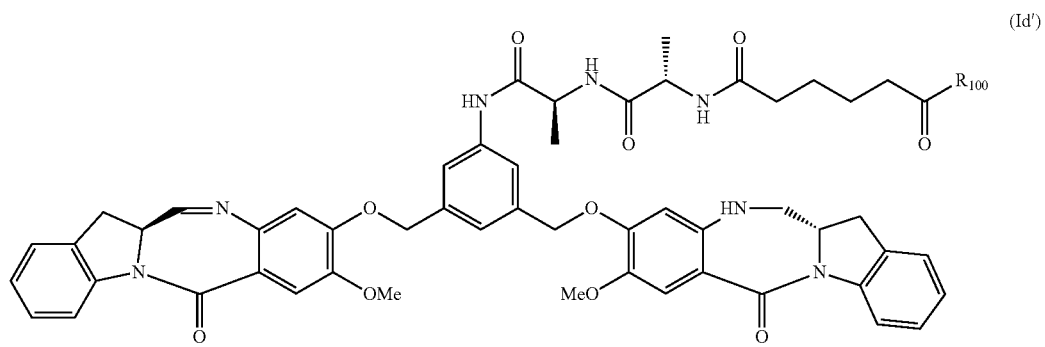

(Id')

or a pharmaceutically acceptable salt thereof, said method comprising the steps of:

(1) reacting a compound of formula (1d) with a halogenating reagent, a sulfonating reagent or an esterification reagent, to form a compound of formula (12d),

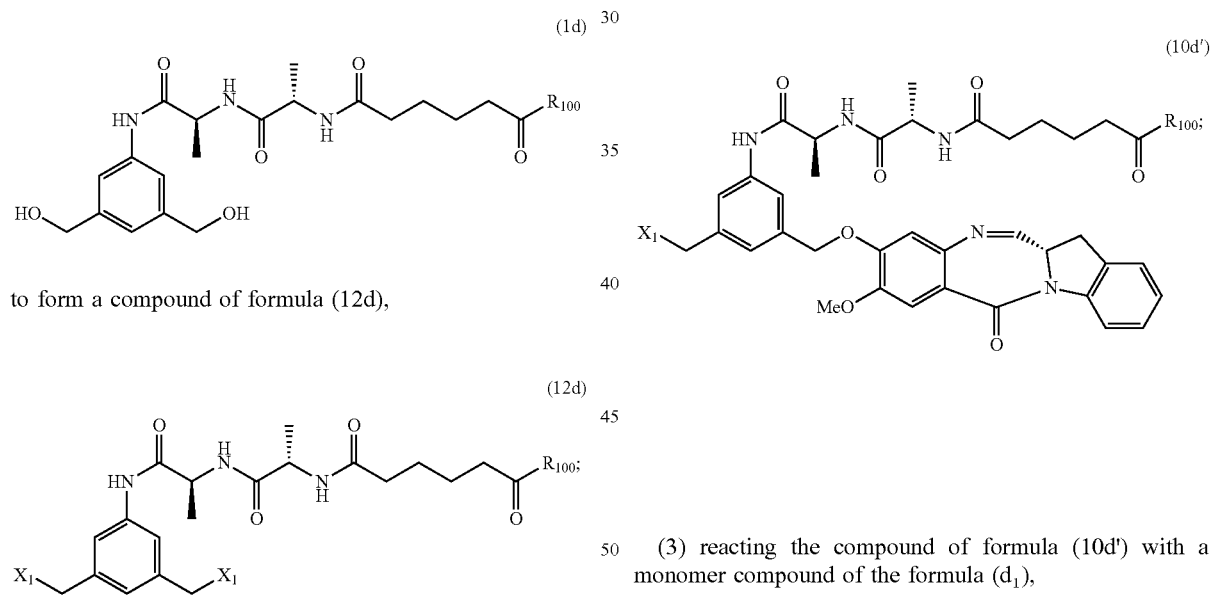

(2) reacting the compound of formula (12d) with a monomer compound of the formula ($a_1$), to form a compound of a formula (10d'), (3) reacting the compound of formula (10d') with a monomer compound of the formula ($d_1$),

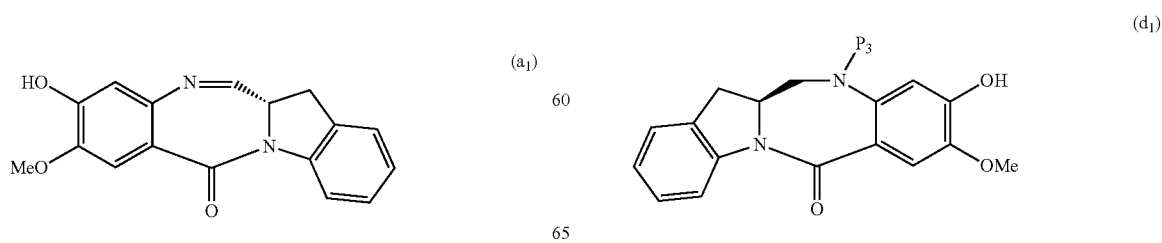

to form a compound of formula (18d),

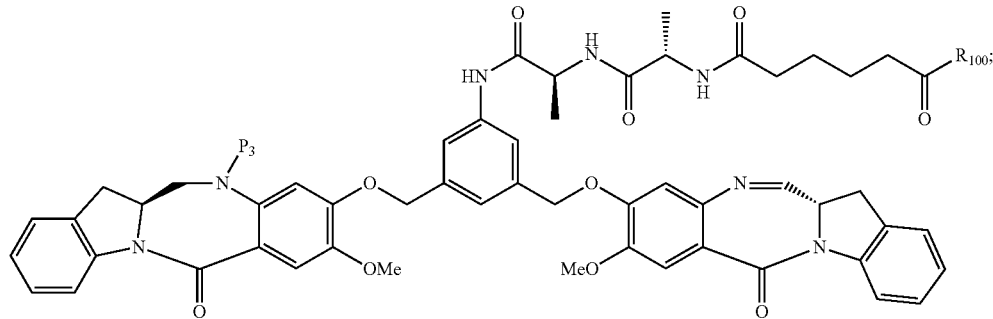
(18d)

and (4) when $P_3$ is an amine protecting group, reacting the compound of formula (18d) with an amine deprotecting reagent to form the compound of formula (Id'), wherein $X_1$ is —Br, —I, —Cl, a sulfonate ester or an activated ester; $P_3$ is H or an amine protecting group; and $R_{100}$ is ($C_1$-$C_3$) alkoxy.

Also provided in the nineteenth embodiment is a method of preparing a compound of formula (IA),

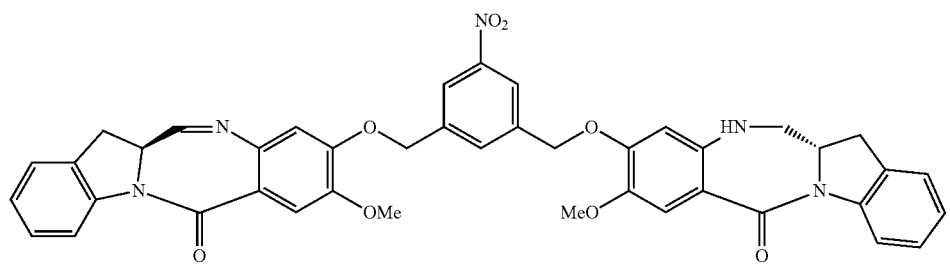
(IA)

or a pharmaceutically acceptable salt thereof, said method comprising the steps of:

(1) reacting a compound of formula (1A) with a halogenating reagent, a sulfonating reagent or an esterification reagent,

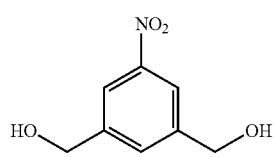
(1A)

to form a compound of formula (12A),

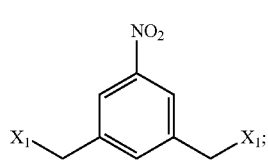
(12A)

(2) reacting the compound of formula (12A) with a monomer compound of the formula ($a_1$),

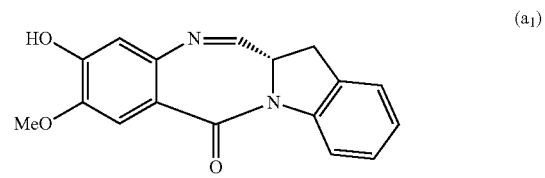 [SMILES: COc1cc2c(cc1O)N=C[C@@H]1Cc3ccccc3N1C2=O]
($a_1$)

to form a compound of a formula (10A'),

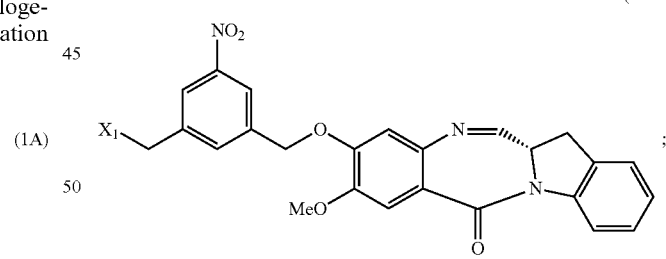
(10A')

(3) reacting the compound of formula (10A') with a monomer compound of the formula ($d_1$),

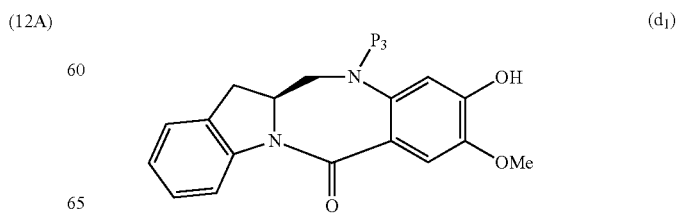
($d_1$)

to form a compound of formula (18A),

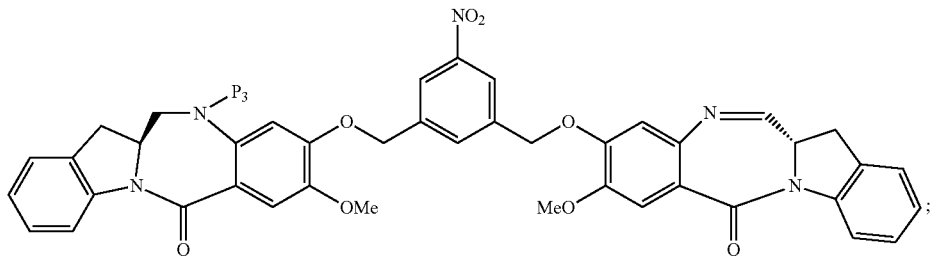

and (4) reacting the compound of formula (11A) with an amine deprotecting reagent to form the compound of formula (IA), wherein $X_1$ is —Br, —I, —Cl, a sulfonate ester or an activated ester; $P_3$ is H or an amine protecting group.

In a specific embodiment, for methods of the nineteenth embodiment, $X_1$ is —Br, —I, or a sulfonate ester.

In a specific embodiment, for methods of the nineteenth embodiment, $P_3$ is H and the compound of (10d') or (10A) is reacted with the monomer compound of ($d_1$) to form a compound of (Id') or (IA), respectively.

In another specific embodiment, for methods of the nineteenth embodiment, $P_3$ is $P_2$; the monomer compound is represented by formula ($c_1$):

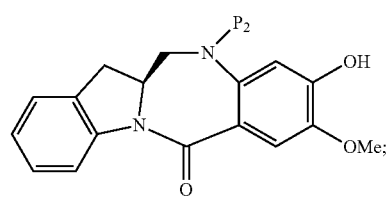

and the compound of formula (18d) or (18A) is represented by formula (11d) or (11A), respectively:

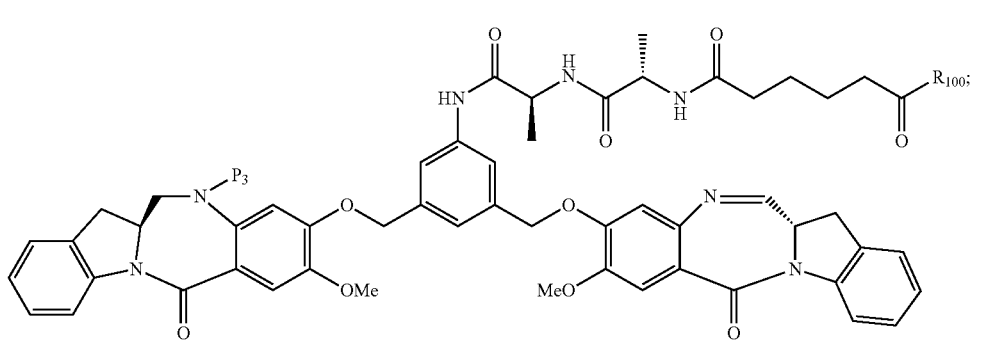

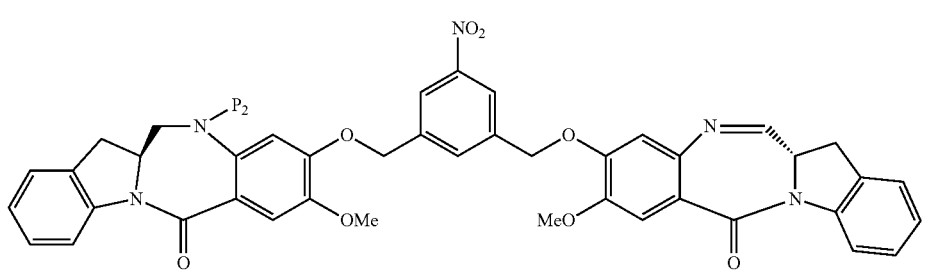

wherein $P_2$ is an amine protecting group.

The conditions and reagents for the method of nineteenth embodiment are as described above in the sixteenth, seventeenth, thirteenth and/or fourteenth embodiment(s) and any specific embodiments described therein.

In a twentieth embodiment, the present invention provides a method of preparing a compound a compound of formula (Id'),

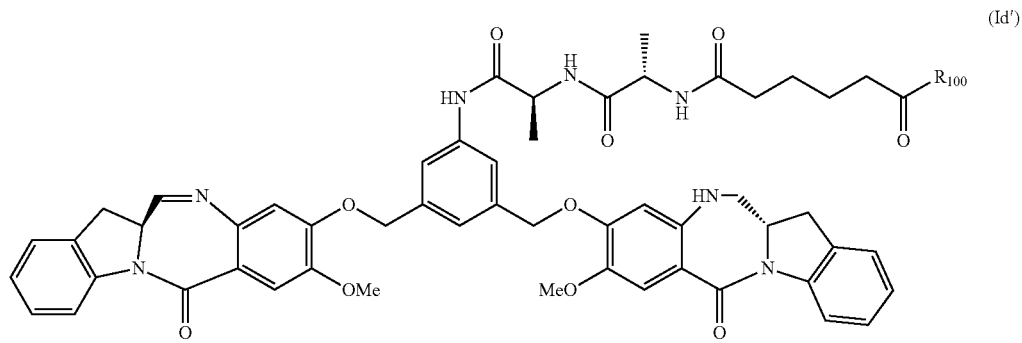
(Id')

or a pharmaceutically acceptable salt thereof, said method comprising the steps of:

(1) reacting a halogenating reagent, a sulfonating reagent or an esterification reagent with a compound of formula (1d), (1d)

to form a compound of formula (12d),

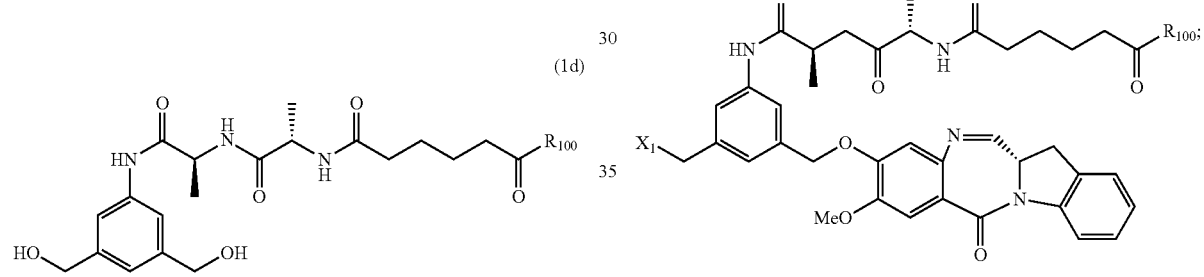
(12d)

(2) reacting the compound of formula (12d) with a monomer compound of the formula ($a_1$), ($a_1$)

to form a compound of a formula (10d'), (10d')

(3) reacting the compound (10d') with an imine reducing reagent to form a compound (7d'),

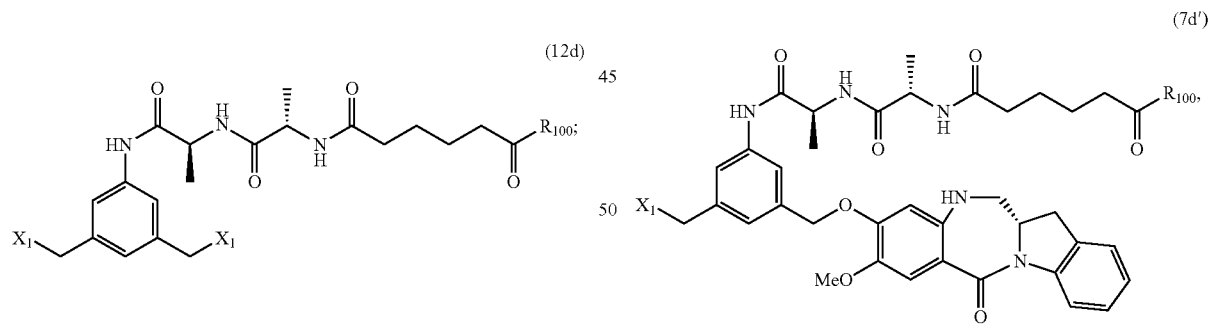
(7d')

(4) reacting the compound of formula (7d') with a monomer compound of the formula ($a_1$),

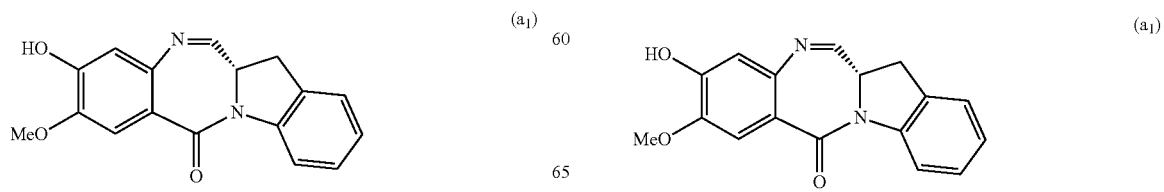
($a_1$)

to form a compound of formula (Id'), or a pharmaceutically acceptable salt thereof, wherein $X_1$ is —Br, —I, —Cl, a sulfonate ester or an activated ester; and $R_{100}$ is ($C_1$-$C_3$) alkoxy.

Also provided in the twentieth embodiment is a method of preparing a compound of (IA),

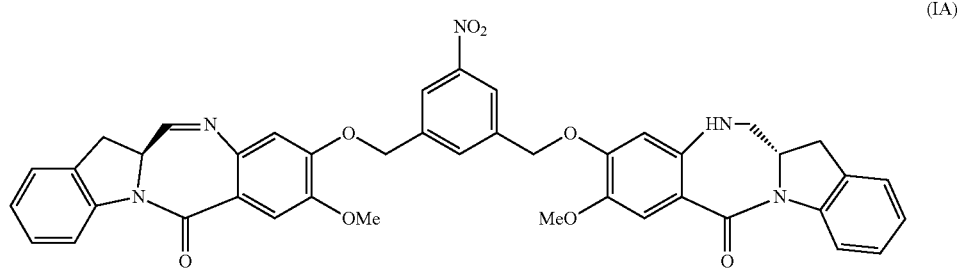 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

(IA)

or a pharmaceutically acceptable salt thereof, said method comprising the steps of:

(1) reacting a halogenating reagent, a sulfonating reagent or a second esterification reagent with a compound of formula (1A),

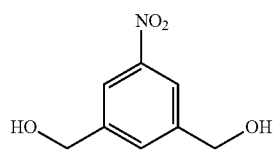

(1A)

to form a compound of formula (12A),

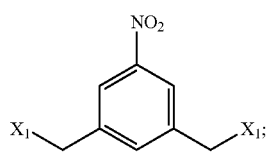

(12A)

(2) reacting the compound of formula (12A) with a monomer compound of the formula ($a_1$),

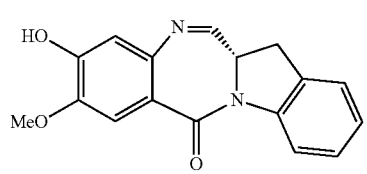

($a_1$)

to form a compound of a formula (10A'),

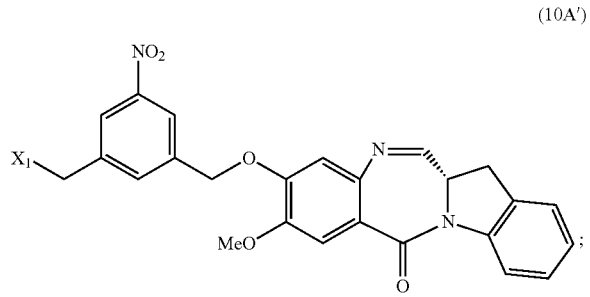

(10A')

(3) reacting the compound (10A') with an imine reducing reagent to form a compound (7A'),

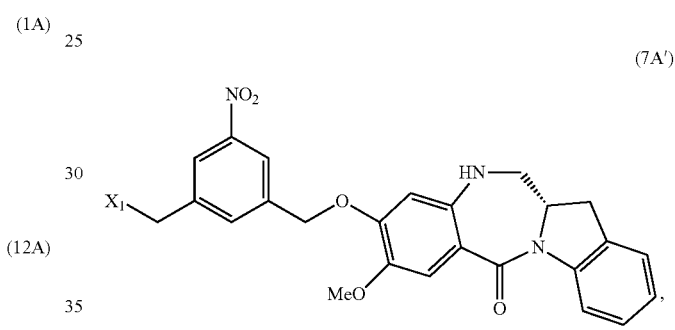

(7A')

(4) reacting the compound of formula (7A') with a monomer compound of the formula ($a_1$),

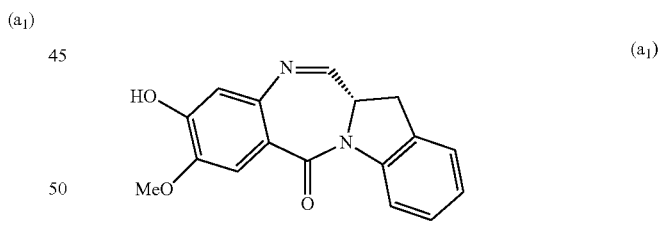

($a_1$)

to form a compound of formula (IA'), or a pharmaceutically acceptable salt thereof, wherein $X_1$ is —Br, —I, —Cl, a sulfonate ester or an activated ester.

In a specific embodiment, for methods of the twentieth embodiment, $X_1$ is —Br, —I, or a sulfonate ester.

The conditions and reagents for the method of twentieth embodiment are as described above in the sixteenth, seventeenth, eighteenth and/or eighth embodiment(s) and any specific embodiments described therein.

In a twenty-first embodiment, the present invention provides a method of preparing a compound of formula (Id'),

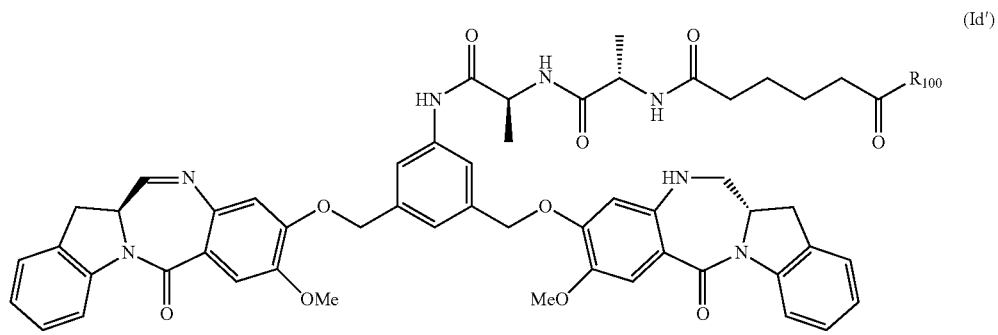
(Id')

or a pharmaceutically acceptable salt thereof, said method comprising the steps of:

(1) reacting a halogenating reagent, a sulfonating reagent or an esterification reagent with a compound of formula (1d),

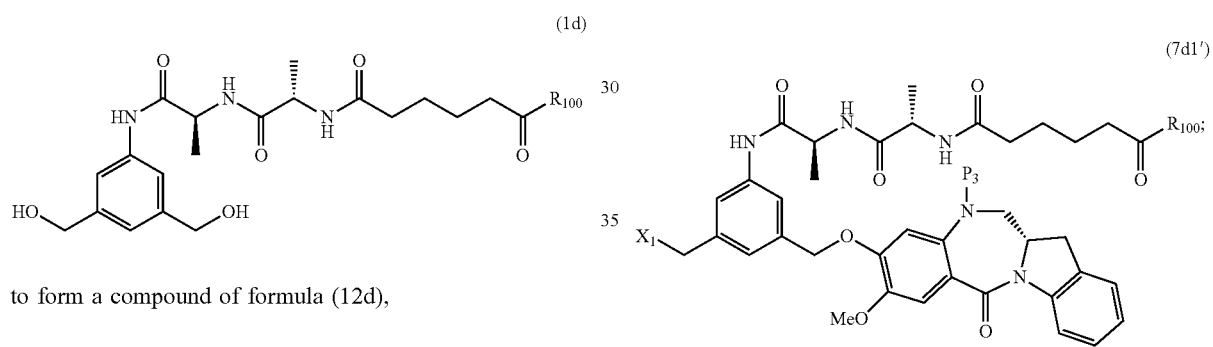

to form a compound of formula (12d), to form a compound of a formula (7d1'), (3) reacting the compound of formula (7d1') with a monomer compound of the formula ($a_1$), (2) reacting the compound of formula (12d) with a monomer compound of the formula ($d_1$),

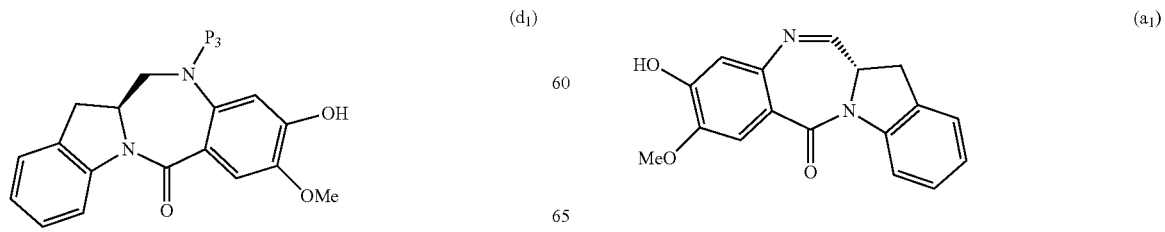

to form a compound of formula (18d),

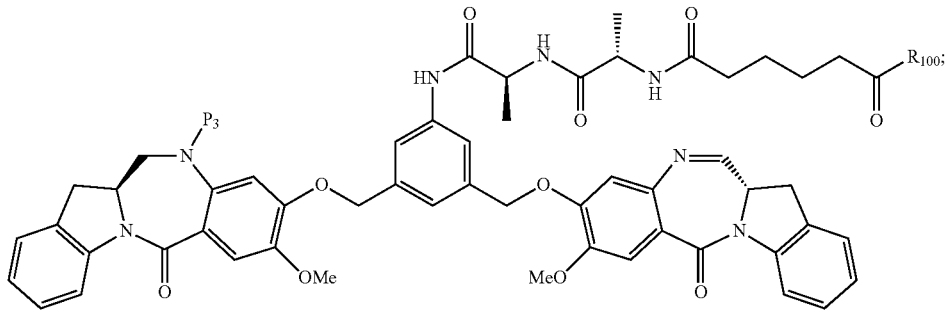

and
(4) when $P_3$ is an amine protecting group, reacting the compound of formula (18d) with an amine deprotecting reagent to form the compound of formula (Id'); wherein $X_1$ is —Br, —I, —Cl, a sulfonate ester or an activated ester; $P_3$ is H or an amine protecting group.

Also provided in the twenty-first embodiment is a method of preparing a compound of formula (1A),

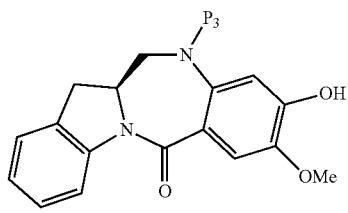

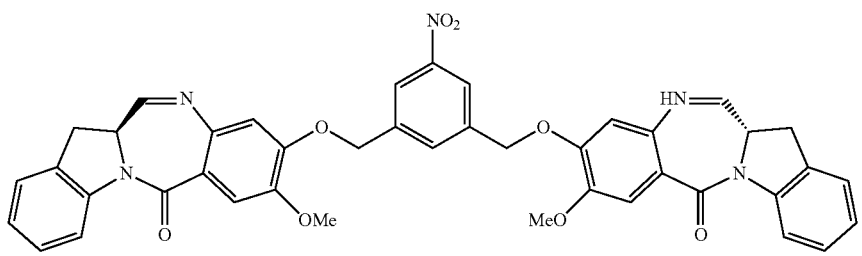

or a pharmaceutically acceptable salt thereof, said method comprising the steps of:

(1) reacting a halogenating reagent, a sulfonating reagent or an esterification reagent with a compound of formula (1A),

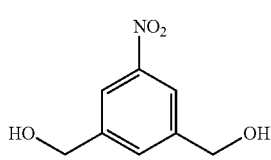

to form a compound of formula (12A),

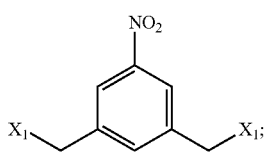

(2) reacting the compound of formula (12A) with a monomer compound of the formula ($d_1$), to form a compound of a formula (7A1'),

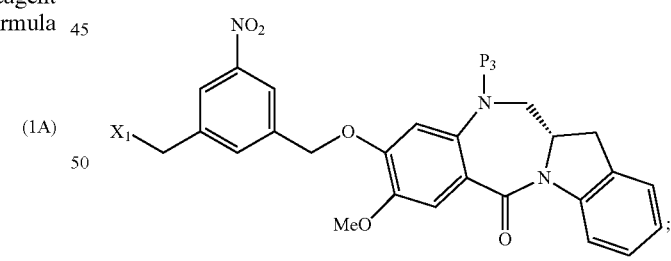

(3) reacting the compound of formula (7A1') with a monomer compound of the formula ($a_1$),

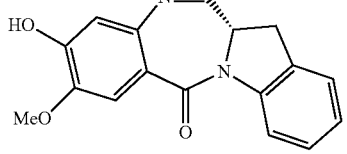

to form a compound of formula (18A),

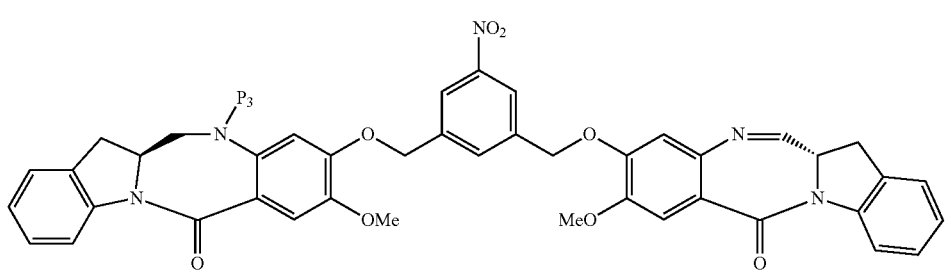

and (4) when $P_3$ is an amine protecting group, reacting the compound of formula (18A) with an amine deprotecting reagent to form the compound of formula (IA); wherein $X_1$ is —Br, —I, —Cl, a sulfonate ester or an activated ester; $P_3$ is H or an amine protecting group.

In one embodiment, for methods of the twenty-first embodiment, $P_3$ is H.

In another embodiment, for methods of the twenty-first embodiment, $X_1$ is —Br, —Cl or a sulfonate ester.

The conditions and reagents for the methods of twenty-first embodiment are as described above in the sixteenth, seventeenth, eighteenth, eighth and/or fourteenth embodiment(s) and any specific embodiments described therein.

In a twenty-second embodiment, the present invention provides a method of preparing a compound of formula (13d),

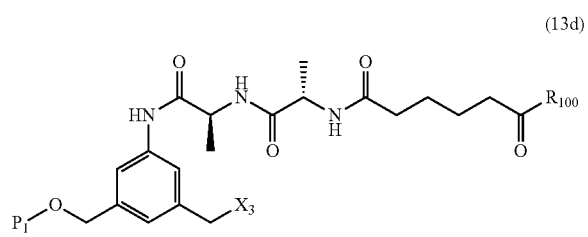

or a salt thereof, said method comprising reacting a chlorinating reagent with a compound of formula (2d),

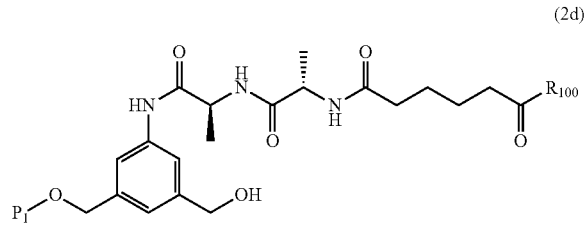

wherein $P_1$ is an alcohol protecting group; $X_3$ is —Cl; and $R_{100}$ is $(C_1$-$C_3)$alkoxy.

Also provided in the twenty-second embodiment is a method of preparing a compound of formula (13A),

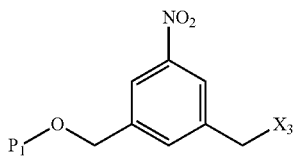

or a salt thereof, said method comprising reacting a chlorinating reagent with a compound of formula (2A),

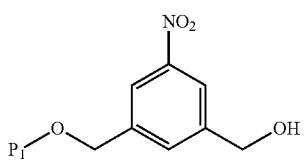

wherein $P_1$ is an alcohol protecting group and $X_3$ is —Cl.

In another specific embodiment, for methods of the twenty-second embodiment, the alcohol protecting group is pivaloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris(4-tert-butylphenyl)methyl. Preferably, the alcohol protecting group is methoxymethyl, tetrahydropyranyl, 2-methoxyethoxymethyl, p-methoxybenzyl, benzyloxymethyl, or 2,2,2-trichloroethoxycarbonyl. Even more preferably, the alcohol protecting group is 2,2,2-trichloroethoxycarbonyl.

In another specific embodiment, the alcohol protecting group is a silyl protecting group. For example, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

In one embodiment, the base is used. The base can be a non-nucleophilic base. Examples of non-nucleophilic base include, but are not limited to, triethylamine, imidazole, diisopropylethylamine (DIPEA), pyridine, 2,6-lutidine, dimethylformamide, 1,8-diazabicyclo[5.4.0]undec-7-ene (DBU), or tetramethylpiperidine. Preferably, the non-nucleophilic base is pyridine.

Any suitable organic solvents can be used for the methods of the twenty-second embodiment. Exemplary solvents include, but are not limited to, DMF, CH$_2$Cl$_2$, dichloroethane, THF, dimethylacetamide, etc. In certain embodiments, DMF is used as the solvent.

In a twenty-third embodiment, the present invention provides a method of preparing a compound of formula (14d),

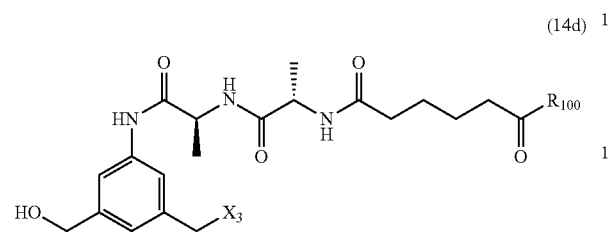

(14d)

or a salt thereof, said method comprising reacting a compound of formula (13d)

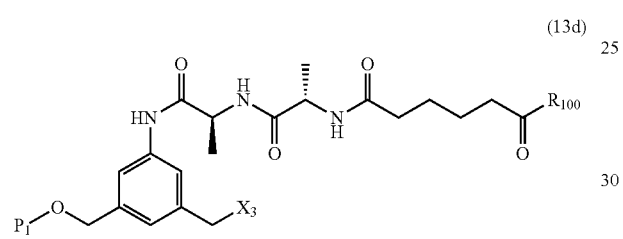

(13d)

with an alcohol deprotecting reagent, wherein P$_1$ is an alcohol protecting group; X$_3$ is —Cl; and R$_{100}$ is (C$_1$-C$_3$) alkoxy.

Also provided in the twenty-third embodiment is a method of preparing a compound of formula (14A),

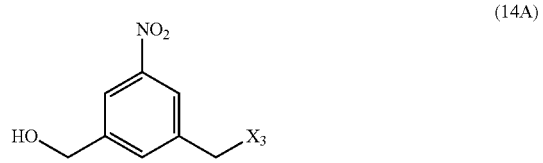

(14A)

or a salt thereof, said method comprising reacting a compound of formula (13A)

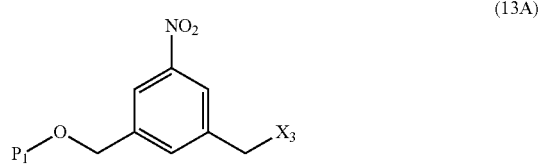

(13A)

with an alcohol deprotecting reagent, wherein P$_1$ is an alcohol protecting group; and X$_3$ is —Cl.

In another specific embodiment, for methods of the twenty-third embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, or periodic acid. Preferably, the alcohol deprotecting reagent is hydrogen fluoride pyridine.

In a twenty-fourth embodiment, the present invention provides a method of preparing a compound of formula (15d):

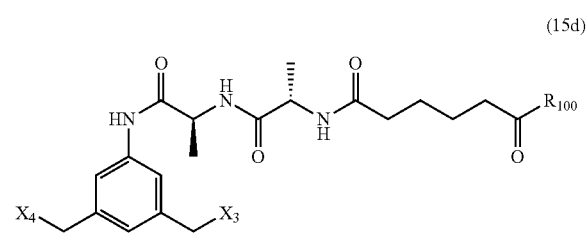

(15d)

or a salt thereof, said method comprising reacting a sulfonating reagent or an esterification reagent with a compound of formula (14d),

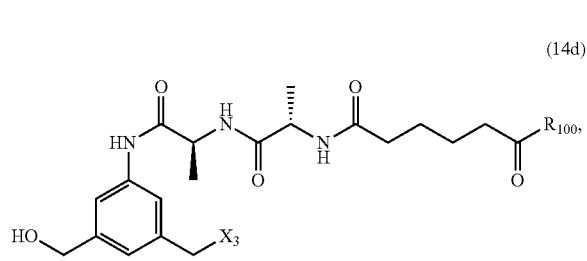

(14d)

wherein X$_3$ is —Cl; X$_4$ is a sulfonate ester or an activated ester; and R$_{100}$ is (C$_1$-C$_3$)alkoxy.

Also provided in the twenty-fourth embodiment is a method of preparing a compound of formula (15A),

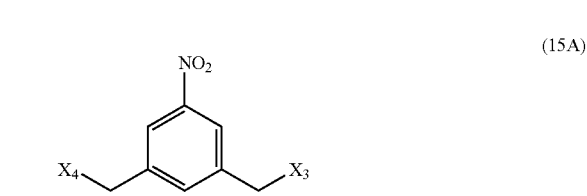

(15A)

or a salt thereof, said method comprising reacting a sulfonating reagent with a compound of formula (14A),

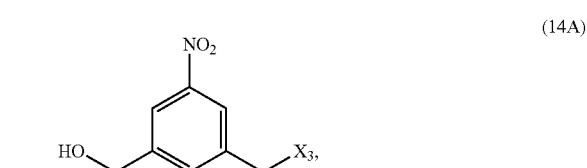

(14A)

wherein X$_3$ is —Cl; and X$_4$ is a sulfonate ester or an activated ester.

In a specific embodiment, for methods of the twenty-fourth embodiment, X$_4$ is a sulfonate ester.

In another specific embodiment, for methods of the twenty-fourth embodiment, the sulfonating reagent is methanesufonyl anhydride, methanesufonyl chloride, p-toluenesulfonyl chloride, 4-bromobenzenesulfonyl chloride, or trifluoromethanesulfonyl anhydride.

In another specific embodiment, for methods of the twenty-fourth embodiment, the sulfonate ester is mesylate, tosylate, brosylate, or triflate. Preferably, the sulfonate ester is mesylate.

In another embodiment, for methods of the twenty-fourth embodiment, a base is used. The base can be a non-nucleophilic base. Examples of non-nucleophilic base include, but are not limited to, triethylamine, imidazole, diisopropylethylamine, pyridine, 2,6-lutidine, dimethylformamide, 1,8-diazabicyclo[5.4.0]undec-7-ene (DBU), or tetramethylpiperidine. Preferably, the non-nucleophilic base is diisopropylethylamine.

In a twenty-fifth embodiment, the present invention provides a method of preparing a compound of formula (20d):

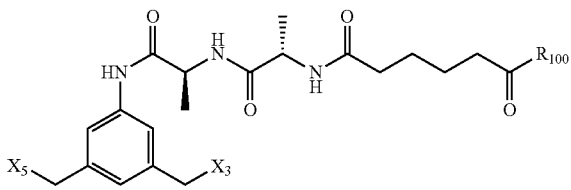
(20d)

or a salt thereof, said method comprising reacting a brominating or iodinating reagent with a compound of formula (14d),

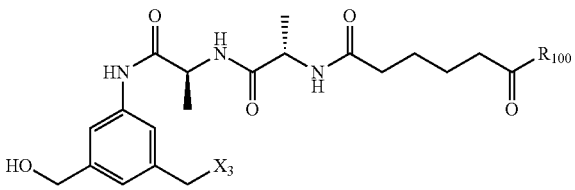
(14d)

wherein $X_3$ is —Cl; $X_5$ is —Br or —I; and $R_{100}$ is $(C_1$-$C_3)$ alkoxy.

Also provided in the twenty-fifth embodiment is a method of preparing a compound of formula (20A):

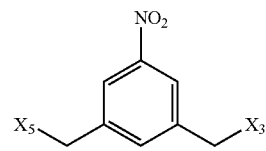
(20A)

or a salt thereof, said method comprising reacting a brominating or iodinating reagent with a compound of formula (14A),

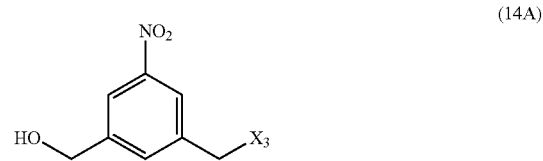
(14A)

wherein $X_3$ is —Cl; $X_5$ is —Br or —I; and $R_{100}$ is $(C_1$-$C_3)$ alkoxy.

In a specific embodiment, for methods of the twenty-fifth embodiment, the brominating or iodinating reagent is bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In a twenty-sixth embodiment, the present invention provides a method of preparing a compound of formula (16d):

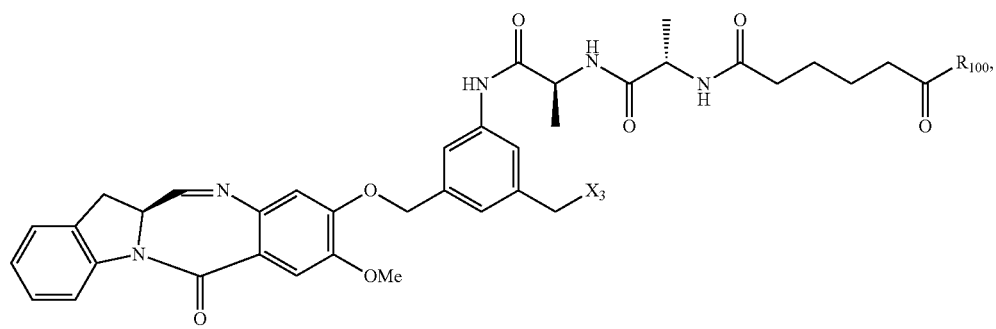
(16d)

or a salt thereof, said method comprising reacting a compound of formula (15d)

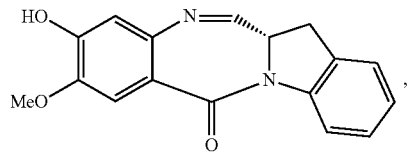
(15d)

with a monomer compound of formula (a₁),

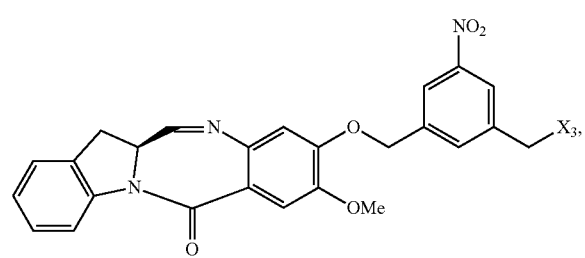
(a₁)

wherein $X_3$ is —Cl; $X_4$ is a sulfonate ester or an activated ester; and $R_{100}$ is $(C_1-C_3)$alkoxy.

Also provided in the twenty-sixth embodiment is a method of preparing a compound of formula (16A),

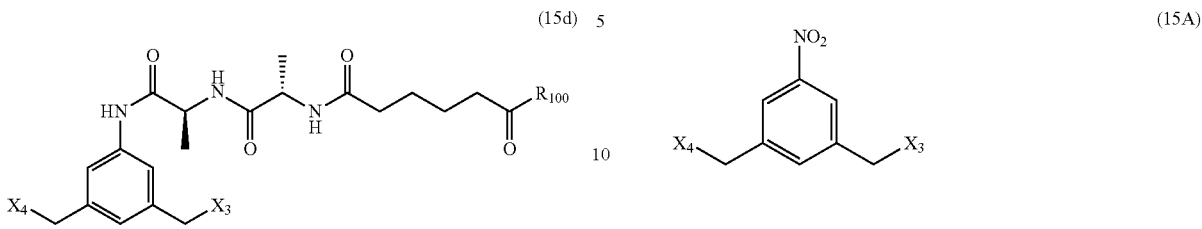
(16A)

or a salt thereof, said method comprising reacting a compound of formula (15A)

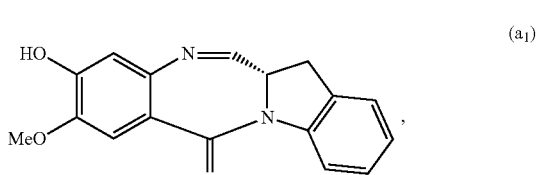
(15A)

with a monomer compound of formula (a₁),

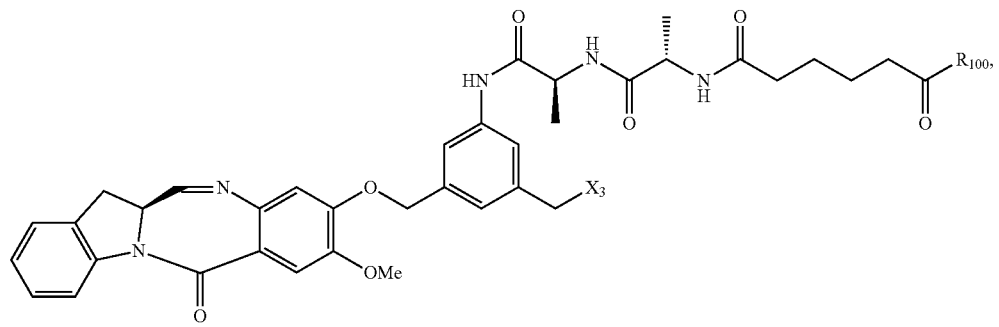
(a₁)

wherein $X_3$ is —Cl; and $X_4$ is a sulfonate ester or an activated ester.

In a specific embodiment, for methods of the twenty-sixth embodiment, $X_4$ is a sulfonate ester.

In an embodiment, for methods of the twenty-sixth embodiment, a base is used. In specific embodiment, the base is sodium carbonate, potassium carbonate, cesium carbonate, sodium hydride, or potassium hydride. Preferably, the base is potassium carbonate.

Any suitable organic solvents can be used for the methods of the twenty-sixth embodiment. Exemplary solvents include, but are not limited to, DMF, $CH_2Cl_2$, dichloroethane, THF, dimethylacetamide, etc. In certain embodiments, dimethylacetamide is used as the solvent.

In a twenty-seventh embodiment, the present invention provides a method of preparing a compound of formula (16d), (16d)

or a salt thereof, said method comprising reacting a compound of formula (20d)

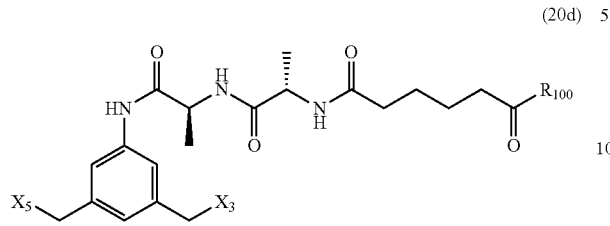
(20d)

with a monomer compound of formula (a₁),

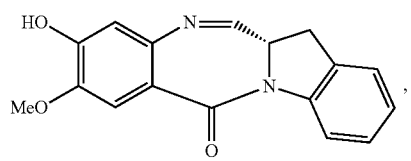
(a₁)

wherein $X_3$ is —Cl; $X_5$ is —Br or —I; and $R_{100}$ is ($C_1$-$C_3$) alkoxy.

Also provided in the twenty-seventh embodiment is a method of preparing a compound of formula (16A),

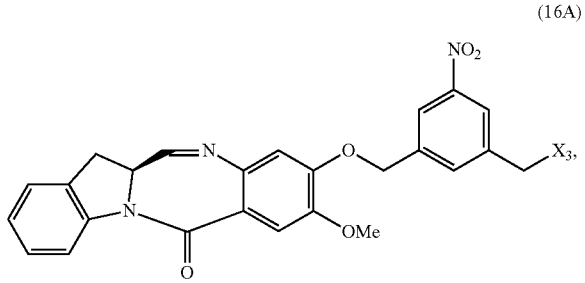
(16A)

or a salt thereof, said method comprising reacting a compound of formula (20A)

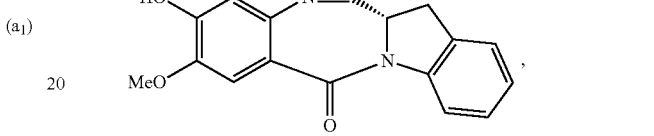
(20A)

with a monomer compound of formula (a₁),

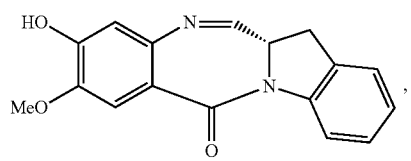
(a₁)

wherein $X_3$ is —Cl and $X_5$ is —Br or —I.

In a specific embodiment, for methods of the twenty-seventh embodiment, the compound of formula (20d) or (20A) is reacted with the monomer compound of formula (a₁) in the presence of a base. Any suitable base can be used. In one embodiment, the base is sodium carbonate, potassium carbonate, cesium carbonate, sodium hydride, or potassium hydride. More specifically, the base is potassium carbonate.

In one embodiment, for methods of the twenty-seventh embodiment, any suitable solvent can be used for the reactions of compounds of formula (20d) or (20A) with the monomer compounds of formula (a₁). In a specific embodiment, the reaction is carried out in a polar aprotic solvent. More specifically, the aprotic solvent is dimethylacetamide.

In a twenty-eighth embodiment, the present invention provides a method of preparing a compound of formula (16d),

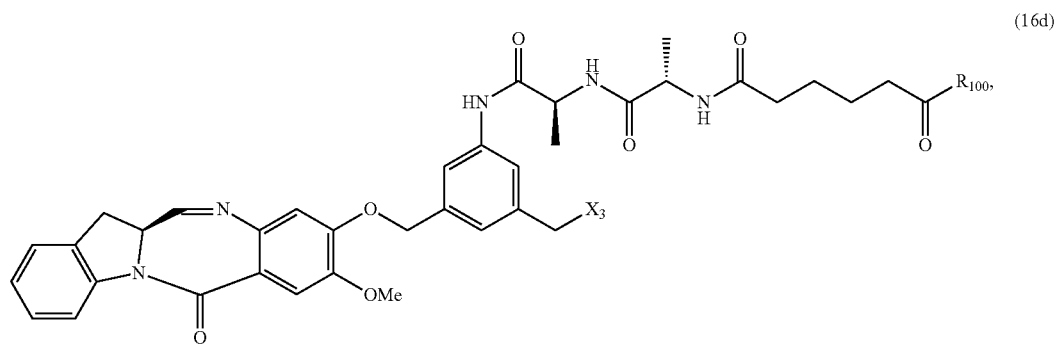
(16d)

or a salt thereof, said method comprising reacting a compound of formula (14d)

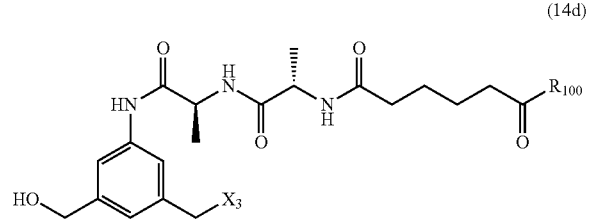
(14d)

with a monomer compound of formula (a₁),

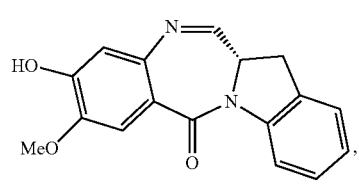
(a₁)

wherein $X_3$ is —Cl; and $R_{100}$ is $(C_1-C_3)$alkoxy.

Also included in the twenty-eighth embodiment is a method of preparing a compound of formula (16A),

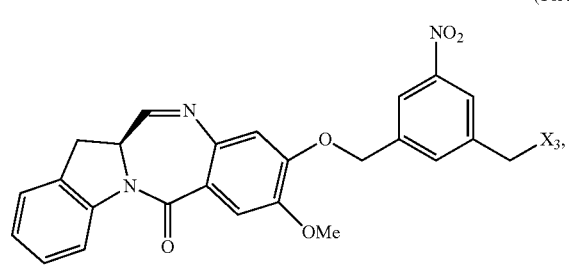
(16A)

or a salt thereof, said method comprising reacting a compound of formula (14A)

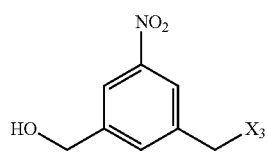
(14A)

with a monomer compound of formula (a₁),

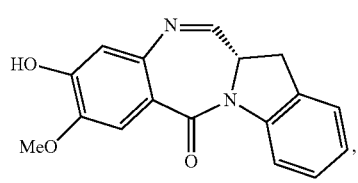
(a₁)

wherein $X_3$ is —Cl.

In a specific embodiment, for methods of the twenty-eighth embodiment, the compound of formula (14d) or (14A) is reacted with a monomer of formula (a₁) in the presence of an alcohol activating agent. In one embodiment, the alcohol activating agent is a trialkylphosphine, triarylphosphine, or triheteroarylphosphine. In a specific embodiment, the alcohol activating agent is trimethylphosphine, tributylphosphine, tri(o-tolyl)phosphine, tri(m-tolyl)phosphine, tri(p-tolyl)phosphine, tri(2-pyridyl)phosphine, tri(3-pyridyl)phosphine, tri(4-pyridyl)phosphine, or [4-(3,3,4,4,5,5,6,6,7,7,8,8,9,9,10,10,10-heptadecafluorodecyl)phenyl]diphenylphosphine. In another embodiment, the alcohol activating agent can be a phosphine-like reagent, such as (tributylphosphoranylidene)acetonitrile, (cyanomethylene)tributylphosphorane (CMBP), or (cyanomethylene)trimethylphosphorane (CMMP). In a more specific embodiment, the alcohol activating agent is triphenylphosphine. In one embodiment, the alcohol activating agent can be polymer-bound or polymer-supported, such as polymer-bound or polymer-supported trialkyl phosphine, triarylphosphine (e.g., triphenylphosphine), or triheteroarylphosphine.

In another specific embodiment, for methods of the twenty-eighth embodiment, the compound of formula (14d) or (14A) is reacted with a monomer of formula (a₁) in the presence of an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis(2,2,2-trichloroethyl)azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl)azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In yet another specific embodiment, for methods of the twenty-eighth embodiment, the compound of formula (14d) or (14A) is reacted with a monomer of formula (a₁) in the presence of triphenylphosphine and an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD). More specifically, the azodicarboxylate is DIAD.

In a twenty-ninth embodiment, the present invention provides a method of preparing a compound of formula (18d):

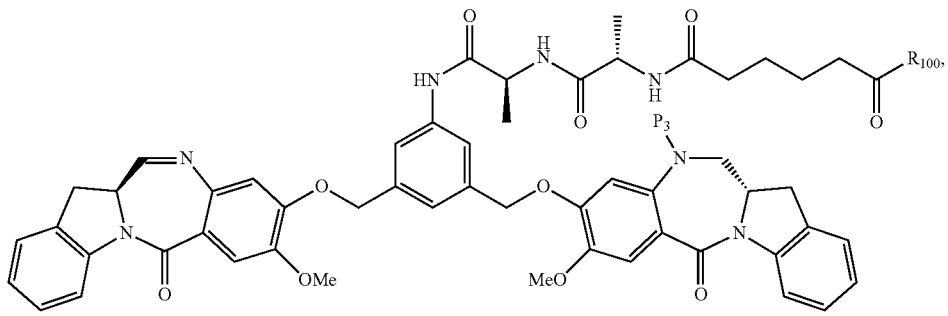

(18d)

a pharmaceutically acceptable salt thereof, said method comprising reacting a compound of formula of (16d):

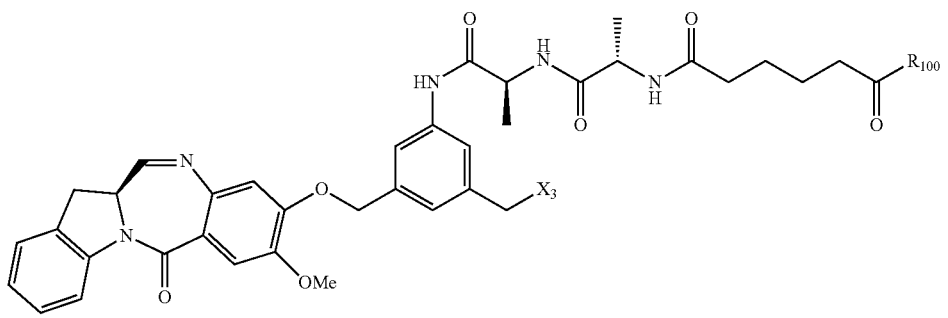

(16d)

with a reduced monomer of formula (d₁):

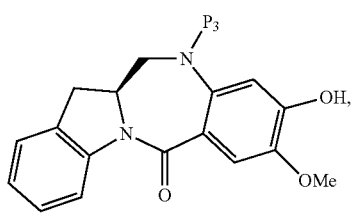

(d₁)

wherein $X_3$ is —Cl; $P_3$ is H or an amine protecting group; and $R_{100}$ is $(C_1-C_3)$alkoxy.

Also provided in the twenty-ninth embodiment is a method of preparing a compound of formula (18A), a pharmaceutically acceptable salt thereof, said method comprising reacting a compound of formula of (16A):

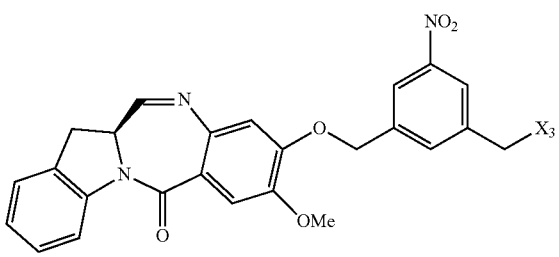

(16A)

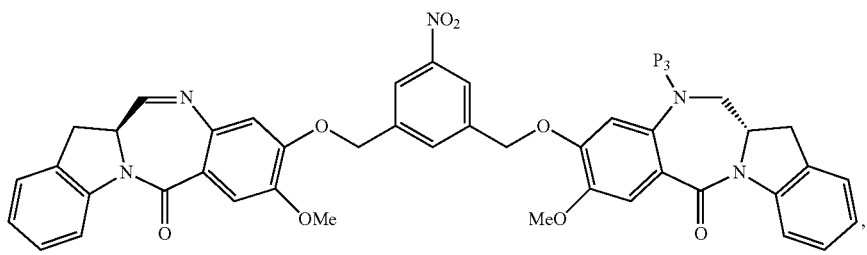

(18A)

with a reduced monomer of formula (d₁):

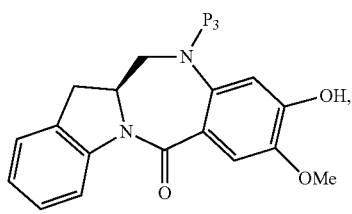

wherein X₃ is —Cl; and P₃ is H or an amine protecting group.

In one embodiment, for methods of the twenty-ninth embodiment, the reaction between the compound of formula (16d) or (16A) and the reduced monomer of formula (d₁) is carried out in the presence of a base. In specific embodiment, the base is sodium carbonate, potassium carbonate, cesium carbonate, sodium hydride, or potassium hydride. Preferably, the base is potassium carbonate.

Any suitable organic solvents can be used for the methods of the twenty-ninth embodiment. In one embodiment, the solvent is a polar aprotic solvent. Exemplary solvents include, but are not limited to, dimethylformamide (DMF), CH₂Cl₂, dichloroethane, THF, dimethylacetamide, etc. In certain embodiments, dimethylformamide or dimethylacetamide is used as the solvent.

In a specific embodiment of the twenty-ninth embodiment, the compound of formula (16d) or (16A) is reacted with reduced monomer of formula (d₁), wherein P₃ is H, to form a compound of formula (Id') or (IA), respectively:

In another specific embodiment of the twenty-ninth embodiment, P₃ is an amine protecting group. Any suitable amine protecting group can be used in the method described above. In one embodiment, the amine protecting group is 2-trimethylsilylethyl, (2-phenyl-2-trimethylsilyl)ethyl, tri-isopropylsiloxy, 2-(trimethylsilyl)ethoxymethyl, allyloxycarbonyl, 9-fluorenylmethoxycarbonyl, 2-(trimethylsilyl)ethoxycarbonyl, or 2, 2,2,2-trichloroethoxycarbonyl.

When P₃ is an amine protecting group, the compound of formula (18d) or (18A) is further reacted with an amine deprotecting reagent to form a compound of formula (Id') or (IA), respectively.

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirtieth embodiment, the present invention provides a method for preparing a compound of formula (17d):

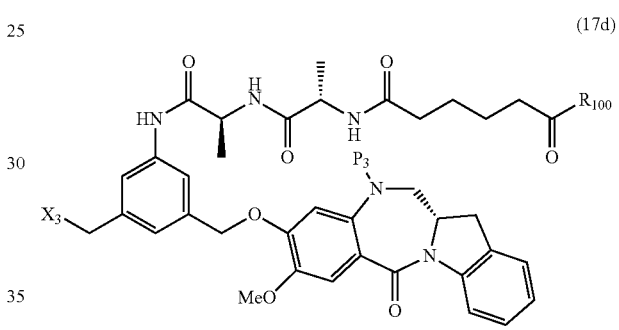

or a salt thereof, said method comprising reacting a compound of formula (15d)

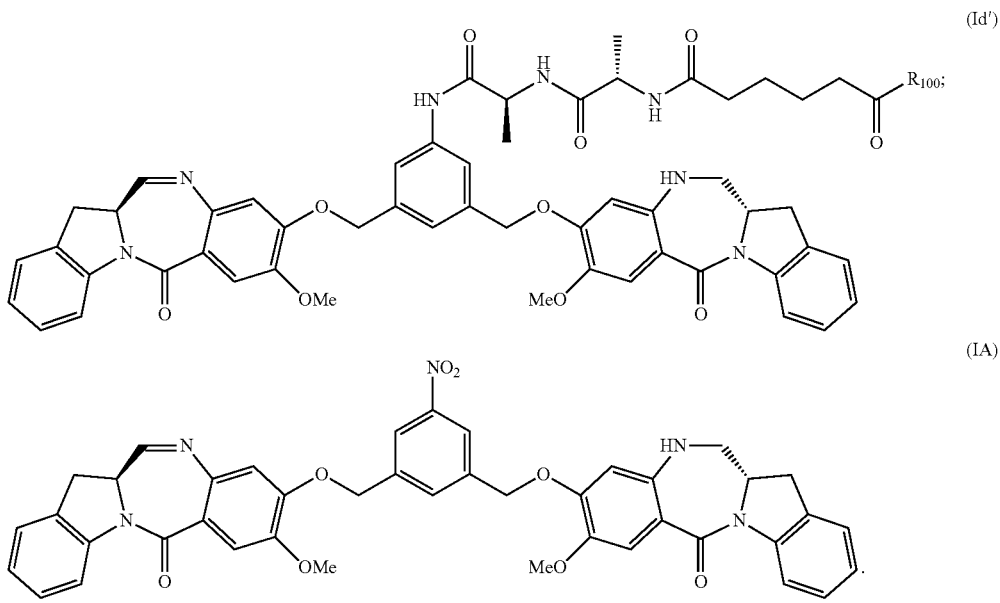

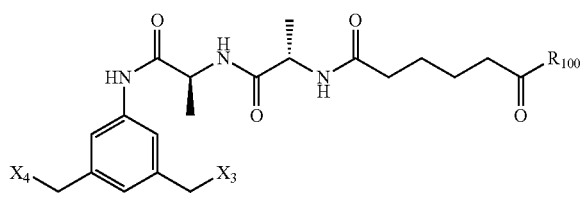

(15d)

with a monomer compound of formula (d₁),

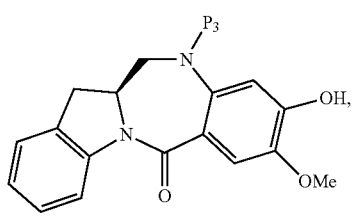

(d₁)

wherein $X_3$ is —Cl; $X_4$ is a sulfonate ester or an activated ester; $P_3$ is H or an amine protecting group; and $R_{100}$ is $(C_1-C_3)$alkoxy. In one embodiment, $X_4$ is an activated ester.

Also included in the thirtieth embodiment is a method of preparing a compound of formula (17A),

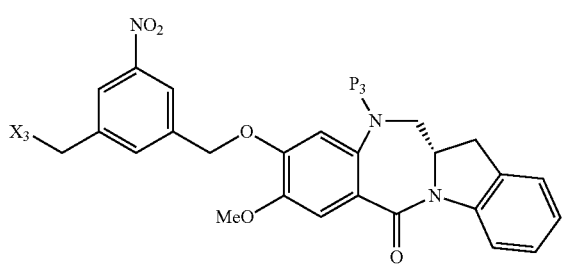

(17A)

or a salt thereof, said method comprising reacting a compound of formula (15A)

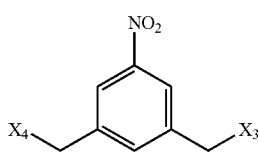

(15A)

with a monomer compound of formula (d₁),

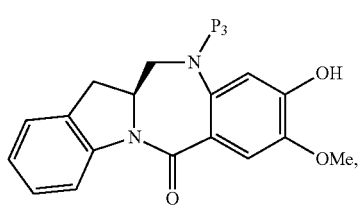

(d₁)

wherein $X_3$ is —Cl; $X_4$ is a sulfonate ester or an activated ester; and $P_3$ is H or an amine protecting group. In one embodiment, $X_4$ is an activated ester.

In an embodiment, for methods of the thirtieth embodiment, a base is used. In specific embodiment, the base is sodium carbonate, potassium carbonate, cesium carbonate, sodium hydride, or potassium hydride. Preferably, the base is potassium carbonate.

Any suitable organic solvents can be used for the methods of the thirtieth embodiment. Exemplary solvents include, but are not limited to, DMF, $CH_2Cl_2$, dichloroethane, THF, dimethylacetamide, etc. In certain embodiments, dimethylacetamide is used as the solvent.

In a specific embodiment of the thirtieth embodiment, $P_3$ is H and the compound of formula (15d) or (15A) is reacted with the monomer compound of formula (d₁) to form a compound of formula (17d') or (17A'), respectively.

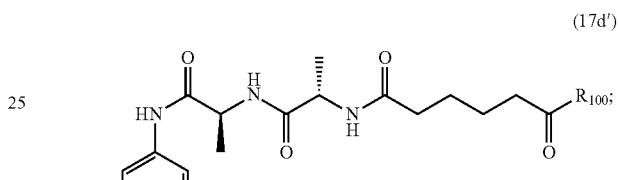

(17d')

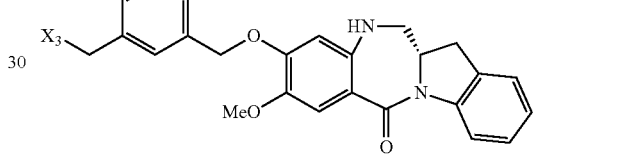

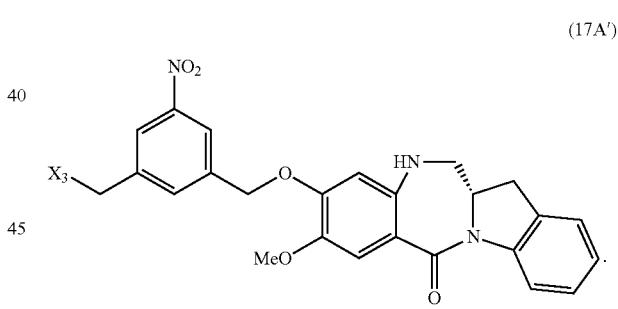

(17A')

In another specific embodiment of the thirtieth embodiment, $P_3$ is an amine protecting group and the method further comprises the step of reacting the compound of formula (17d) or (17A) with an amine deprotecting reagent to form a compound of formula (17d') or (17A'), respectively.

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirty-first embodiment, the present invention provides a method of preparing a compound of formula (17d),

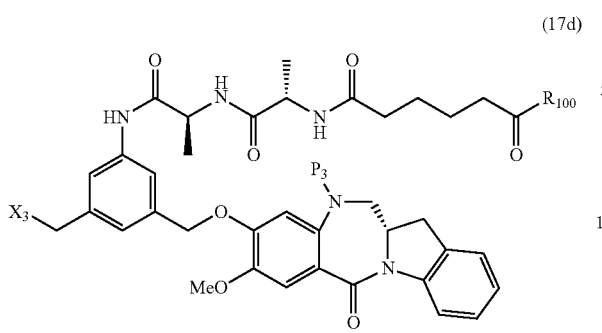
(17d)

or a salt thereof, said method comprising reacting a compound of formula (14d)

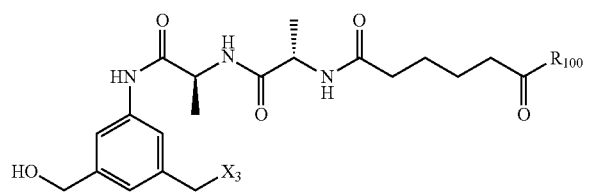
(14d)

with a monomer compound of formula (d₁),

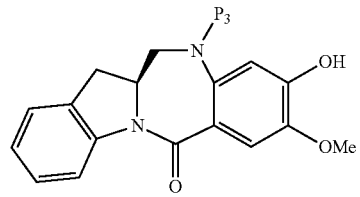
(d₁)

wherein $X_3$ is —Cl; $P_3$ is H or an amine protecting group; and $R_{100}$ is $(C_1-C_3)$alkoxy.

Also included in the thirty-first embodiment is a method of preparing a compound of formula (17A),

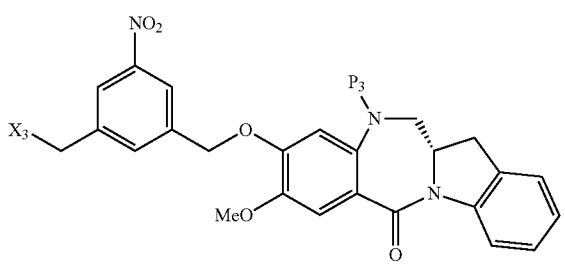
(17A)

or a salt thereof, said method comprising reacting a compound of formula (14A)

(14A)

with a monomer compound of formula (d₁),

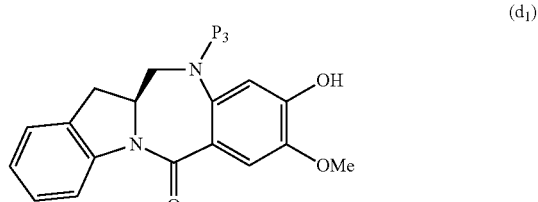
(d₁)

wherein $X_3$ is —Cl; and $P_3$ is H or an amine protecting group.

In a specific embodiment, for methods of the thirty-first embodiment, the compound of formula (14d) or (14A) is reacted with a monomer of formula (d₁) in the presence of an alcohol activating agent. In a specific embodiment, the alcohol activating agent is trimethylphosphine, tributylphosphine, tri(o-tolyl)phosphine, tri(m-tolyl)phosphine, tri(p-tolyl)phosphine, tri(2-pyridyl)phosphine, tri(3-pyridyl) phosphine, tri(4-pyridyl)phosphine, or [4-(3,3,4,4,5,5,6,6,7,7,8,8,9,9,10,10,10-Heptadecafluorodecyl)phenyl] diphenylphosphine. In another embodiment, the alcohol activating agent can be a phosphine-like reagent, such as (tributylphosphoranylidene)acetonitrile, (cyanomethylene) tributylphosphorane (CMBP), or (cyanomethylene)trimethylphosphorane (CMMP). In a more specific embodiment, the alcohol activating agent is triphenylphosphine. In one embodiment, the alcohol activating agent can be polymer-bound or polymer-supported, such as polymer-bound or polymer-supported trialkyl phosphine, triarylphosphine (e.g., triphenylphosphine), or triheteroarylphosphine.

In another specific embodiment, for methods of the thirty-first embodiment, the compound of formula (14d) or (14A) is reacted with a monomer of formula (d₁) in the presence of an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis (2,2,2-trichloroethyl) azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl)azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In yet another specific embodiment, for methods of the thirty-first embodiment, the compound of formula (14d) or (14A) is reacted with a monomer of formula (d₁) in the presence of triphenylphosphine and an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl) dipiperidine (ADDP), and ditertbutyl azodicarboxylate (DTAD). More specifically, the azodicarboxylate is DIAD.

In a thirty-second embodiment, the present invention provides a method of preparing a compound of formula (17d):

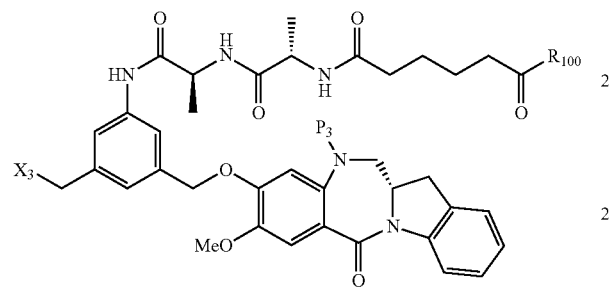
(17d)

or a salt thereof, said method comprising reacting a compound of formula (20d)

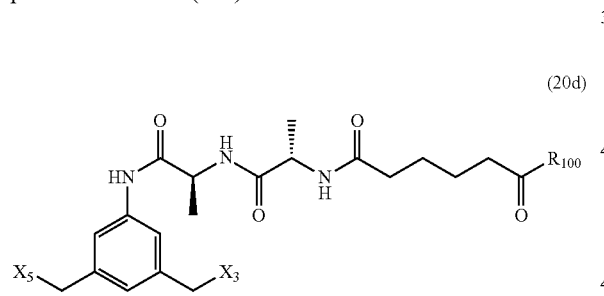
(20d)

with a monomer compound of formula (d₁),

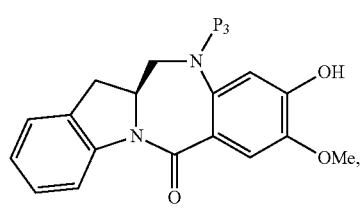
(d₁)

wherein $X_3$ is —Cl; $X_5$ is —Br or —I; $P_3$ is H or an amine protecting group; and $R_{100}$ is $(C_1\text{-}C_3)$alkoxy.

Also provided in the thirty-second embodiment is a method of preparing a compound of formula (17A):

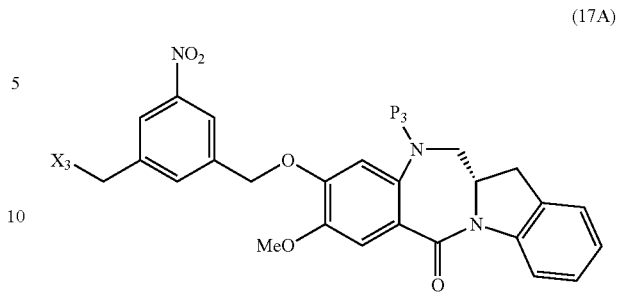
(17A)

or a salt thereof, said method comprising reacting a compound of formula (20A)

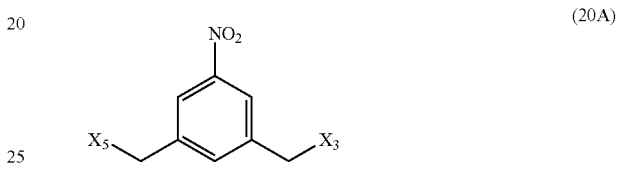
(20A)

with a monomer compound of formula (d₁),

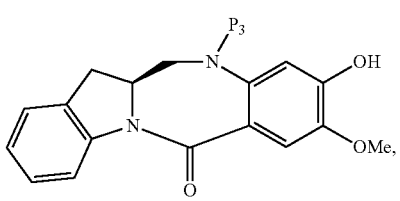
(d₁)

wherein $X_3$ is —Cl; $X_5$ is —Br or —I; and $P_3$ is H or an amine protecting group.

In one embodiment, for methods of the thirty-second embodiment, the compound of formula (20d) or (20A) is reacted with the monomer compound of formula (d₁) in the presence of a base. Any suitable base can be used. In one embodiment, the base is sodium carbonate, potassium carbonate, cesium carbonate, sodium hydride, or potassium hydride. More specifically, the base is potassium carbonate.

In another embodiment, for methods of the thirty-second embodiment, any suitable solvent can be used for the reactions of compounds of formula (20d) or (20A) with the monomer compounds of formula (d₁). In a specific embodiment, the reaction is carried out in a polar aprotic solvent. More specifically, the aprotic solvent is dimethylacetamide.

In a specific embodiment of the thirty-second embodiment, $P_3$ is H and the compound of formula (20d) or (20A) is reacted with the monomer compound of formula (d₁) to form a compound of formula (17d') or (17A'), respectively.

(17d') 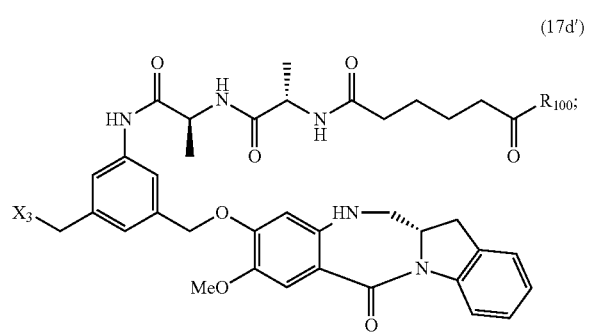 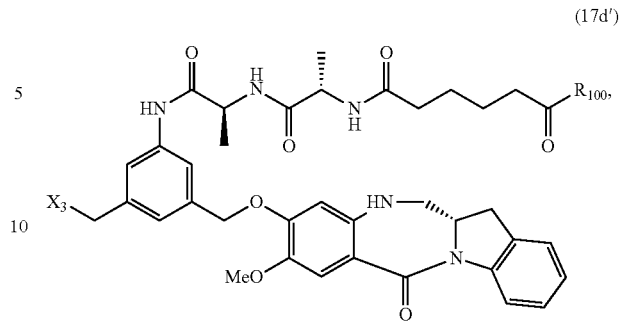

or a salt thereof, said method comprising reacting a compound of formula (16d)

(16d) 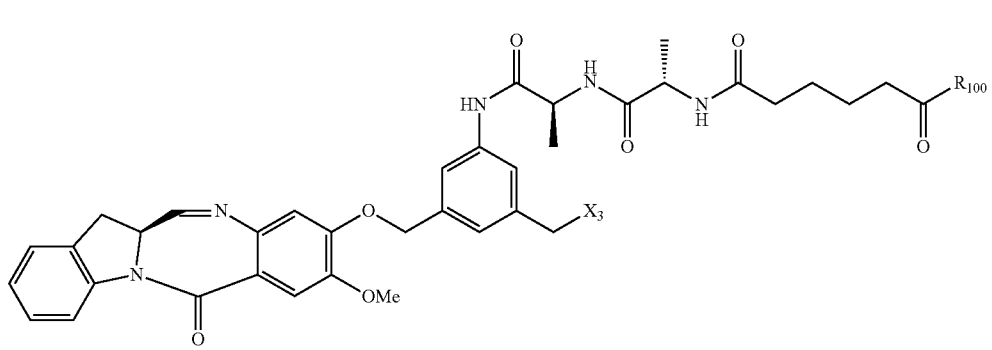

with an imine reducing agent, wherein $X_3$ is —Cl; and $R_{100}$ is $(C_1$-$C_3)$alkoxy.

Also included in the thirty-third embodiment is a method of preparing a compound of formula (17A'):

(17A') 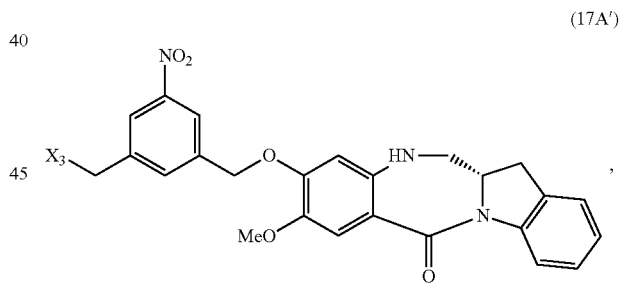

or a salt thereof, said method comprising reacting a compound of formula (16A)

(16A) 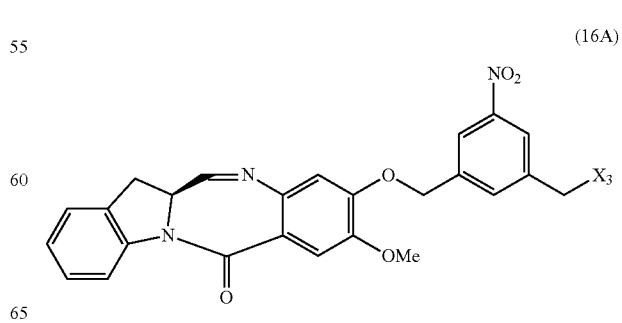

-continued (17A') 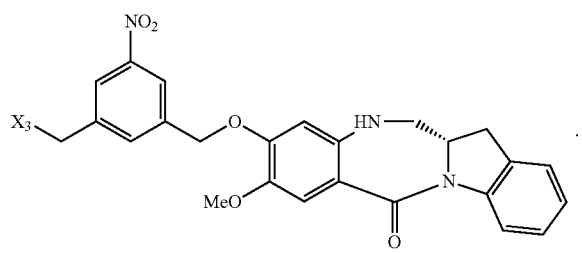

In another specific embodiment of the thirty-second embodiment, $P_3$ is an amine protecting group, the method further comprises the step of reacting the compound of formula (17d) or (17A) with an amine deprotecting reagent to form a compound of formula (17d') or (17A'), respectively.

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirty-third embodiment, the present invention provides a method of preparing a compound of formula (17d'):

with an imine reducing agent, wherein $X_3$ is —Cl.

In one specific embodiment, for methods of the thirty-third embodiment, the imine reducing agent is a hydride reducing agent. Examples of suitable hydride reducing agents include, but are not limited to, sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH$_4$), potassium borohydride (KBH$_4$), or sodium bis(2-methoxyethoxy)aluminumhydride (Red-Al). In one particular embodiment, the hydride reducing agent is sodium triacetoxy borohydride (NaBH(OAc)$_3$).

In a thirty-fourth embodiment, the present invention provides a method of preparing a compound of formula (18d),

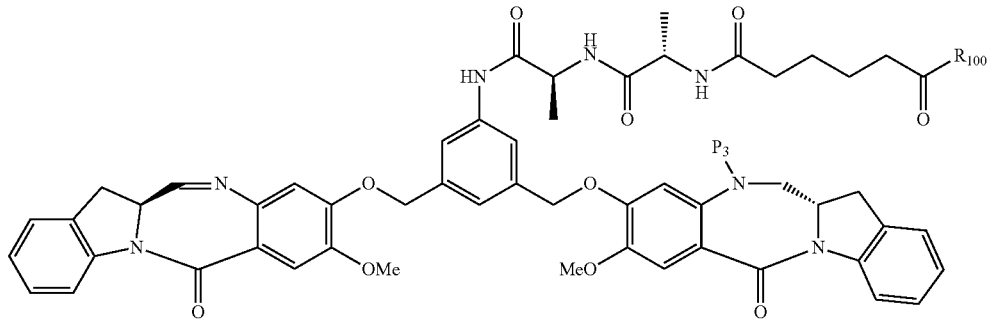

(18d)

or a pharmaceutically acceptable salt thereof, said method comprising reacting a compound of formula of (17d):

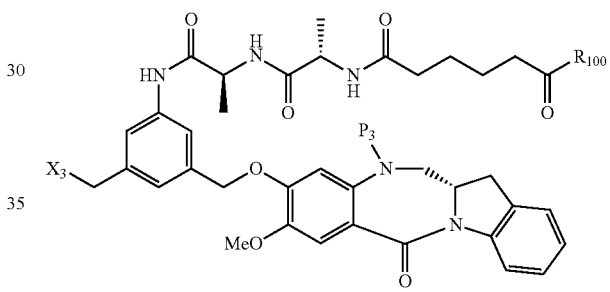

(17d)

with a monomer of formula (a$_1$):

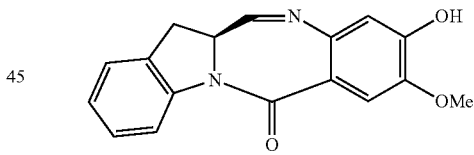

(a$_1$)

wherein X$_3$ is —Cl; P$_3$ is H or an amine protecting group; and R$_{100}$ is (C$_1$-C$_3$)alkoxy.

Also provided in the thirty-fourth embodiment is a method of preparing a compound of formula (18A),

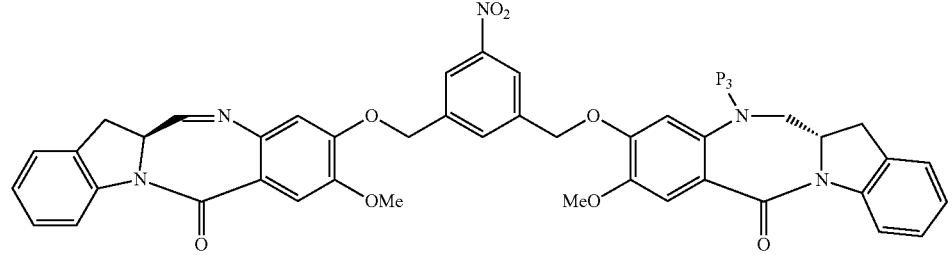

(18A)

or a pharmaceutically acceptable salt thereof, said method comprising reacting a compound of formula of (17A):

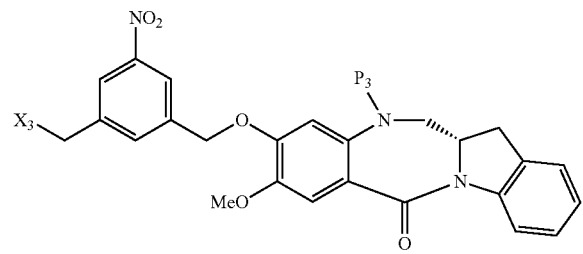
(17A)

with a monomer of formula ($a_1$):

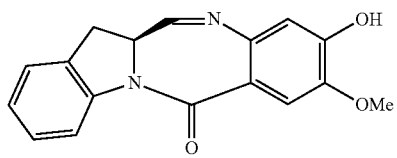
($a_1$)

wherein $X_3$ is —Cl; and $P_3$ is H or an amine protecting group.

In one embodiment, for methods of the thirty-fourth embodiment, the reaction between the compound of formula (17d) or (17A) and the monomer of formula ($a_1$) is carried out in the presence of a base. In specific embodiment, the base is sodium carbonate, potassium carbonate, cesium carbonate, sodium hydride, or potassiumhydride. Preferably, the base is potassium carbonate.

Any suitable organic solvents can be used for the methods of the thirty-fourth embodiment. In one embodiment, the solvent is a polar aprotic solvent. Exemplary solvents include, but are not limited to, dimethylformamide (DMF), $CH_2Cl_2$, dichloroethane, THF, dimethylacetamide, etc. In certain embodiments, dimethylformamide or dimethylacetamide is used as the solvent.

In a specific embodiment of the thirty-fourth embodiment, the compound of formula (17d) or (17A) is reacted with the monomer of formula ($a_1$), wherein $P_3$ is H, to form a compound of formula (Id') or (IA), respectively.

In another specific embodiment of the thirty-fourth embodiment, $P_3$ is an amine protecting group. Any suitable amine protecting group can be used in the method described above. In one embodiment, the amine protecting group is 2-trimethylsilylethyl, (2-phenyl-2-trimethylsilyl)ethyl, tri-isopropylsiloxy, 2-(trimethylsilyl)ethoxymethyl, allyloxycarbonyl, 9-fluorenylmethoxycarbonyl, 2-(trimethylsilyl)ethoxycarbonyl, or 2, 2,2,2-trichloroethoxycarbonyl.

When $P_3$ is an amine protecting group, the compound of formula (18d) or (18A) is further reacted with an amine deprotecting reagent to form a compound of formula (Id') or (IA), respectively.

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirty-fifth embodiment, the present invention provides a method of preparing a compound of formula (18d),

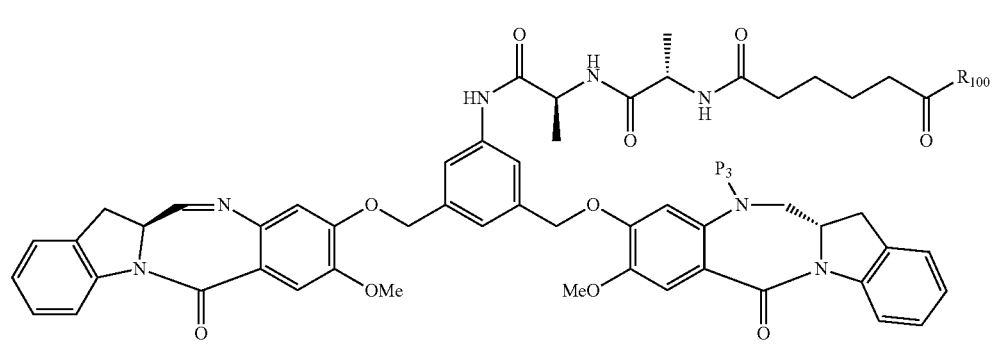
(18d)

or a pharmaceutically acceptable salt thereof, said method comprising the steps of:

(1) reacting a sulfonating reagent or an esterification reagent with the compound of formula (14d):

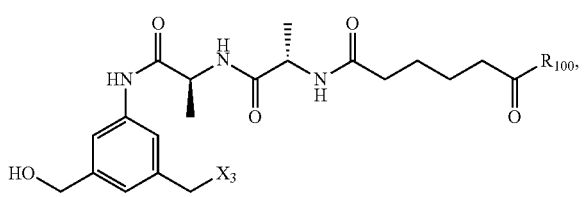
(14d)

or a salt thereof, to form a compound of formula (15d):

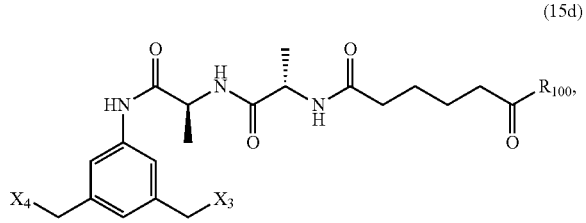
(15d)

or a salt thereof;

(2) reacting the compound of formula (15a) with a monomer compound of formula ($a_1$),

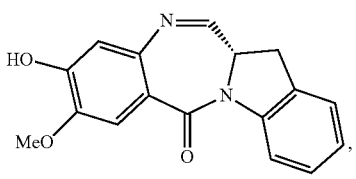
(a₁), to form a compound of formula (16d):

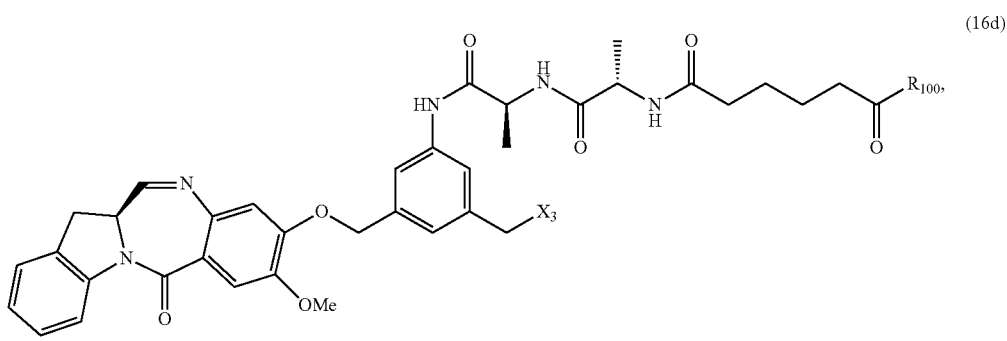
(16d)

or a salt thereof; and
(3) reacting the compound of formula of (16d) with a reduced monomer of formula (d₁):

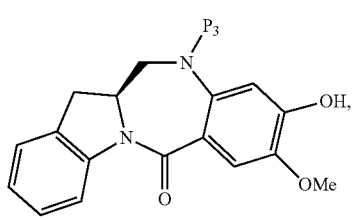
(d₁)

to form a compound of formula (18d), or a pharmaceutically acceptable salt thereof, wherein $X_3$ is —Cl; $X_4$ is a sulfonate ester or an activated ester; $P_1$ is an alcohol protecting group; $P_3$ is H or an amine protecting group; and $R_{100}$ is $(C_1-C_3)$ alkoxy. In one embodiment, $X_4$ is a sulfonate ester.

Also included in the thirty-fifth embodiment is a method of preparing a compound of formula (18A), or a pharmaceutically acceptable salt thereof, said method comprising the steps of:
(1) reacting a sulfonating reagent or an esterification reagent with the compound of formula (14A):

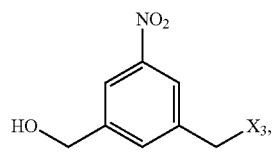
(14A)

or a salt thereof, to form a compound of formula (15A):

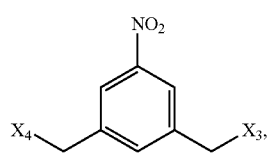
(15A)

or a salt thereof;
(2) reacting the compound of formula (15A) with a monomer compound of formula (a₁),

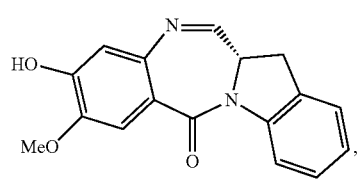
(a₁)

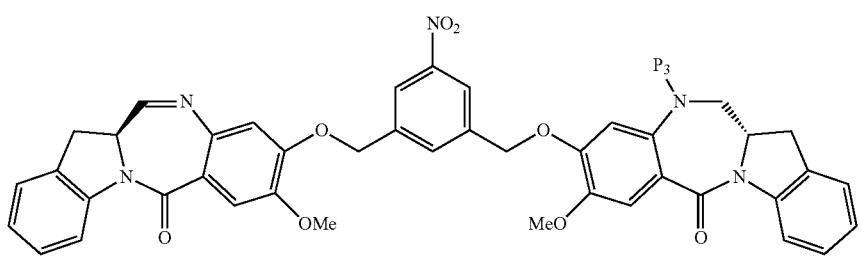
(18A)

to form a compound of formula (16A):

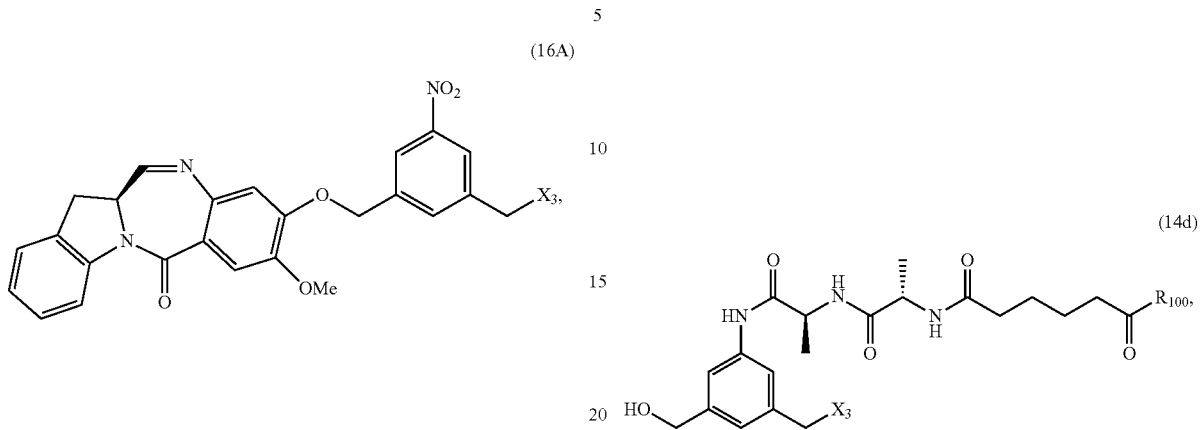

or a salt thereof; and
(3) reacting the compound of formula of (16A) with a reduced monomer of formula (d₁):

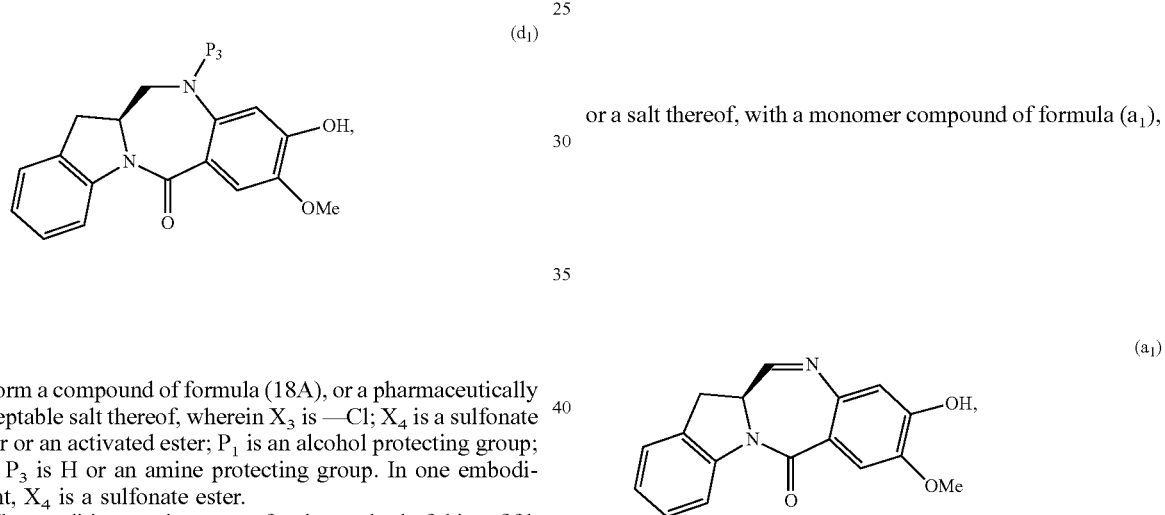

to form a compound of formula (18A), or a pharmaceutically acceptable salt thereof, wherein $X_3$ is —Cl; $X_4$ is a sulfonate ester or an activated ester; $P_1$ is an alcohol protecting group; and $P_3$ is H or an amine protecting group. In one embodiment, $X_4$ is a sulfonate ester.

The conditions and reagents for the method of thirty-fifth embodiment are as described above in the twenty-fourth, twenty-sixth and/or twenty-ninth embodiment(s) and any specific embodiments described therein.

In a thirty-sixth embodiment, the present invention provides a method of preparing a compound of formula (18d), or a pharmaceutically acceptable salt thereof, said method comprising the steps of:

(1) reacting the compound of formula (14d):

or a salt thereof, with a monomer compound of formula (a₁),

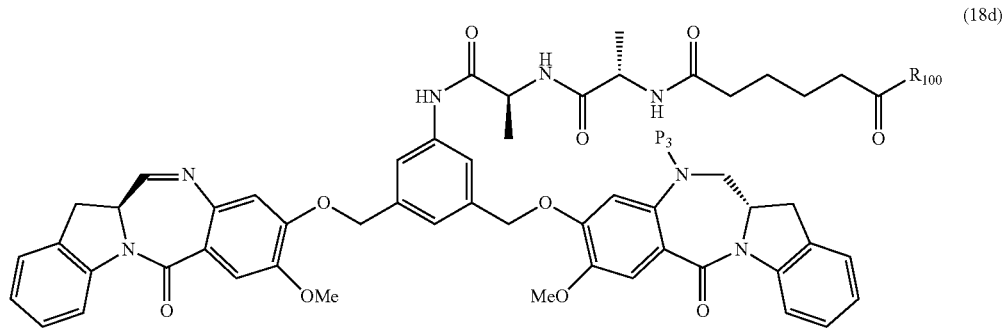

to form a compound of formula (16d):

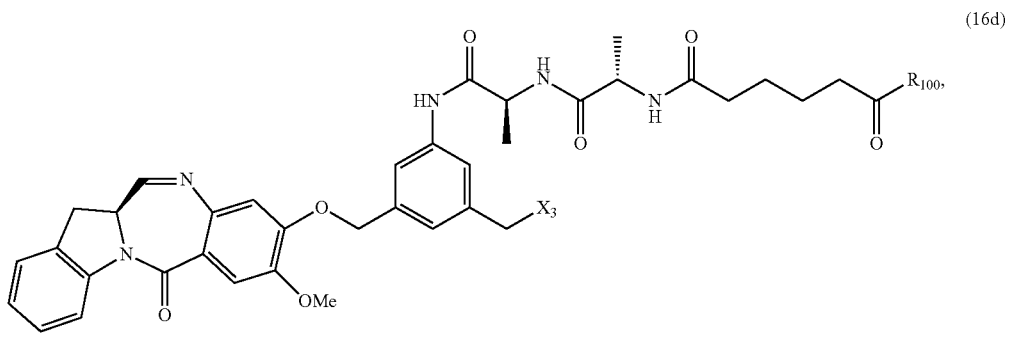

or a salt thereof; and
(2) reacting the compound of formula of (16d) with a reduced monomer of formula ($d_1$):

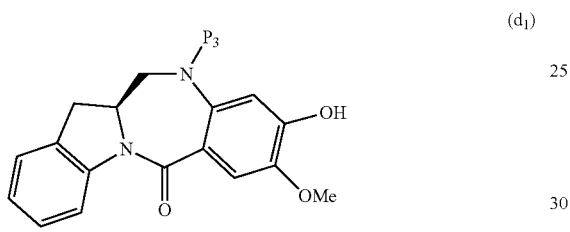

to form a compound of formula (18d), or a pharmaceutically acceptable salt thereof, wherein $X_3$ is —Cl; $P_1$ is an alcohol protecting group; $P_3$ is H or an amine protecting group; and $R_{100}$ is ($C_1$-$C_3$)alkoxy.

Also provided in the thirty-sixth embodiment is a method of preparing a compound of formula (18A),

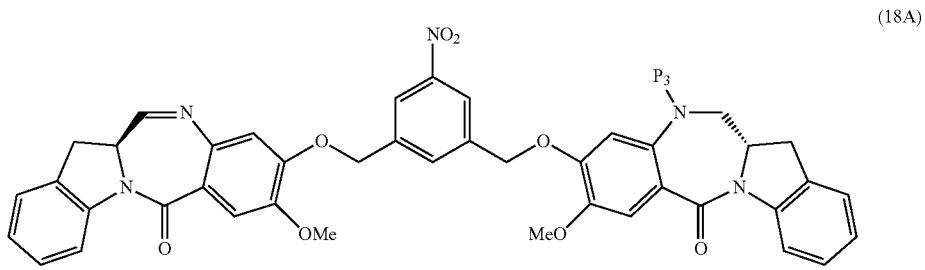

or a pharmaceutically acceptable salt thereof, said method comprising the steps of:
(1) reacting the compound of formula (14A):

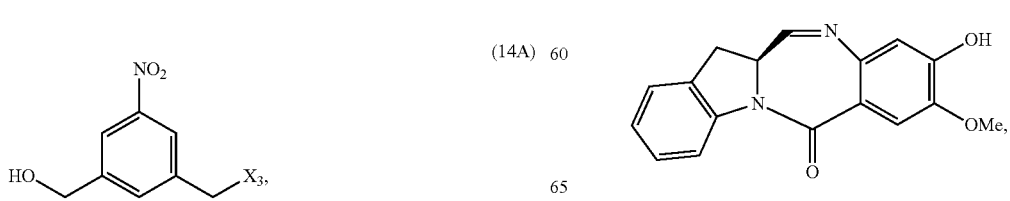

or a salt thereof, with a monomer compound of formula ($a_1$), to form a compound of formula (16A):

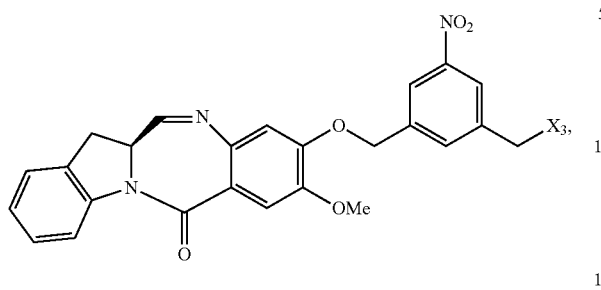

(16A)

or a salt thereof; and (2) reacting the compound of formula of (16A) with a reduced monomer of formula (d₁):

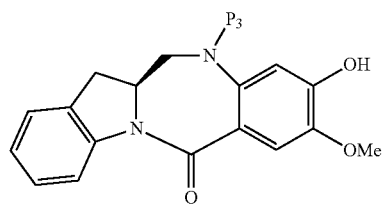

(d₁)

to form a compound of formula (18A), or a pharmaceutically acceptable salt thereof, wherein $X_3$ is —Cl; $P_1$ is an alcohol protecting group; and $P_3$ is H or an amine protecting group.

The conditions and reagents for the method of thirty-sixth embodiment are as described above in the twenty-eighth, and/or twenty-ninth embodiment(s) and any specific embodiments described therein.

In a thirty-seventh embodiment, the present invention provides a method of preparing a compound of formula (18d), or a pharmaceutically acceptable salt thereof, said method comprising the steps of:

(1) reacting a halogenating reagent with the compound of formula (14d):

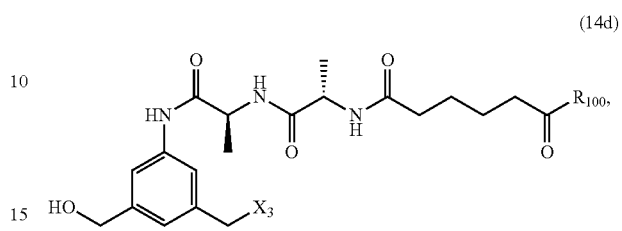

(14d)

or a salt thereof, to form a compound of formula (20d):

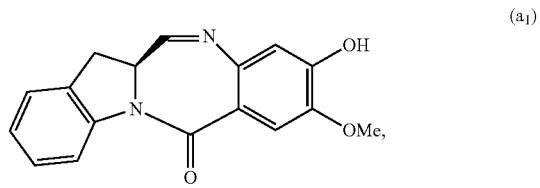 [SMILES: COc1cc2c(cc1O)N=C[C@@H]1Cc3ccccc3N1C2=O]

(20d)

or a salt thereof;

(2) reacting a compound of formula (20d) or a salt thereof with a monomer compound of formula (a₁),

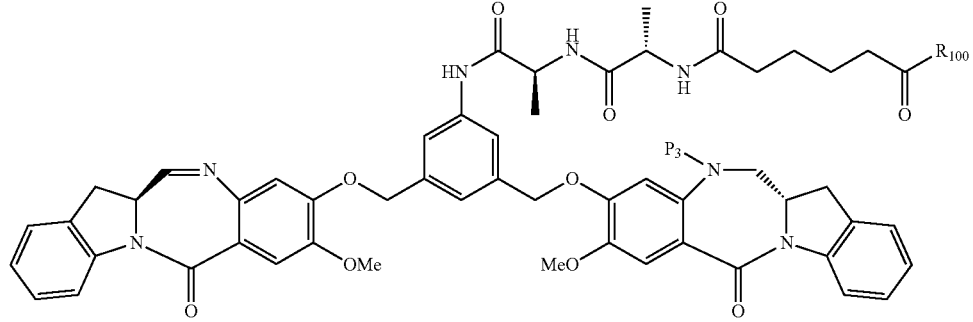

(a₁)

(18d)

to form a compound of formula (16d):

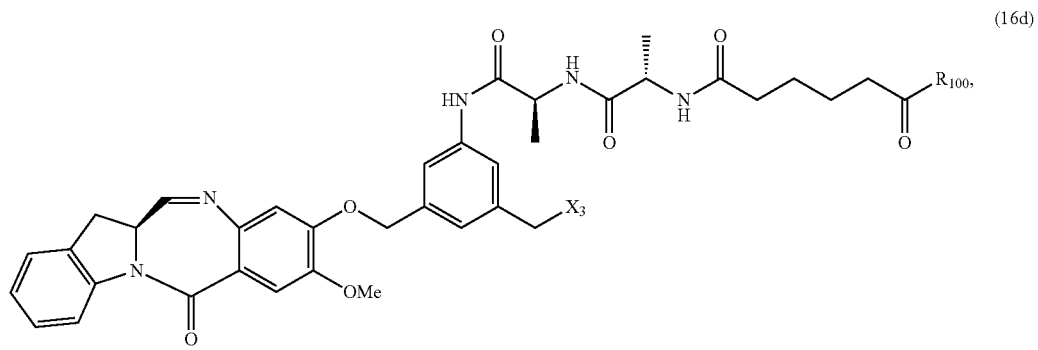

or a salt thereof; and (3) reacting the compound of formula of (16d) with a reduced monomer of formula (d₁):

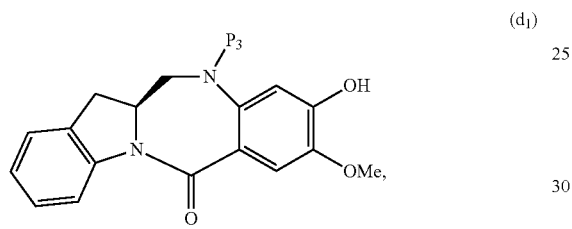

to form a compound of formula (18d), or a pharmaceutically acceptable salt thereof, wherein $X_3$ is —Cl; $X_5$ is —Br or —I; $P_3$ is H or an amine protecting group; and $R_{100}$ is $(C_1$-$C_3)$alkoxy.

Also provided in the thirty-seventh embodiment is a method of preparing a compound of formula (18A),

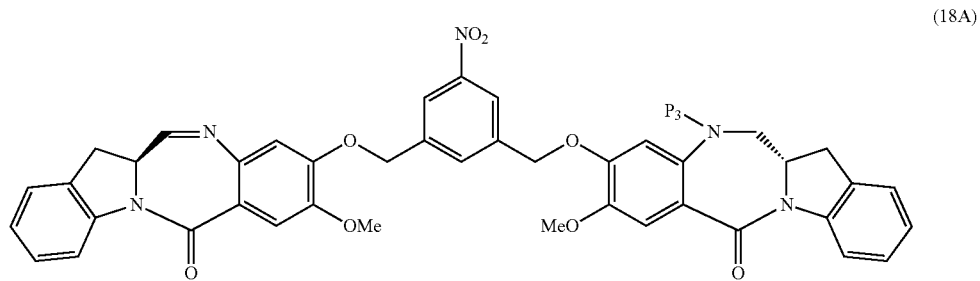

or a pharmaceutically acceptable salt thereof, said method comprising the steps of:

(1) reacting a halogenating reagent with the compound of formula (14A):

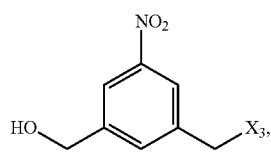

or a salt thereof, to form a compound of formula (20A):

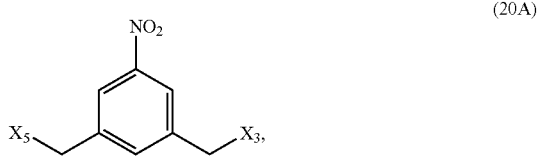

or a salt thereof;

(2) reacting a compound of formula (20A) or a salt thereof with a monomer compound of formula (a₁),

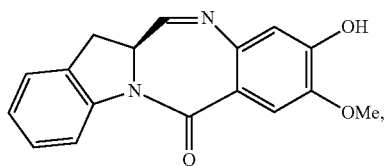

to form a compound of formula (16A):

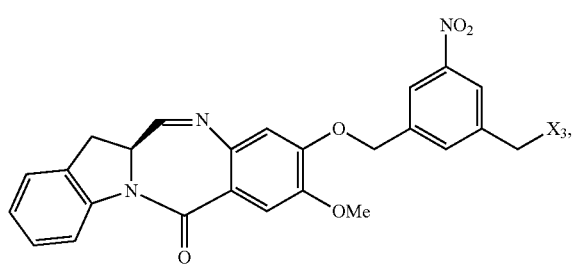

or a salt thereof; and (3) reacting the compound of formula of (16A) with a reduced monomer of formula ($d_1$):

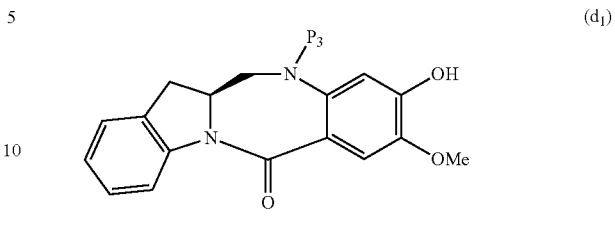

to form a compound of formula (18A), or a pharmaceutically acceptable salt thereof, wherein $X_3$ is —Cl; $X_5$ is —Br or —I; and $P_3$ is H or an amine protecting group.

The conditions and reagents for the method of thirty-seventh embodiment are as described above in the twenty-fifth, twenty-seventh, and/or twenty-ninth embodiment(s) and any specific embodiments described therein.

In a specific embodiment, for the methods of the thirty-fifth, thirty-sixth and thirty-seventh embodiments, $P_3$ is H, the compound of formula (16d) or (16A) is reacted with reduced monomer of formula ($d_1$) to form a compound of formula (Id') or (IA) respectively:

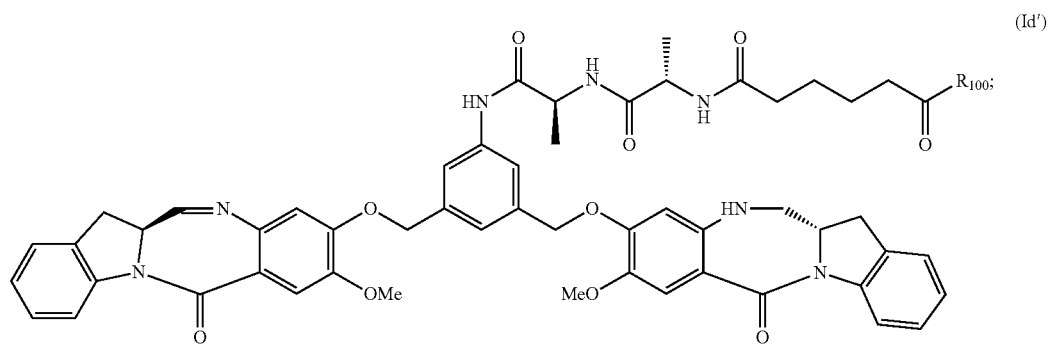

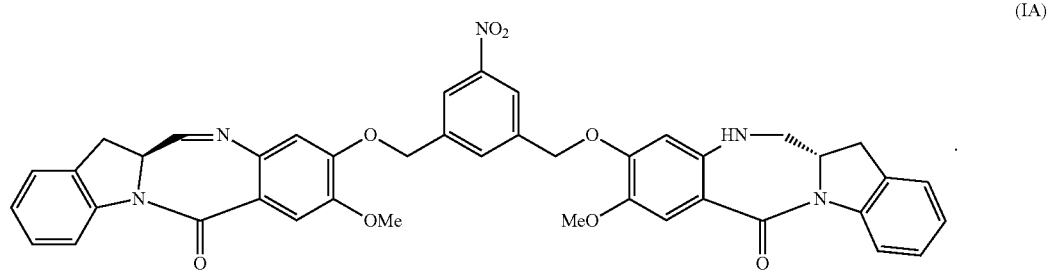

In another specific embodiment, for the methods of thirty-fifth, thirty-sixth and thirty-seventh embodiments, $P_3$ is an amine protecting group and the methods further comprise reacting the compound of formula (18d) or (18A) with an amine deprotecting reagent to form a compound of formula (Id') or (IA) respectively.

In a thirty-eighth embodiment, the present invention provides a method of preparing a compound of formula (18d),

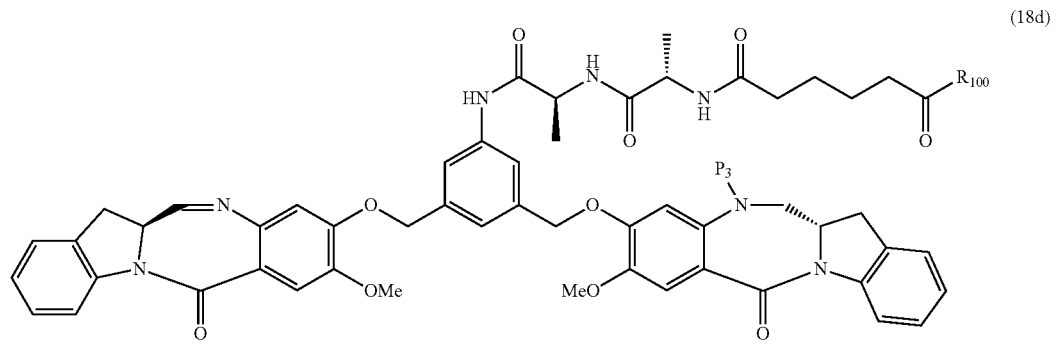

(18d)

or a pharmaceutically acceptable salt thereof, said method comprising the steps of:

(1) reacting a sulfonating reagent or an esterification reagent with the compound of formula (14d):

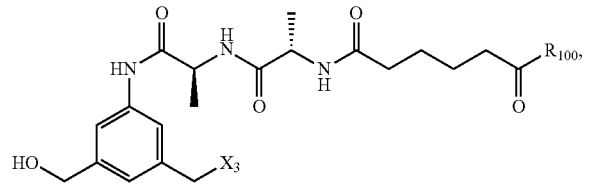

(14d)

or a salt thereof, to form a compound of formula (15d):

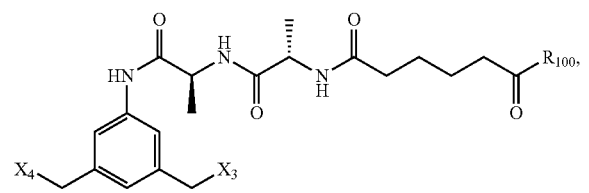

(15d)

or a salt thereof;

(2) reacting the compound of formula (15d) with a reduced monomer compound of formula ($d_1$),

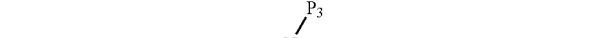

($d_1$)

to form a compound of formula (17d):

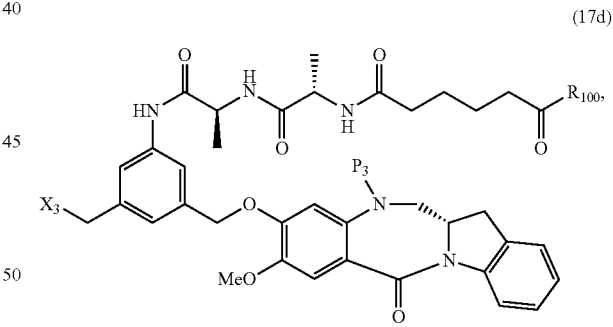

(17d)

or a salt thereof; and (3) reacting the compound of formula of (17d) with a monomer of formula ($a_1$):

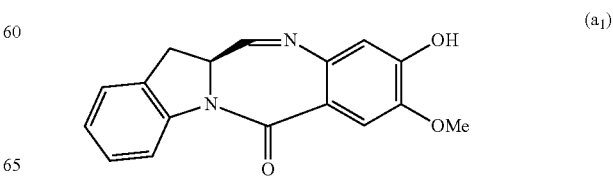

($a_1$)

to form a compound of formula (18d), or a pharmaceutically acceptable salt thereof, wherein $X_3$ is —Cl; $X_4$ is a sulfonate ester or an activated ester; $P_1$ is an alcohol protecting group; $P_3$ is H or an amine protecting group; and $R_{100}$ is ($C_1$-$C_3$) alkoxy. In one embodiment, $X_4$ is a sulfonate ester.

Also provided in the thirty-eighth embodiment is a method of preparing a compound of formula (18A), (1) reacting a sulfonating reagent or an esterification reagent with the compound of formula (14A):

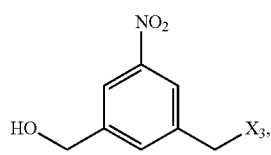
(14A)

or a salt thereof, to form a compound of formula (15A):

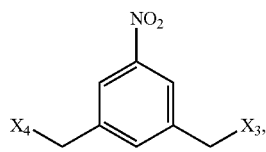
(15A)

or a salt thereof;

(2) reacting the compound of formula (15A) with a reduced monomer compound of formula ($d_1$),

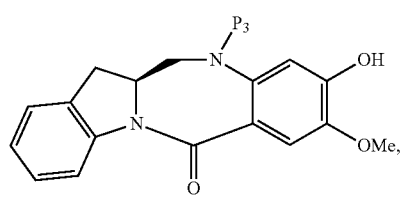
($d_1$)

to form a compound of formula (17A):

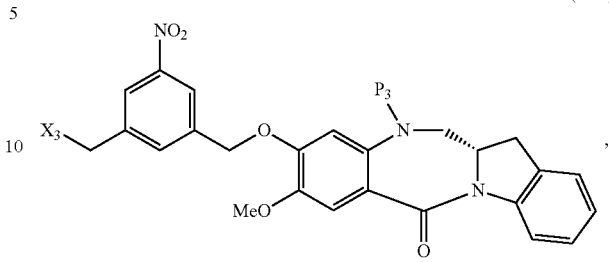
(17A)

or a salt thereof; and (3) reacting the compound of formula of (17A) with a monomer of formula ($a_1$):

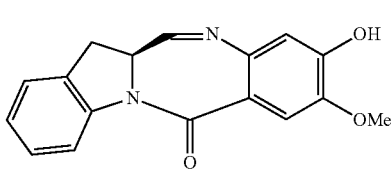
($a_1$)

to form a compound of formula (18A), or a pharmaceutically acceptable salt thereof, wherein $X_3$ is —Cl; $X_4$ is a sulfonate ester or an activated ester; $P_1$ is an alcohol protecting group; and $P_3$ is H or an amine protecting group. In one embodiment, $X_4$ is a sulfonate ester.

The conditions and reagents for the method of thirty-eighth embodiment are as described above in the twenty-fifth, thirtieth and/or thirty-fourth embodiment(s) and any specific embodiments described therein.

In a thirty-ninth embodiment, the present invention provides method of preparing a compound of formula (18d),

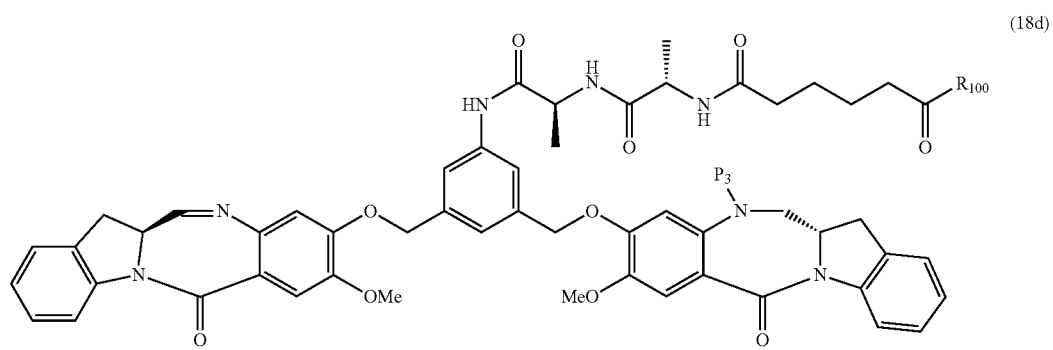
(18d)

or a pharmaceutically acceptable salt thereof, said method comprising the steps of:

(1) reacting the compound of formula (14d):

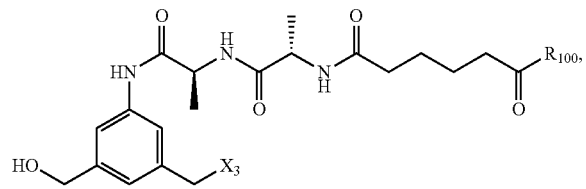

(14d)

or a salt thereof, with a reduced monomer compound of formula ($d_1$),

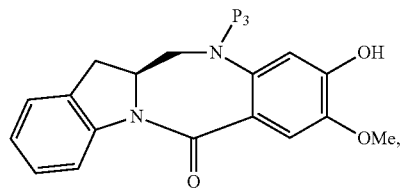

($d_1$)

to form a compound of formula (17d):

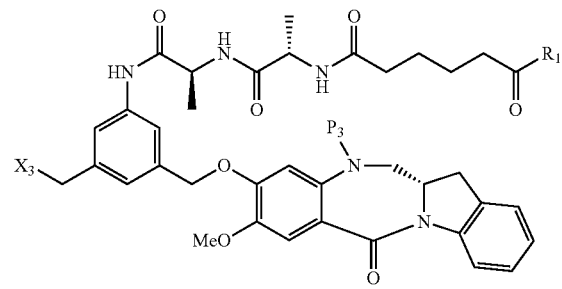

(17d)

or a salt thereof; and
(2) reacting the compound of formula of (17d) with a monomer of formula ($a_1$):

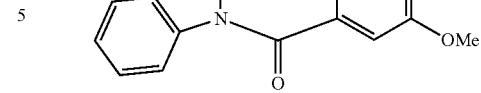

($a_1$)

to form a compound of formula (18d), or a pharmaceutically acceptable salt thereof, wherein $X_3$ is —Cl; $P_1$ is an alcohol protecting group; $P_3$ is H or an amine protecting group; and $R_{100}$ is ($C_1$-$C_3$)alkoxy.

Also provided in the thirty-ninth embodiment is a method of preparing a compound of formula (18A),

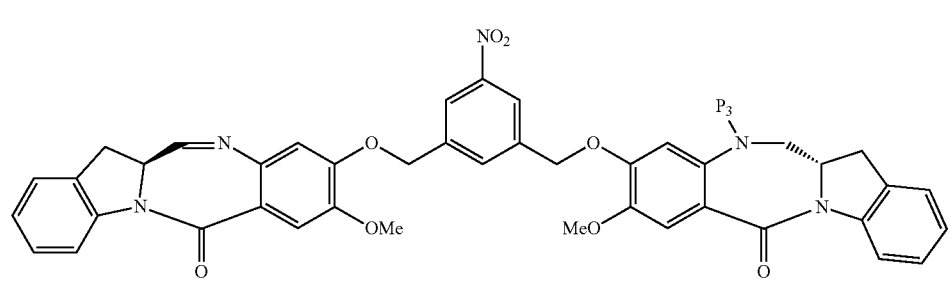

(18A)

or a pharmaceutically acceptable salt thereof, said method comprising the steps of:

(1) reacting the compound of formula (14A):

(14A)

NO$_2$

HO

X$_3$, or a salt thereof, with a reduced monomer compound of formula ($d_1$), ($d_1$)

to form a compound of formula (17A):

(17A)

or a salt thereof; and (2) reacting the compound of formula of (17A) with a monomer of formula (a₁):

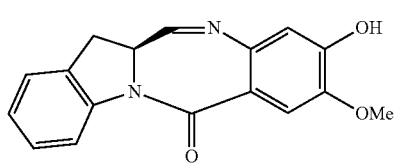

to form a compound of formula (18A), or a pharmaceutically acceptable salt thereof, wherein $X_3$ is —Cl; $P_1$ is an alcohol protecting group; and $P_3$ is H or an amine protecting group.

The conditions and reagents for the method of thirty-ninth embodiment are as described above in the thirty-first and/or thirty-fourth embodiment(s) and any specific embodiments described therein.

In a fortieth embodiment, the present invention provides a method of preparing a compound of formula (18d),

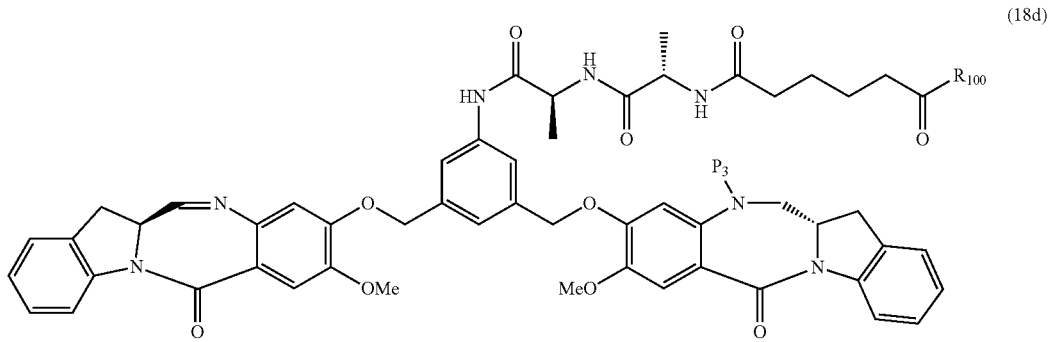

or a pharmaceutically acceptable salt thereof, said method comprising the steps of:

(1) reacting a brominating or iodinating reagent with the compound of formula (14d):

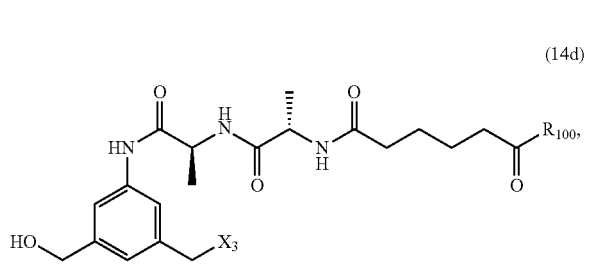

or a salt thereof, to form a compound of formula (20d):

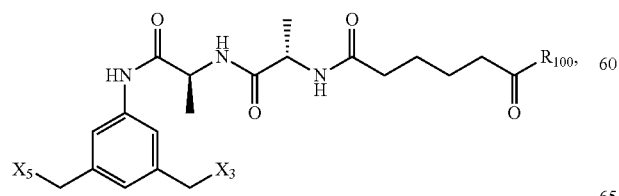

or a salt thereof;

(2) reacting the compound of formula (20d) with a reduced monomer compound of formula (d₁),

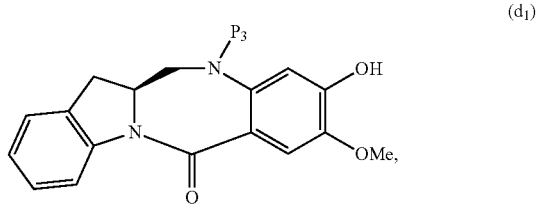

to form a compound of formula (17d):

(17d)

or a salt thereof; and (3) reacting the compound of formula of (17d) with a monomer of formula (a₁):

(a₁)

to form a compound of formula (18d), or a pharmaceutically acceptable salt thereof, wherein $X_3$ is —Cl; $X_5$ is —Br or —I; $P_1$ is an alcohol protecting group; $P_3$ is H or an amine protecting group; and $R_{100}$ is $(C_1$-$C_3)$alkoxy.

Also provided in the fortieth embodiment is a method of preparing a compound of formula (18A),

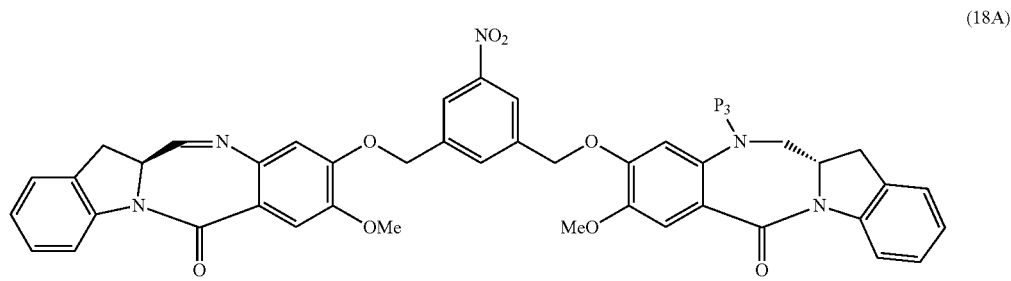

(18A)

or a pharmaceutically acceptable salt thereof, said method comprising the steps of:

(1) reacting a brominating or iodinating reagent with the compound of formula (14A):

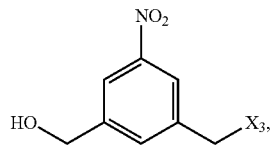

(14A)

or a salt thereof, to form a compound of formula (20A):

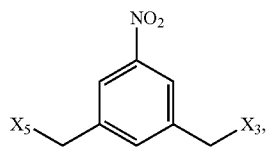

(20A)

or a salt thereof;

(2) reacting the compound of formula (20A) with a reduced monomer compound of formula ($d_1$),

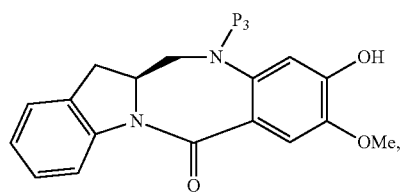

($d_1$)

to form a compound of formula (17A):

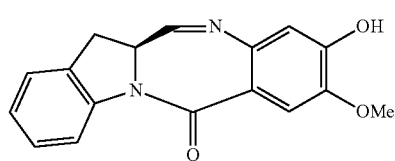

(17A)

or a salt thereof; and (3) reacting the compound of formula of (17A) with a monomer of formula ($a_1$):

($a_1$)

to form a compound of formula (18A), or a pharmaceutically acceptable salt thereof, wherein $X_3$ is —Cl; $X_5$ is —Br or —I; $P_1$ is an alcohol protecting group; and $P_3$ is H or an amine protecting group.

The conditions and reagents for the method of fortieth embodiment are as described above in the twenty-fifth, thirty-second and/or thirty-fourth embodiment(s) and any specific embodiments described therein.

In a specific embodiment, for the methods of the thirty-eighth, thirty-ninth and fortieth embodiments, $P_3$ is H, the compound of formula (17d) or (17A) is reacted with the monomer of formula ($a_1$) to form a compound of formula (Id') or (IA) respectively.

In another specific embodiment, for the methods of thirty-eighth, thirty-ninth and fortieth embodiments, $P_3$ is an amine protecting group and the methods further comprise reacting the compound of formula (18d) or (18A) with an amine deprotecting reagent to form a compound of formula (Id') or (IA) respectively.

In a forty-first embodiment, the present invention provides a method of preparing a compound of formula (Id'),

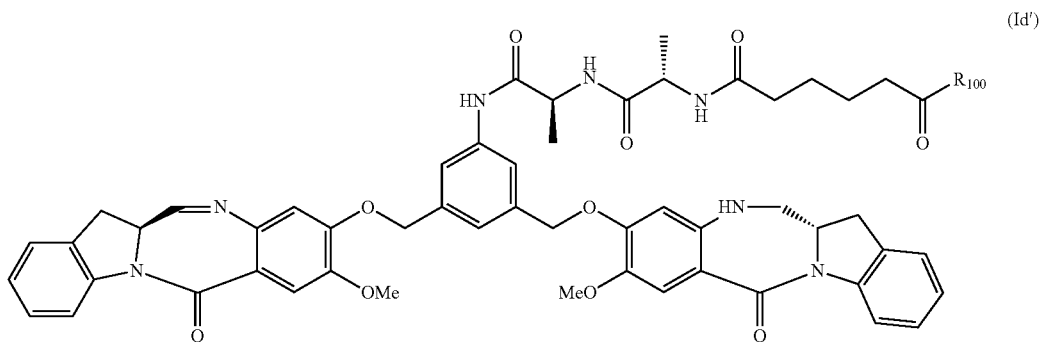

(Id')

or a pharmaceutically acceptable salt thereof, said method comprising the steps of:

(1) reacting a sulfonating reagent or an esterification reagent with the compound of formula (14d):

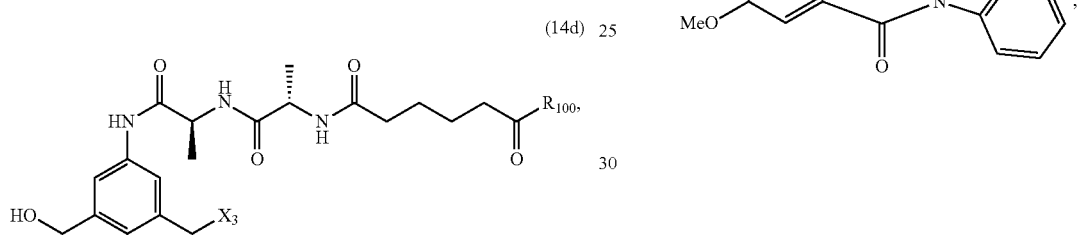

(14d)

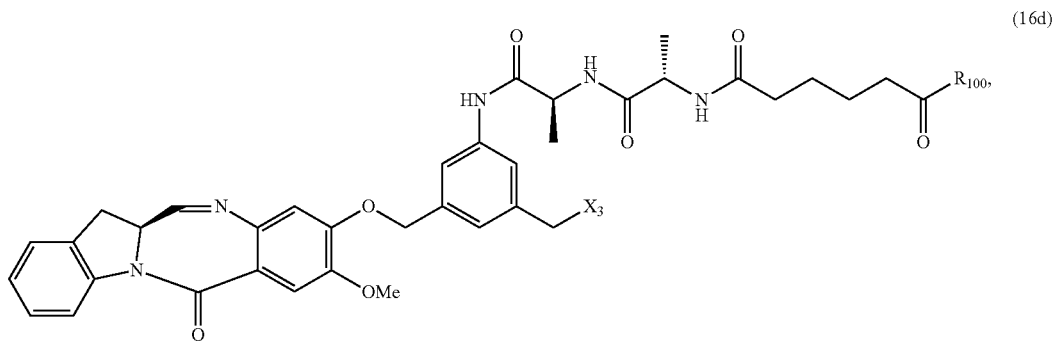

(a₁)

or a salt thereof, to form a compound of formula (15d):

(15d)

or a salt thereof;

(2) reacting the compound of formula (15d) with a monomer compound of formula (a₁), to form a compound of formula (16d):

(16d)

or a salt thereof;

(3) reacting the compound of formula (16d) with an imine reducing agent to form a compound of formula (17d'):

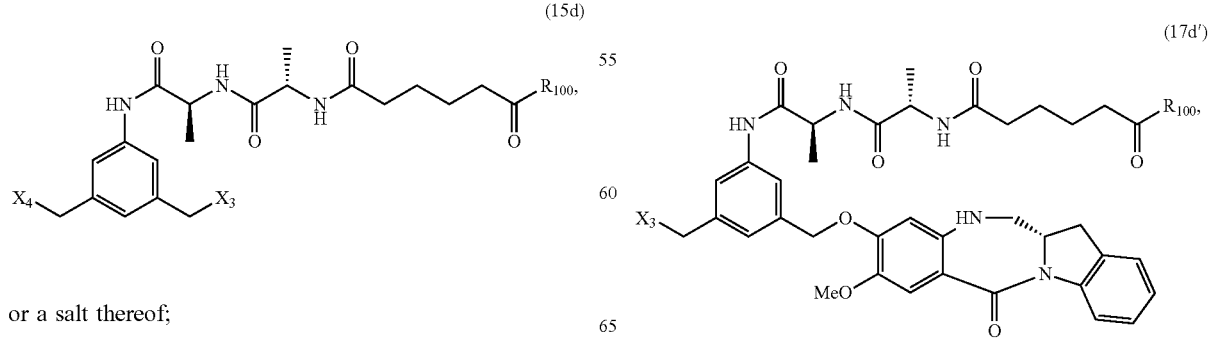

(17d')

or a salt thereof; and (4) reacting the compound of formula (17d') with a monomer of formula (a₁):

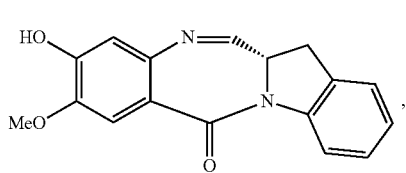

to form the compound of formula (Id'); wherein $X_3$ is —Cl; $X_4$ is a sulfonate ester or an activated ester; $P_1$ is an alcohol protecting group; $P_2$ is an amine protecting group; and $R_{100}$ is ($C_1$-$C_3$)alkoxy. In one embodiment, $X_4$ is a sulfonate ester.

Also provided in the forty-first embodiment is a method of preparing a compound of formula (IA),

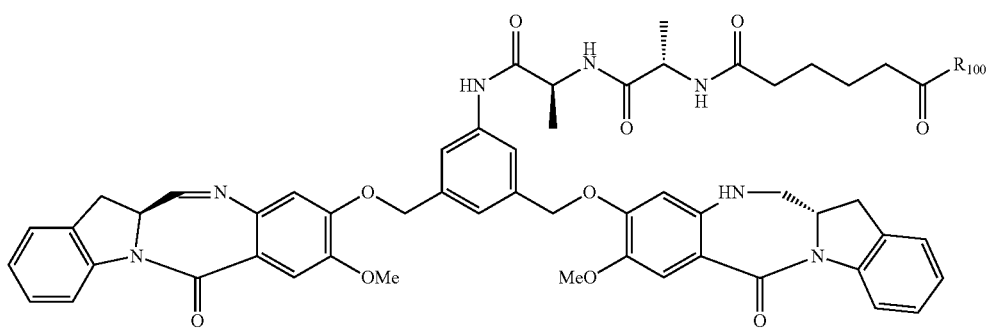

or a pharmaceutically acceptable salt thereof, said method comprising the steps of:

(1) reacting a sulfonating reagent or an esterification reagent with the compound of formula (14A):

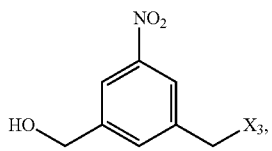

or a salt thereof, to form a compound of formula (15A):

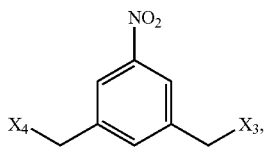

or a salt thereof;

(2) reacting the compound of formula (15A) with a monomer compound of formula (a₁),

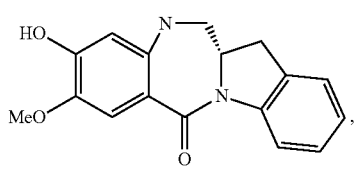

to form a compound of formula (16d):

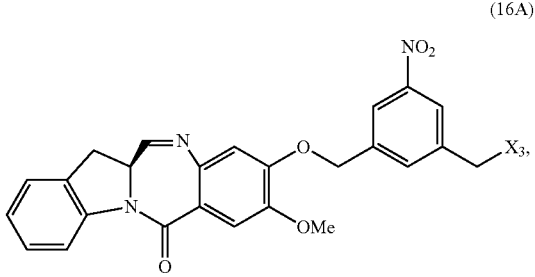

or a salt thereof;

(3) reacting the compound of formula (16A) with an imine reducing agent to form a compound of formula (17A'):

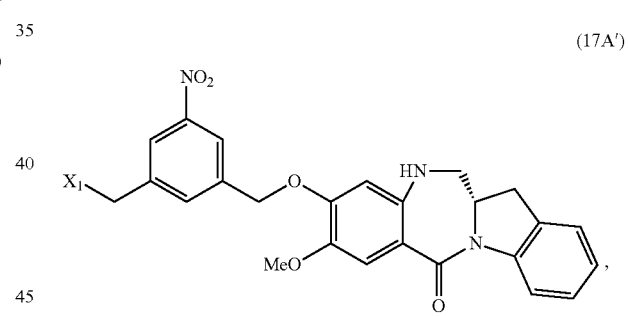

or a salt thereof; and (4) reacting the compound of formula (17A') with a monomer of formula (a₁):

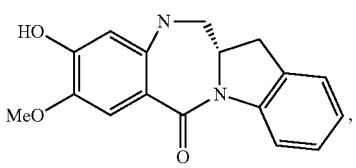

to form the compound of formula (IA); wherein $X_3$ is —Cl; $X_4$ is a sulfonate ester or an activated ester; $P_1$ is an alcohol protecting group; and $P_2$ is an amine protecting group. In one embodiment, $X_4$ is a sulfonate ester.

The conditions and reagents for the method of forty-first embodiment are as described above in the twenty-fourth, twenty-sixth and/or thirty-fourth embodiment(s) and any specific embodiments described therein.

In a forty-second embodiment, the present invention provides a method of preparing a compound of formula (Id'),

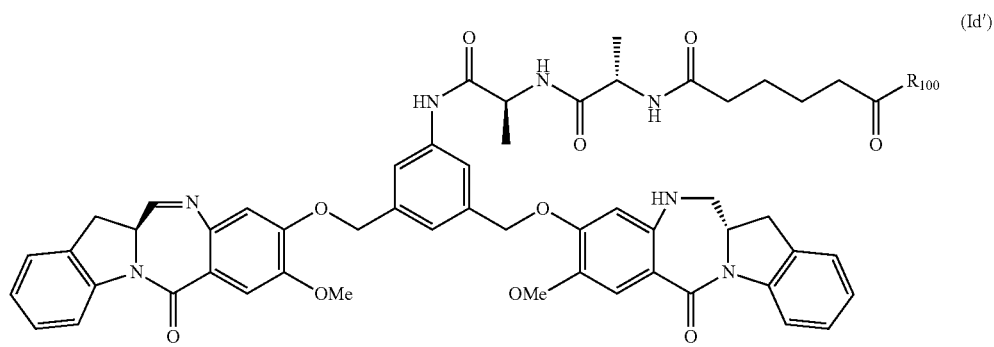

(Id')

or a pharmaceutically acceptable salt thereof, said method comprising the steps of:
(1) reacting the compound of formula (14d):

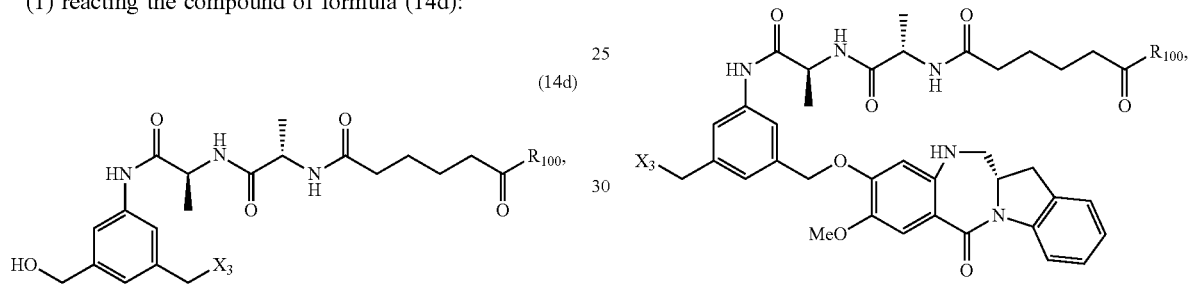

(14d)

or a salt thereof, with a monomer compound of formula (a₁),

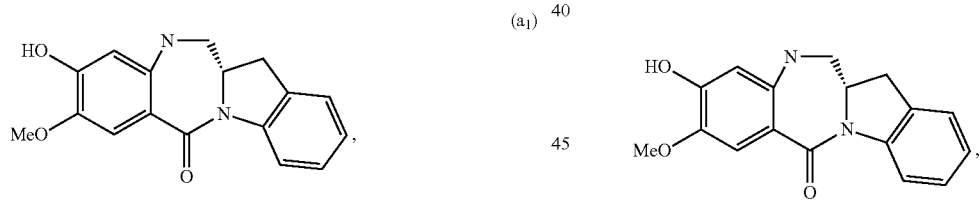

(a₁)

to form a compound of formula (16d):

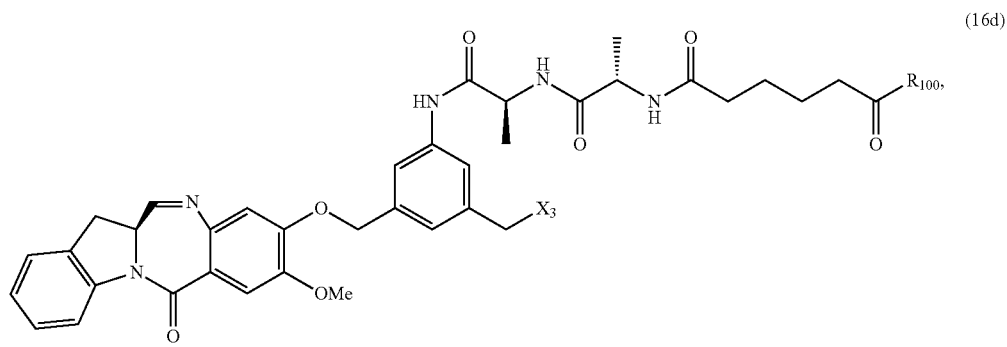

(16d)

or a salt thereof;

(2) reacting the compound of formula (16d) with an imine reducing agent to form a compound of formula (17d'):

(17d')

or a salt thereof; and
(3) reacting the compound of formula (17d') with a monomer of formula (a₁):

(a₁)

to form the compound of formula (Id'); wherein $X_3$ is —Cl; $P_1$ is an alcohol protecting group; and $R_{100}$ is $(C_1\text{-}C_3)$alkoxy.

Also provided in the forty-second embodiment is a method of preparing a compound of formula (IA),

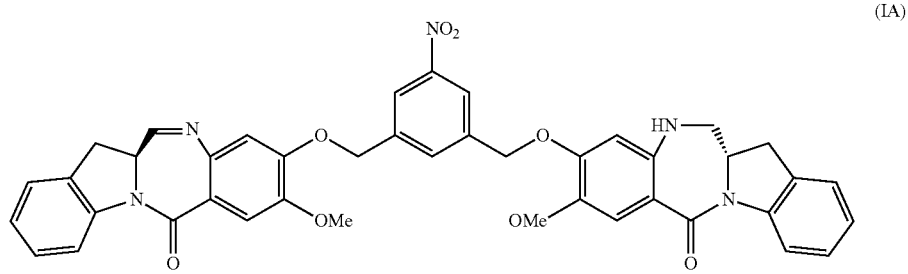 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]
(IA)

or a pharmaceutically acceptable salt thereof, said method comprising the steps of:

(1) reacting the compound of formula (14A):

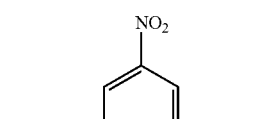
(14A)

or a salt thereof, with a monomer compound of formula $(a_1)$,

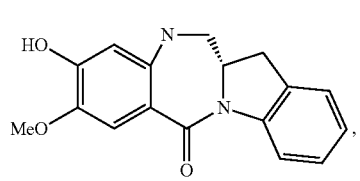
$(a_1)$ to form a compound of formula (16A):

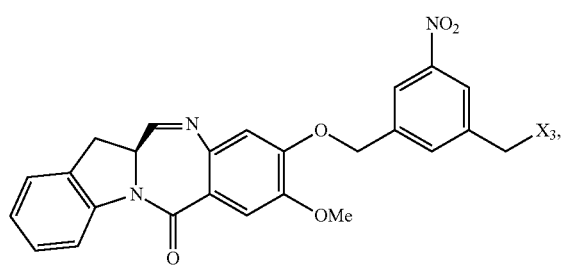
(16A)

or a salt thereof;

(2) reacting the compound of formula (16A) with an imine reducing agent to form a compound of formula (17A'):

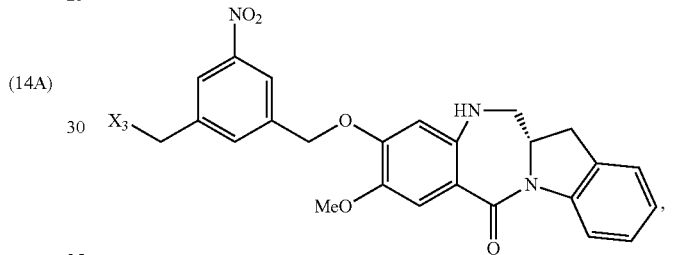
(17A')

or a salt thereof; and (3) reacting the compound of formula (17A') with a monomer of formula $(a_1)$:

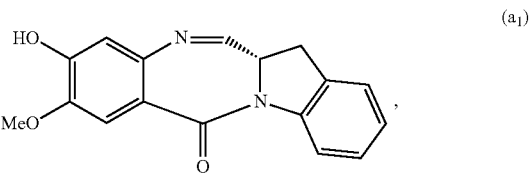 [SMILES: COc1cc2c(cc1O)N=C[C@@H]1Cc3ccccc3N1C2=O]
$(a_1)$ to form the compound of formula (IA); wherein $X_3$ is —Cl; and $P_1$ is an alcohol protecting group.

The conditions and reagents for the method of forty-second embodiment are as described above in the twenty-eighth, thirty-third and/or thirty-fourth embodiment(s) and any specific embodiments described therein.

In a forty-third embodiment, the present invention provides a method of preparing a compound of formula (Id'),

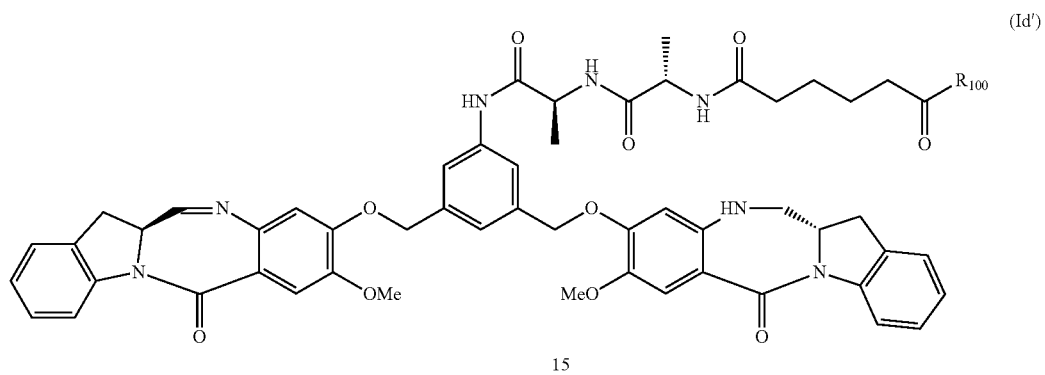

or a pharmaceutically acceptable salt thereof, said method comprising the steps of:

(1) reacting a halogenating reagent with the compound of formula (14d):

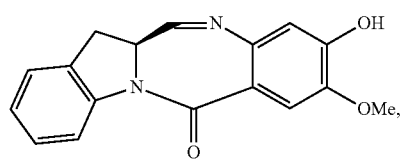

or a salt thereof, to form a compound of formula (20d):

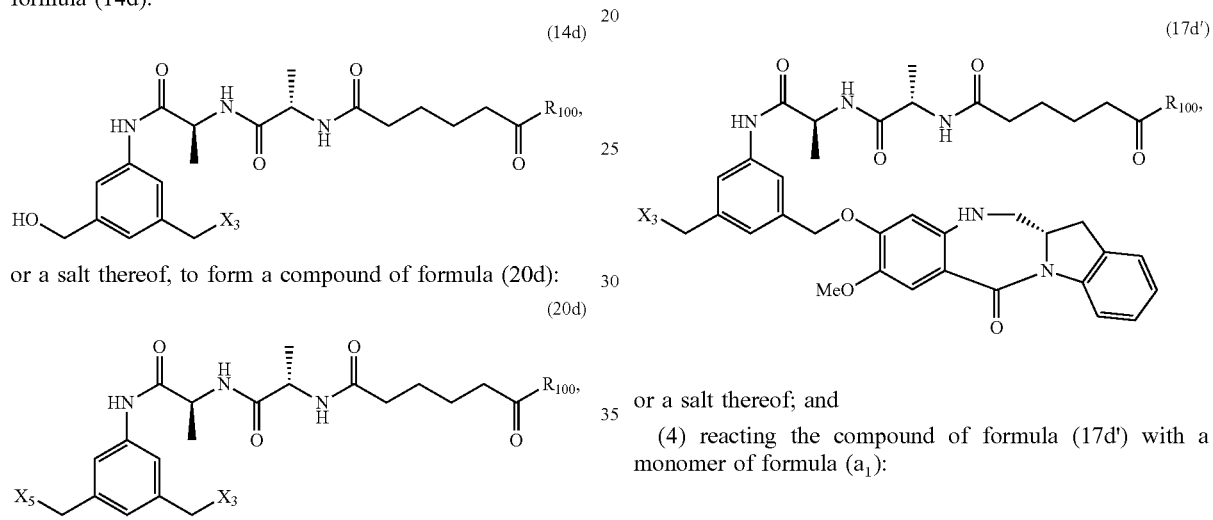

or a salt thereof;

(2) reacting a compound of formula (20d) or a salt thereof with a monomer compound of formula (a₁), to form a compound of formula (16d):

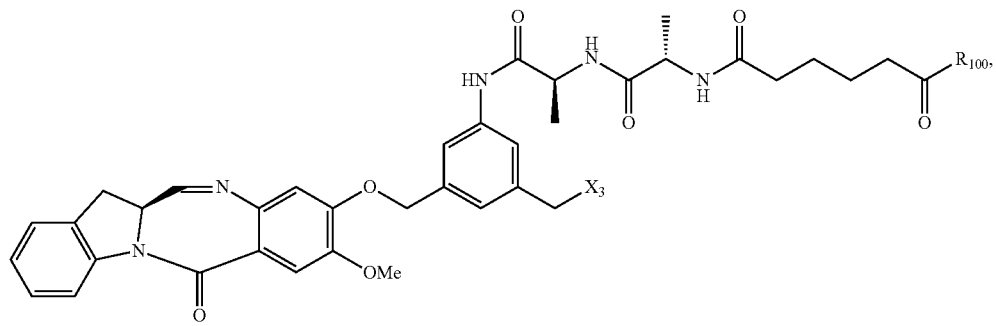

(3) reacting the compound of formula (16d) with an imine reducing agent to form a compound of formula (17d'):

or a salt thereof; and (4) reacting the compound of formula (17d') with a monomer of formula (a₁):

to form the compound of formula (Id'); wherein $X_3$ is —Cl; $X_5$ is —Br or —I; and $R_{100}$ is $(C_1$-$C_3)$alkoxy.

Also provided in the forty-third embodiment is a method of preparing a compound of formula (IA),

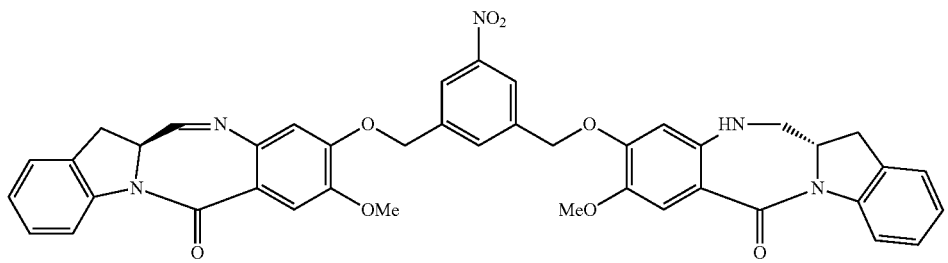

(IA)

or a pharmaceutically acceptable salt thereof, said method comprising the steps of:

(1) reacting a halogenating reagent with the compound of formula (14A):

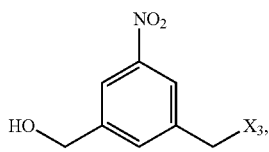

(14A)

or a salt thereof, to form a compound of formula (20d):

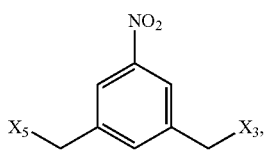

(20A)

or a salt thereof;

(2) reacting a compound of formula (20A) or a salt thereof with a monomer compound of formula ($a_1$),

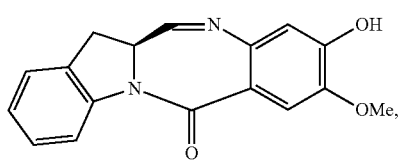

($a_1$)

to form a compound of formula (16A):

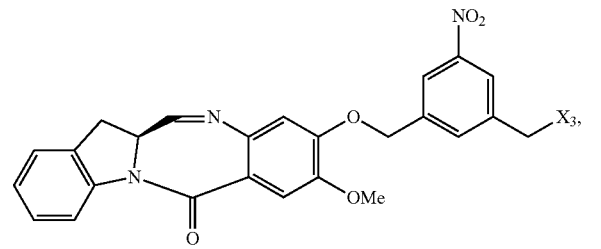

(16A)

(3) reacting the compound of formula (16A) with an imine reducing agent to form a compound of formula (17A'):

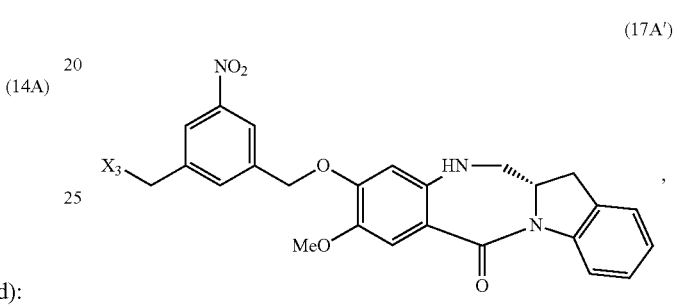

(17A')

or a salt thereof; and (4) reacting the compound of formula (17A') with a monomer of formula ($a_1$):

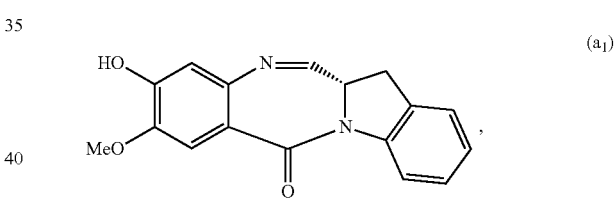

($a_1$)

to form the compound of formula (IA); wherein $X_3$ is —Cl.

The conditions and reagents for the method of the forty-third embodiment are as described above in the twenty-fifth, twenty-seventh, thirty-third and/or thirty-fourth embodiment(s) and any specific embodiments described therein.

In one embodiment, for methods of the thirty-fifth, thirty-sixth, thirty-seventh, thirty-eighth, thirty-ninth, fortieth, forty-first, forty-second and forty-third embodiments described above, the compound (14d) of a salt thereof is prepared a method comprising the following steps:

(1) reacting a chlorinating reagent with a compound of formula (2d),

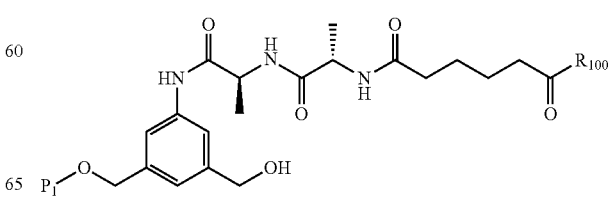

(2d)

to form a compound a compound of formula (13d),

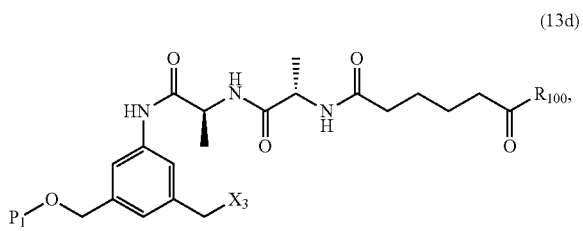
(13d)

or a salt thereof; and (2) reacting the compound of formula (13d) with an alcohol deprotecting reagent to form the compound of formula (14d) or a salt thereof, wherein $X_3$ is —Cl; and $P_1$ is an alcohol protecting group.

In another embodiment, for methods of the thirty-fifth, thirty-sixth, thirty-seventh, thirty-eighth, thirty-ninth, fortieth, forty-first, forty-second and forty-third embodiments described above, the compound (14A) of a salt thereof is prepared a method comprising the following steps:

(1) reacting a chlorinating reagent with a compound of formula (2A),

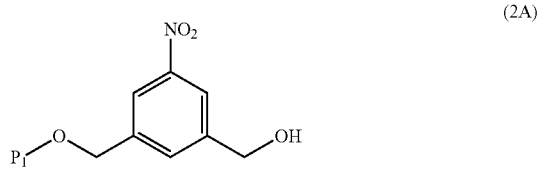
(2A)

to form a compound a compound of formula (13A),

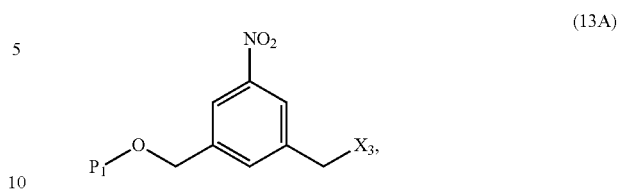
(13A)

or a salt thereof; and (2) reacting the compound of formula (13A) with an alcohol deprotecting reagent to form the compound of formula (14A) or a salt thereof.

The conditions and reagents for the method of preparing compound of formula (14d) or (14A) above are as described above in the twenty-second and/or twenty-third embodiment(s) and any specific embodiments described therein.

In another embodiment, for the methods described above, the compound of formula (2d) is prepared by reacting a compound of formula (1d) with an alcohol protecting reagent.

In another embodiment, for the methods described above, the compound of formula (2A) is prepared by reacting a compound of formula (1A) with an alcohol protecting reagent.

The conditions and reagents for the method of preparing compound of formula (2d) or (2A) above are as described above in the first embodiment and any specific embodiments described therein.

In a forth-fourth embodiment, the present invention provides a method of

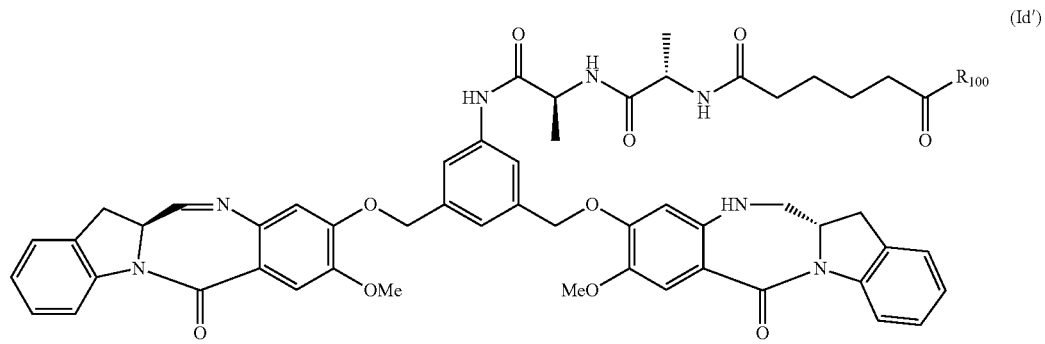
(Id')

or a pharmaceutically acceptable salt thereof, said method comprising the steps of:

(1) reacting a compound of formula (IA):

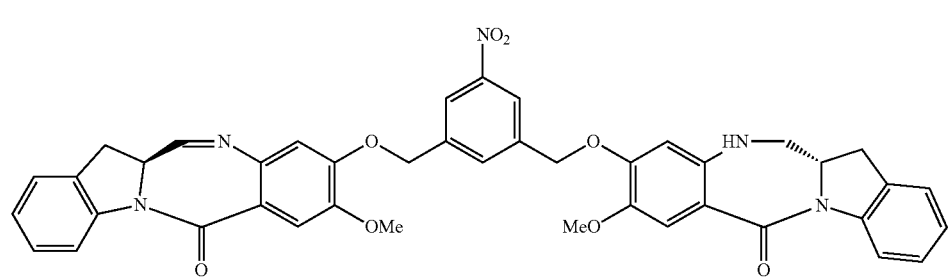
(IA)

with a reducing agent to form a compound of formula (IB):

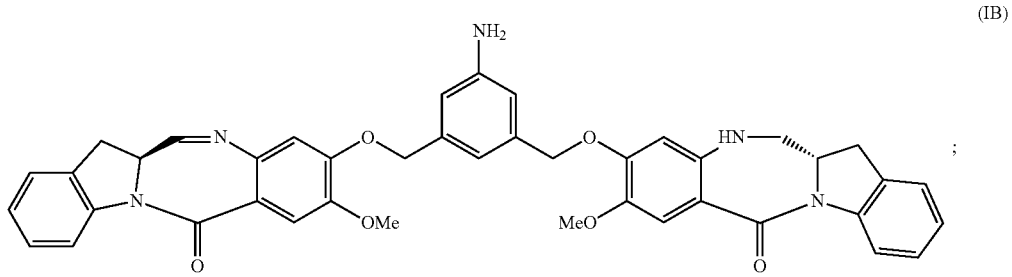 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

(IB)

and (2) reacting the compound of formula (IB) with a compound of formula (L1):

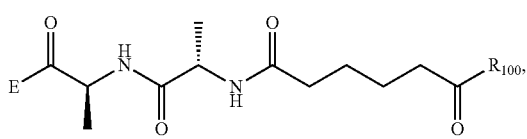

(L1)

to form the compound of formula (Id), wherein E is —OH, halide or —C(=O)E is an activated ester; and $R_{100}$ is $(C_1$-$C_3)$alkoxy.

Any reducing reagent that can convert a nitro (—$NO_2$) group to an amine (—$NH_2$) group can be used in step (1). In one embodiment, the reducing reagent is selected from the group consisting of: hydrogen gas, sodium hydrosulfite, sodium sulfide, stanneous chloride, titanium (II) chloride, zinc, iron and samarium iodide. In a specific embodiment, the reducing reagent is Fe/$NH_4Cl$ or Zn/$NH_4Cl$.

In a specific embodiment, for the method of forty-fourth embodiment, E is —OH and the reaction of the compound of formula (IB) and the compound of formula (L1) is carried out in the presence of an activating agent.

In one embodiment, the activating agent is a carbodiimide, a uronium, an active ester, a phosphonium, 2-alkyl-1-alkylcarbonyl-1,2-dihydroquinoline, 2-alkoxy-1-alkoxycarbonyl-1,2-dihydroquinoline, or alkylchloroformate. In a specific embodiment, the activating agent is a carbodiimide. In a more specific embodiment, the activating agent is dicyclohexylcarbodiimide (DCC), 1-ethyl-3-(3-dimethylaminopropyl)carbodiimide (EDC), or diisopropylcarbodiimide (DIC). In another specific embodiment, the activating agent is N-ethoxycarbonyl-2-ethoxy-1,2-dihydroquinoline.

In one embodiment, for methods described above, $R_{100}$ is methoxy.

The method of the present invention can also be any combination of the methods described above (e.g., methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighty, thirty-ninth, fortieth, forty-first, forty-second, forty-third and forty-fourth embodiment). For example, the combination of the methods of the first and second embodiments, the combination of methods of the first, second, and third embodiments, the combination of the methods of the fourth and fifth embodiments, the combination of the methods of the fourth, fifth and sixth embodiments, the combination of the methods of the sixth and eighth embodiments, the combination of the methods of thirteenth and fourteenth embodiments, the combination of the methods of thirteenth, fourteenth and fifteenth embodiments, and the combination of the methods of the seventeenth and eighteenth embodiments are also included in the present invention. The variable definitions described in any of the specific embodiments below also apply to any combination of methods described above.

The reactions described herein in the methods of the present invention can be carried out in any suitable solvent(s). In one embodiment, the solvent is an organic solvent. Exemplary organic solvents include, but are not limited to, dichloromethane, dichloroethane, DMF, DMA, acetone, acetonitrile, THF, DMSO, ethyl acetate etc., or a combination thereof.

The reactions described herein in the methods of the present invention can be carried out at any suitable temperature. In one embodiment, the reaction can be carried out at room temperature. In another embodiment, the reaction can carried out at a low temperature, such as 0° C. In yet another embodiment, the reaction can be carried out at an elevated temperature, such as about 40° C., about 50° C. etc.

In certain embodiment, the indolinobenzodiazepine dimer compound of formula (Id') and (IA) can be prepared according to Schemes 1-10 shown below, wherein L' is

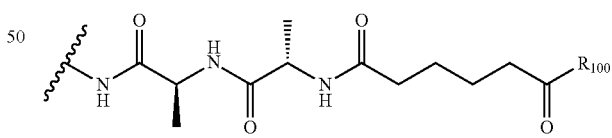

for formula (Id'); and —$NO_2$ for formula (IA). In one embodiment, $R_{100}$ is —OMe.

Scheme 1

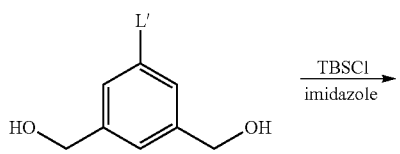

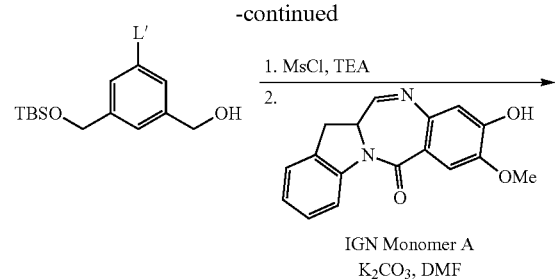
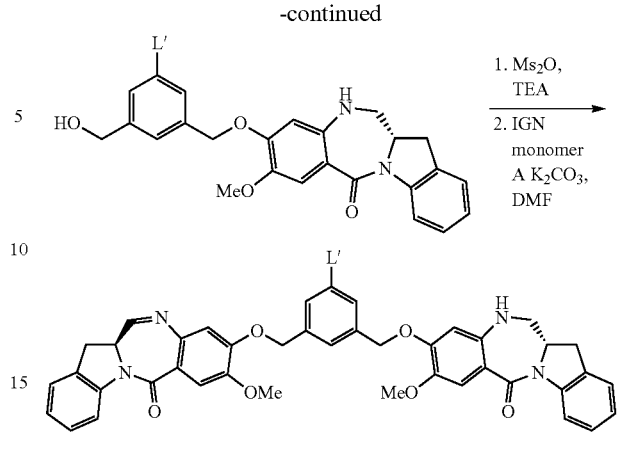
Scheme 2
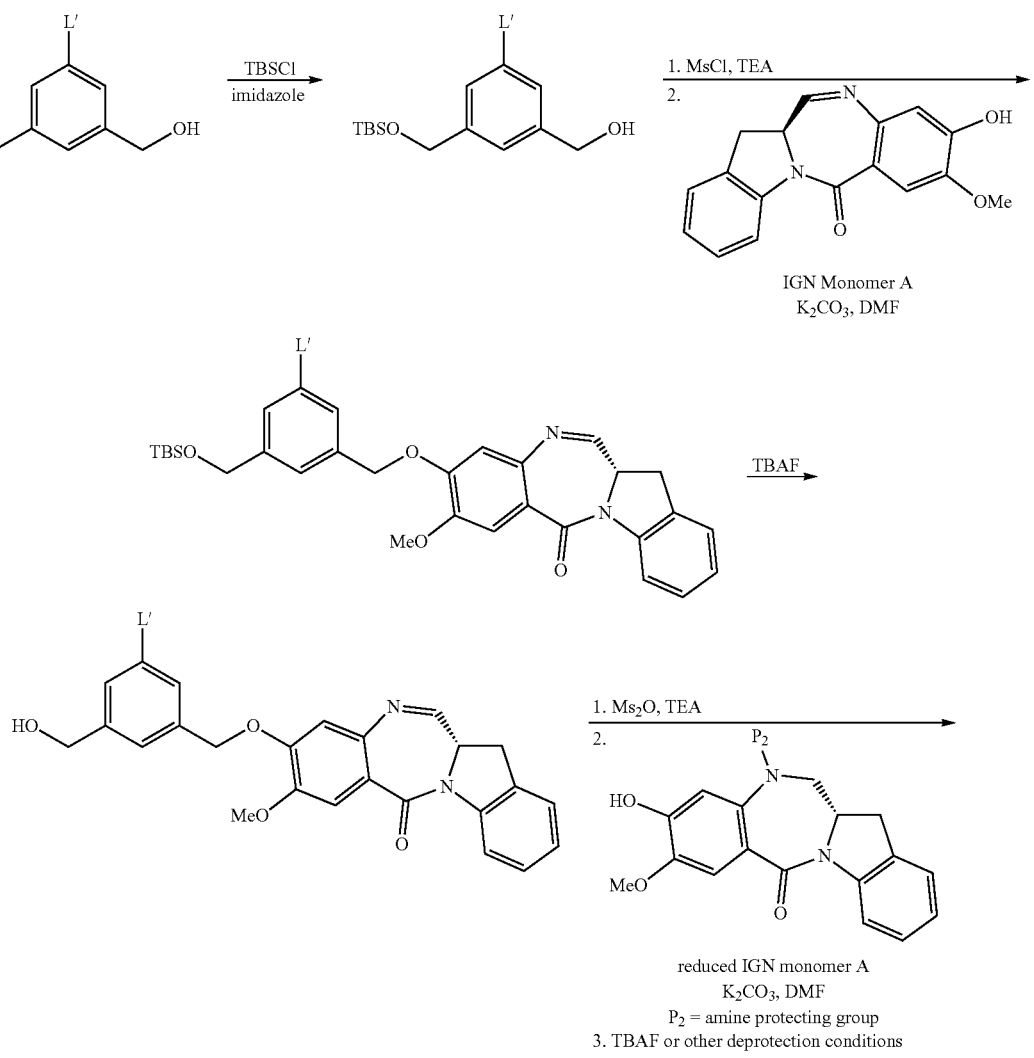

-continued
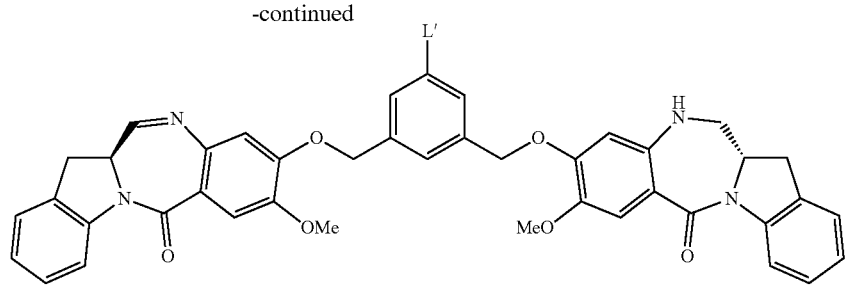
Scheme 3
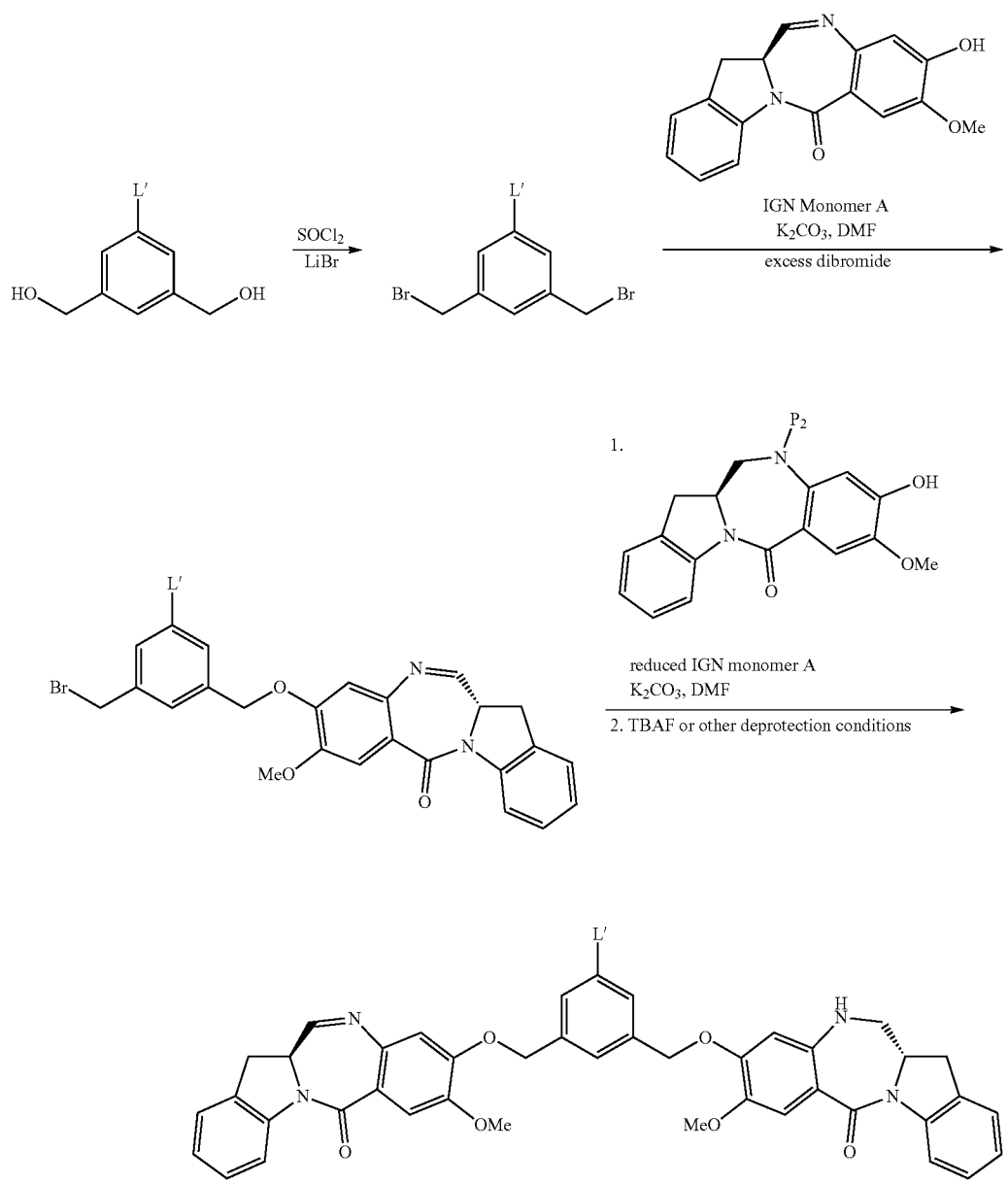

Scheme 4
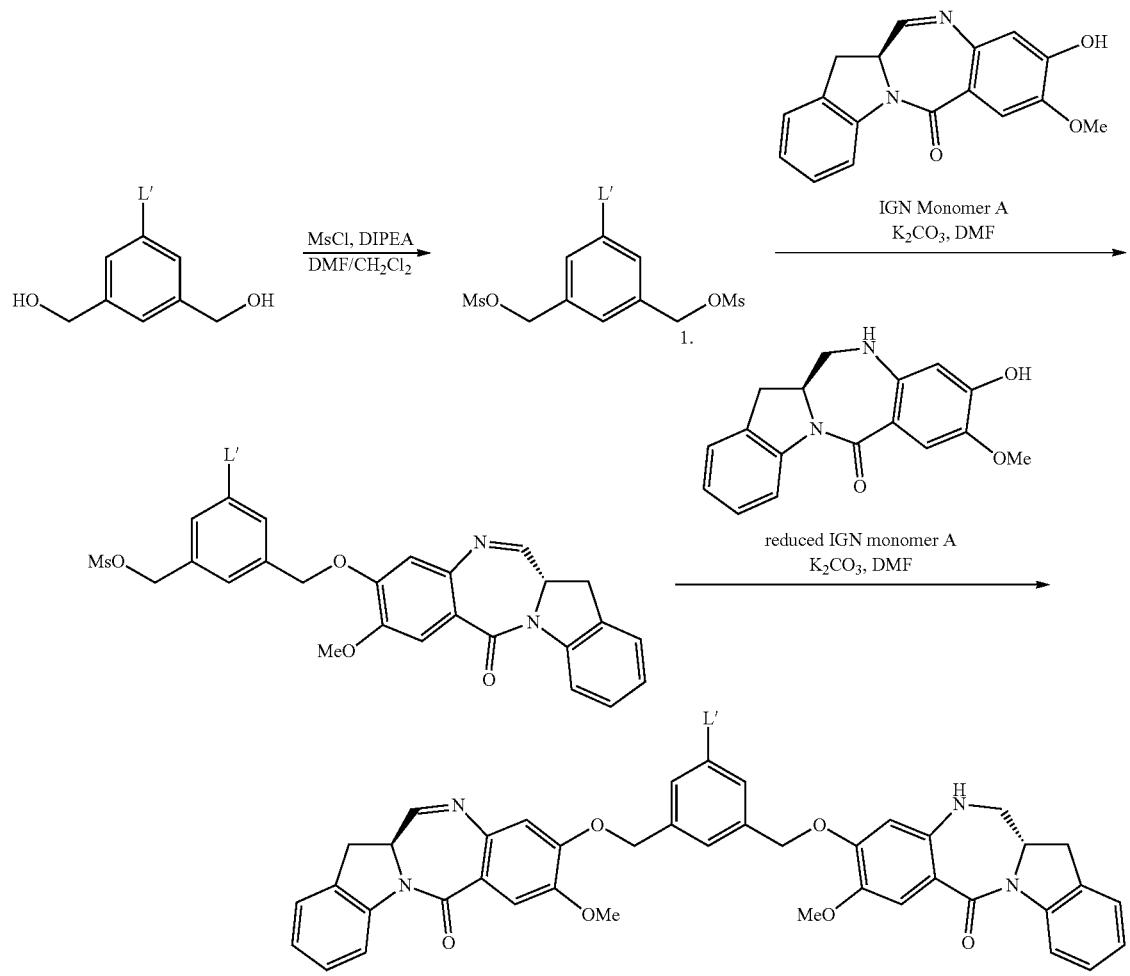
Scheme 5
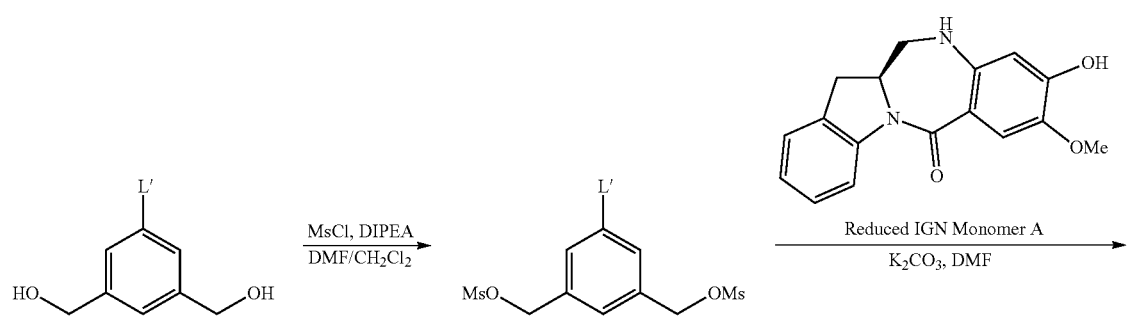

199 200
-continued
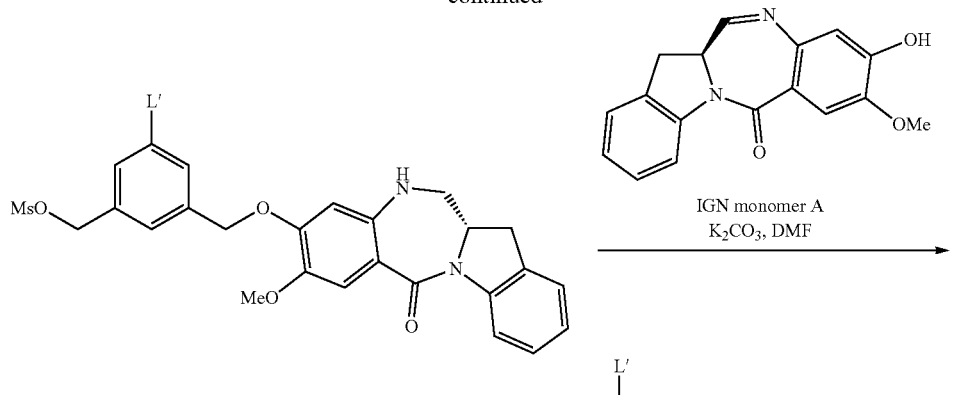
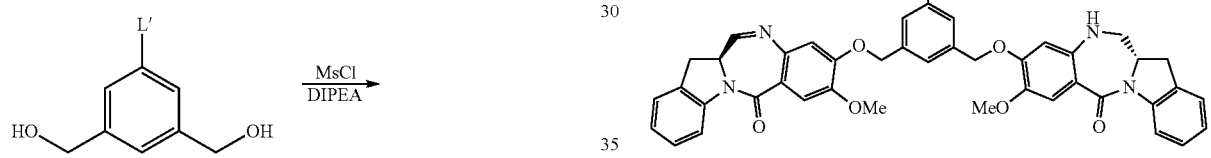
Scheme 6
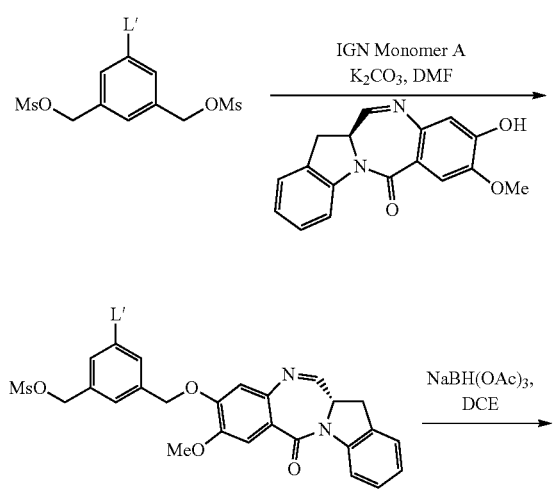
-continued
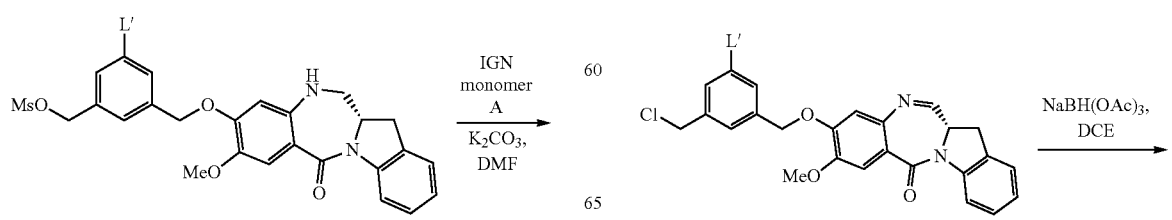
Scheme 7
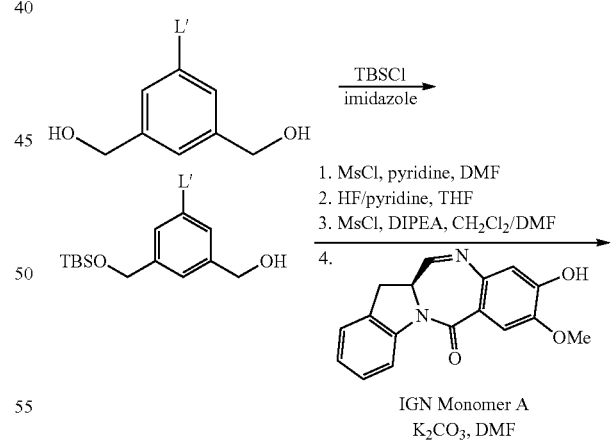

201
-continued
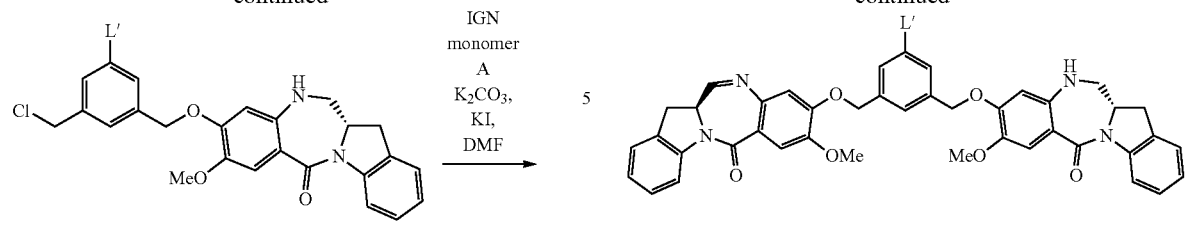
202
-continued
Scheme 8
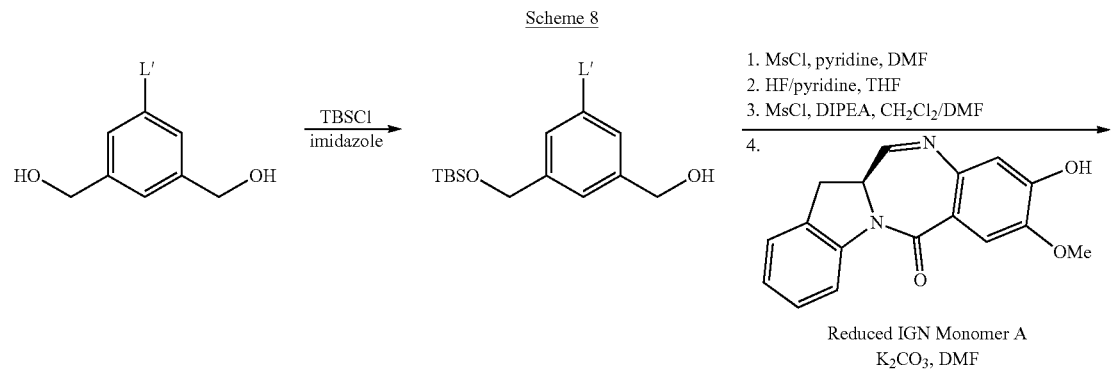
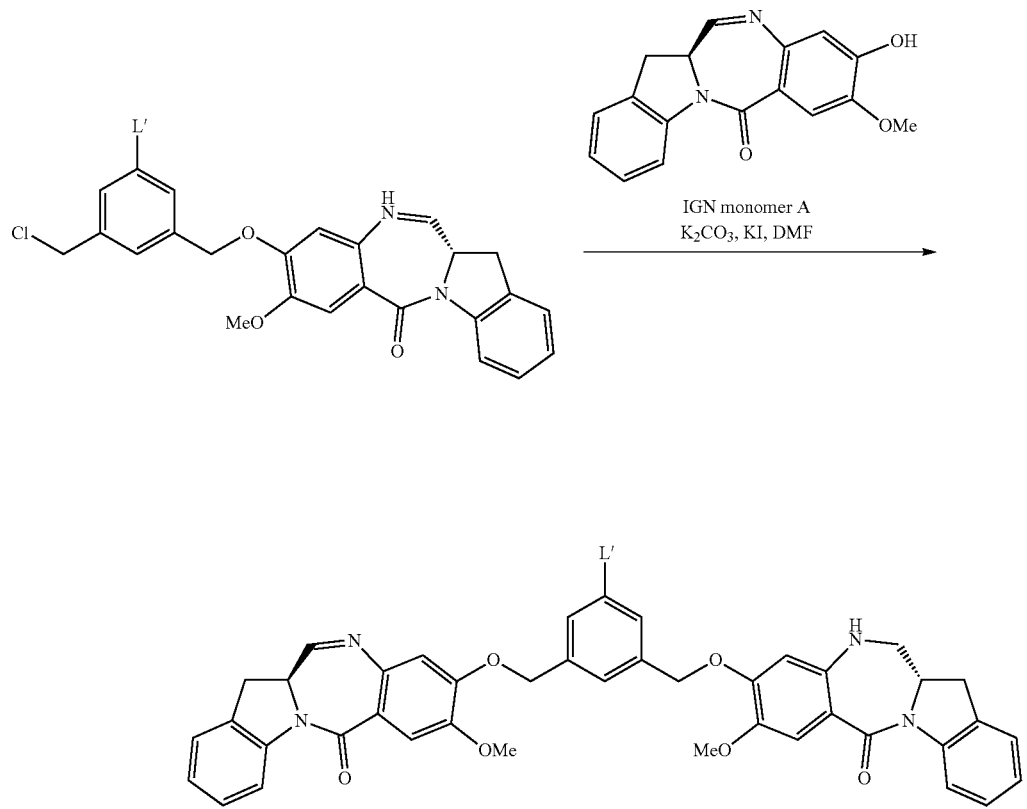

Scheme 9
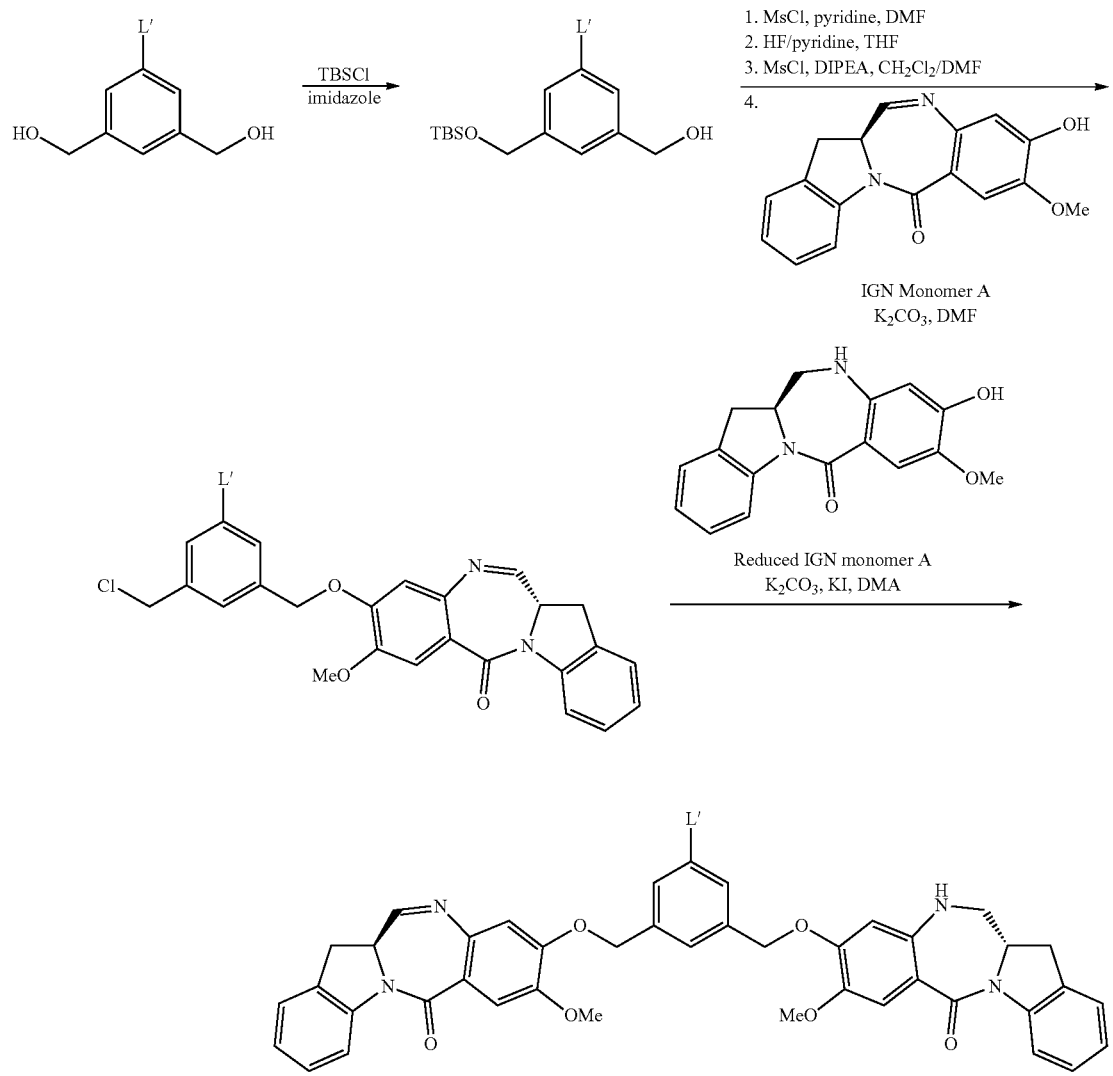
Scheme 10
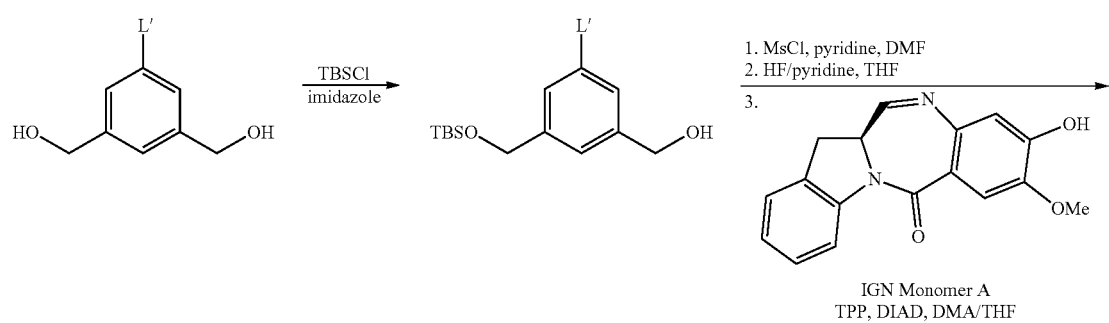

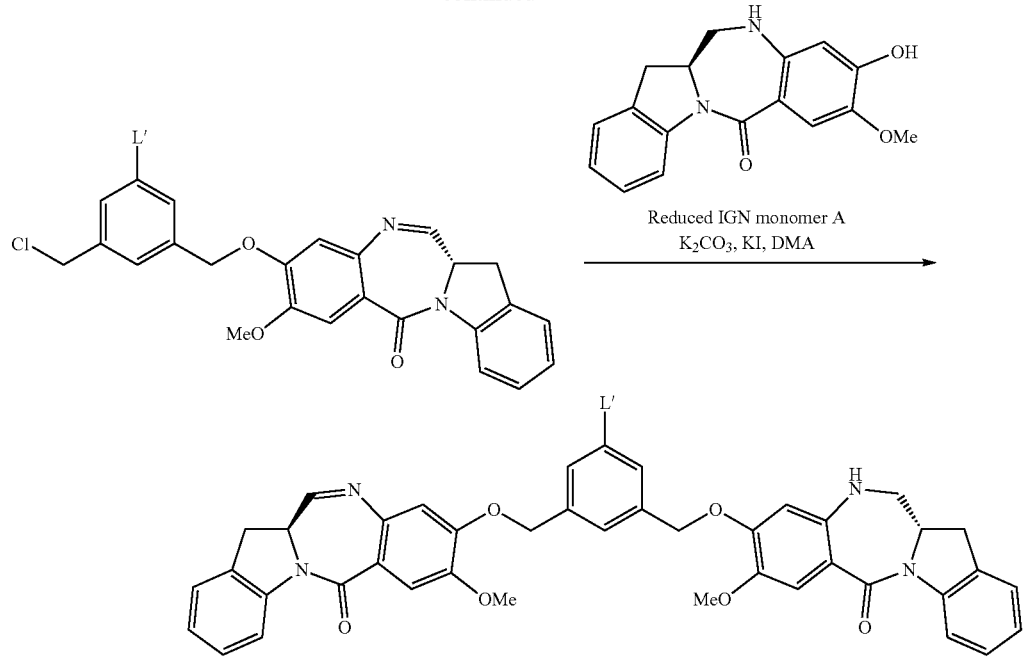
Scheme 11
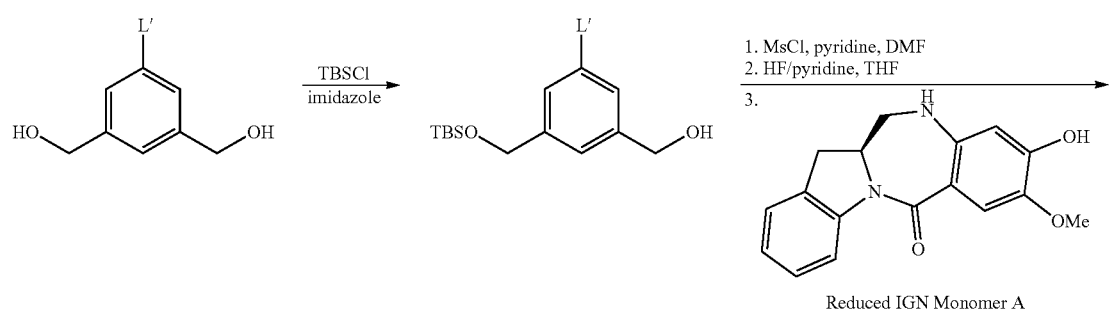
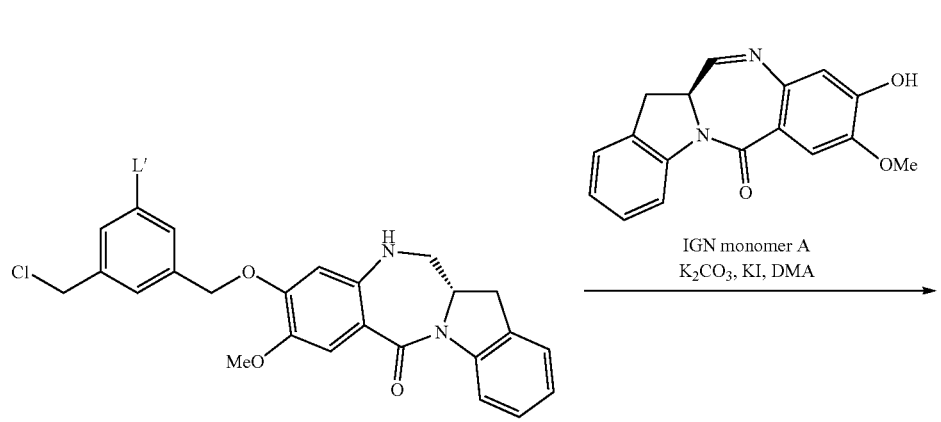

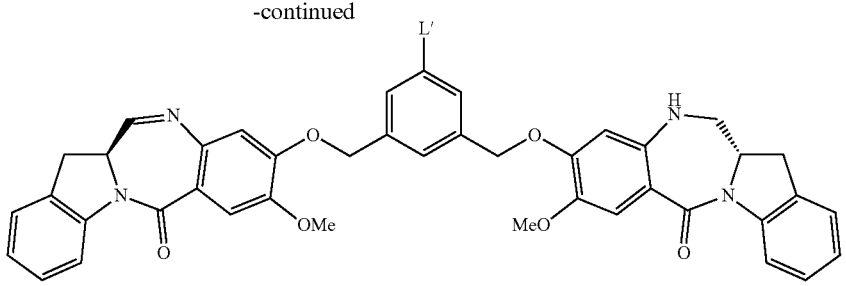

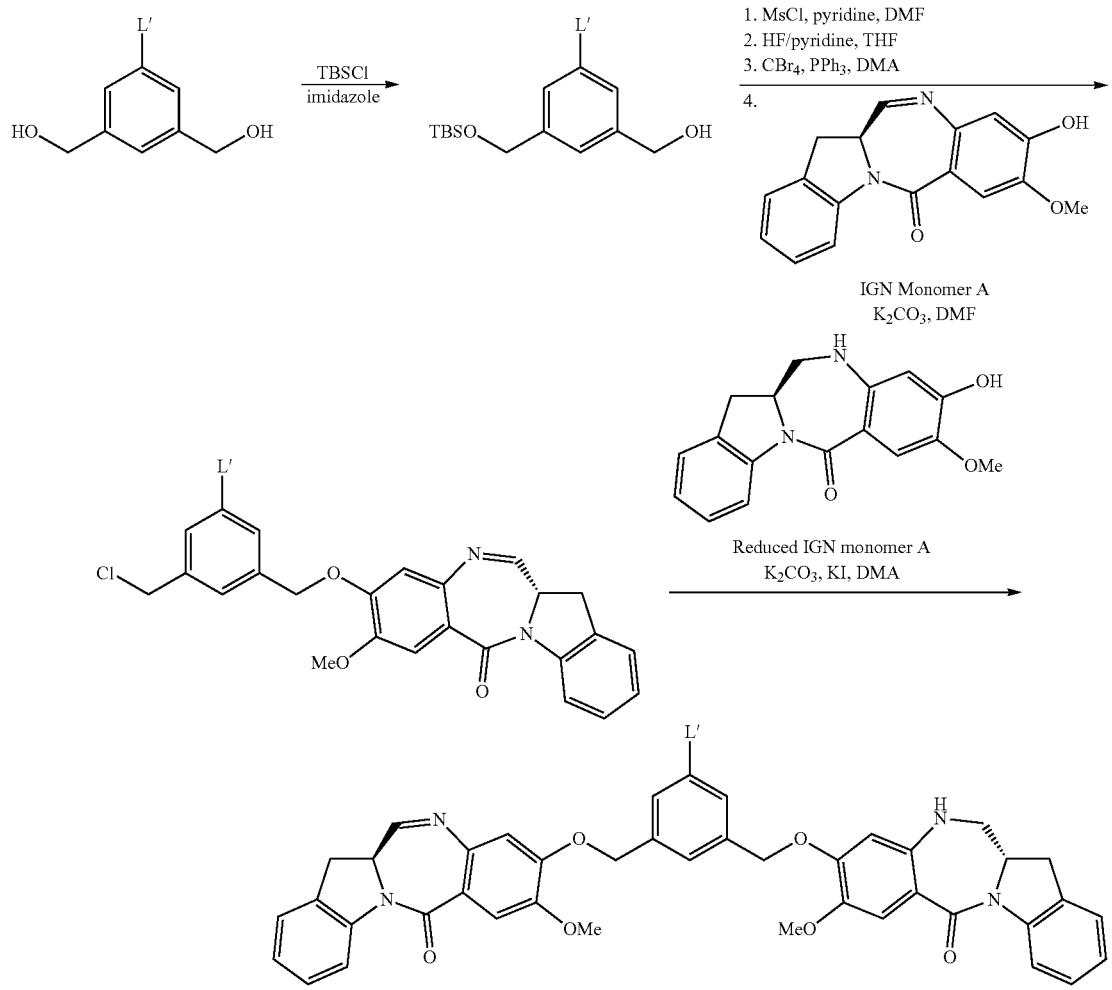

Scheme 12

Compounds of the Invention

The present invention also provides novel compounds described herein. In certain embodiments, the compounds of the present invention are compounds of formulas (1d), (1A), (2d), (2A), (2d"), (2A"), (3d), (3A), (3d"), (3A"), (4d), (4A), (4d"), (4A"), (5d), (5A), (5d"), (5A"), (6d), (6A), (7d), (7A), (7d'), (7A'), (7d1'), (7A1'), (7d"), (7A"), (7d'''), (7A'''), (9d), (9A), (10d), (10A), (10d'), (10A'), (11d), (11A), (12d), (12A), (13d), (13A), (14d), (14A), (15d), (15A), (16d), (16A), (17d), (17A), (17d'), (17A'), (18d), (18A), (20d), (20A), ($c_1$), ($d_1$), (Id'), (IA), and (IB), wherein the variables are as described above.

In a 1$^{st}$ specific embodiment, for compound of formula (1d), (2d), (2d"), (3d), (3d"), (4d), (4d"), (5d), (5d"), (6d), (7d), (7d'), (7d1'), (7d"), (7d'''), (9d), (10d), (10d'), (11d), (12d), (13d), (14d), (15d), (16d), (17d), (17d'), (18d), (20d), or (Id'), $R_{100}$ is —OMe.

In a 2$^{nd}$ specific embodiment, for compound of formula (2d), (3d), (4d), (5d), (13d), (2A), (3A), (4A), (5A), (13A), $P_1$ is a silyl protecting group; and the remaining variables are as described in first to forty-fourth embodiments or the 1$^{st}$ specific embodiment above. More specifically, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimetheythylsilyl (TEOC), or [2-(trimethylsilyl)ethoxy]methyl. Even more specifically, the silyl protecting group is triethylsilyl, triisopropylsilyl, or tert-butyldimethylsilyl. In another even more specific embodiment, the silyl protecting group is tert-butyldimethylsilyl.

In a 3$^{rd}$ specific embodiment, for compound of formula (3d), (3d"), (7d'), (7d1'), (12d), (10d'), (3A), (3A"), (7A'), (7A1'), (12A), or (10A'), $X_1$ is a sulfonate ester; and the remaining variables are as described above in the first to forty-fourth embodiments or in the 1$^{st}$ or 2$^{nd}$ specific embodiment. More specifically, the sulfonate ester is mesylate, tosylate, brosylate, or triflate. Even more specifically, the sulfonate ester is mesylate.

In a 4$^{th}$ specific embodiment, for compound of formula (3d), (3d"), (7d'), (7d1'), (12d), (10d'), (3A), (3A"), (7A'), (7A1'), (12A), or (10A'), $X_1$ is —Br or —I; and the remaining variables are as described above in the first to forty-fourth embodiments or in the 1$^{st}$ or 2$^{nd}$ specific embodiment. More specifically, $X_1$ is —Br.

In a 5$^{th}$ specific embodiment, for compound of formula (7d), (10d), (7A), or (10A), $X_2$ is a sulfonate ester; and the remaining variables are as described above in the first to forty-fourth embodiments or in the 1$^{st}$ specific embodiment. More specifically, the sulfonate ester is mesylate, tosylate, brosylate, or triflate. Even more specifically, the sulfonate ester is mesylate.

In a 6$^{th}$ specific embodiment, for compound of (7d") or (7A"), $X_2'$ is —Br or —I, and the remaining variables are as described above in the first to forty-fourth embodiments or in the 1$^{st}$ specific embodiment.

In a 7$^{th}$ specific embodiment, for the compound of formula (2d"), (3d"), (4d"), (5d"), (2A"), (3A"), (4A"), or (5A"), $P_1'$ is acetate, allyl, methoxymethyl, tetrahydrofuranyl, tetrahydropyranyl, 5-dibenzosuberyl, 1-ethoxyethyl, 1-methyl-1-methoxyethyl, 2-(phenylselenyl)ethyl, trityl/triphenylmethyl, or tris(4-tert-butylphenyl)methyl; and the remaining variables are as described above in the first to forty-fourth embodiments or in the 1$^{st}$, 3$^{rd}$, or 4$^{th}$ specific embodiment. In another specific embodiment, $P_1'$ is a silyl protecting group; the remaining variables are as described above in the first to forty-fourth embodiments or in the 1$^{st}$, 3$^{rd}$, or 4$^{th}$ specific embodiment. In a more specific embodiment, $P_1'$ is dimethylisopropylsilyl, diethylisopropylsilyl, dimethylhexylsilyl, trimethylsilyl, triethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl(TEOC), or [2-(trimethylsilyl)ethoxy]methyl. Even more specifically, $P_1'$ is triethylsilyl, triisopropylsilyl, or tert-butyldimethylsilyl. In another more specific embodiment, $P_1'$ is tert-butyldimethylsilyl.

In a 8$^{th}$ specific embodiment, for the compound of formula (13d), (14d), (15d), (16d), (17d), (17d'), (20d), (13A), (14A), (15A), (16A), (17A), (17A'), or (20A), $X_3$ is chlorine; and the remaining variables are as described above in the first to forty-fourth embodiments or in the 1$^{st}$ or 2$^{nd}$ specific embodiment.

In a 9$^{th}$ specific embodiment, for the compound of formula (15d) or (15A), $X_4$ is a sulfonate ester; and the remaining variables are as described above in the first to forty-fourth embodiments or in the 1$^{st}$ or 8$^{th}$ specific embodiment. More specifically, the sulfonate ester is mesylate, tosylate, brosylate, or triflate. Even more specifically, the sulfonate ester is mesylate.

In a 10$^{th}$ specific embodiment, for the compound of formula ($c_1$), (11d) or (11A), $P_2$ is an amine protecting group selected from 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, and 2, 2,2,2-trichloroethoxycarbonyl; and the remaining variables are as described above in the first to forty-fourth embodiments or in the 1$^{st}$ specific embodiment.

In a 11$^{th}$ specific embodiment, for the compound of formula ($d_1$), (7d1'), (17d), (18d), (7A1'), (17A) or (18A), $P_3$ is H or an amine protecting group selected from 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2, 2,2,2-trichloroethoxycarbonyl; and the remaining variables are as described above in the first to forty-fourth embodiments or in the 1$^{st}$ or 8$^{th}$ specific embodiment.

In a 12$^{th}$ specific embodiment, for the compound of (20d) or (20A), $X_5$ is —Br; and the remaining variables are as described above in the first to forty-fourth embodiments or in the 1$^{st}$ or 8$^{th}$ specific embodiment.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument and LCMS were acquired on an Agilent 1260 Infinity LC with an Agilent 6120 single quadrupole MS using electrospray ionization and UPLC were acquired on a Waters, Acquity system with a single quadrupole MS Zspray™ (column: Acquity BEH C18, 2.1 ×50 mm, 1.7 μm, method: 2.5 min, flow rate 0.8 mL/min, solvent A: water, solvent B: MeCN, 5 to 95% of MeCN over 2.0 mm and 95% MeCN for 0.5 mm).

The following solvents, reagents, protecting groups, moieties and other designations may be referred to by their abbreviations in parenthesis:

Me=methyl; Et=ethyl; Pr=propyl; i-Pr=isopropyl; Bu=butyl; t-Bu=tert-butyl; Ph =phenyl, and Ac=acetyl
AcOH or HOAc=acetic acid
ACN or CH$_3$CN=acetonitrile
Ala=alanine
Ar=argon
aq=aqueous
Bn=benzyl
Boc or BOC=tert-butoxycarbonyl
CBr$_4$=carbontetrabromide
Cbz or Z=benzyloxycarbonyl
DCM or CH$_2$Cl$_2$=dichloromethane
DCE=1,2-dichloroethane
DMAP=4-dimethylaminopyridine
DI water=deionized water
DIBAL=diisobutylaluminum hydride
DIEA or DIPEA=N,N-diisopropylethylamine
DMA=N,N-dimethylacetamide
DMF=N,N-dimethylformamide
DMSO=dimethyl sulfoxide
DTT=dithiothreitol
EDC=1-ethyl-3-(3-dimethylaminopropyflcarbodiimide EEDQ=N-Ethoxycarbonyl-2-ethoxy-1,2-dihydroquinoline
ESI or ES=electrospray ionization
EtOAc=ethylacetate
Gly=glycine
g=grams
h=hour
HATU=N,N,N'N'-tetramethyl-O-(7-azabenzotriazol-1-yl) uronium hexaphosphate
HPLC=high-performance liquid chromatography
HOBt or HOBT=1-hydroxybenzotriazole
LAH=lithium aluminum hydride
LC=liquid chromatography
LCMS=liquid chromatography mass spectrometry
min=minutes
mg=miligrams
mL=mililiters
mmol=milimoles
μg=micrograms
μL=microliters
μmol=micromoles
Me=methyl
MeOH=methanol
MeI=methyliodide
MS=mass spectrometry
MsCl=methanesulfonyl chloride (mesyl chloride)
Ms$_2$O=methanesulfonic anhydride
MTBE=Methyl tert-butyl ether
NaBH(OAc)$_3$=sodium triacetoxyborohydride
NHS=N-hydroxysuccinamide
NMR=nuclear magnetic resonance spectroscopy
PPh$_3$=triphenylphosphine
PTLC=preparative thin layer chromatography
rac=racemic mixture
R$_f$=retardation factor
RPHPLC or RP-HPLC=reverse phase high-performance liquid chromatography
RT or rt=room temperature (ambient, about 25° C.)
sat or sat'd=saturated
STAB=sodium triacetoxyborohydride (NaBH(OAc)$_3$)
TBSCl or TBDMSCl=tert-butyldimethylsilyl chloride
TBS=tert-butyldimethylsilyl
TCEP.HCl=tris(2-carboxyethyl)phosphine hydrochloride salt
TEA=triethylamine (Et$_3$N)
TFA=trifluoroacetic acid
THF=tetrahydrofuran
TLC=thin layer chromatography Example 1

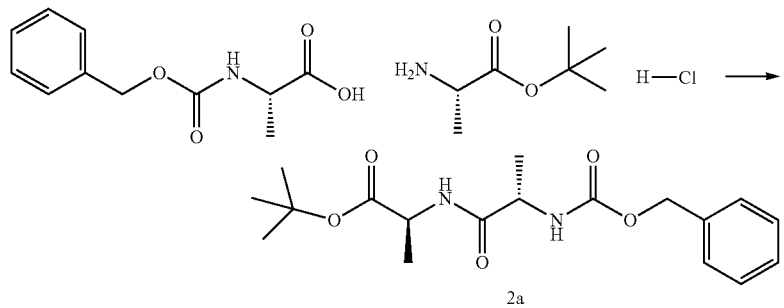

(S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC.HCl (4.72 g, 24.64 mmol), HOBt (3.43 g, 22.40 mmol), and DIPEA (9.75 mL, 56.0 mmol) were added. The reaction stirred under argon, at room temperature overnight. The reaction mixture was diluted with dichloromethane and then washed with saturated ammonium chloride, saturated sodium bicarbonate, water, and brine. The organic layer was dried over sodium sulfate and concentrated. The crude oil was purified by silica gel chromatography (Hexanes/Ethyl Acetate) to yield compound 2a (6.7 g, 85% yield). $^1$H NMR (400 MHz, CDCl$_3$): δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

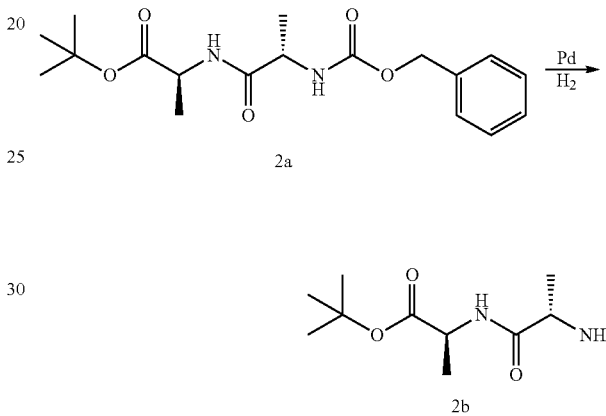

Compound 2a (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 2b (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

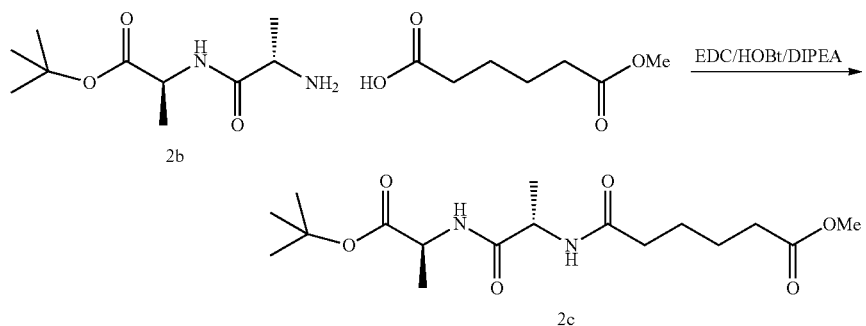

Compound 2b (4.02 g, 18.59 mmol) and mono methyl-adipate (3.03 mL, 20.45 mmol) were dissolved in anhydrous DMF (62.0 mL). EDC.HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and concentrated. The compound was azeotroped with acetonitrile (5×), then pumped on the high vacuum at 35° C. to give compound 2c (6.66 g, 100% yield). The crude material was taken onto next step without purification. ¹H NMR (400 MHz, CDCl₃): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

Compound 2c (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 2d as a sticky solid (5.88 g, 100% yield). ¹H NMR (400 MHz, CDCl₃): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

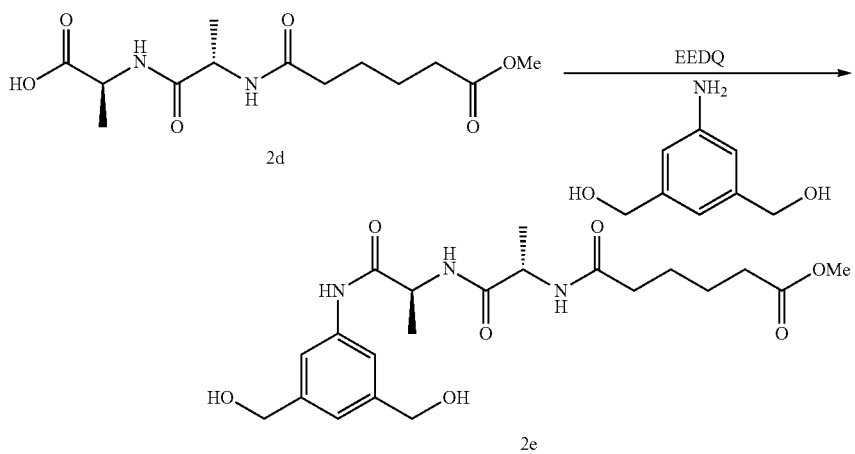

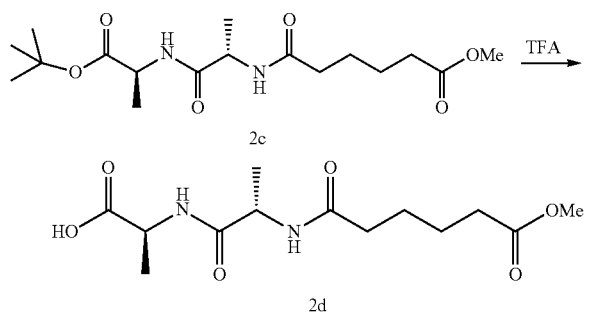

Compound 2d (5.6 g, 18.52 mmol) was dissovled in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature overnight. The solvent was concentrated and ethyl acetate was added. The resulting slurry was filtered, washed with ethyl acetate and dried under vacuum/N₂ to give compound 2e (2.79 g, 36% yield). ¹H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

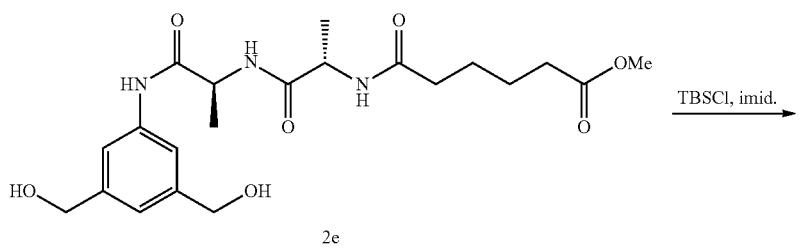

2e

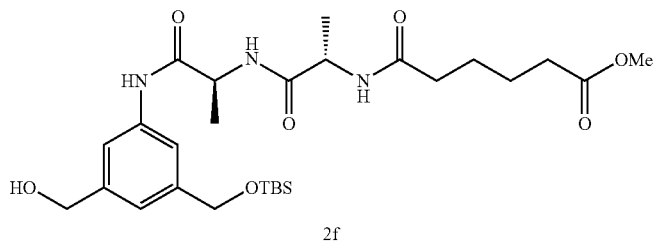

2f

Diol 2e (1.0 g, 2.286 mmol) was dissolved in anhydrous DMF (7.6 mL). TBSCl (0.482 g, 3.20 mmol) and imidazole (0.467 g, 6.86 mmol) were added and the reaction was stirred at room temperature for 2 hrs. The reaction was quenched with saturated ammonium chloride and diluted with water and EtOAc. The aqueous layer was extracted once with EtOAc and the combined organic layers were washed with water and brine, dried over sodium sulfate, filtered and concentrated. The crude residue was purified by silica gel flash chromatography (DCM/MeOH) to obtain compound 2f (360 mg, 28% yield). LCMS (8 min method, 40-98%)=2.35 min. Mass observed (ESI$^+$): 574.4 (M+Na)$^+$.

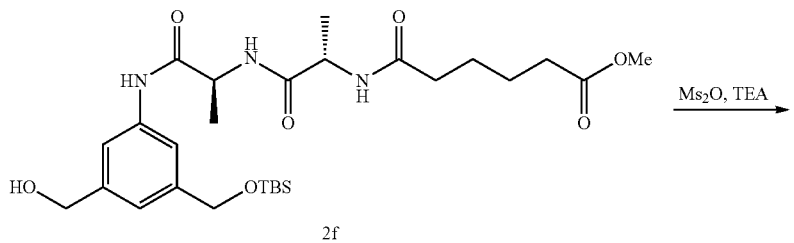

2f

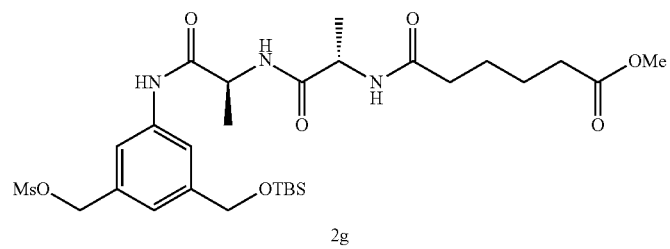

2g

Compound 2f (360 mg, 0.652 mmol) was dissolved in anhydrous dichloromethane (6.52 mL) and cooled in an acetone/ice bath. Triethylamine (227 μL, 1.631 mmol) and methanesulfonic anhydride (146 mg, 0.816 mmol) were added. The reaction stirred at −10° C. in the acetone/ice bath for 1 hr. The reaction was diluted with cold EtOAc and quenched with ice water. The organic layer was washed with ice water and then dried over sodium sulfate and magnesium sulfate, filtered and concentrated to give crude compound 2g as a fluffy solid (390 mg, 95% yield). LCMS (8 min method, 40-98%)=2.81 min; 5.86 min (8 min method, 5-98%). Mass observed (ESI$^-$): 628.0 (M−H)$^-$.

217

218

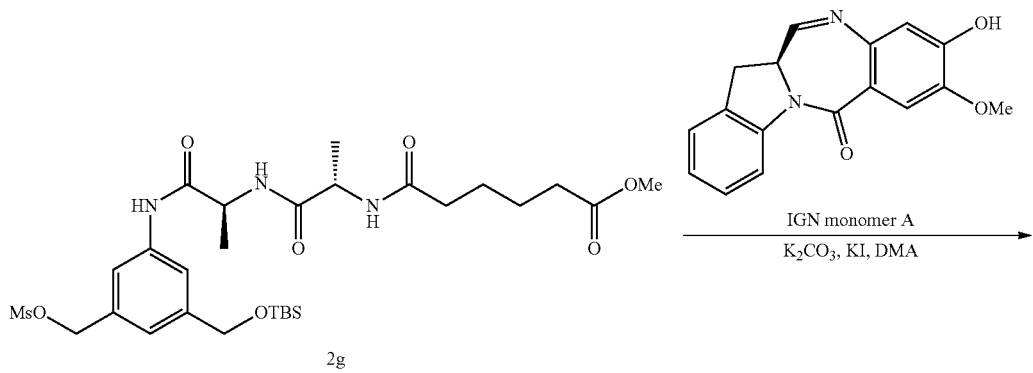

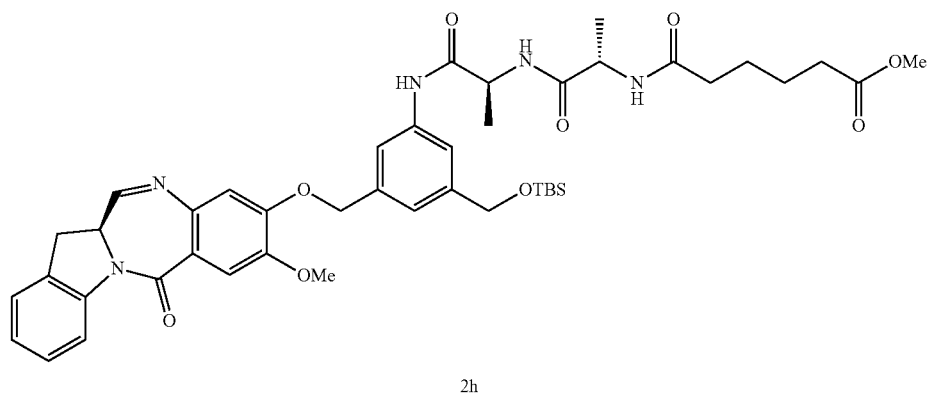

Mesylate 2g (390 mg, 0.619 mmol) and IGN monomer A (264 mg, 0.897 mmol) were dissolved in anhydrous DMA (7.47 mL). Potassium carbonate (207 mg, 1.495 mmol) and potassium iodide (51.4 mg, 0.310 mmol) were added and the reaction was stirred overnight at room temperature. The reaction was precipitated with water, filtered and the filter cake washed with water. The solid was redissolved in DCM, washed with water, dried over magnesium sulfate and concentrated to give crude compound 2h (568 mg, 111% yield). The product was carried on without further purification. LCMS (8 min method, 5-98%)=6.23 min. Mass observed (ESI$^+$): 827.8 (M+H)$^+$.

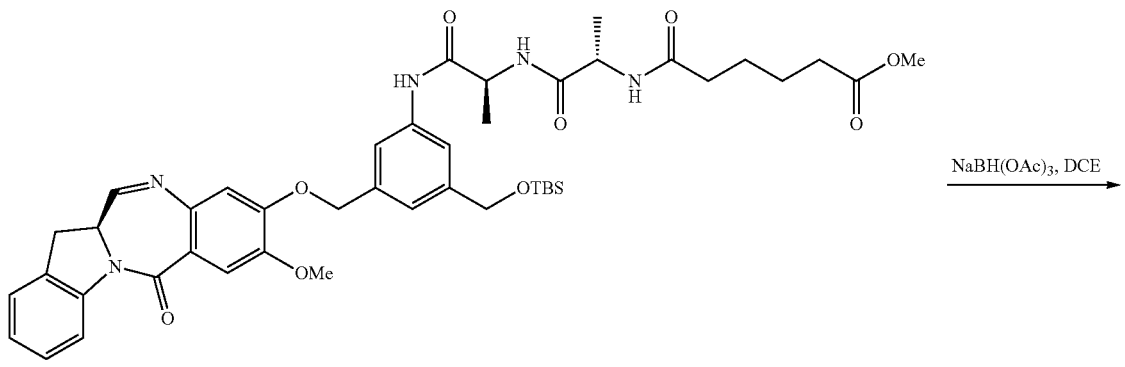

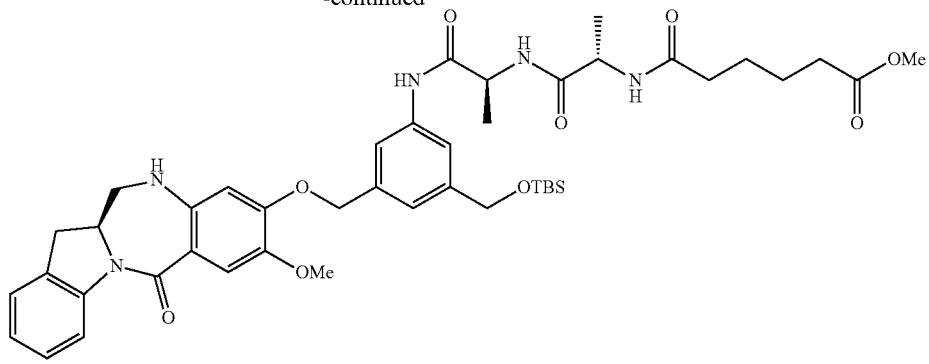

2i

Compound 2h (0.513 g, 0.619 mmol) was dissolved in DCE (7.74 mL). NaBH(OAc)₃ (0.276 g, 1.239 mmol) was added and the mixture stirred at room temperature for 1.5 h. The reaction was diluted with DCM, quenched with saturated ammonium chloride and washed with brine. The organic layer was dried over magnesium sulfate, filtered and concentrated to give compound 2i. LCMS (15 min method)=9.93 min

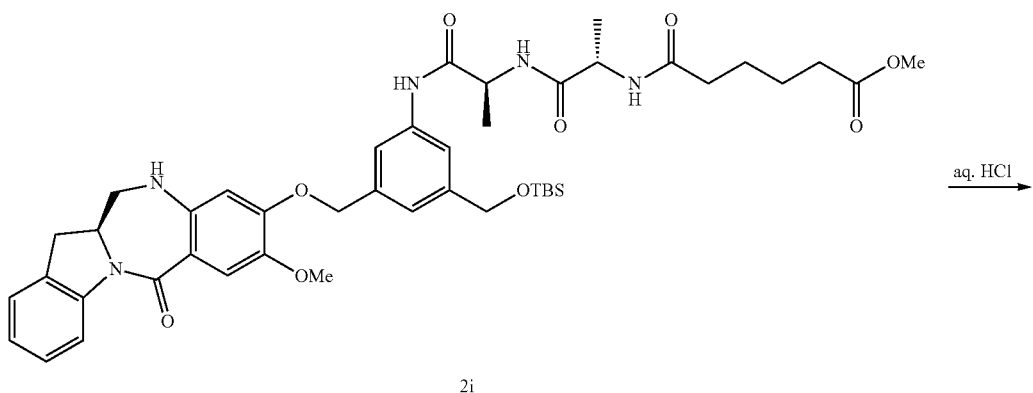

2j

Compound 2i (514 mg, 0.619 mmol) was dissolved in THF (3.44 mL). 5 M aqueous HCl (1.24 mL, 6.19 mmol) was added at room temperature and the reaction stirred for 1 h. The reaction mixture was diluted with DCM/MeOH (20:1) and the organic layer was washed with saturated sodium bicarbonate, brine, dried over magnesium sulfate, filtered and concentrated. The crude residue was purified by silica gel chromatography (DCM/MeOH) to give compound 2j (210 mg, 47% yield). LCMS (8 min method, 5-98%)=4.56 min. Mass observed (ESI⁺): 715.8 (M+H)⁺.

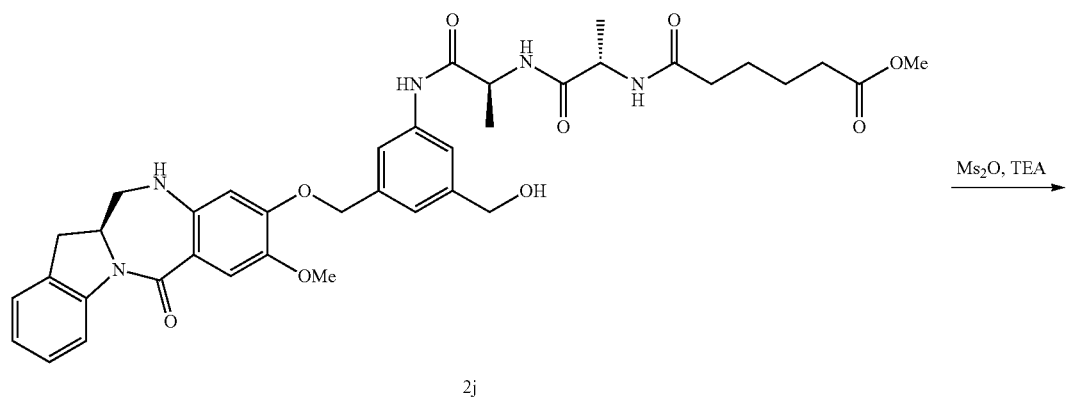

2j

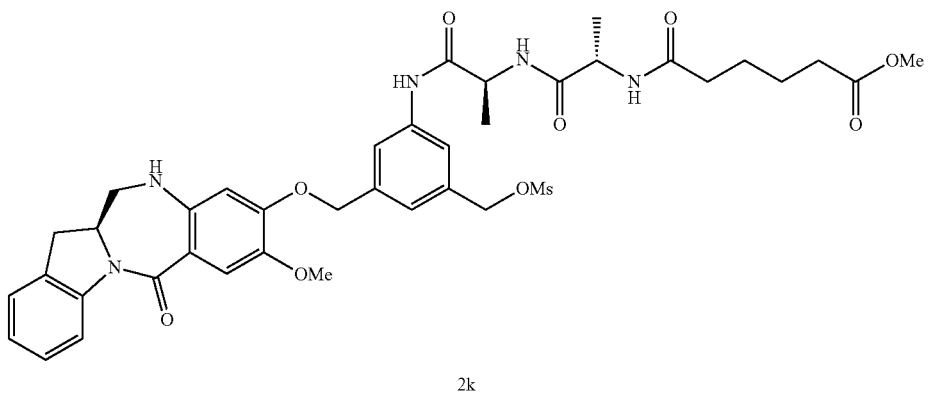

2k

Compound 2j (210 mg, 0.293 mmol) was dissolved in DCM (3.95 mL) and DMF (500 µL) and cooled to −10° C. (ice-acetone bath). TEA (57.2 µL, 0.411 mmol) and methanesulfonic anhydride (46.6 mg, 0.260 mmol) were added and the reaction as stirred for 3 h under Ar. The reaction was quenched with cold water at −5° C. and diluted with EtOAc. The aqueous layer was extracted with cold EtOAc (2×) and the combined organics were washed with cold water (2×). The organic layer was dried over anhydrous sodium/magnesium sulfate, filtered and concentrated. The crude product 2k was pumped on the high vacuum and taken onto next step without purification. LCMS (8 min method, 5-98%)=5.06 min. Mass observed (ESI⁻): 791.8 (M−H)⁻.

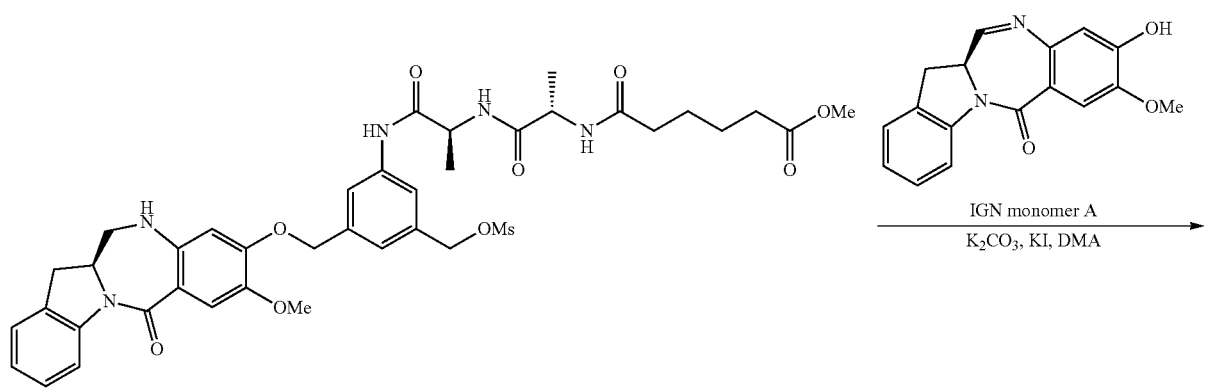

2k

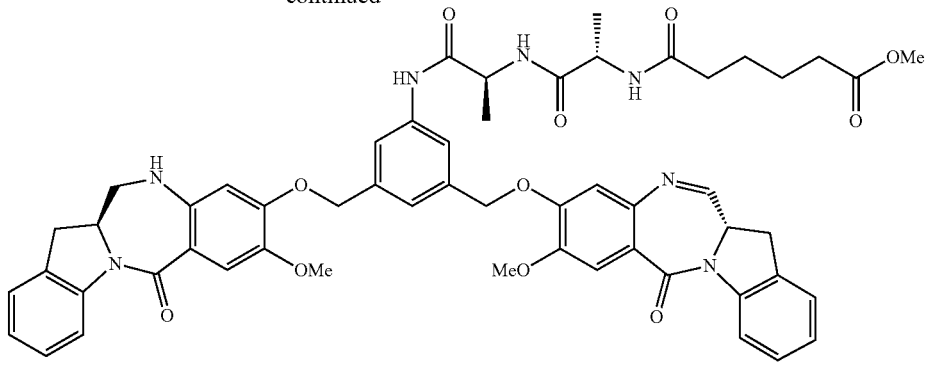

21

Compound 2k (233 mg, 0.293 mmol) was dissolved in DMA (1.95 mL). IGN monomer A (103 mg, 0.352 mmol) and potassium carbonate (60.7 mg, 0.440 mmol) were added at room temperature and the reaction stirred overnight. DI water was added to the reaction mixture and the resulting solid was filtered and washed with water. The solid was redissolved in DCM/MeOH (20:1), washed with water, dried over magnesium sulfate, filtered and concentrated. The crude residue was purified by RPHPLC (ACN/H$_2$O) to give 2l (44 mg, 15% yield). LCMS (8 min method, 5-98%)=5.4 min. Mass observed (ESI$^+$): 991.7 (M+H)$^+$.

Example 2

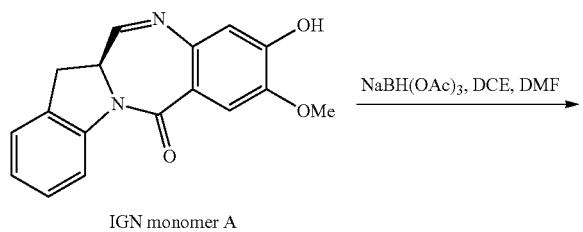

IGN monomer A

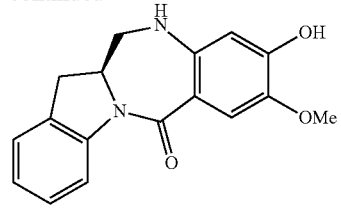

reduced IGN monomer A

To a solution of IGN monomer A (1.0 g, 3.4 mmol) in DCE (10 mL) and DMF (4 mL) was added sodium triacetoxyborohydride (1.1 g, 5.1 mmol, 1.5 equiv) and the reaction was stirred until completion of starting material. Upon completion of the starting material after 2h at room temperature, the reaction was quenched with sat. ammonium chloride (10 mL), and then the layers were separated. The aqueous layer was extracted once with dichloromethane (10 mL) and the combined organic layers were washed with water (2×10 mL) and brine (10 mL). The organic layer was dried over magnesium sulfate, filtered and the solvent was removed in vacuo to give a white/brown powder. The powder was washed with EtOAc (2×10 mL) and dried under vacuum to give reduced IGN monomer A as a white solid (0.87 g, 2.9 mmol, 87% yield) which was used in the next step without further purification. UPLCMS (2.5 min method)=1.34 min. Mass observed (ESI$^+$): 297.4 (M+H)$^+$. $^1$H NMR (400 MHz, DMSO-d$_6$): δ 9.44 (s, 1H), 8.20 (d, J=8.1 Hz, 1H), 7.30-7.23 (m, 2H), 7.22-7.12 (m, 1H), 7.01 (td, J=7.4, 1.1 Hz, 1H), 6.21 (s, 1H), 6.17 (d, J=6.6 Hz, 1H), 4.37 (tdd, J=10.1, 4.4, 1.9 Hz, 1H), 3.70 (s, 3H), 3.58-3.39 (m, 2H), 3.31-3.15 (m, 2H), 2.88 (dd, J=16.9, 4.4 Hz, 1H).

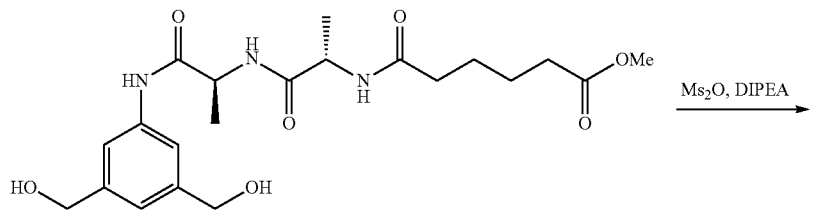

2e

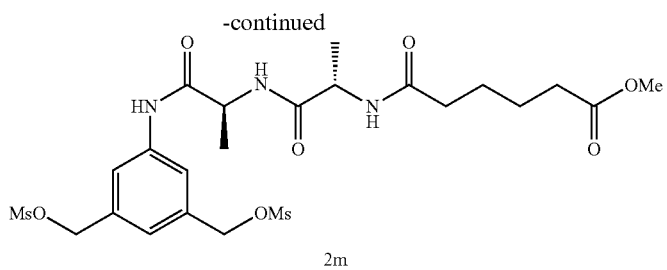

2m

A solution of 2e (5.53 g, 12.6 mmol) in DCM (81 mL) and DMF (64.9 mL) was cooled down to 0° C. and then DIPEA (6.13 mL, 37.9 mmol, 3.0 equiv.) was added followed by a solution of methanesulfonic anhydride (5.06 g, 29.1 mmol, 2.3 equiv.) in DCM (15 mL)/DMF (1 mL) dropwise. The reaction was stirred for 1h before quenching with cold water. After washing with water and brine the solution was dried over magnesium sulfate, filtered, and the solvent was removed in vacuo to give an orange oil which was triturated in diethyl ether to give bis mesylate 2m (6.4 g, 10.8 mmol, 85% yield). LCMS (8 min method)=4.019 min. Mass observed (ESI$^+$): 594.8 (M+H)$^+$. The crude material was carried on to the next step without further purification.

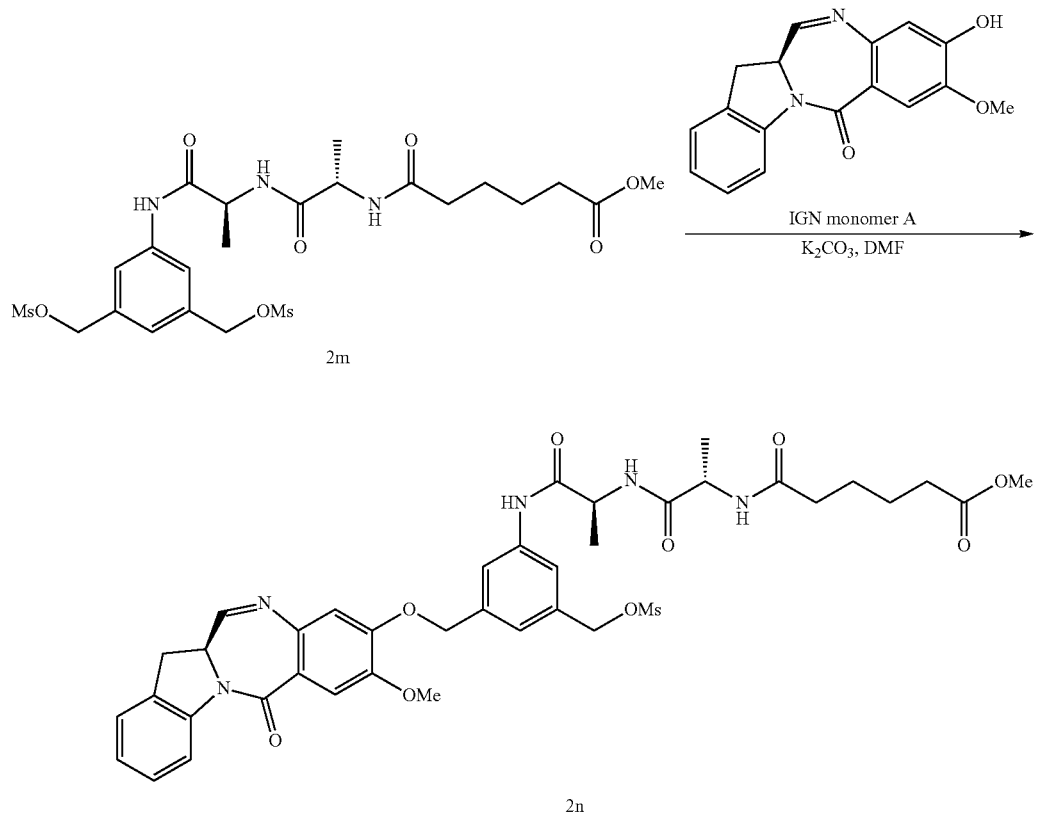

To a solution of 2m (0.52 g, 0.88 mmol) and IGN monomer A (0.18 g, 0.61 mmol, 0.7 equiv.) in DMF (7 mL) was added potassium carbonate (0.24 g, 1.75 mmol, 2.0 equiv.) and the reaction was stirred at room temperature for 12 h. The reaction was quenched with water (30 mL) and was extracted with DCM (3×15 mL). The organic layers were combined and washed with water (3×60 mL), brine (60 mL), dried over magnesium sulfate, filtered and the solvent was removed in vacuo to give a crude yellow oil. The material was purified by silica gel chromatography (DCM/(MeCN/MeOH (4/1) from 100/0 to 65/35) to give desired product 2n (0.09 g, 0.12 mmol, 13% yield). UPLCMS (2.5 min method)=1.46 min. Mass observed (ESI$^+$): 792.6 (M+H)$^+$.

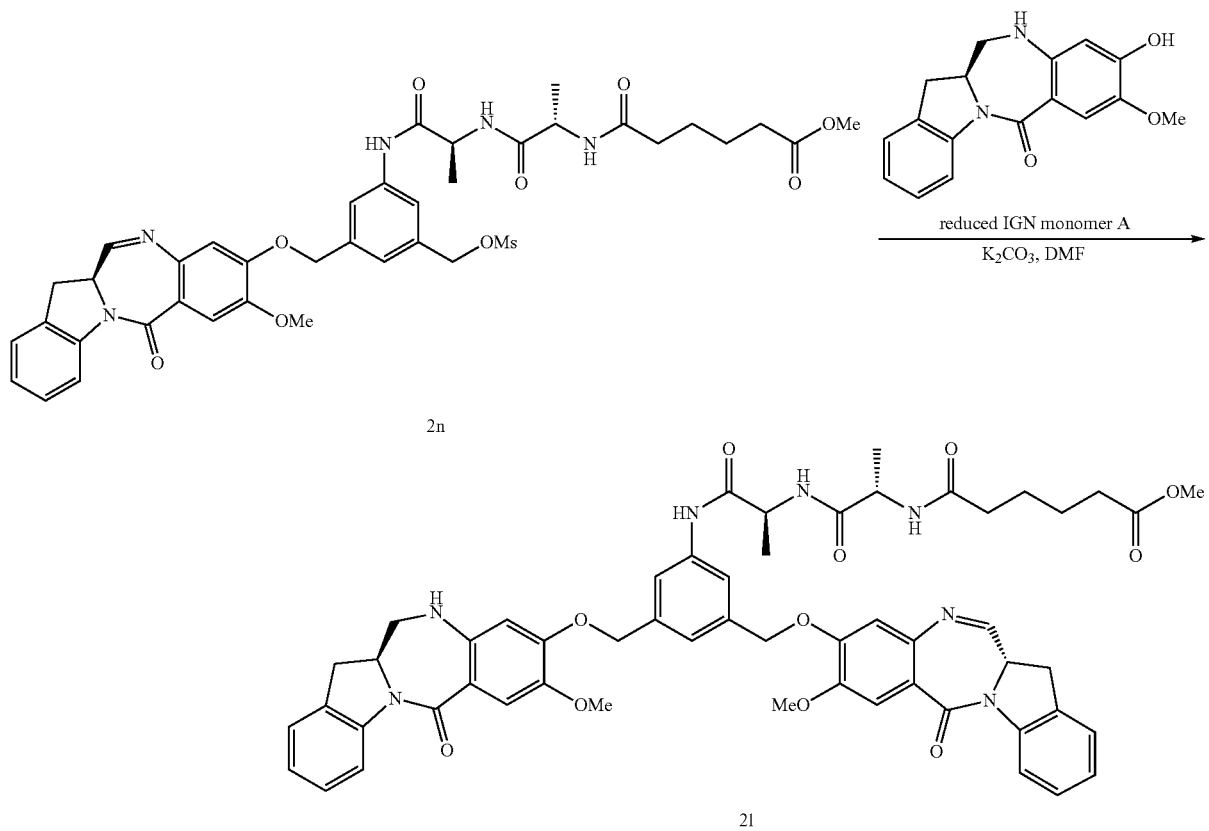

To a solution of 2n (0.05 g, 0.06 mmol) in DMF (0.48 mL, 6.2 mmol) was added potassium carbonate (0.02 g, 0.12 mmol, 2.0 equiv.) followed by reduced IGN monomer A (0.02 g, 0.07 mmol, 1.1 equiv.). The reaction was stirred at room temperature for 12 h. The reaction was quenched with water and the resulting solid was filtered and washed with water. The solid was redissolved in DCM/MeOH (20:1), washed with water, dried with magnesium sulfate, filtered and concentrated. The crude residue was purified by RPHPLC (ACN/H$_2$O) to give 2l (0.03 g, 0.04 mmol, 55% yield). LCMS (8 min method, 5-98%)=5.4 min. Mass observed (ESI$^+$): 991.7 (M+H)$^+$. $^1$H NMR (400 MHz, DMSO-d$_6$, reported as a mixture of water adducts): δ 10.10 (d, J=3.7 Hz, 1H), 8.27 (d, J=8.0 Hz, 1H), 8.21-8.10 (m, 1H), 8.05 (d, J=7.4 Hz, 1H), 7.78 (dt, J=8.5, 1.8 Hz, 2H), 7.43-7.13 (m, 7H), 7.16-6.98 (m, 2H), 6.49 (s, 1H), 6.36 (d, J=13.1 Hz, 0.4H), 6.16 (d, J=6.2 Hz, 0.4H), 5.80 (s, 0.4H), 5.67 (s, 0.4H), 5.57 (d, J=5.6 Hz, 0.4H), 5.35-5.09 (m, 2H), 5.03 (t, J=5.9 Hz, 2H), 4.81-4.72 (m, 0.4H), 4.60 (dt, J=9.7, 5.0 Hz, 0.2H), 4.51-4.36 (m, 2H), 4.39-4.23 (m, 1H), 4.17 (td, J=9.7, 2.9Hz, 0.4H), 3.93 (s, 0.4H), 3.83-3.74 (m, 5H), 3.62 (s, 2H), 3.75-3.44 (m, 2H), 3.32 (d, J=11.6 Hz, 1H), 3.19-3.07 (m, 1H), 2.95 (dd, J=17.1, 4.3 Hz, 1H), 2.38-2.29 (m, 1H), 2.18 (m, 1H), 1.56 (m, J=3.9 Hz, 4H), 1.41-1.31 (m, 3H), 1.30-1.14 (m, 3H).

Example 3

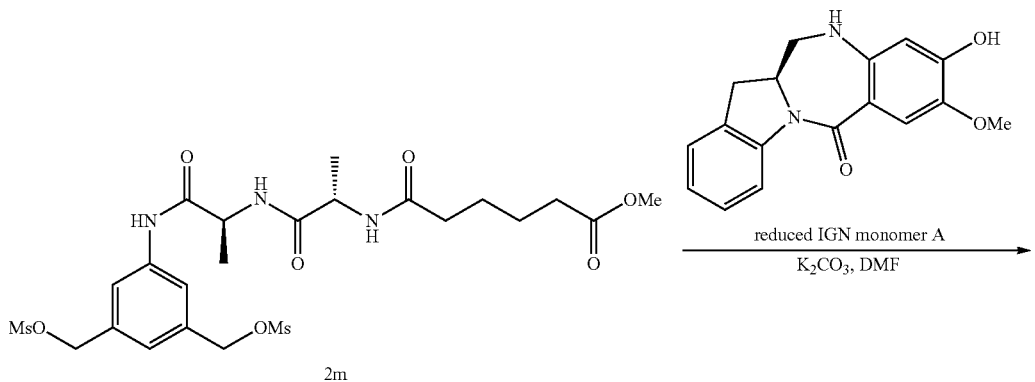

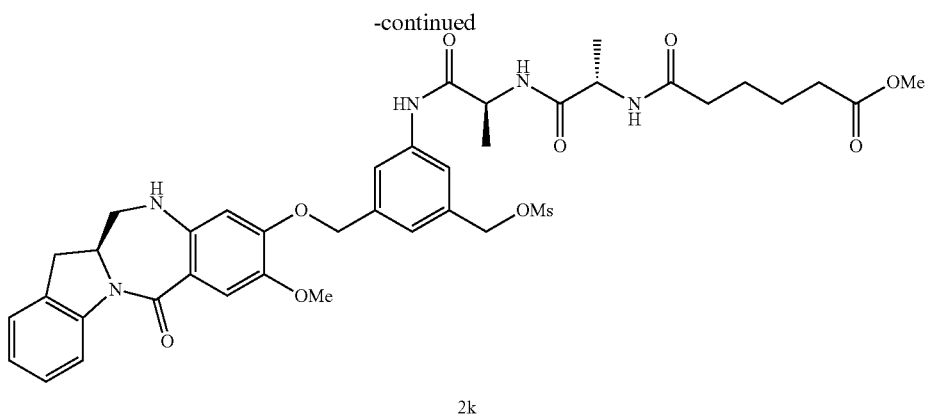

2k

To a solution of 2m (0.88 g, 1.47 mmol) in DMF (11 mL) was added reduced IGN monomer A (0.26 g, 0.88 mmol, 0.6 equiv.) followed by potassium carbonate (0.41 mg, 2.95 mmol, 2.0 equiv.). After the reaction was stirred for 12 h, the reaction was diluted with water (50 mL) and EtOAc (30 mL). The aqueous layer was extracted with EtOAc (3×10 mL). The combined organic layers were washed with brine (20 mL), dried over magnesium sulfate and filtered. The solvent was removed and the crude mixture was purified by silica gel chromatography (DCM/MeOH) to give desired product 2k (0.11 g, 0.14 mmol, 10% yield). LCMS (8 min method)=5.013 min. Mass observed (ESI$^+$): 794.3 (M+H)$^+$.

To a solution of 2k (0.11 g, 0.14 mmol) in DMF (2 mL) was added potassium carbonate (0.04 g, 0.29 mmol, 2.0 equiv.) IGN monomer A (0.04 g, 0.14 mmol, 1.0 equiv.) was added and the reaction was stirred at rt for 12 h. The reaction was quenched with water (10 mL) and the resulting solid was filtered and washed with water. The solid was redissolved in DCM/MeOH (20:1), washed with water (10 mL), dried with magnesium sulfate, filtered and concentrated. The crude residue was purified by RPHPLC (ACN/H$_2$O) to give 2l (0.08 g, 0.09 mmol, 59% yield). LCMS (8 min method, 5-98%)=5.4 min. Mass observed (ESI$^+$): 991.7 (M+H)$^+$.

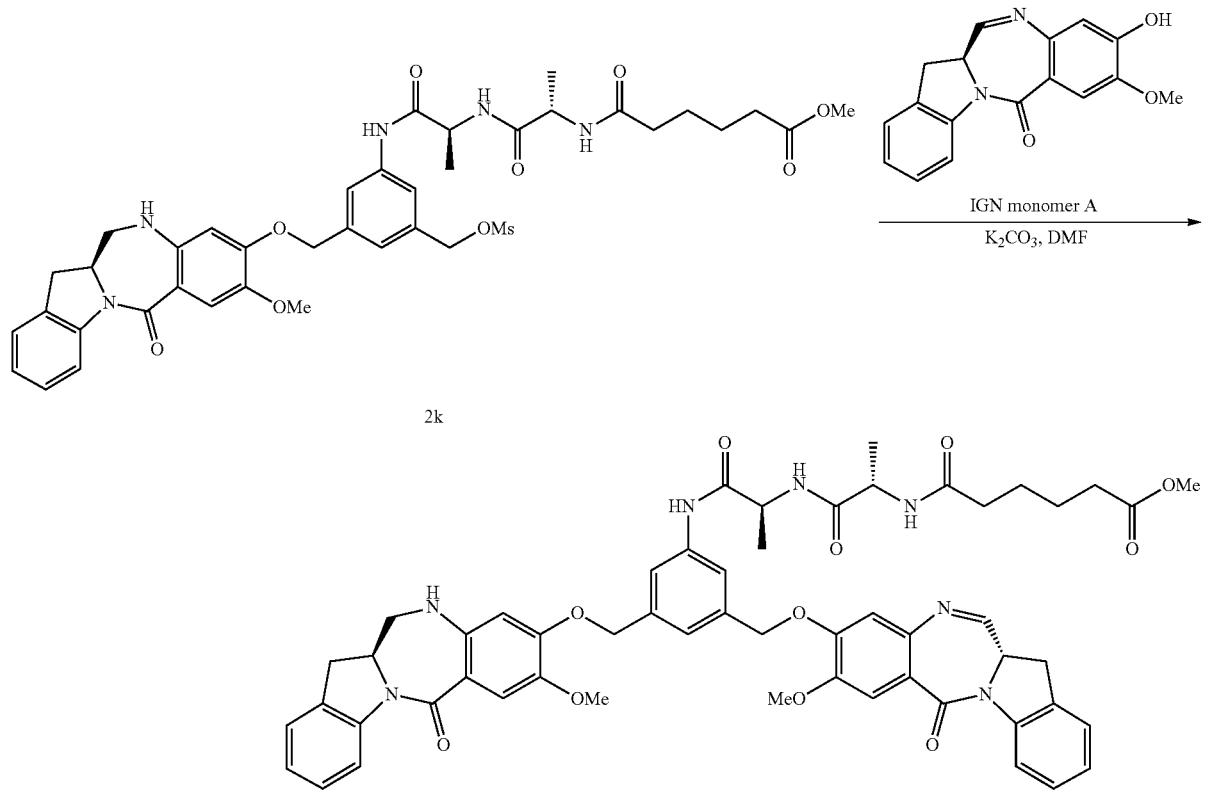

Example 4

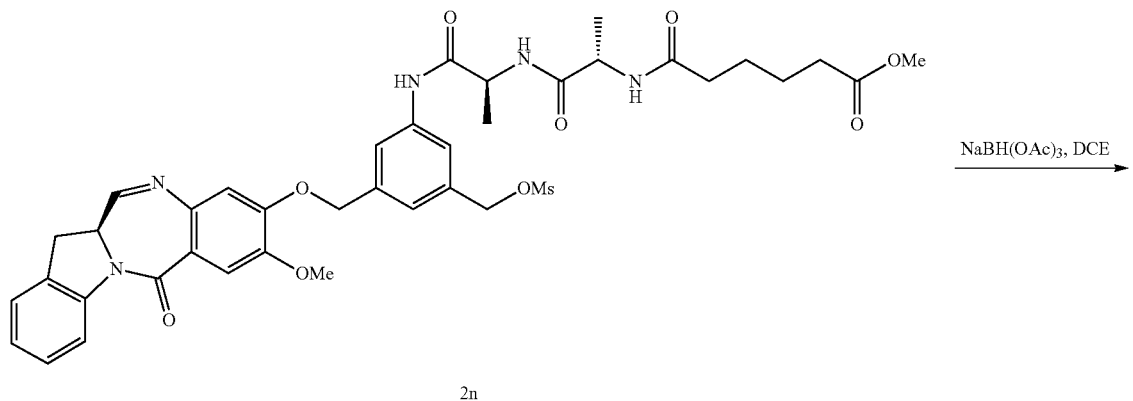

To a solution of 2n (0.1 g, 0.13 mmol) in DCE (2 mL) was added sodium triacetoxyborohydride (0.03 g, 0.13 mmol, 1.0 equiv.) and the reaction was stirred at rt for 2 h. The reaction was quenched with saturated ammonium chloride (2 mL) and the layers were separated. The aqueous layer was extracted with DCM (5 mL) and the combined organic layers were washed with water, brine, dried over magnesium sulfate and filtered. The crude yellow solid was purified using silica gel chromatography (EtOAc/MeOH (95/5)) to afford the desired reduced product 2k (0.035 g, 0.044 mmol, 35% yield). LCMS (8 min method)=5.021 min. Mass observed (ESI$^+$): 794.3 (M+H)$^+$.

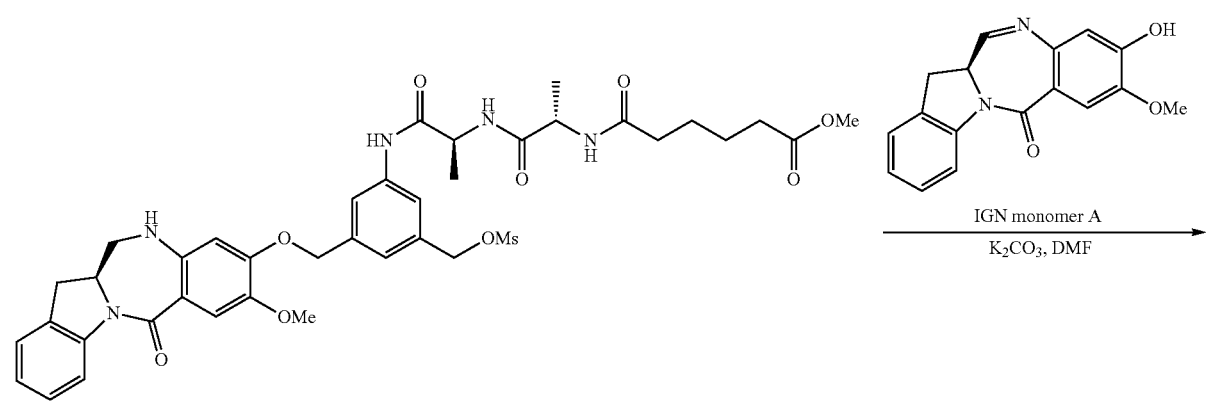

-continued

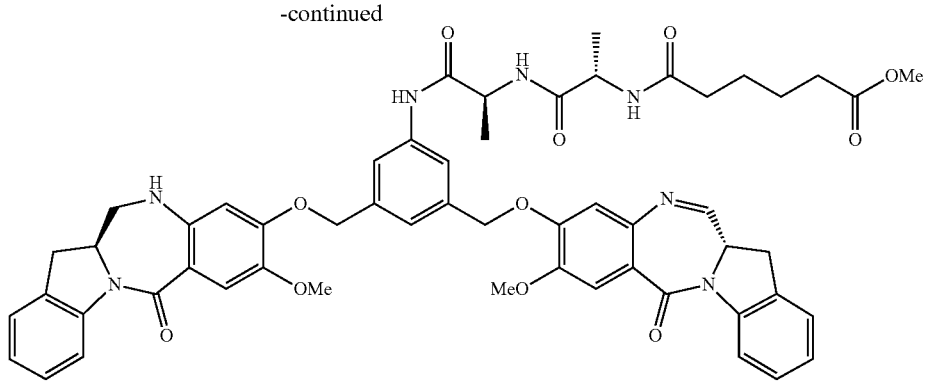

21

To a solution of 2k (0.035 g, 0.044 mmol) in DMF (1.0 mL) was added potassium carbonate (0.013 g, 0.09 mmol, 2.0 equiv.). IGN monomer A (0.013 g, 0.04 mmol, 1.0 equiv.) was added and the reaction was stirred at room temperature for 12 h. The reaction was quenched with water (10 mL) and the resulting solid was filtered and washed with water. The solid was redissolved in DCM/MeOH (20:1, 20 mL), washed with water (20 mL), dried with magnesium sulfate, filtered and concentrated. The crude residue was purified by RPHPLC (ACN/H$_2$O) to give 2l (0.017 g, 0.01 mmol, 38% yield). LCMS (8 min method, 5-98%)=5.4 min). Mass observed (ESI$^+$): 991.7 (M+H)$^+$.

Example 5

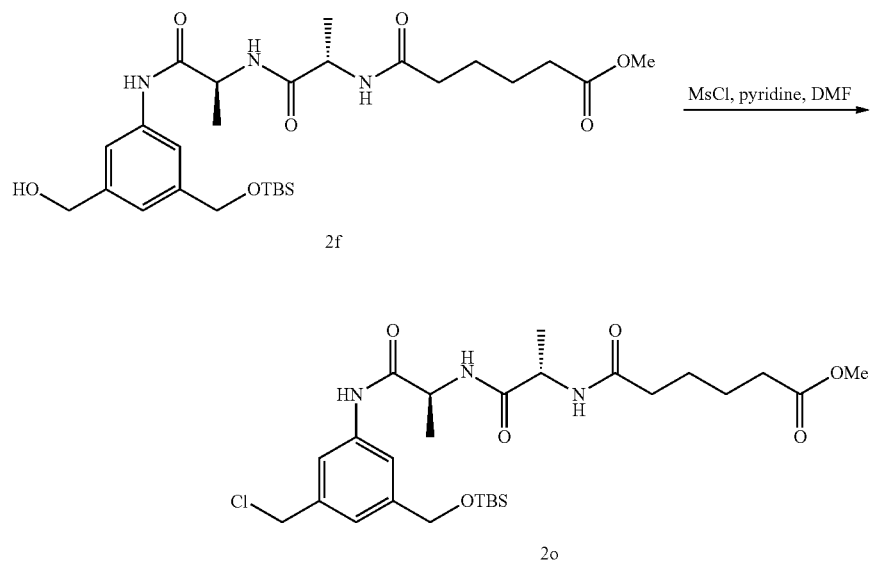

To a solution of 2f (8.8 g, 16.0 mmol) in DMF (100 mL) was added pyridine (4.51 ml, 55.8 mmol, 3.5 equiv.). The reaction was cooled down to 0° C. then methanesulfonyl chloride (2.5 mL, 31.9 mmol, 2.0 equiv.) was added dropwise and reaction stirred for 2 h. The mixture was quenched with sat. sodium bicarbonate (30 mL), EtOAc was added and the layers were separated. The aqueous layer was extracted with EtOAc (3×50 mL) and the combined organic layers were washed with water, brine, dried over magnesium sulfate and filtered. The solvent was removed and the crude white solid 2o was used in the next step without purification (6.2 g, 10.9 mmol, 68%). UPLCMS (2.5 min method)=1.96 min. Mass observed (ESI$^+$): 570.7 (M+H)$^+$.

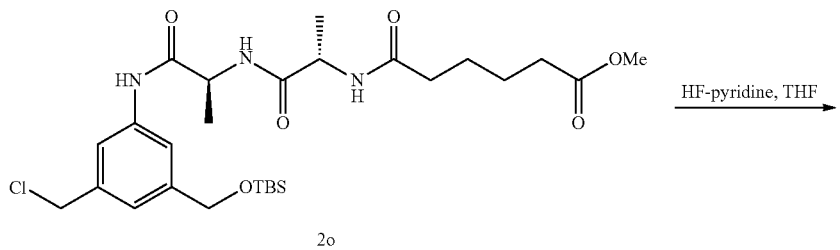

2o

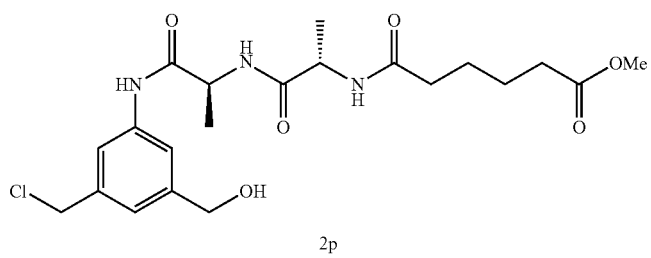

2p

To a solution of 2o (1.7 g, 2.98 mmol) in THF (36.6 mL) was added DIPEA (2.1 mL, 11.9 mmol, 4.0 equiv.) followed by HF-pyridine (0.84 mL, 6.0 mmol, 2.0 equiv.). The reaction was stirred at room temperature for 3 h. The reaction was quenched with sat. sodium bicarbonate (20 mL) and then the layers were separated. The aqueous layer was extracted with EtOAc (3×10 mL). The combined organic layers were washed with brine (30 mL), dried over magnesium sulfate, filtered and the solvent removed in vacuo to give a crude white oil which was purified by silica gel chromatography (DCM/MeOH) to give desired product 2p as a white solid (0.75 g, 1.6 mmol, 55% yield). UPLCMS (2.5 min method)=1.23 min. Mass observed (ESI$^+$): 456.4 (M+H)$^+$.

To a solution of 2p (0.65 g, 1.43 mmol) in DCM (10 mL) and DMF (2 mL) was added DIPEA (0.51 mL, 2.85 mmol, 2.0 equiv.) and the reaction was cooled down to 0° C. A solution of methanesulfonic anhydride (0.3 g, 1.71 mmol) in DCM (2 mL) was added slowly. The reaction was completed after 30 min, quenched with water (20 mL), the layers were extracted, aqueous layer washed with DCM (2×10 mL). Organic layers were combined, washed with water (20 mL), brine (10 mL), dried over magnesium sulfate and filtered. The solvent was removed in vacuo to give desired product 2q (0.76 g, 1.42 mmol, 100% yield) which was carried crude into the next step without further purification. UPLCMS (2.5 min method)=1.37 min. Mass observed (ESI$^+$): 534.4 (M+H)$^+$.

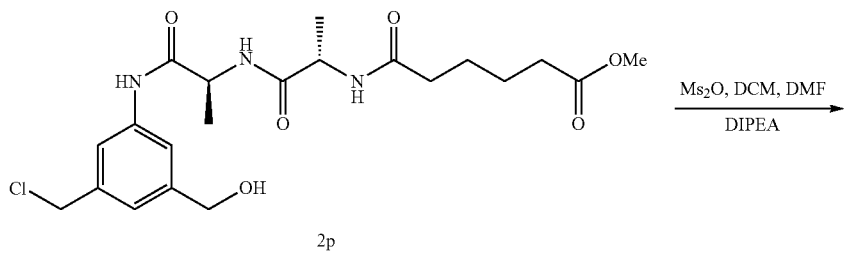

2p

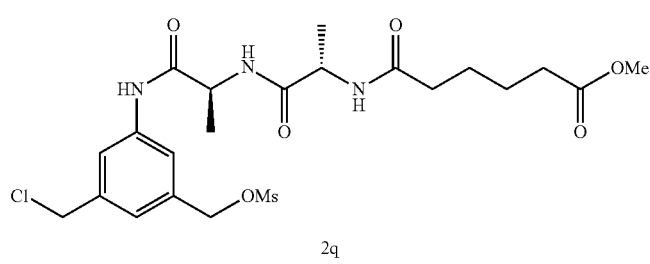

2q

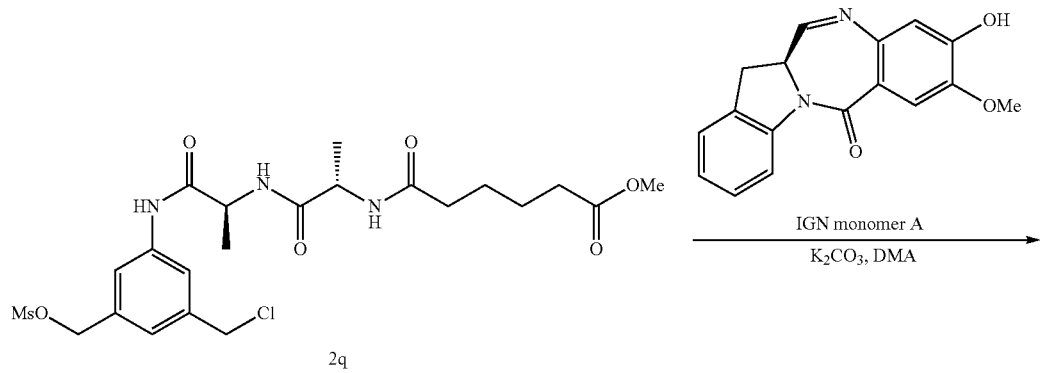

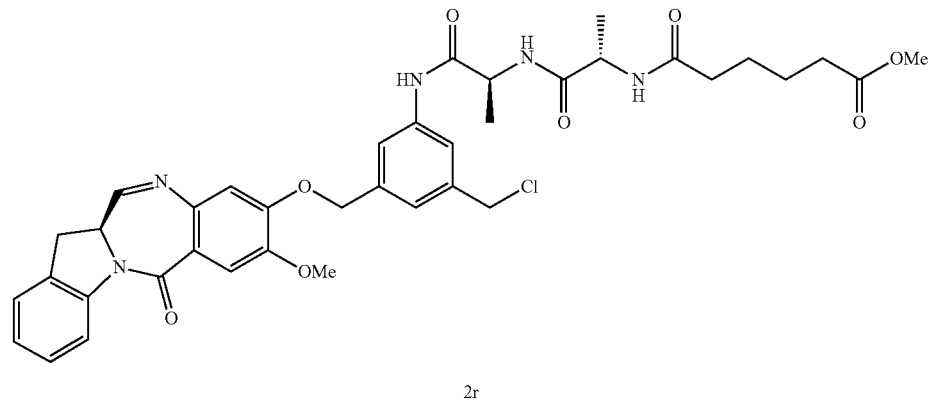

To a solution of 2q (0.76 g, 1.42 mmol) in DMA (13 mL) was added potassium carbonate (0.59 g, 4.27 mmol) followed by a solution of IGN monomer A (0.5 g, 1.71 mmol) in DMA (1 mL). The reaction was stirred at room temperature for 12 h. The reaction was quenched with water (30 mL) and the mixture was stirred for 10 min. The solid was filtered and then dissolved in DCM/MeOH (9/1, 20 mL) and washed with brine (10 mL). The organic layer was separated and dried over magnesium sulfate, filtered and concentrated in vacuo to give a crude yellow solid 2r (0.76 g, 1.04 mmol, 73% yield) which was carried crude into the next step without further purification. UPLCMS (2.5 min method)=1.55 min. Mass observed (ESI+): 732.9 (M+H)+.

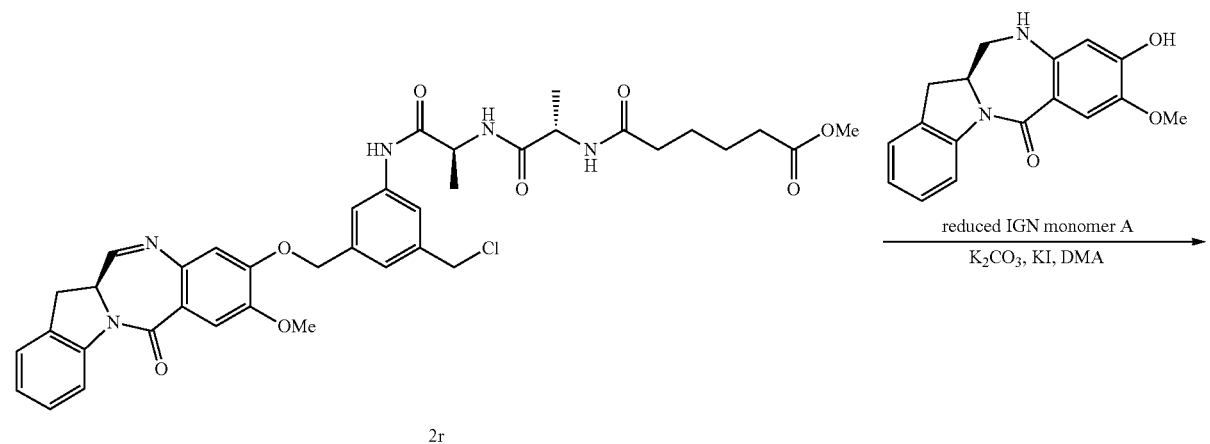

-continued

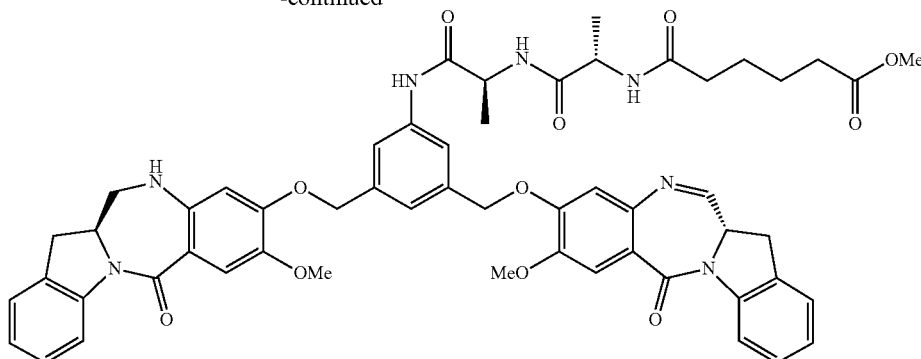

21

To a solution of 2r (0.26 g, 0.36 mmol) in DMA (10 mL) was added potassium iodide (0.06 g, 0.355 mmol, 1.0 equiv.), reduced IGN monomer A (0.1 g, 0.37 mmol, 1.05 equiv.) and potassium carbonate (0.15 g, 1.06 mmol, 3.0 equiv.). The reaction was warmed up to 40° C. and stirred for 4 h. The reaction was quenched with water (20 mL) and the mixture stirred for 10 min. The resulting solid was filtered. The solid was redissolved in DCM/MeOH (20:1, 20 mL), washed with water (20 mL), dried with magnesium sulfate, filtered and concentrated. The crude residue was purified by RPHPLC (ACN/H$_2$O) to give 2l (0.097 g, 0.097 mmol, 28% yield). LCMS (8 min method, 5-98%)=5.4 min. Mass observed (ESI$^+$): 991.7 (M+H)$^+$.

Example 6

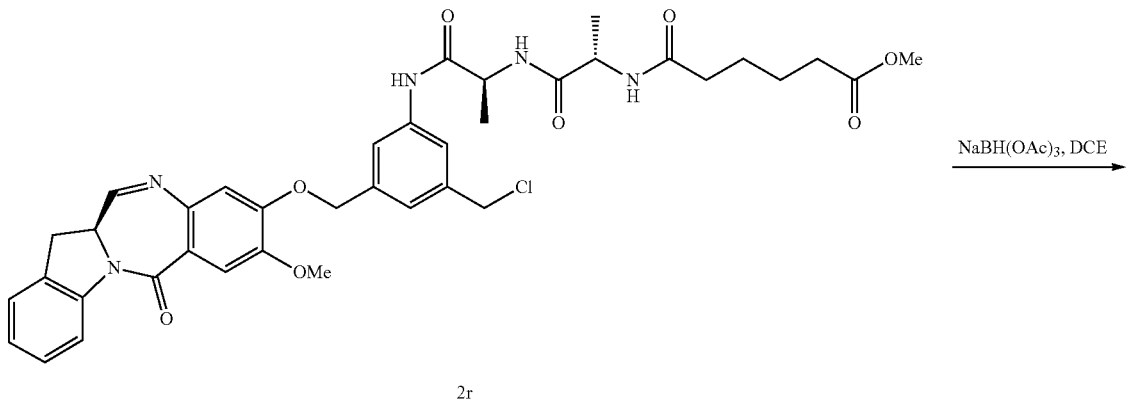

2r

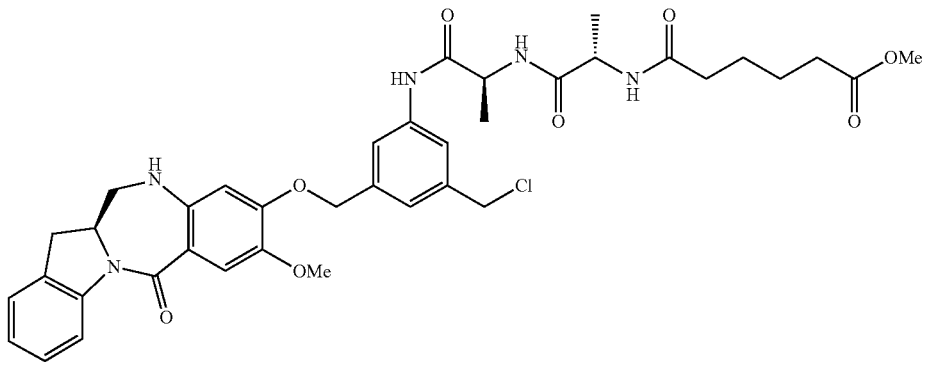

2s

To a solution of 2r (0.76 g, 1.04 mmol) in DCE (10 mL) was added DMF (3.0 mL) followed by addition of sodium triacetoxyborohydride (0.33 g, 1.56 mmol) at 0° C. The reaction was stirred at room temperature for 4 h. The reaction was quenched with sat ammonium chloride (20 mL) and the layers were separated. The aqueous layer was extracted with DCM (3×10 mL) and the combined organic layers were washed with water (10 mL), brine (10 mL), dried over magnesium sulfate, filtered and the solvent removed in vacuo to give the desired crude material 2s as an oil (0.65 g, 0.88 mmol, 85% yield) which was used in the next step without further purification. UPLCMS (2.5 min method)=1.80 min. Mass observed (ESI+): 735.3 (M+H)+.

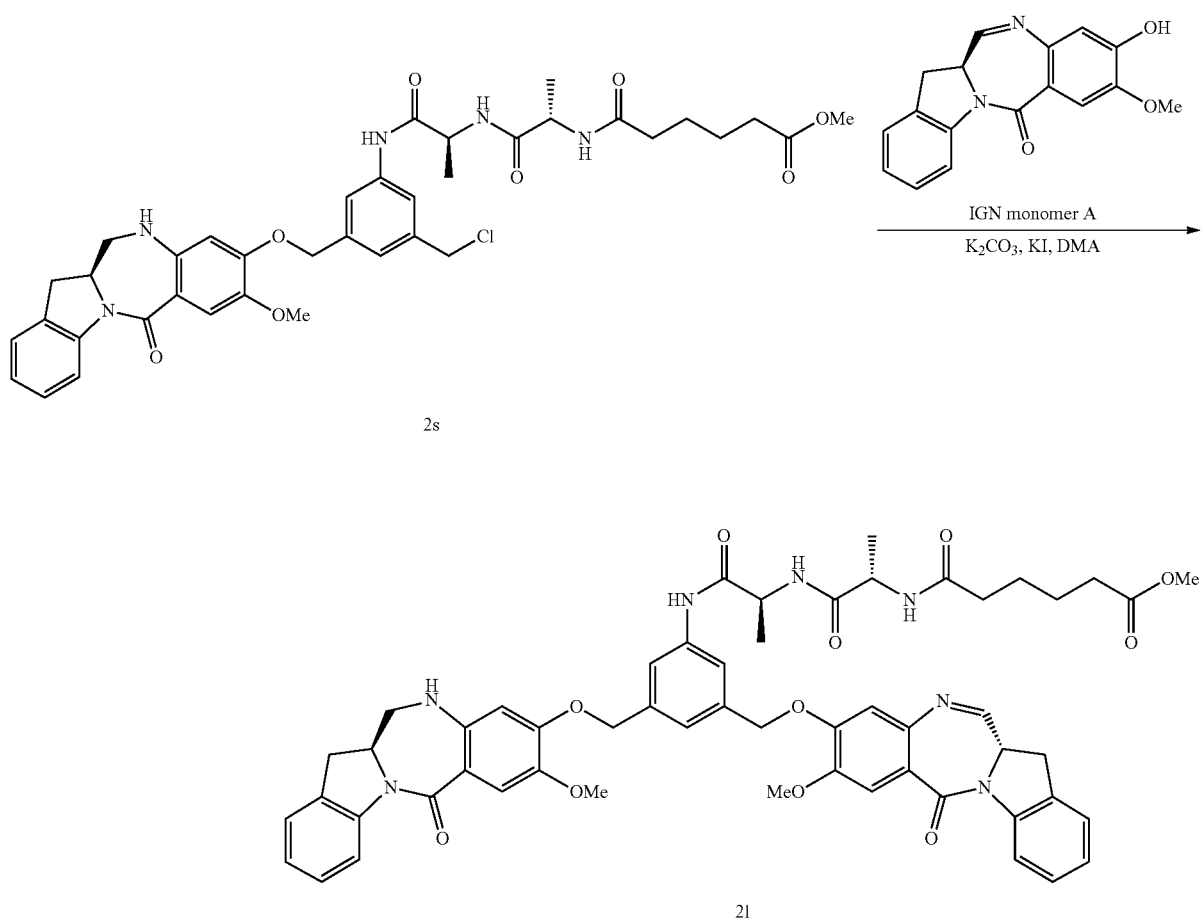

To a solution of 2s (0.65 g, 0.88 mmol) in DMA (15 mL) was added potassium carbonate (0.25 g, 1.78 mmol, 2.0 equiv.) followed by potassium iodide (0.073 g, 0.44 mmol, 0.5 equiv.) and a solution of IGN monomer A (0.29 g, 0.974 mmol, 1.1 equiv.) in DMA (2 mL) was added to the reaction mixture at room temperature. The reaction was heated at 40° C. for 5 h. The reaction was quenched with water (30 mL) and then solid was filtered off. The solid was redissolved in DCM/MeOH (20:1, 30 mL), washed with water (20 mL), dried with magnesium sulfate, filtered and concentrated. The crude residue (0.78 g) was purified by RPHPLC (ACN/H₂O) to give 2l (0.43 g, 0.43 mmol, 49% yield). LCMS (8 min method, 5-98%)=5.4 min. Mass observed (ESI+): 991.7 (M+H)+.

Example 7

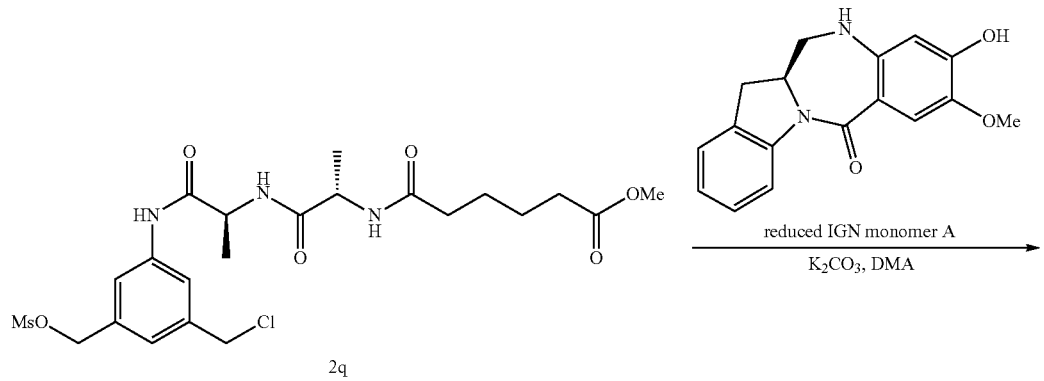

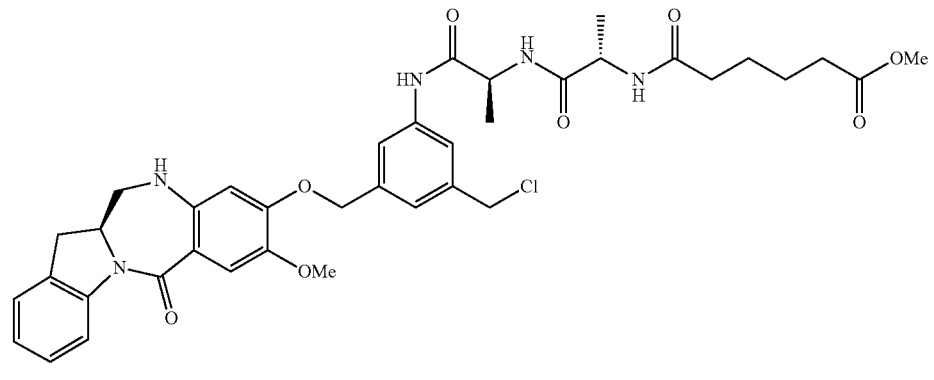

To a solution of 2q (0.14 g, 0.27 mmol) in DMA (3 mL) was added potassium carbonate (0.11 g, 0.81 mmol) followed by a solution of reduced IGN monomer A (0.084 g, 0.28 mmol) in DMA (1 mL). The reaction was stirred at room temperature for 12 h. The reaction was quenched with water (20 mL) and the mixture stirred for 10 min. The solid was filtered and then dissolved in DCM/MeOH (9/1, 20 mL) and washed with brine (10 mL). The organic layer was separated and dried over magnesium sulfate, filtered and solvent removed in vacuo. The crude material was purified by silica gel chromatography using DCM (MeOH/EtOAc, 1/4) to give desired product 2s (0.08 g, 0.11 mmol, 40% yield). UPLCMS (2.5 min method)=1.63 min. Mass observed (ESI$^+$): 735.2 (M+H)$^+$

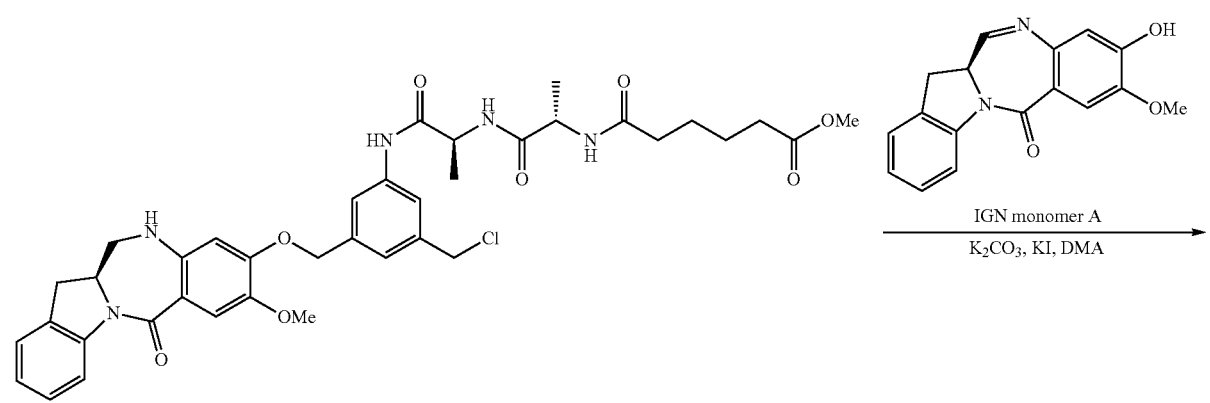

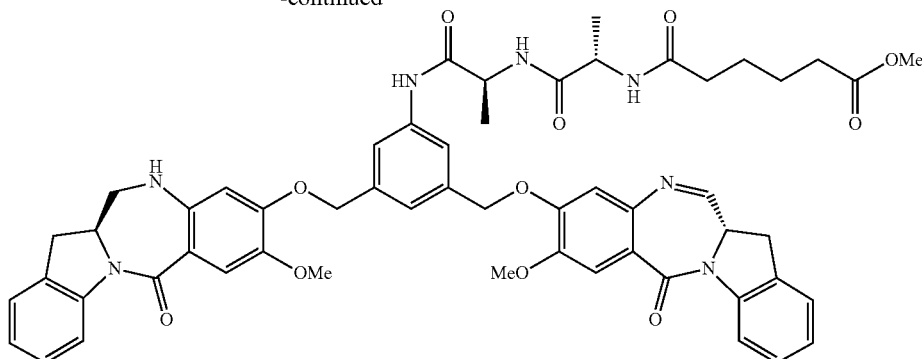

21

To a solution of 2s (0.06 g, 0.09 mmol) in DMA (2 mL) was added potassium carbonate (0.025 g, 0.18 mmol) followed by potassium iodide (0.007 g, 0.044 mmol). A solution of IGN monomer A (0.03 g, 0.097 mmol) in DMA (1 mL) was added to the reaction mixture at room temperature. The reaction was heated at 40° C. for 5h. The reaction was cooled down and quenched with water (20 mL) and the solid was filtered off. The solid was redissolved in DCM/MeOH (20:1, 20 mL), washed with water (10 mL), dried with magnesium sulfate, filtered and concentrated. The crude residue (0.07 g) was purified by RPHPLC (ACN/H$_2$O) to give 2l (0.035 g, 0.035 mmol, 51% yield). LCMS (8 min method, 5-98%)=5.4 min. Mass observed (ESI$^+$): 991.7 (M+H)$^+$.

Example 8

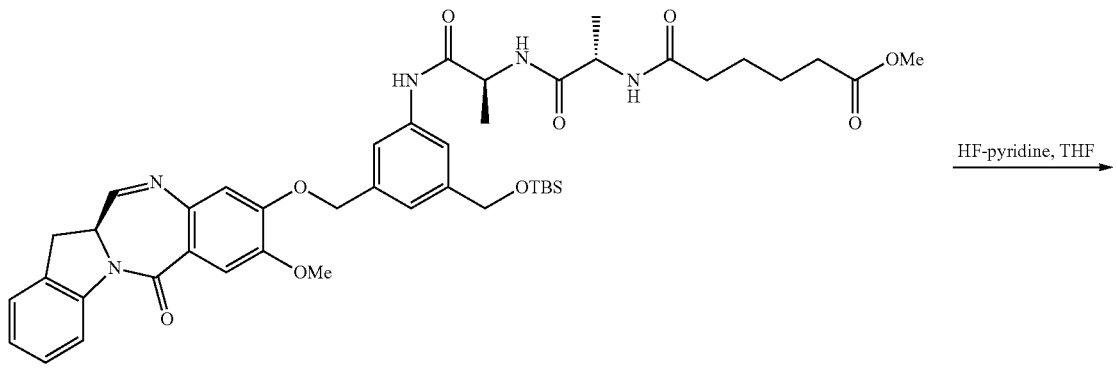

2h

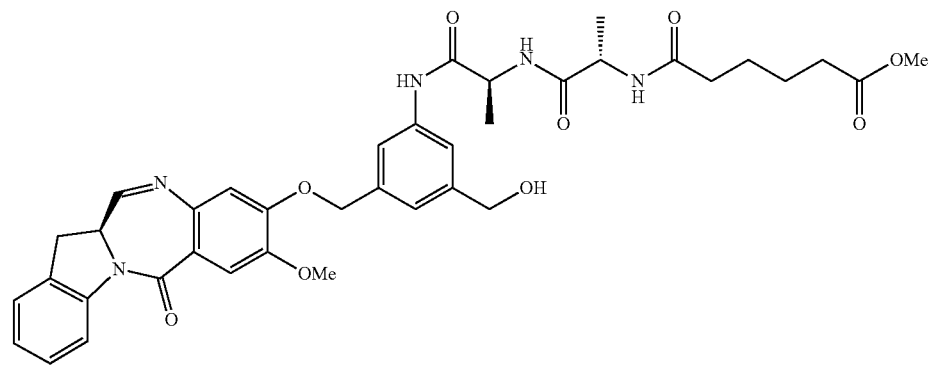

2t

To a solution of 2h (0.85 g, 1.027 mmol) in THF (9 mL) was added DIPEA (0.54 mL, 3.1 mmol, 3.0 equiv.) followed by HF-pyridine (0.3 mL, 2.053 mmol, 2.0 equiv.) at room temperature. The reaction was stirred for 3 h at room temperature. The reaction was quenched with sat. sodium bicarbonate (10 mL), the layers were separated and the aqueous layer extracted with DCM (3×10 mL). The combined organic layers were washed with brine (10 mL), dried over magnesium sulfate, and filtered. The solvent was removed in vacuo to give crude product as a solid which was washed with EtOAc to give the desired product 2t (0.64 g, 0.89 mmol, 87% yield). UPLCMS (2.5 min method)=1.36 min. Mass observed (ESI$^+$): 714.6 (M+H)$^+$.

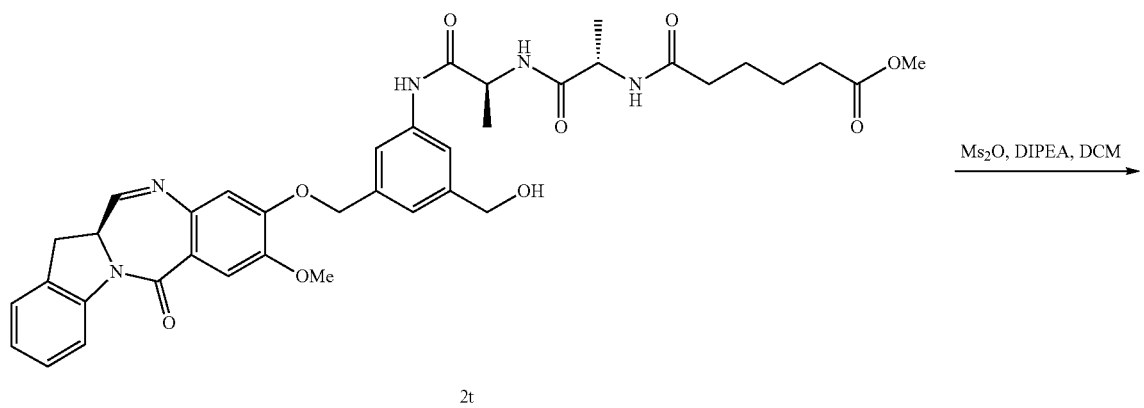

2t

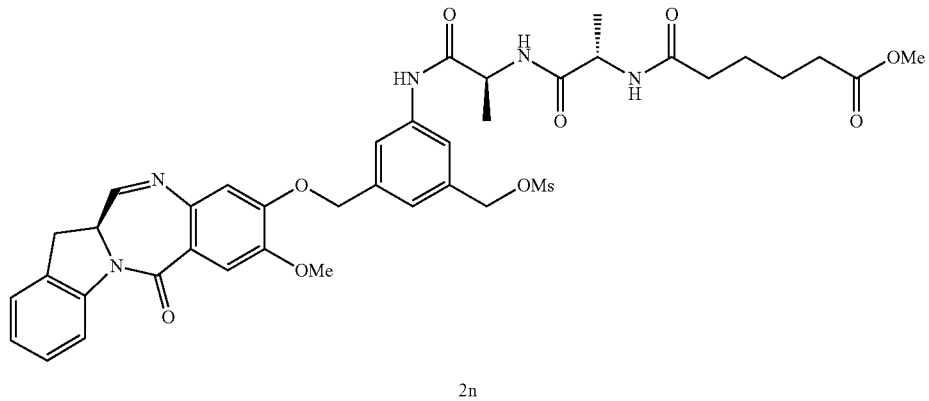

2n

To a solution of 2t (0.23 g, 0.322 mmol) in dichloromethane (3 mL) was added DIPEA (0.11 ml, 0.644 mmol, 2.0 equiv.) followed by methanesulfonic anhydride (0.084 g, 0.48 mmol, 1.5 equiv.) as a solution in DCM (1 mL) at 0° C. The reaction was stirred for 1 h. The reaction was quenched with water (3 mL) and diluted with DCM (3 mL). The layers were separated and the organic layer was washed with brine (3 mL), dried over magnesium sulfate and filtered. The solvent was removed in vacuo and the crude material 2n (0.25 g, 0.31 mmol, 98% yield) was used in the next step without further purification. UPLCMS (2.5 min method)=1.45 min. Mass observed (ESI$^+$): 792.5 (M+H)$^+$.

249 250

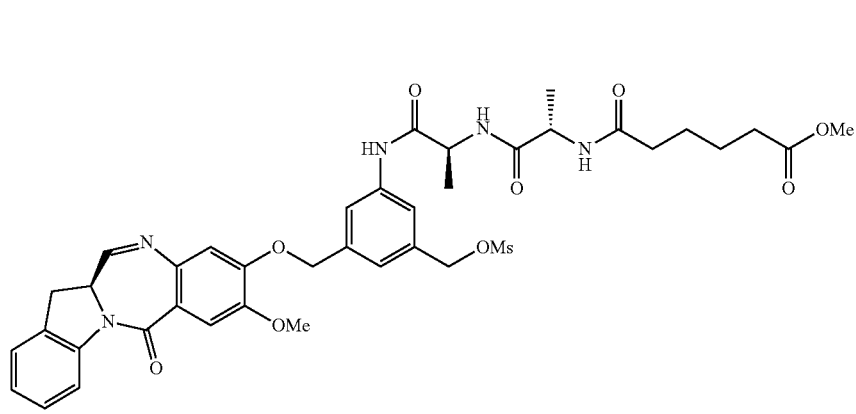

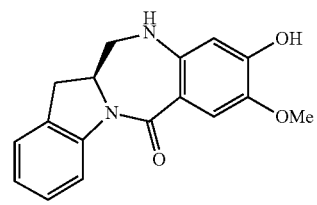

2n

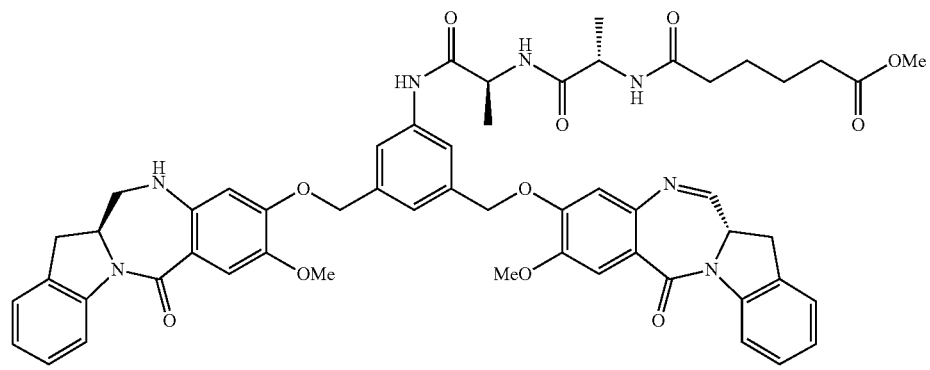

2l

To a solution of 2n (0.02 g, 0.027 mmol) in DMF (0.2 ml) was added potassium carbonate (0.007 g, 0.053 mmol, 2.0 equiv.) followed by reduced IGN monomer A (0.009 g, 0.029 mmol, 1.1 equiv.) and the reaction was stirred at room temperature for 18 h. Water (3 mL) was added to the reaction mixture and the resulting solid was filtered. The solid was redissolved in DCM/MeOH (20:1, 5 mL), washed with water (5 mL), dried with magnesium sulfate, filtered and concentrated. The crude residue was purified by RPHPLC (ACN/H$_2$O) to give 2l (0.005 g, 0.005 mmol, 19% yield). LCMS (8 min method, 5-98%)=5.4 min. Mass observed (ESI$^+$): 991.7 (M+H)$^+$.

Example 9

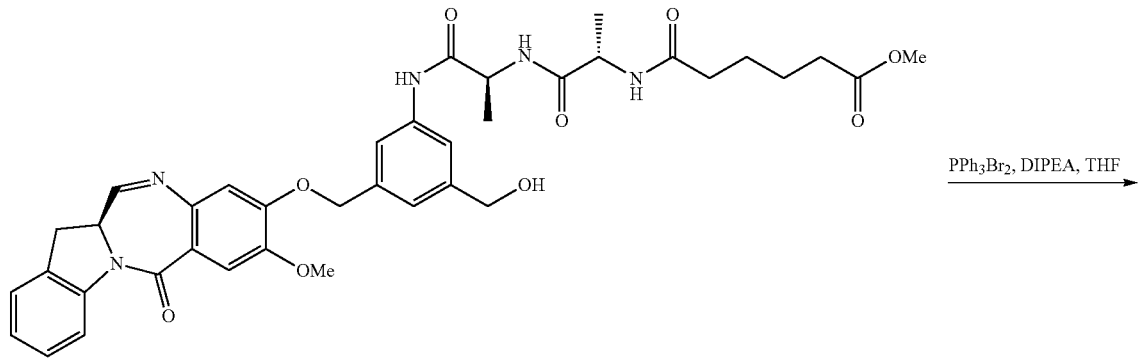

2t

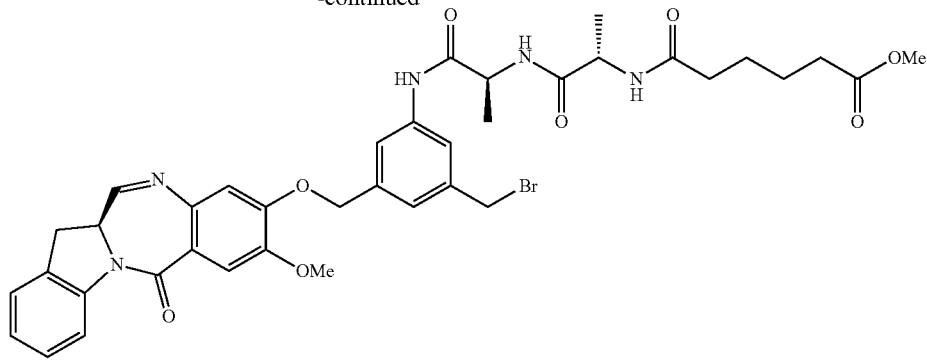

2u

To a solution of 2t (0.02 g, 0.031 mmol) in THF (2 mL) was added DIPEA (0.016 mL, 0.092 mmol, 3.0 equiv.) followed by a solution of dibromotriphenylphosphorane (0.03 g, 0.062 mmol, 2.0 equiv.) in THF (0.5 mL). The reaction was stirred at room temperature for 12 h. The reaction was stopped by evaporation of solvent and then the crude material was purified by silica gel chromatography to give 2u (0.006 g, 0.007 mmol, 25% yield). UPLCMS (2.5 min method)=1.56 min. Mass observed (ESI$^+$): 778.2 (M+H)$^+$.

To a solution of 2u (0.006 g, 7.73 μmol) in DMA (1 mL) was added reduced IGN monomer A (0.003 g, 9.27 μmol) followed by potassium carbonate (0.002 g, 0.015 mmol) and the reaction was stirred at room temperature for 18 h. Water (3 mL) was added to the reaction mixture and the resulting solid was filtered and washed with water. The solid was redissolved in DCM/MeOH (20:1, 5 mL), washed with water (5 mL), dried with magnesium sulfate, filtered and concentrated. The crude residue was purified by RPHPLC (ACN/H$_2$O) to give 2l (0.001 g, 0.001 mmol, 13% yield). LCMS (8 min method, 5-98%)=5.4 min. Mass observed (ESI$^+$): 991.7 (M+H)$^+$.

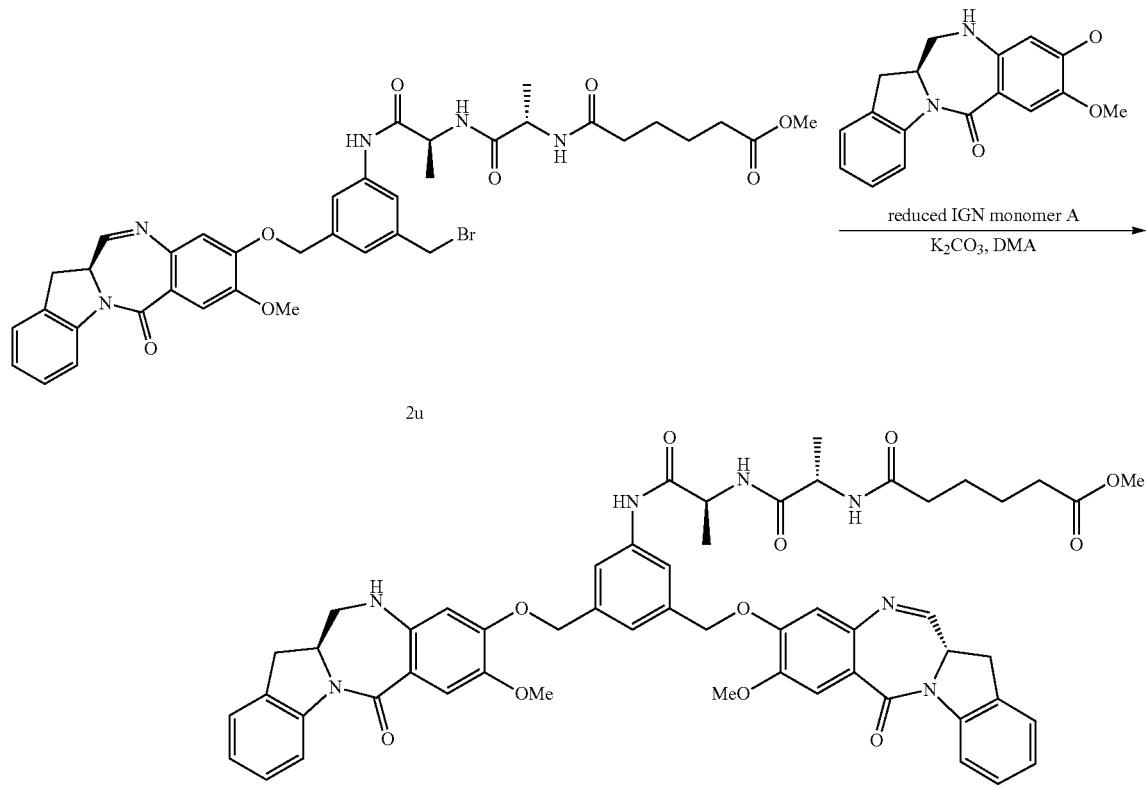

Example 10

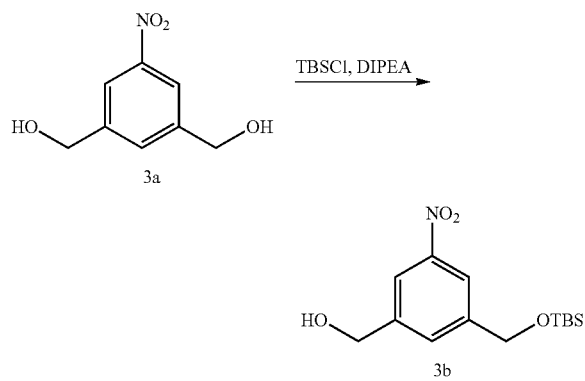

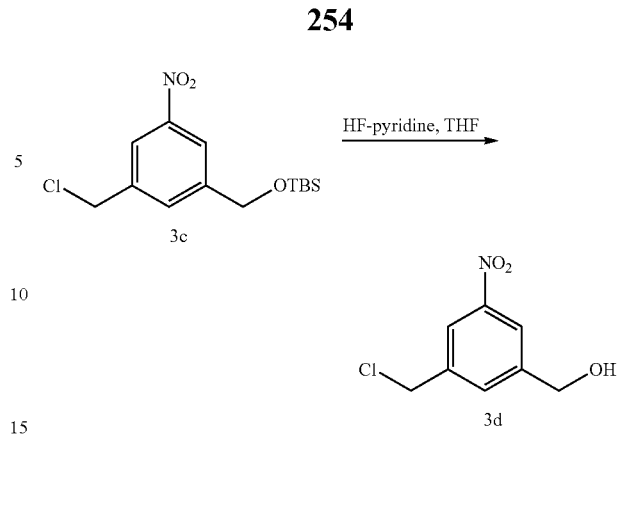

To a solution of (5-nitro-1,3-phenylene)dimethanol 3a (4.0 g, 21.84 mmol) in DCM (40 mL) and DMF (5 mL) was added DIPEA (3.86 mL, 21.84 mmol, 1.0 equiv.) followed by TBSCl (3.29 g, 21.84 mmol, 1.0 equiv.) as a solution in DMF (5 mL). The reaction was stirred at 0° C. for 1 h. The reaction was quenched with sat ammonium chloride (20 mL) and the layers were separated. The aqueous layer was extracted with DCM (2×20 mL) and the combined organic layers were washed with water (2×50 mL), brine, dried over magnesium sulfate, filtered and solvent was removed in vacuo to give a crude yellow oil. The crude product was purified by silica gel chromatography (DCM/MeOH) to give desired product 3b (3.69 g, 12.41 mmol, 57% yield). UPLCMS (2.5 min method)=1.96 min. Mass observed (ESI$^+$): 298.5 (M+H)$^+$.

To a solution of 3c (2.0 g, 6.33 mmol) in THF (38.9 mL) was added DIPEA (5.5 mL, 31.6 mmol, 5.0 equiv.) followed by HF-pyridine (2.7 mL, 19.0 mmol, 3.0 equiv.) and the reaction was stirred at room temperature for 2 h. The reaction was then quenched with sat. sodium bicarbonate (100 mL). The layers were separated and then the aqueous layer was extracted with EtOAc (3×20 mL). The combined organic layers were then washed with water (30 mL), brine (30 mL), dried over magnesium sulfate and filtered. The excess of solvent was removed in vacuo to give desired product 3d (1.1 g, 5.46 mmol, 86% yield). UPLCMS (2.5 min method)=1.31 min. Mass observed (ESI$^+$): 202.4 (M+H)$^+$.

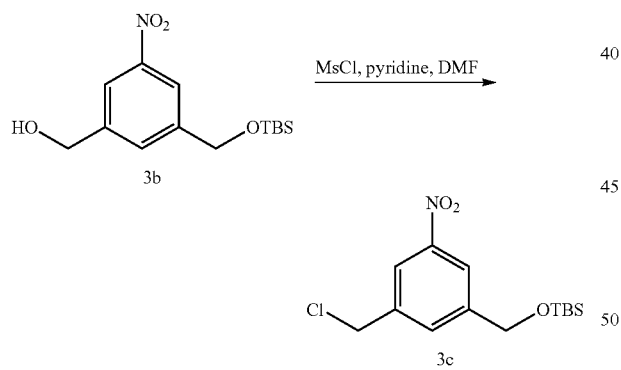

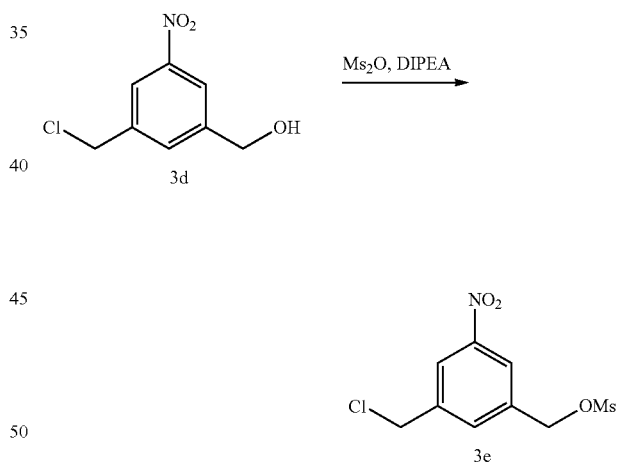

To a solution of 3b (2.0 g, 6.72 mmol) in DMF (50 mL) was added pyridine (1.6 ml, 20.17 mmol, 3.0 equiv.) followed by methanesulfonyl chloride (1.1 mL, 13.45 mmol, 2.0 equiv.) at 0° C. The reaction was warmed to rt and was stirred for 3 h. The reaction was quenched with sat. sodium bicarbonate (20 mL) and the layers were separated. The aqueous layer was extracted with EtOAc (3×30 mL). The combined organic layers were washed with water (2×100 mL), brine (100 mL), dried over magnesium sulfate and filtered. The solvent removed in vacuo and the crude material 3c (2.0 g, 6.7 mmol, 94% yield) was carried crude onto the next step. UPLCMS (2.5 min method)=2.22 min. Mass observed (ESI$^+$): 316.7 (M+H)$^+$.

To a solution of 3d (1.0 g, 4.96 mmol) in DCM (10 mL) was added DIPEA (2.6 mL, 14.9 mmol, 3.0 equiv.) at 0° C. then a solution of methanesulfonic anhydride (1.1 g, 6.45 mmol, 1.3 equiv.) in DCM was added to the reaction mixture. The reaction was stirred for 1 h. The reaction was quenched with water (10 mL) and the layers were separated and the aqueous layer was extracted with DCM (2×20 mL). The combined organic layers were washed with sat. sodium bicarbonate (10 mL), brine (20 mL), dried over magnesium sulfate and filtered. The solvent was removed in vacuo and the crude material 3e (1.3 g, 4.65 mmol, 94% yield) was used in the next step without further purification. UPLCMS (2.5 min method)=1.51 min. Mass observed (ESI$^+$): 280.6 (M+H)$^+$.

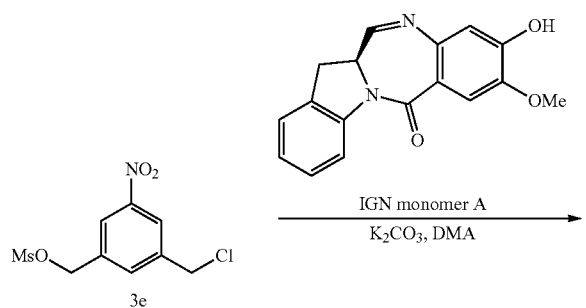

To a solution of 3e (0.4 g, 1.43 mmol) and potassium carbonate (0.6 g, 4.29 mmol, 3.0 equiv.) in DMA (13.4 mL) was added a solution of IGN monomer A (0.46 g, 1.57 mmol, 1.1 equiv.) in DMA (2 mL) at room temperature and the reaction was stirred for 5 h. The reaction was quenched with water (30 mL), the layers were separated and the aqueous layer was extracted with EtOAc (3×30 mL). The combined organic layers were washed with water (30 mL), brine (30 mL), dried over magnesium sulfate and the solvent was removed in vacuo. The crude oil was purified over silica gel chromatography using DCM/MeOH to give compound 3f (0.37 g, 0.77 mmol, 54% yield). UPLCMS (2.5 min method)=1.69 min. Mass observed (ESI⁺): 478.3 (M+H)⁺.

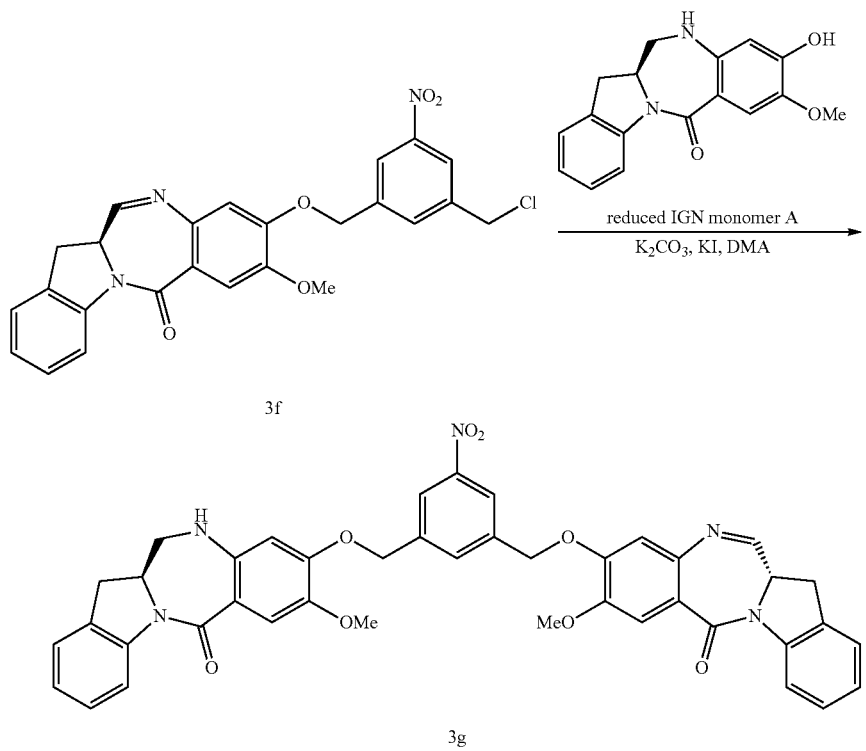

-continued

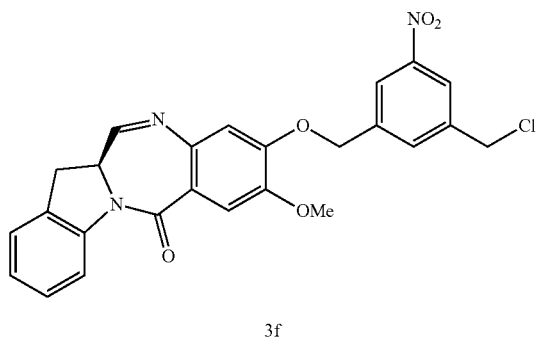

3f

To a solution of 3f (0.11 g, 0.23 mmol) in DMA (3.0 mL) was added potassium carbonate (0.095 g, 0.69 mmol, 3.0 equiv.), followed by potassium iodide (0.02 g, 0.11 mmol, 0.5 equiv.). A solution of reduced IGN monomer A (0.07 g, 0.25 mmol, 1.1 equiv.) in DMA (1 mL) was added. The reaction was then gently heated at 35° C. for 5 h. The reaction was quenched with water, and the solid was filtered off. The solid was redissolved in DCM/MeOH (20:1), washed with water, dried with magnesium sulfate, filtered and concentrated. The crude residue (0.13 g) was purified by RPHPLC (ACN/H$_2$O) to give 3g (0.063 g, 0.085 mmol, 36% yield). UPLCMS (2.5 min method)=1.79 min. Mass observed (ESI⁺): 738.3 (M+H)⁺. ¹H NMR (400 MHz, DMSO-d$_6$, reported as a mixture of water adducts)¹H NMR (400 MHz, DMSO-d6): δ 8.43-8.36 (m, 2H), 8.27 (d, J=8.1 Hz, 1H), 8.13-8.02 (m, 2H), 7.44-7.14 (m, 6H), 7.14-6.99 (m, 2H), 6.79 (s, 0.5H), 6.56 (s, 0.5H), 6.50 (d, J=2.2 Hz, 1H), 6.39 (d, J=6.9 Hz, 1H), 6.17 (d, J=6.8 Hz, 0.5H), 5.69 (s, 0.5H), 5.59 (d, J=5.7 Hz, 0.5H), 5.47-5.27 (m, 4H), 5.03

(t, J=6.1 Hz, 0.5H), 4.77 (dd, J=9.1, 6.8 Hz, 0.5H), 4.61 (dt, J=9.7, 5.1 Hz, 0.15H), 4.50-4.39 (m, 0.5H), 4.27 (dd, J=10.9, 4.2 Hz, 0.5H), 4.16 (td, J=9.6, 2.9 Hz, 0.5H), 3.95 (s, 0.5H), 3.89-3.76 (m, 6H), 3.76-3.44 (m, 4H), 3.20-3.08 (m, 1H), 2.96 (dd, J=17.0, 4.4 Hz, 1H).

Example 11

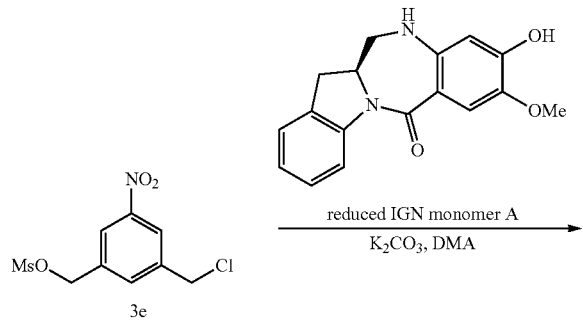

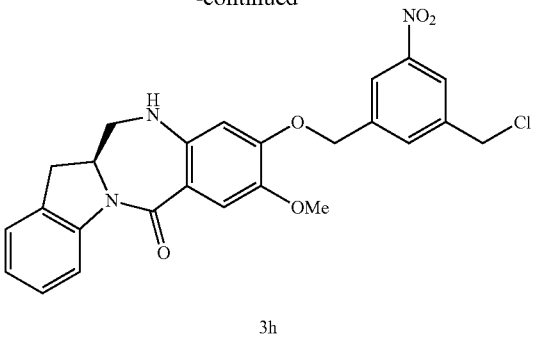

To a solution of 3e (0.45 g, 1.61 mmol) in DMA (15.1 mL) was added potassium carbonate (0.67 g, 4.83 mmol, 3.0 equiv.) followed by a solution of reduced IGN monomer A (0.5 g, 1.69 mmol, 1.1 equiv.) in DMA (2 mL). The reaction was stirred at room temperature for 5h. The reaction was quenched with water (30 mL) and the mixture was stirred for 10 min. The solid was filtered and then dissolved in DCM/MeOH (9/1, 30 mL) and washed with brine (20 mL). The organic layer was separated and dried over magnesium sulfate, filtered and the solvent removed in vacuo. The crude material was purified by silica gel chromatography using Hexane/EtOAc to give compound 3h (0.28 g, 0.58 mmol, 36% yield) as colorless oil. UPLCMS (2.5 min method)=1.82 min. Mass observed (ESI$^+$): 480.3 (M+H)$^+$.

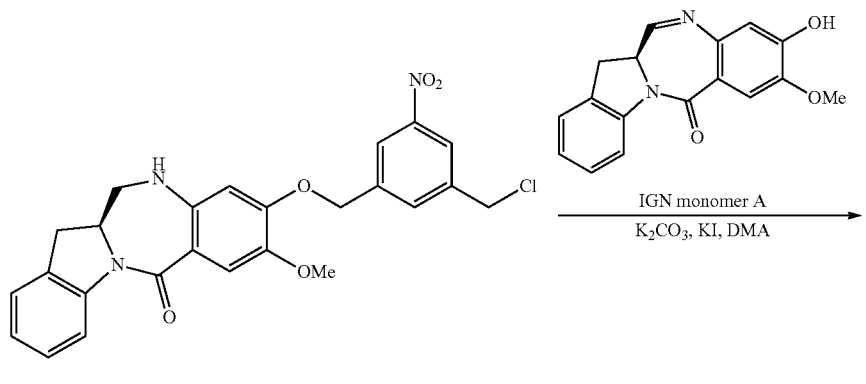

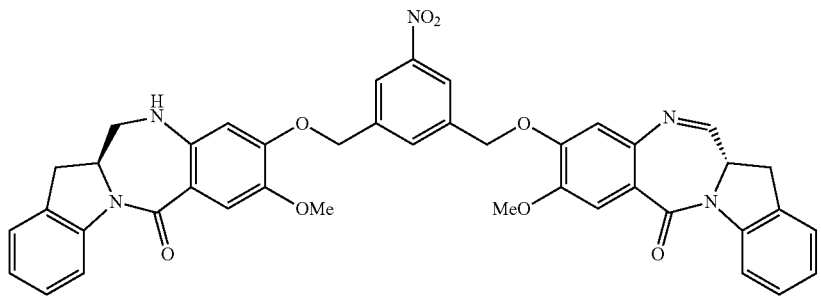

To a solution of 3h (0.27 g, 0.56 mmol) in DMA (10 mL) was added potassium carbonate (0.16 g, 1.12 mmol, 2.0 equiv.) followed by potassium iodide (0.05 g, 0.28 mmol, 0.05 equiv.). A solution of IGN monomer A (0.18 g, 0.62 mmol, 1.1 equiv.) in DMA (2 mL) was added to the reaction mixture at room temperature. The reaction was then stirred at 40° C. for 3h. The reaction was quenched with water (20 mL) and the solid was filtered off and washed with water. The crude yellow solid was dissolved in DCM/MeOH (9/1, 30 mL) and then washed with water (10 mL), dried over magnesium sulfate and filtered. The solvent was removed in vacuo to give a crude yellow solid. The crude product was purified by silica gel chromatography using DCM/MeOH (0% to 5% MeOH/DCM) to give the product 3g as a yellow powder (0.35 g, 0.48 mmol, 86% yield). UPLCMS (2.5 min method)=1.79 mm (2.5 min method). Mass observed (ESI$^+$): 738.4 (M+H)$^+$.

Example 12

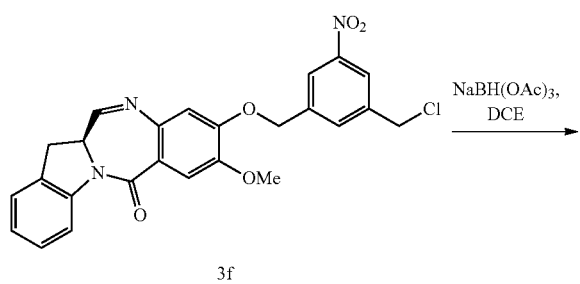

3h

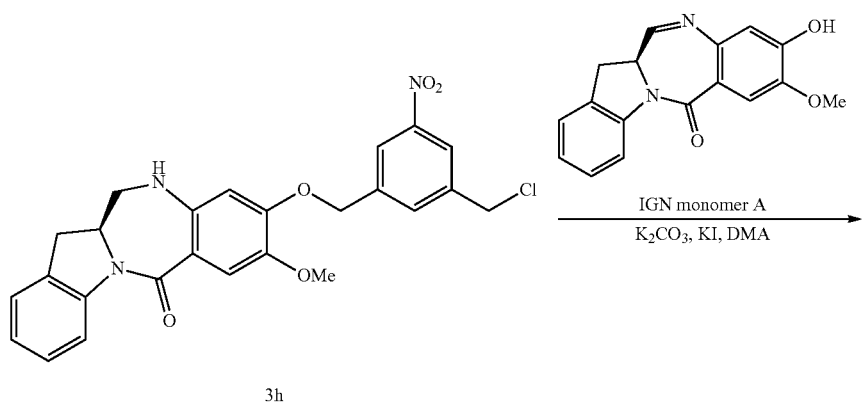

To a solution of 3f (0.15 g, 0.31 mmol) in DCE (2 mL) was added sodium triacetoxyborohydride (0.067 g, 0.31 mmol, 1.0 equiv.) and the reaction was stirred at room temperature for 1 h. The reaction was quenched with sat ammonium chloride (1 mL) and then the layers were separated. The aqueous layer was extracted with DCM (3×10 mL) and the combined organic layers were washed with brine (20 mL), dried over magnesium sulfate, filtered and the solvent removed in vacuo. The crude brown oil was purified by silica gel chromatography to give desired product 3h (0.08 g, 0.16 mmol, 52% yield). UPLCMS (2.5 min method)=1.80 min. Mass observed (ESI$^+$): 480.5 (M+H)$^+$.

3h

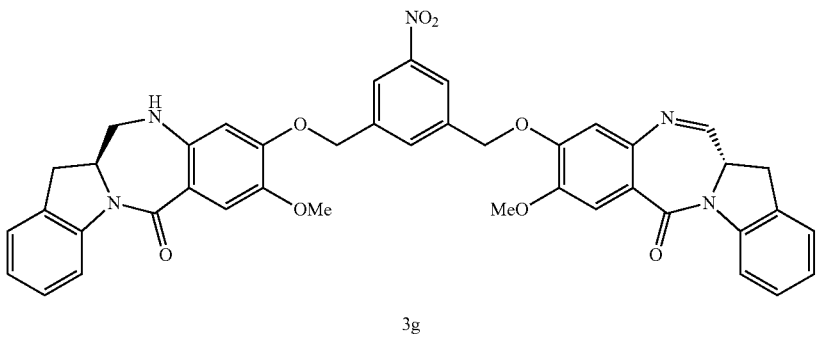

3g

To a solution of 3h (0.07 g, 0.16 mmol) in DMA (2 mL) was added potassium carbonate (0.07 g, 0.47 mmol, 3.0 equiv.) followed by potassium iodide (0.013 g, 0.08 mmol, 0.05 equiv.) and then a solution of IGN monomer A (0.05 g, 0.17 mmol, 1.1 equiv.) in DMA (0.5 mL) was added. The reaction was stirred at room temperature for 12h. Water (20 mL) was added to the mixture and the mixture was stirred for 10 mm at which point the solid was filtered. The solid was solubilized in DCM (10 mL) and then washed with brine (10 mL). The organic layer was dried over magnesium sulfate and filtered. The solvent was removed to obtain a yellow oil (0.09 g, 0.12 mmol, 80% yield). UPLCMS (2.5 min method)=1.79 mm (2.5 min method). Mass observed (ESI$^+$): 738.5 (M+H)$^+$.

Example 13

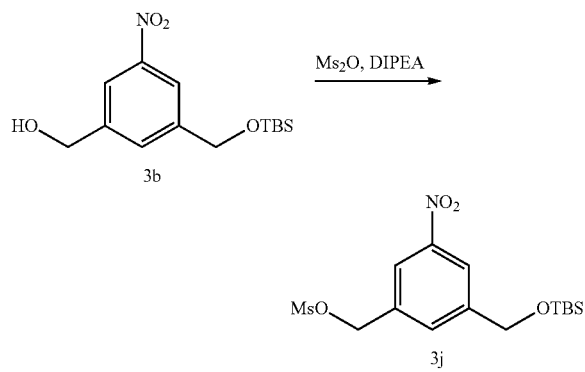

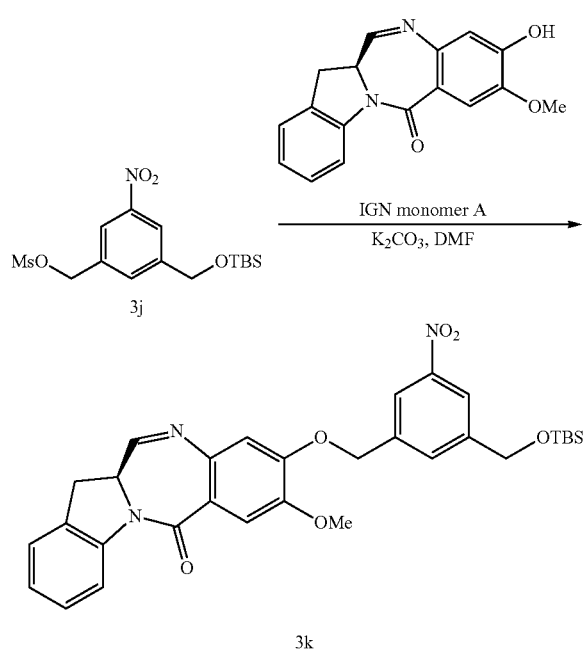

To a solution of 3b (1.00 g, 3.4 mmol) in DCM (33 mL) was added DIPEA (1.781 ml, 10.09 mmol, 3.0 equiv.), followed by a solution of methanesulfonic anhydride (0.703 g, 4.03 mmol, 1.2 equiv.) at 0° C. The reaction was stirred for 1 h. The solvent was evaporated to give the crude product 3j (1.2 g, 3.2 mmol, 95% yield) which was used in the next step without further purification. UPLCMS (2.5 min method)=2.04 min. Mass observed (ESI$^+$): 376.5 (M+H)$^+$.

To a solution of 3j (1.24 g, 3.30 mmol) in DMF (26 mL) was added potassium carbonate (0.91 g, 6.60 mmol, 2.0 equiv.) followed by IGN monomer A (0.97 g, 3.30 mmol, 1.0 equiv.) at room temperature for 12 h. The reaction was quenched with water (60 mL) and the solid was filtered off and then dissolved in DCM/MeOH (20/1, 20 mL). The organic layer was washed with brine, dried over magnesium sulfate and filtered. The solvent was removed in vacuo and the crude material was purified over silica gel chromatography to give the desired product 3k (1.3 g, 2.27 mmol, 69% yield). UPLCMS (2.5 min method)=2.12 mm (2.5 min method). Mass observed (ESI$^+$): 574.4 (M+H)$^+$.

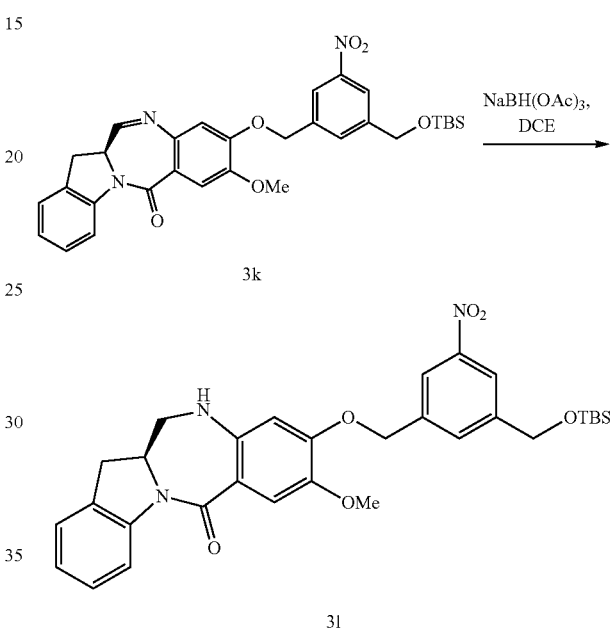

3k (0.63 g, 1.1 mmol) was dissolved in anhydrous DCE (11 mL). Sodium triacetoxyborohydride (0.70 g, 3.3 mmol, 3.0 equiv.) was added and the reaction mixture was stirred for 1 h at room temperature. The mixture was quenched with sat ammonium chloride (10 mL). The layers were separated and the aqueous layer was extracted with DCM (2×20 mL). The combined organic layers were washed with brine (20 mL), dried over anhydrous magnesium sulfate, filtered and concentrated to obtain 3l (0.58 g, 1.0 mmol, 92% yield). UPLCMS (8.0 min method)=7.797 min (8.0 min method). Mass observed (ESI$^+$): 576.3 (M+H)$^+$.

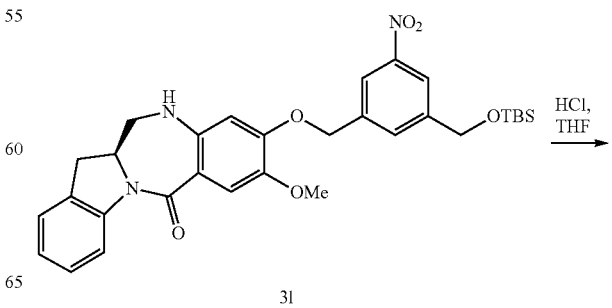

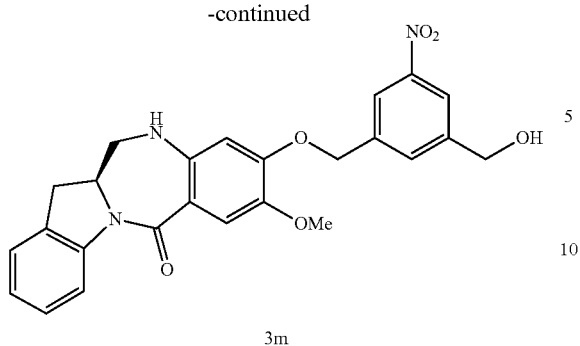

3m

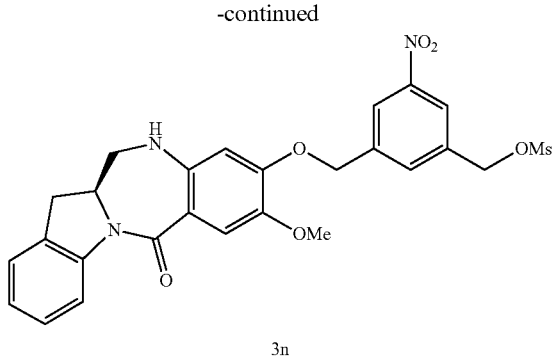

3n

A solution of 3l (0.58 g, 1.0 mmol) was dissolved in anhydrous THF (5 mL) and 5 M aqueous hydrochloride acid solution (2.01 mL, 10.07 mmol) was added. The mixture was stirred at room temperature for 2 h. The reaction was quenched with sat. sodium bicarbonate (5 mL) and the layers were separated and the aqueous layer was extracted with DCM (2×10 mL). The combined organic layers were washed with brine (20 mL), dried over magnesium sulfate and concentrated to give a bright orange solid. The resulting solid was purified by silica gel chromatography (DCM/MeOH) to give compound 3m (0.33 g, 0.71 mmol, 71% yield). UPLCMS (8.0 min method)=5.166 min. Mass observed (ESI+): 462.1 (M+H)+.

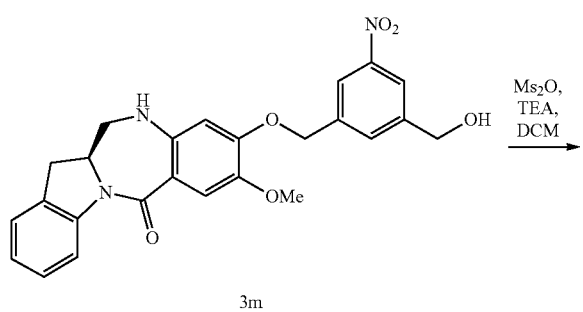

3m 3m (0.1 g, 0.22 mmol) was dissolved in anhydrous DCM (1.5 mL) and anhydrous DMF (0.7 mL). The reaction was cooled to 0° C. and triethylamine (0.12 mL, 0.88 mmol) and methanesulfonic anhydride (0.08 g, 0.44 mmol) were added. The reaction was stirred at 0° C. for 1 h. The reaction mixture was diluted with ethyl acetate (20 mL), washed with water (2×20 mL), dried over magnesium sulfate, filtered and concentrated. The compound was initially purified by silica gel chromatography (DCM/EtOAc) followed by additional purification by RPPHPLC (MeCN/water) to give the desired product 3n (0.041 g, 0.076 mmol, 34% yield). Mass observed (ESI+): 540.3 (M+H)+.

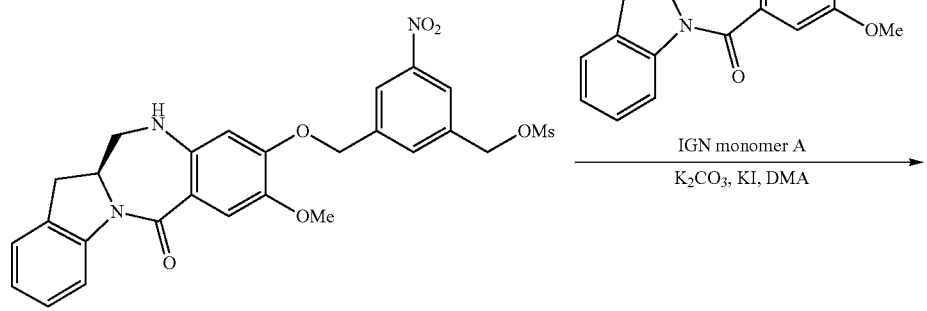

3n

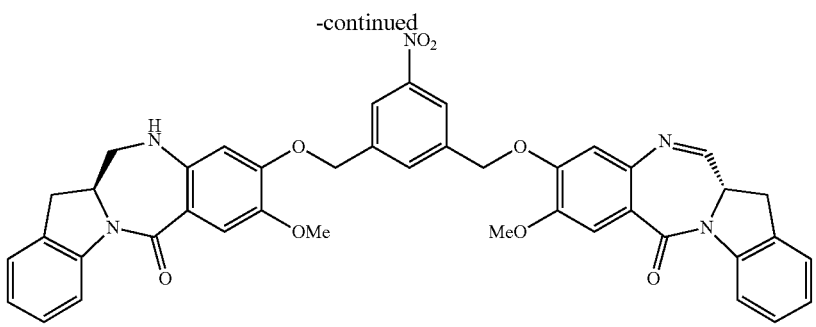

3g

Compound 3n (0.041 g, 0.076 mmol) and IGN monomer A (0.027 g, 0.091 mmol) were dissolved in anhydrous DMA (0.5 mL). Potassium carbonate (0.012 g, 0.091 mmol) and potassium iodide (0.006 g, 0.038 mmol) were added and the mixture stirred for 12 h. Water (5 mL) was added to the reaction mixture. The solid was filtered off and then redissolved in DCM (20 mL) and washed with water (10 mL). After drying over magnesium sulfate, filtration and concentration, the solid was purified by RPHPLC (ACN/H$_2$O) to give 3g (0.012 g, 0.016 mmol, 21% yield). UPLCMS (2.5 min method)=1.79 min. Mass observed (ESI$^+$): 738.5 (M+H)$^+$.

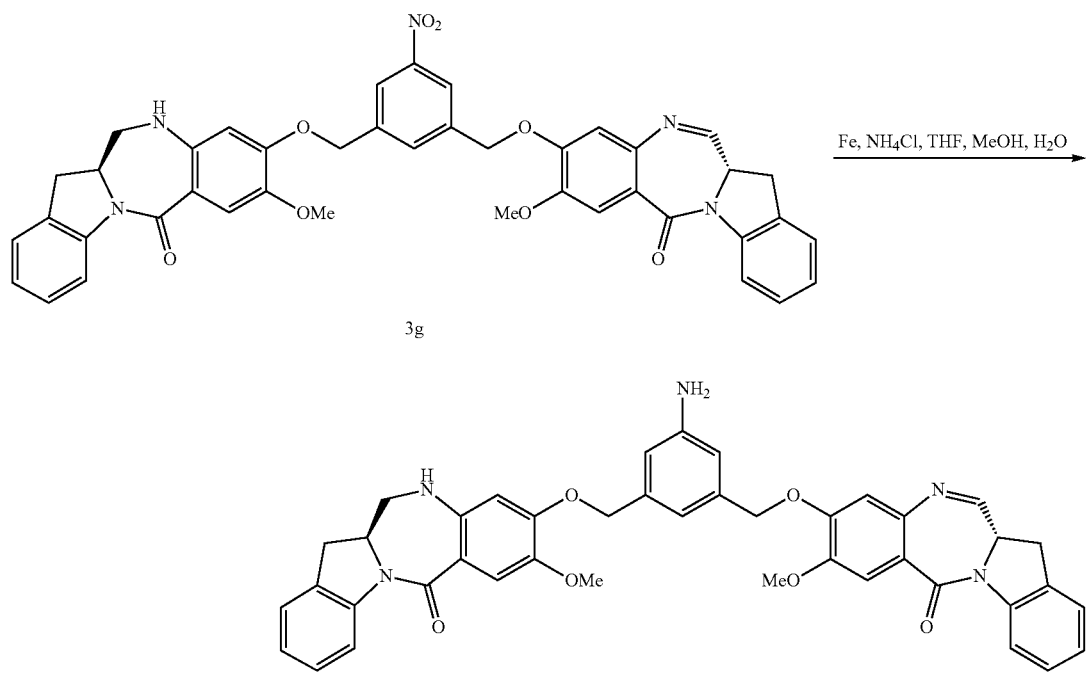

Compound 3g (0.017 g, 0.023 mmol) was dissolved in anhydrous THF (1 mL), anhydrous MeOH (0.5 mL) and water (0.1 mL). Ammonium chloride (0.012 g, 0.23 mmol, 10.0 equiv.) and iron (0.006 g, 0.115 mmol, 5.0 equiv.) were added. The mixture was stirred at 60° C. for 2 h. The reaction mixture was cooled to room temp, filtered through Celite and rinsed with 20% MeOH/DCM (10 mL). The filtrate was concentrated and the crude product was purified by silica gel chromatography (DCM/MeOH) to give compound 3o as a white solid (0.012 g, 0.018 mmol, 76% yield). UPLCMS (2.5 min method)=1.84 min. Mass observed (ESI$^+$): 708.5 (M+H)$^+$. $^1$H NMR (400 MHz, DMSO-d6, reported as a mixture of water adducts, T=330K): δ 8.26 (d, J=7.9 Hz, 1H), 8.17 (d, J=7.8 Hz, 1H), 8.03 (d, J=4.5 Hz, 1H), 7.49 (s, 1H), 7.42-7.33 (m, 2H), 7.36-7.08 (m, 4H), 7.09-6.95 (m, 2H), 6.76-6.64 (m, 3H), 6.47 (s, 1H), 6.15 (d, J=6.5 Hz, 1H), 5.11 (m, 2H), 4.98 (m, 2H), 4.58 (dt, J=9.9, 4.7 Hz, 1H), 4.47-4.36 (m, 1H), 3.87 (m, 1H), 3.76 (s, 3H), 3.71-3.46 (m, 4H), 3.39-3.28 (m, 1H), 2.93 (dd, J=16.8, 4.7 Hz, 1H).

Example 14

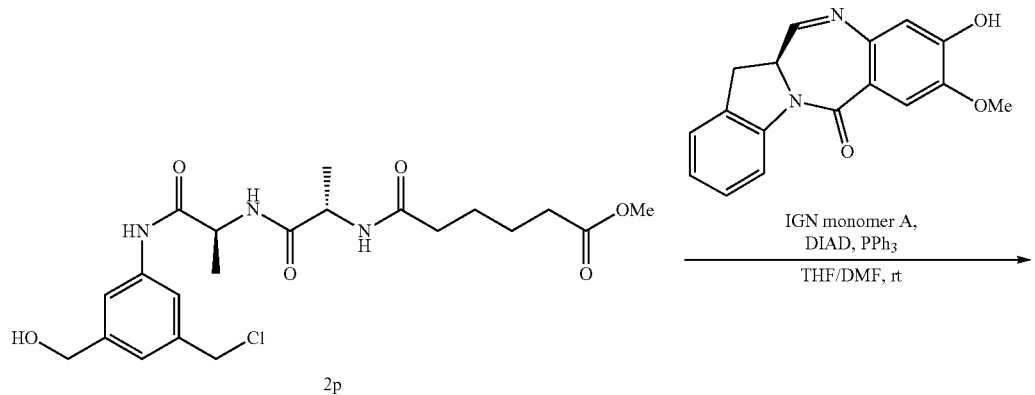

Compound 2p (0.03 g, 0.066 mmol, 1.0 equiv.) and IGN monomer A (0.021 g, 0.072 mmol, 1.1 equiv.) were dissolved in THF (0.65 mL) and DMF (0.3 mL). Triphenylphosphine was added (0.021 g, 0.079 mmol, 1.2 equiv.), followed by a slow addition of DIAD (0.015 mL, 0.079 mmol, 1.2 equiv.). The reaction was stirred at rt under argon for 2 h. The reaction mixture was concentrated and water (~2 mL) was added to triturate the product. The precipitate was filtered and the remaining solid was washed with water. The crude residue was purified by RPHPLC (C18 column, MeCN/water, gradient, 40% to 60%) to give compound 2r as a white fluffy solid (0.015 g, 0.02 mmol, 31% yield). UPLCMS (2.5 min method)=1.62 min. Mass observed (ESI$^+$)=732.9 (M+H)$^+$.

Example 15

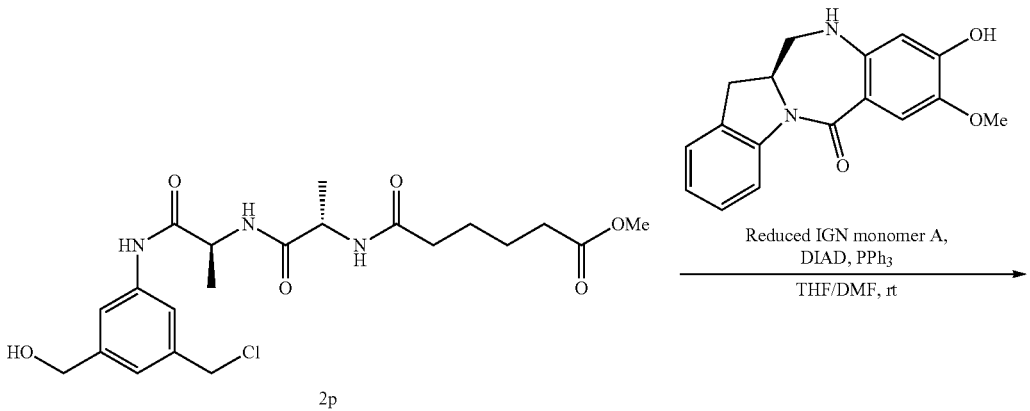

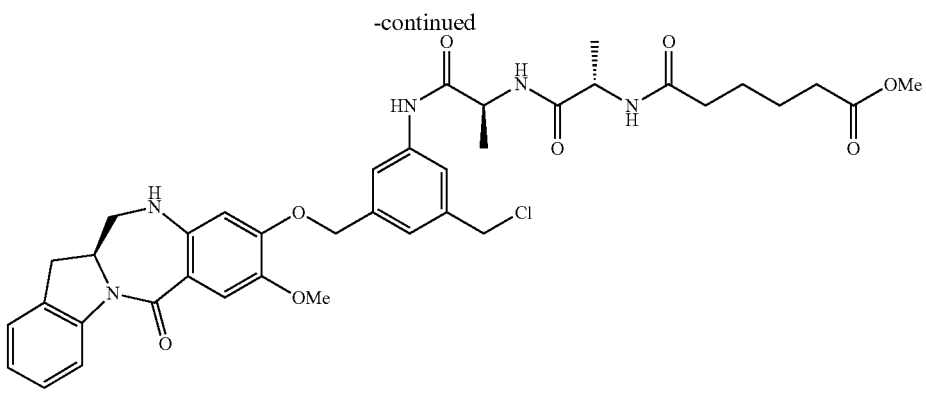

2s

Compound 2p (0.03 g, 0.066 mmol, 1.0 equiv.) and reduced IGN monomer A (0.02 g, 0.072 mmol, 1.1 equiv.) were dissolved in THF (0.66 mL) and DMF (0.1 mL). Triphenylphosphine (0.021 g, 0.079 mmol, 1.2 equiv.) was added, followed by a slow addition of DIAD (0.015 mL, 0.079 mmol, 1.2 equiv.). The reaction mixture was stirred at rt under argon for 2 h. The reaction mixture was diluted with DCM and was washed with water (2×). The organic layer was dried over magnesium sulfate, filtered and concentrated. The crude residue was purified by RPHPLC (C18 column, MeCN/water, gradient, 40% to 65%) to yield 2s as a white fluffy solid (0.017 g, 0.02 mmol, 35% yield). UPLCMS (2.5 min method)=1.71 min. Mass observed (ESI$^+$)=735.4 (M+H)$^+$.

Example 16

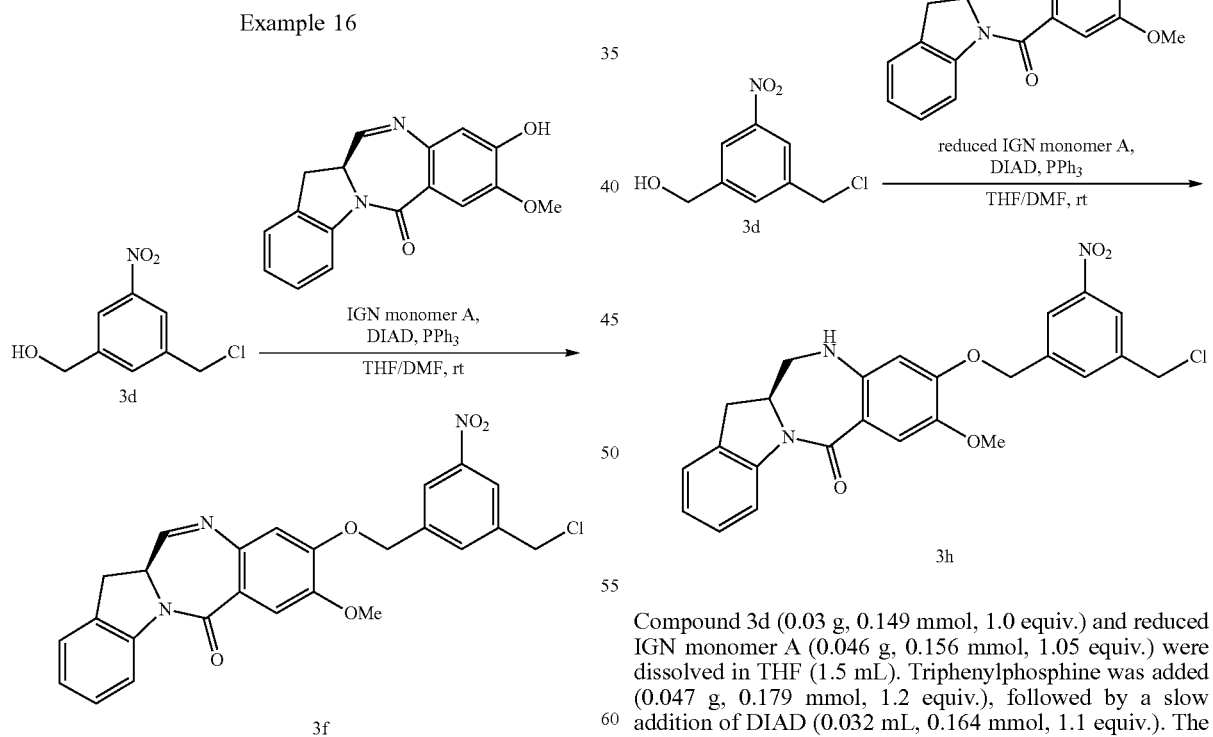

Compound 3d (0.03 g, 0.149 mmol, 1.0 equiv.) and IGN monomer A (0.046 g, 0.156 mmol, 1.05 equiv.) were dissolved in THF (1.5 mL) and DMF (0.3 mL). Triphenylphosphine was added (0.047 g, 0.179 mmol, 1.2 equiv.), followed by a slow addition of DIAD (0.032 mL, 0.164 mmol, 1.1 equiv.). The reaction was stirred at rt under argon for 12 h. The reaction mixture was concentrated and water (~2 mL) was added to triturate the product. The precipitate was filtered and the remaining solid was washed with water. The crude residue was purified by silica gel chromatography (hexane/EtOAc) to give compound 3f as a white yellow solid (0.013 g, 0.027 mmol, 18% yield). UPLCMS (2.5 min method)=1.80 min. Mass observed (ESI$^+$)=478.4 (M+H)$^+$.

Example 17

Compound 3d (0.03 g, 0.149 mmol, 1.0 equiv.) and reduced IGN monomer A (0.046 g, 0.156 mmol, 1.05 equiv.) were dissolved in THF (1.5 mL). Triphenylphosphine was added (0.047 g, 0.179 mmol, 1.2 equiv.), followed by a slow addition of DIAD (0.032 mL, 0.164 mmol, 1.1 equiv.). The reaction was stirred at rt under argon for 2 h. The reaction mixture was concentrated and coevaporated with toluene (2×). The crude residue was purified by silica gel chromatography (hexane/EtOAc) to give compound 3h as a orange yellow solid (0.055 g, 0.115 mmol, 77% yield). UPLCMS (2.5 min method)=1.90 min. Mass observed (ESI$^+$)=480.5 (M+H)$^+$.

Example 18

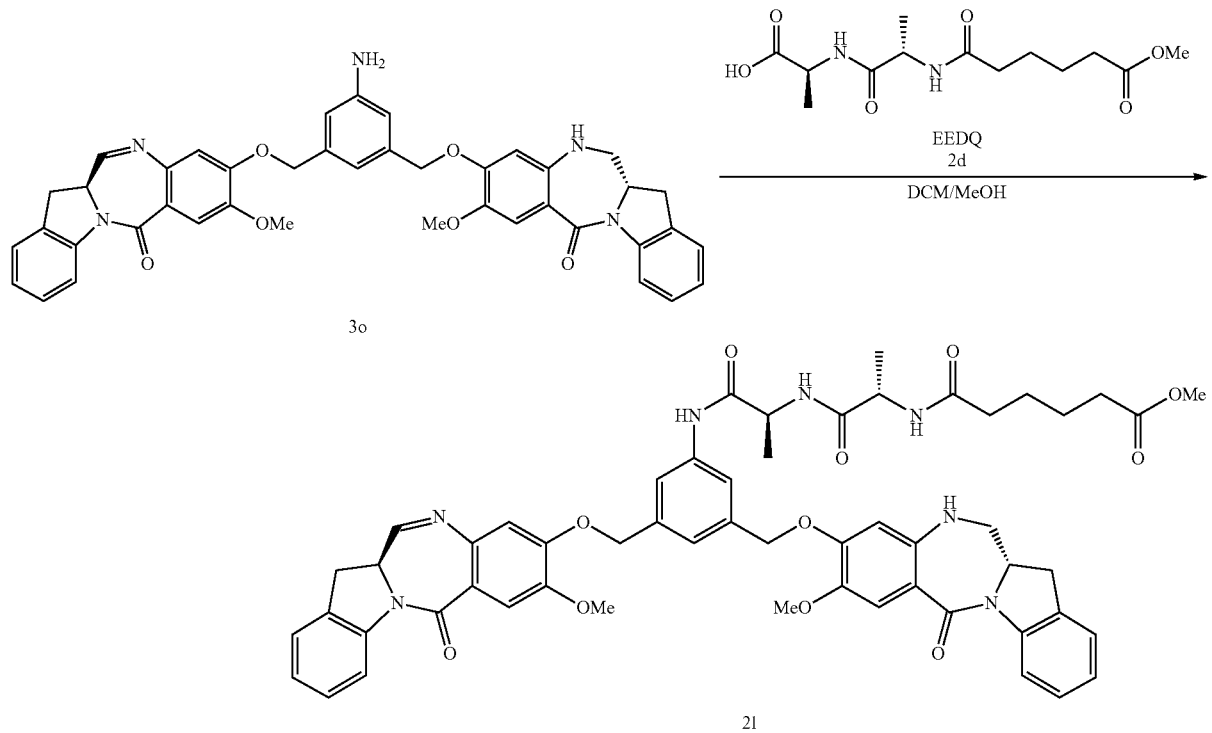

To a solution of 2d (0.024 g, 0.078 mmol, 1.1 equiv.) in DCM (1 mL) was added EEDQ (0.019 g, 0.078 mmol, 1.1 equiv.). The reaction was stirred for 5 min and MeOH (0.1 mL) was added, followed by a solution of 3o (0.05 g, 0.071 mmol) in DCM (1 mL). The reaction was stirred at rt for 2 h or until completion of starting material. The reaction was concentrated to form a white precipitate to which MTBE (5 mL) was added and the resulting mixture was stirred for 30 mm at room temperature. The solid was filtered off to give compound 2l which was then purified by RPHPLC (C18 column, MeCN/water) to give 2l (0.023 g, 0.023 mmol, 33% yield). UPLCMS (2.5 min method)=1.75 min. Mass observed (ESL$^+$)=993.2 (M+H)$^+$.

Example 19

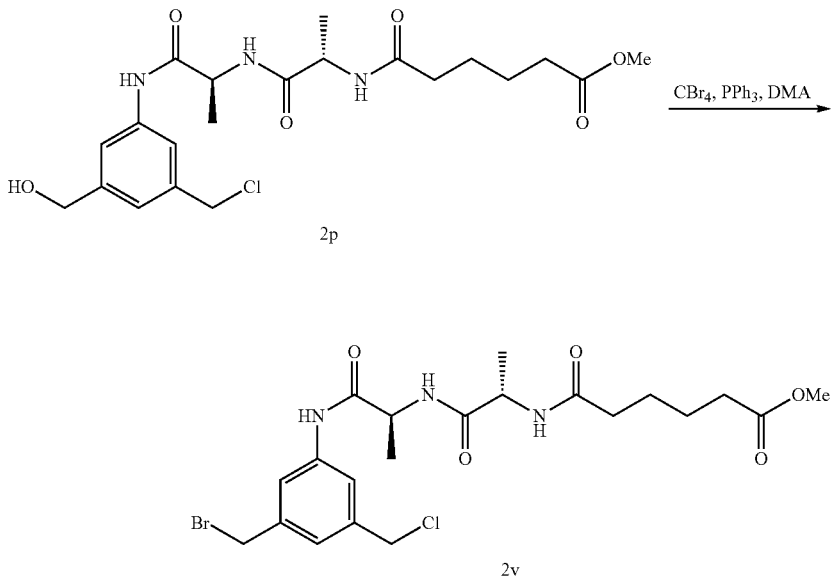

To a solution of 2p (0.05 g, 0.110 mmol, 1.0 equiv.) in DMA (1 mL), was added carbon tetrabromide (0.044 g, 0.132 mmol, 1.2 equiv.) followed by triphenylphosphine (0.043 g, 0.164 mmol, 1.5 equiv.) and the reaction was stirred at room temperature for 2 h. The solvent was removed to give a white solid which was triturated with MTBE and the solid was filtered off to give compound 2v. (0.03 g, 0.058 mmol, 57% yield, 52% purity), which was carried onto the next step without further purification. UPLCMS (2.5 min method) =1.59 min. Mass observed (ESI$^+$)=518.2 (M+H)$^+$.

-continued

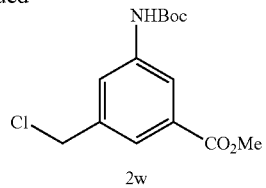

2w

To a slurry of compound 2v (14.7 g, 0.052 mol, 1.0 equiv., prepared as described described in literature, see: *Beilstein J. Org. Chem.* 2014, 10, 535-543) in DCM and (100 mL) DMF (1 ml), was charged with SOCl$_2$ (12.6 g, 0.104 mol, 2.0 equiv.) in one portion. The resulting solution was stirred at 35° C. overnight resulting in a thick tan slurry. The slurry was filtered and the solid was dried to give 7.5 g as an off-white solid. NMR revealed cleavage of the Boc protecting group. The dark filtrate was charged with solid sodium carbonate (10.6 g, 0.1 mol) followed by buffering to pH~6-7 by further addition of sodium bicarbonate. To the resulting solution Boc$_2$O (12.7 g, 0.058 mol, 1.1 equiv.) was added and was stirred for 0.5 h. The filtered solid (7.5 g) was added to the reaction mixture, followed by the addition of Boc$_2$O (6.5 g, 0.030 mol, 1.7 equiv.) (pH~6) and continued to stir at rt overnight. Then sat. sodium bicarbonate (10 mL) was added to reach pH 6~7. Additional Boc$_2$O (9.3 g, 42.6 mmol), and DMAP (0.2 g, 1.63 mmol) were added and continued to stir overnight. The dark reaction was filtered to remove some precipitate. The DCM layer was washed with 1 N HCl to remove un-Boc product, which was basified and extracted with DCM and recovered 3.0 g colorless crispy solid (un-Boc product). The DCM layer was washed with brine and concentrated to a dark slush. The crude product

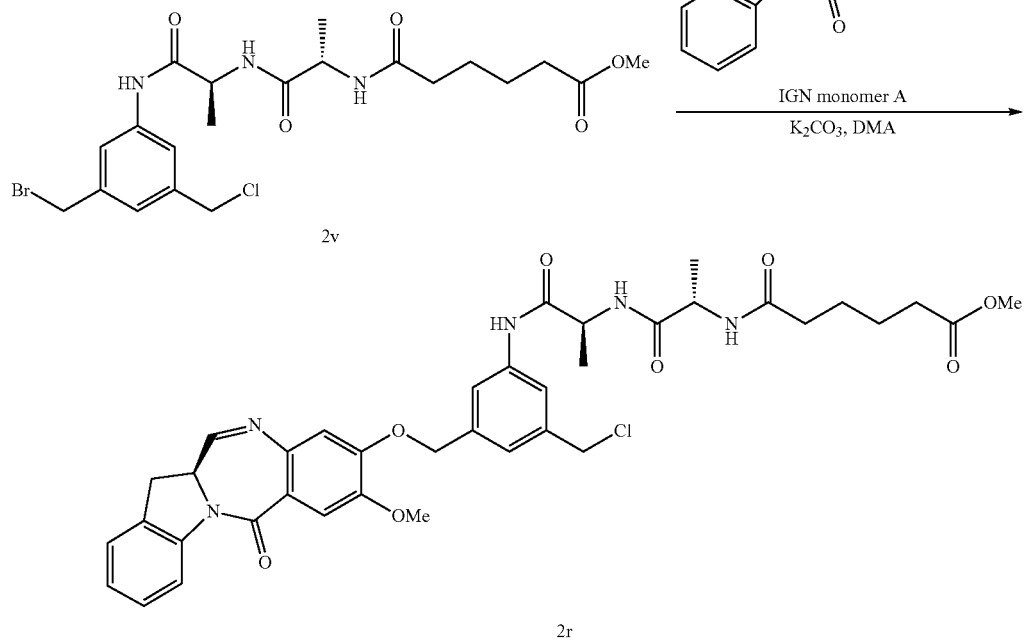

To a solution of 2v (0.03 g, 0.043 mmol, 1.0 equiv.) in DMA (0.5 mL) was added potassium carbonate (0.012 g, 0.087 mmol, 2.0 equiv.) followed by IGN monomer A (0.013 g, 0.046 mmol, 1.05 equiv.). The reaction mixture was stirred for 4 h at room temperature. The reaction mixture was diluted with water (5 mL) and the solid was filtered off. The solid was dissolved in DCM/MeOH (9/1, 2 mL). The organic layer was washed with water (10 mL), brine (10 mL), and dried over magnesium sulfate. After filtration and solvent removal, the crude product was purified by RPHPLC (C18 column, MeCN/water) to give 2r (0.011 g, 0.015 mmol, 35% yield). UPLCMS (2.5 min method)=1.62 min. Mass observed (ESI$^+$)=733.2 (M+H)$^+$.

Example 20

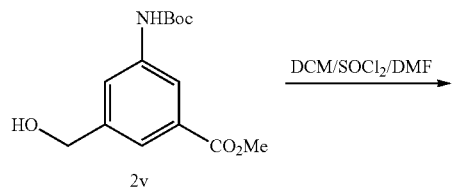

was purified by silica gel chromatography (EtOAc/Hexanes) to give 2w as a pale brown solid (9.5 g, 0.031 mmol, 62% yield). $^1$H NMR (400 MHz, CDCl$_3$): δ 7.84 (m, 2H), 7.75 (m, 1H), 6.60 (s, 1H, NH), 4.58 (s, 2H), 3.91 (s, 3H), 1.53 (s, 9H).

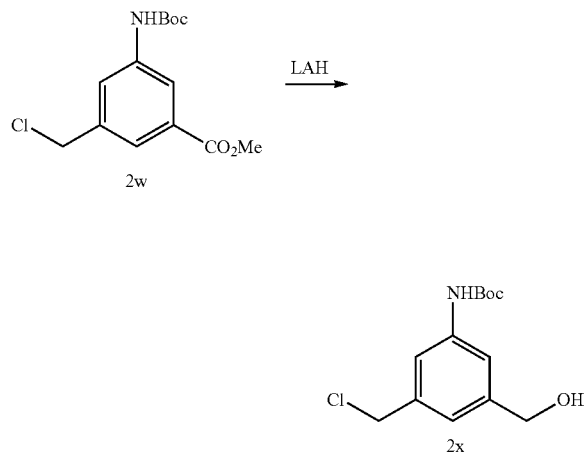

A solution of LAH/THF (0.6M, 60 mL, 1.15 equiv.) was stirred at rt for 30 min and then cooled down to −65° C. with an acetone-dry ice bath. Compound 2w (9.3 g, 0.031 mol, 1.0 equiv.) was slowly added in portions (Ti~−60° C.) resulting in a yellow brown slurry which was stirred for 4 h. The reaction was quenched with water (1.3 mL), 15% NaOH (1.3 mL), and water (4 mL) and was stirred for 20 mm (Ti~5° C.). The reaction was filtered and rinsed with ethyl acetate (~90 mL). The filtrate was washed with brine, and concentrated to yield 2x (8.0 g, 0.029 mol, 93% yield) as brown oil. $^1$H NMR (400 MHz, CDCl$_3$): δ 7.45 (s, 1H), 7.40 (s, 1H), 7.10 (s, 1H), 6.60 (s, 1H, NH), 4.75 (s, 2H), 4.50 (s, 2H), 1.53 (s. 9H).

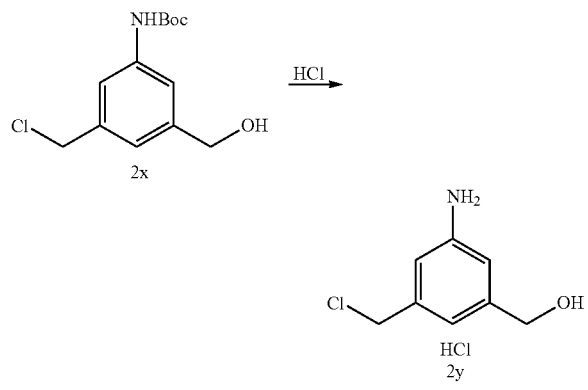

Compound 2x (8.0 g, 0.029 mol, 1.0 equiv.) was dissolved in DCM (20 mL) and cooled in ice-water bath. 4 N HCl/dioxane (15 mL, 1.5 equiv.) was added and the resulting mixture was heated at 50° C. for 1 h and then cooled down to rt. The slurry was concentrated and the solvent switched to heptane. The slurry was filtered, rinsed with hexane, and dried in oven (60° C.) to afford 2y (5.4 g, 0.026 mol, 88% yield) as light brown solid. $^1$H NMR (400 MHz, DMSO-d6): δ 7.45 (s, 1H), 7.25 (s, 2H), 4.76 (s, 2H), 4.52 (s, 2H).

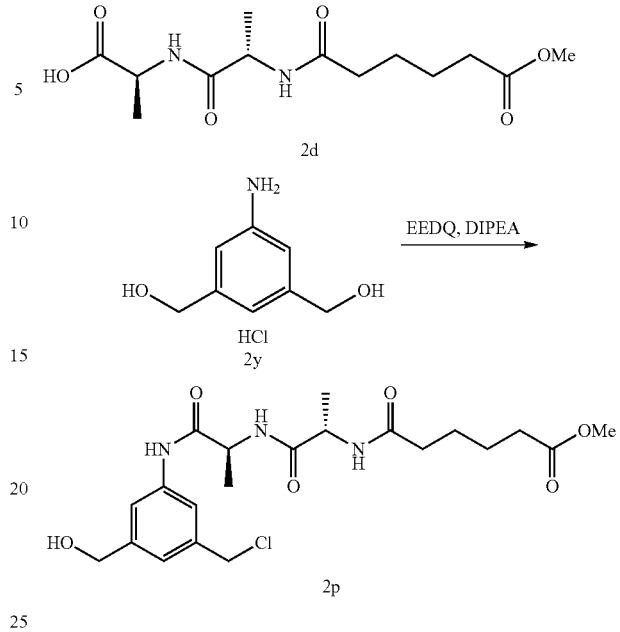

To a solution of 2d (0.969 g, 3.20 mmol, 1.1 equiv.) in DCM (25 mL) was added EEDQ (0.79 g, 3.2 mmol, 1.1 equiv) at room temperature. After 8 min, a solution of 2y (0.5 g, 2.91 mmol, 1.0 equiv.), DIPEA (0.51 mL, 2.91 mmol, 1.0 equiv.) in MeOH (5 mL) was added dropwise over 1 minute. The reaction was stirred for 2 h. The reaction mixture was quenched with water (30 mL), the layers were separated and the aqueous layer extracted with DCM (2×20 mL). The combined organic layers were washed with sat. sodium bicarbonate (20 mL), brine (20 mL), dried over magnesium sulfate, filtered and concentrated to minimal amount of solvent left. The resulting white solid was diluted in MBTE and was filtered to give the desired product 2p as a white solid (0.64 g, 1.40 mmol, 48% yield). UPLCMS (2.5 min method)=1.30 min. Mass observed (ESI$^+$)=456.3 (M+H)$^+$.

The invention claimed is:

1. A method of preparing a compound of formula (17d):

(17d)

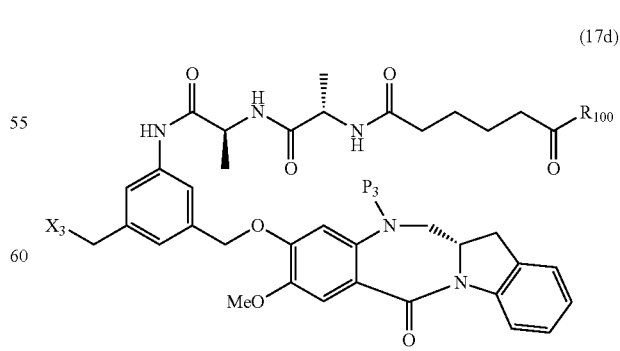

or a salt thereof, said method comprising reacting a compound of formula (14d)

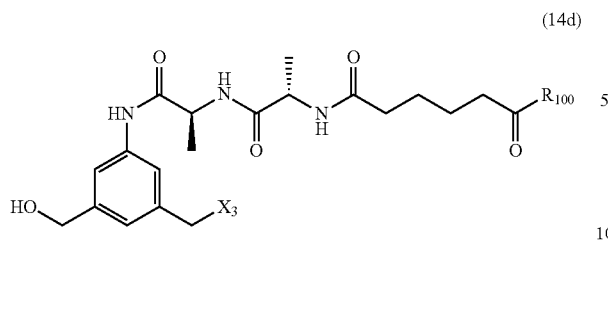
(14d)

with a monomer compound of formula (d₁),

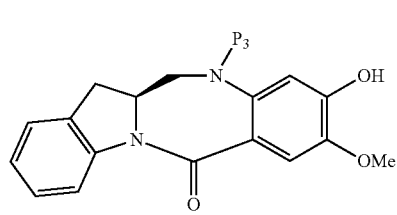
(d₁)

wherein $X_3$ is —Cl; $P_3$ is H or an amine protecting group; and $R_{100}$ is $(C_1\text{-}C_3)$alkoxy.

2. The method of claim 1, wherein the compound of formula (14d) is reacted with a monomer of formula (d₁) in the presence of an alcohol activating agent and an azodicarboxylate.

3. The method of claim 2, wherein the alcohol activating agent is triphenylphosphine.

4. The method of claim 2, wherein the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD).

5. The method of claim 2, wherein the compound of formula (14d) is reacted with the monomer compound of formula (d₁), wherein $P_3$ is H, to form a compound of formula (17d'):

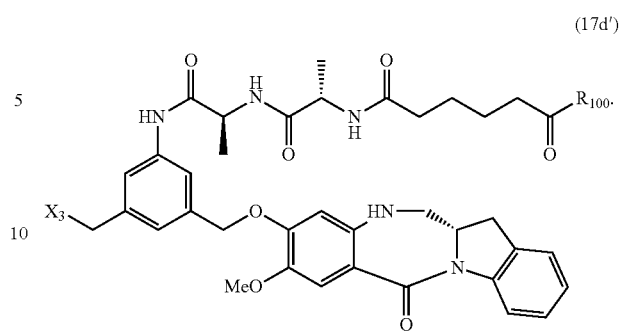
(17d')

6. The method of claim 2, wherein $P_3$ is an amine protecting group and the method further comprises the step of reacting the compound of formula (17d) with an amine deprotecting reagent to form a compound of formula (17d'):

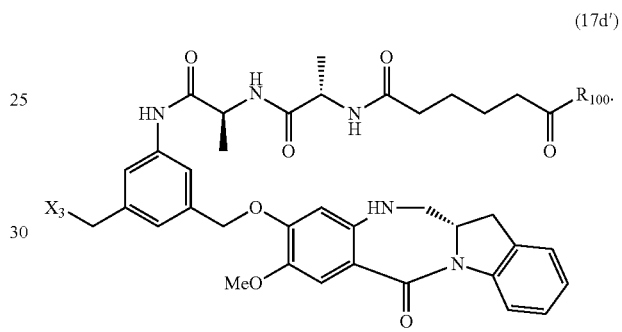
(17d')

7. A method of preparing a compound of formula (18d),

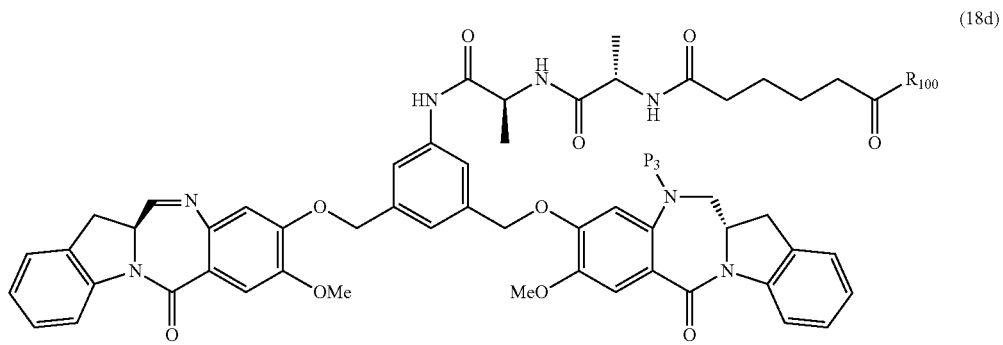
(18d)

or a pharmaceutically acceptable salt thereof, said method comprising the steps of:

(1) reacting the compound of formula (14d):

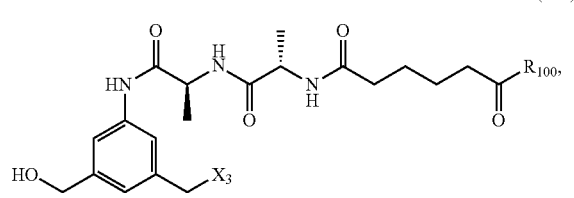
(14d)

or a salt thereof, with a reduced monomer compound of formula ($d_i$),

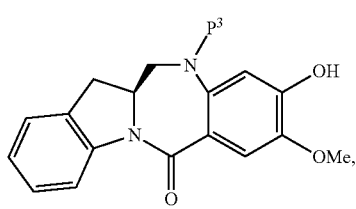 ($d_1$)

to form a compound of formula (17d):

(17d)
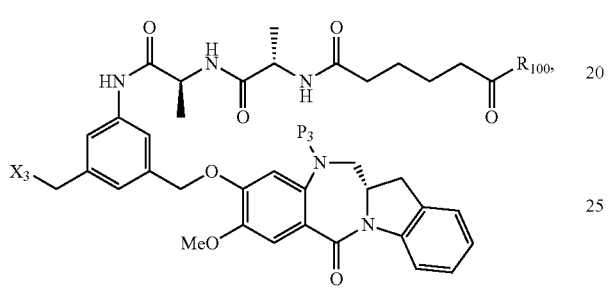

or a salt thereof; and (2) reacting the compound of formula of (17d) with a monomer of formula ($a_1$):

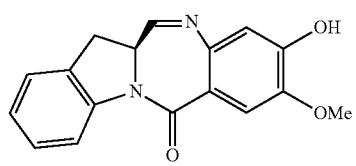 ($a_1$)

to form a compound of formula (18d), or a pharmaceutically acceptable salt thereof, wherein $X_3$ is —Cl; $P_3$ is H or an amine protecting group; and $R_{100}$ is ($C_1$-$C_3$) alkoxy.

8. The method of claim 7, wherein the compound of formula (17d) is reacted with monomer of formula ($a_1$), wherein $P_3$ is H, to form a compound of formula (Id'):

(Id')
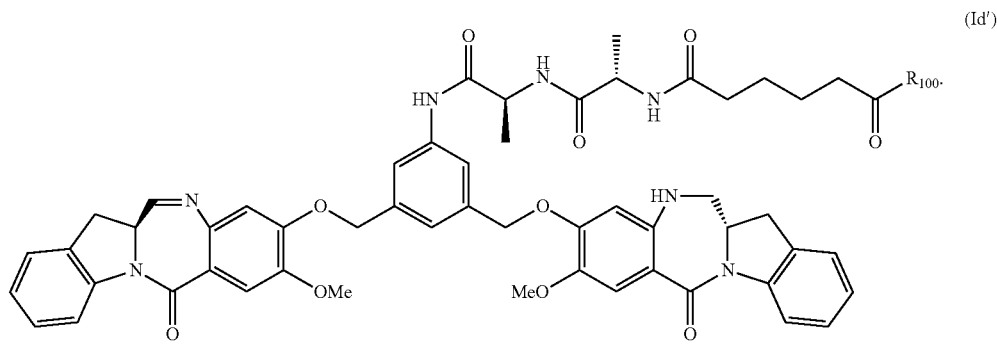

9. The method of claim 8, wherein $P_3$ is an amine protecting group, and the compound of formula (18d) is further reacted with an amine deprotecting reagent to form a compound of formula (Id'):

(Id')
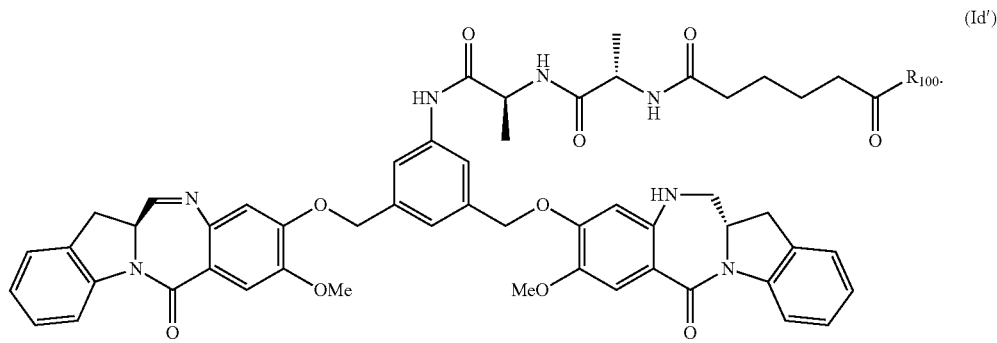

10. The method of claim 7, wherein the compound of formula (14d) or a salt thereof is prepared a method comprising the following steps:
   (1) reacting a chlorinating reagent with a compound of formula (2d),

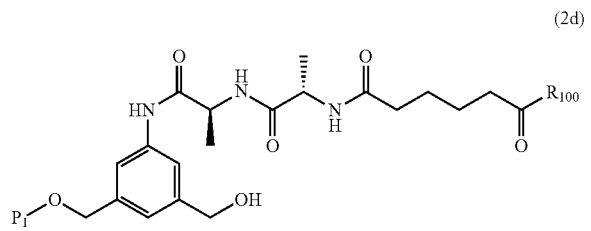

to form a compound a compound of formula (13d),

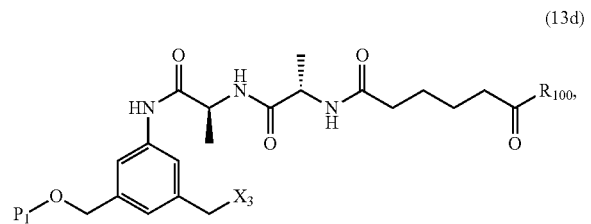

or a salt thereof;
   (2) reacting the compound of formula (13d) with an alcohol deprotecting reagent to form the compound of formula (14d) or a salt thereof; wherein $P_1$ is an alcohol protecting group.

11. The method of claim 10, wherein the compound of formula (2d) is prepared by reacting a compound of formula (id) with an alcohol protecting reagent

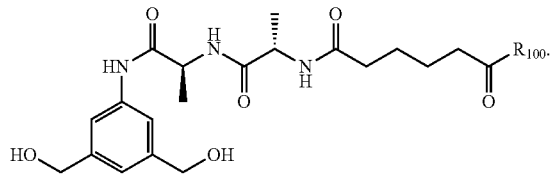

12. The method of claim 7, wherein the compound of formula (14d) is reacted with a monomer of formula ($d_1$) in the presence of an alcohol activating agent.

13. The method claim 12, wherein the alcohol activating agent is triphenylphosphine.

14. The method of claim 12, wherein the compound of formula (14d) is reacted with a monomer of formula ($d_1$) in the presence of an azodicarboxylate.

15. The method of claim 14, wherein the azodicarboxylate is selected from the group consisting of diethyl azodicarboxylate (DEAD), diisopropyl azodicarboxylate (DIAD), 1,1'-(azodicarbonyl)dipiperidine (ADDP), and ditertbutyl azodicarboxylate (DTAD).

16. The method of claim 15, wherein the azodicarboxylate is diisopropyl azodicarboxylate (DIAD).

17. The method of claim 13, wherein the compound of formula (14d) is reacted with a monomer of formula ($d_1$) in the presence of an azodicarboxylate selected from the group consisting of diethyl azodicarboxylate (DEAD), diisopropyl azodicarboxylate (DIAD), 1,1'-(azodicarbonyl)dipiperidine (ADDP), and ditertbutyl azodicarboxylate (DTAD).

18. The method of claim 17, wherein the azodicarboxylate is diisopropyl azodicarboxylate (DIAD).

* * * * *

UNITED STATES PATENT AND TRADEMARK OFFICE
CERTIFICATE OF CORRECTION

PATENT NO. : 10,081,640 B2
APPLICATION NO. : 15/216548
DATED : September 25, 2018
INVENTOR(S) : Baudouin Gérard et al.

It is certified that error appears in the above-identified patent and that said Letters Patent is hereby corrected as shown below:

In Claim 7, at Column 278, please replace the term "$(d_i)$" with "$(d_1)$".

In Claim 10, at Column 281, please replace the following phrase:
"wherein the compound of formula (14d) or a salt thereof is prepared a method comprising the following steps"
With the following phrase:
"wherein the compound of formula (14d) or a salt thereof is prepared using a method comprising the following steps".

In Claim 11, at Column 281, please replace the term "(id)" with "(1d)".

Signed and Sealed this
Twentieth Day of November, 2018

Andrei Iancu
*Director of the United States Patent and Trademark Office*